(12) United States Patent
Bartlett et al.

(10) Patent No.: US 11,186,579 B2
(45) Date of Patent: Nov. 30, 2021

(54) THERAPEUTIC HETEROCYCLIC COMPOUNDS

(71) Applicant: Gilead Sciences, Inc., Foster City, CA (US)

(72) Inventors: Mark J. Bartlett, Castro Valley, CA (US); Britton Kenneth Corkey, Redwood City, CA (US); Kristyna M. Elbel, San Francisco, CA (US); Rao V. Kalla, Cupertino, CA (US); Xiaofen Li, Thousand Oaks, CA (US); Thao Perry, San Jose, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 16/502,721

(22) Filed: Jul. 3, 2019

(65) Prior Publication Data

US 2020/0031834 A1    Jan. 30, 2020

Related U.S. Application Data

(60) Provisional application No. 62/694,923, filed on Jul. 6, 2018.

(51) Int. Cl.
*C07D 487/04* (2006.01)
*C07D 471/04* (2006.01)
*A61K 31/519* (2006.01)

(52) U.S. Cl.
CPC ......... *C07D 487/04* (2013.01); *C07D 471/04* (2013.01); *A61K 31/519* (2013.01)

(58) Field of Classification Search
CPC .................................................. C07D 487/04
See application file for complete search history.

(56) References Cited

U.S. PATENT DOCUMENTS

| | | | |
|---|---|---|---|
| 3,845,770 A | 11/1974 | Theeuwes |
| 4,326,525 A | 4/1982 | Swanson |
| 4,902,514 A | 2/1990 | Barclay |
| 4,943,593 A | 7/1990 | Palfreyman |
| 4,965,288 A | 10/1990 | Palfreyman |
| 4,992,445 A | 2/1991 | Lawter |
| 4,997,854 A | 3/1991 | Kagan |
| 5,001,139 A | 3/1991 | Lawter |
| 5,021,456 A | 6/1991 | Palfreyman |
| 5,023,252 A | 6/1991 | Hseih |
| 5,059,714 A | 10/1991 | Palfreyman |
| 5,120,764 A | 6/1992 | Mccarthy |
| 5,182,297 A | 1/1993 | Palfreyman |
| 5,252,608 A | 10/1993 | Palfreyman |
| 5,616,345 A | 4/1997 | Geoghegan |
| 8,513,184 B2 | 8/2013 | Appleby |
| 8,569,296 B2 | 10/2013 | Liang |
| 8,722,054 B2 | 5/2014 | Apelian |
| 9,670,205 B2 | 6/2017 | Aktoudianakis |
| 2004/0248671 A1 | 12/2004 | Farjanel |
| 2008/0234251 A1 | 9/2008 | Doherty |
| 2008/0306050 A1 | 12/2008 | Doherty |
| 2009/0047249 A1 | 2/2009 | Graupe |
| 2010/0029585 A1 | 2/2010 | Howbert |
| 2010/0143301 A1 | 6/2010 | Desai |
| 2011/0092485 A1 | 4/2011 | Howbert |
| 2011/0098248 A1 | 4/2011 | Halcomb |
| 2011/0118235 A1 | 5/2011 | Howbert |
| 2012/0082658 A1 | 4/2012 | Hershberg |
| 2012/0219615 A1 | 8/2012 | Hershberg |
| 2013/0079327 A1 | 3/2013 | Yamamoto |
| 2013/0165489 A1 | 6/2013 | Cocklin |
| 2013/0217880 A1 | 8/2013 | Yamamoto |
| 2013/0251673 A1 | 9/2013 | Hartman |
| 2013/0267517 A1 | 10/2013 | Guo |
| 2013/0344029 A1 | 12/2013 | Aciro |

(Continued)

FOREIGN PATENT DOCUMENTS

WO    WO2009062285 A1    5/2009
WO    WO2010130034 A1    11/2010

(Continued)

OTHER PUBLICATIONS

Cheong, J.E. et al. (2018). "A Patent Review of IDO1 Inhibitors for Cancer," Expert Opinion on Therapeutic Patents 28(4):317-330.

(Continued)

*Primary Examiner* — John S Kenyon
(74) *Attorney, Agent, or Firm* — Morrison & Foerster LLP

(57) ABSTRACT

Compounds having the following Formula (I), or a pharmaceutically acceptable salt or pharmaceutically acceptable tautomer thereof, and methods of their use and preparation are disclosed:

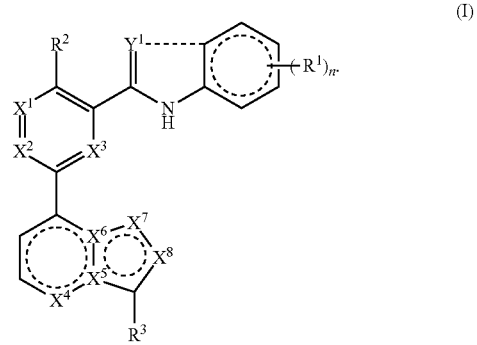

(I)

36 Claims, No Drawings

(56) References Cited

U.S. PATENT DOCUMENTS

| | | |
|---|---|---|
| 2013/0344030 A1 | 12/2013 | Steadman |
| 2014/0030221 A1 | 1/2014 | Aciro |
| 2014/0045849 A1 | 2/2014 | Mcgowan |
| 2014/0066432 A1 | 3/2014 | Howbert |
| 2014/0073642 A1 | 3/2014 | Mcgowan |
| 2014/0088085 A1 | 3/2014 | Burgess |
| 2014/0275167 A1 | 9/2014 | Hartman |
| 2014/0330015 A1 | 11/2014 | Yamamoto |
| 2014/0343032 A1 | 11/2014 | Guo |
| 2014/0350031 A1 | 11/2014 | Mc Gowan |
| 2016/0289229 A1 | 10/2016 | Aktoudianakis |
| 2020/0031801 A1 | 1/2020 | Bartlett |

FOREIGN PATENT DOCUMENTS

| | | | |
|---|---|---|---|
| WO | WO2012003497 A1 | 1/2012 | |
| WO | WO2012003498 A1 | 1/2012 | |
| WO | WO2012145728 A1 | 1/2013 | |
| WO | WO2013006738 A1 | 1/2013 | |
| WO | WO2013006792 A1 | 1/2013 | |
| WO | WO2013159064 A1 | 10/2013 | |
| WO | WO2014006572 A1 | 1/2014 | |
| WO | WO2014023813 A1 | 2/2014 | |
| WO | WO2014033167 A1 | 3/2014 | |
| WO | WO2014033170 A1 | 3/2014 | |
| WO | WO2014033176 A1 | 3/2014 | |
| WO | WO2014037480 A1 | 3/2014 | |
| WO | WO2014056953 A1 | 4/2014 | |
| WO | WO2014076221 A1 | 5/2014 | |
| WO | WO2014128189 A1 | 8/2014 | |
| WO | WO2014131847 A1 | 9/2014 | |
| WO | WO2015001491 A1 | 1/2015 | |
| WO | WO2018039512 A1 | 3/2018 | |
| WO | WO-2019040102 A1 * | 2/2019 | ......... A61K 31/4745 |
| WO | WO2019040102 A1 | 2/2019 | |
| WO | WO2020010223 A1 | 1/2020 | |

OTHER PUBLICATIONS

Cheson, B.D. et al. (Aug. 7, 2008). "Monoclonal Antibody Therapy for B-Cell Non-Hodgkin's Lymphoma," The New England Journal of Medicine 359(6):613-626.

Ferrara, N. et al. (Dec. 1999). "Clinical Applications of Angiogenic Growth Factors and Their Inhibitors," Nature Med. 5(12):1359-1364.

Foster, (Jan. 1, 1984). "Deuterium Isotope Effects in Studies of Drug Metabolism," Trends Pharmacol. Sci. 5(12):524-527.

Gu, Z. et al. (Jul. 6, 2005). "A highly specific inhibitor of matrix metalloproteinase-9 rescues laminin from proteolysis and neurons from apoptosis in transient focal cerebral ischernia," The Journal of Neuroscience 25(27):6401-6408.

International Search Report dated Nov. 26, 2019, for Patent Application No. PCT/US2019/040540, filed Jul. 3, 2019, four pages.

Morton, L.M. et al. (2006). "Lymphoma Incidence Patterns by WHO Subtype in the United States, 1992-2001," Blood 107(1):265-276.

Nicolaou, K.C. et al. (1994). "Calicheamicin η : A Rationally Designed Molecule with Extremely Potent and Selective DNA Cleaving Properties and Apoptosis Inducing Activity," Angew. Chem. Intl. Ed. Engl. 33(2):183-186.

Wierda, W.G. (2006). "Current arid Investigational Therapies for Patients with CLL," Hematology x(x):285-294.

Written Opinion of the International Searching Authority dated Nov. 26, 2019, for Patent Application No. PCT/US2019/040540, filed Jul. 3, 2019, five pages.

Indian Office Action dated Apr. 9, 2021 for IN Application No. 202117000204 filed on Jan. 4, 2021, 5 pages (English Translation).

International Preliminary Report on Patentability dated Jan. 12, 2021, for Patent Application No. PCT/US2019/040540, filed Jul. 3, 2019, 6 pages.

* cited by examiner

THERAPEUTIC HETEROCYCLIC COMPOUNDS

CROSS REFERENCE TO RELATED APPLICATION

This patent application claims the benefit of priority of U.S. Provisional Patent Application Ser. No. 62/694,923, filed Jul. 6, 2018. The contents of this application are incorporated herein by reference.

FIELD

The present disclosure relates generally to inhibitors of indoleamine 2,3-dioxygenase 1 (IDO1) activity and methods of use and manufacture thereof.

BACKGROUND

Catabolism of the essential amino acid tryptophan by the inducible heme-containing enzyme indoleamine 2,3-dioxygenase 1 (IDO1) is a central pathway maintaining the immunosuppressive microenvironment in many cancers. IDO1 catalyzes the degradation of tryptophan to kynurenine, and its effects on immune suppression are due to decreased tryptophan availability and the generation of tryptophan metabolites resulting in multipronged negative effects on cytotoxic T lymphocytes, as well as expansion of immunosuppressive regulatory T cells. IDO1 is elevated in multiple cancers, and is induced by chemotherapy, targeted therapy, or immunotherapy. IDO1 expression in the tumor microenvironment is correlated with poor prognosis in a variety of cancers. IDO1 inhibitors are positioned to potentiate the efficacy of multiple oncology therapeutics including immunotherapies, targeted agents, and chemotherapies. Indeed, epacadostat (INCB24360), a potent and selective IDO1 inhibitor, entered clinical trials and is demonstrating activity in combination with ipilimumab (anti-CTLA4) in melanoma.

In addition to the above, IDO1 has been shown to play a role in chronic infections, HBV, HIV and AIDS, autoimmune diseases or disorders (e.g., rheumatoid arthritis), and immunologic tolerance, such as prevention of fetal rejection in utero. Inhibition of IDO1 may also be an important treatment strategy for patients with neurological or neuropsychiatric diseases or disorders, such as depression.

A need remains for additional therapeutic agents useful to treat proliferative disorders or diseases that are mediated by IDO1.

SUMMARY

The present disclosure provides compounds that function as inhibitors of IDO1. The disclosure also provides compositions, including pharmaceutical compositions, kits that include the compounds, and methods of using and making the compounds. The compounds provided herein are useful in treating diseases, disorders, or conditions that are mediated by IDO1. The disclosure also provides compounds for use in therapy. The disclosure further provides compounds for use in a method of treating a disease, disorder, or condition that is mediated by IDO1. Moreover, the disclosure provides uses of the compounds in the manufacture of a medicament for the treatment of a disease, disorder or condition that is mediated by IDO1.

In some embodiments, provided is a compound having the structure of Formula I:

wherein:
  $Y^1$ is O or N;
  ------ is a single bond that is present or absent,
    wherein ------ is absent when $Y^1$ is O and is present when $Y^1$ is N;
  $X^1$, $X^2$, $X^3$, and $X^4$ are each independently N or CH;
  each indicates that the ring in which it is contained is aromatic;
  one of $X^5$ and $X^6$ is C and one of $X^5$ and $X^6$ is N;
  one of $X^7$ and $X^8$ is $CR^4$ and one of $X^7$ and $X^8$ is N, provided that if $X^5$ is N, $X^8$ is $CR^4$;
  n is 0, 1, 2, 3, or 4;
  each $R^1$ is independently $C_{1-6}$ alkyl or halo;
  $R^2$ is halo, $C_{1-6}$ alkyl, or $C_{1-6}$ haloalkyl;
  $R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;
  $R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and
  each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy, or a pharmaceutically acceptable salt or pharmaceutically acceptable tautomer thereof.

Another embodiment provides a compound having the following Formula Ia:

wherein:

$X^1$, $X^2$, $X^3$, and $X^4$ are each independently N or CH;

each 

indicates that the ring in which it is contained is aromatic;
one of $X^5$ and $X^6$ is C and one of $X^5$ and $X^6$ is N;
one of $X^7$ and $X^8$ is $CR^4$ and one of $X^7$ and $X^8$ is N, provided that if $X^5$ is N, $X^8$ is $CR^4$;

n is 0, 1, 2, 3, or 4;

each $R^1$ is independently $C_{1-6}$ alkyl or halo;

$R^2$ is halo, $C_{1-6}$ alkyl, or $C_{1-6}$ haloalkyl;

$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;

$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy, or a pharmaceutically acceptable salt or pharmaceutically acceptable tautomer thereof Another embodiment provides a compound having the following Formula Ib:

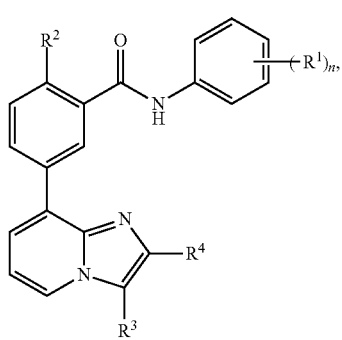

(Ib)

wherein:

n is 0, 1, 2, 3, or 4;

each $R^1$ is independently $C_{1-6}$ alkyl or halo;

$R^2$ is halo, $C_{1-6}$ alkyl or $C_{1-6}$ haloalkyl;

$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;

$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy, or a pharmaceutically acceptable salt or pharmaceutically acceptable tautomer thereof.

Another embodiment provides a compound having the following Formula Ic:

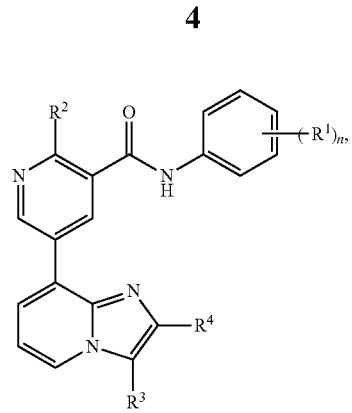

(Ic)

wherein:

n is 0, 1, 2, 3, or 4;

each $R^1$ is independently $C_{1-6}$ alkyl or halo;

$R^2$ is halo, $C_{1-6}$ alkyl or $C_{1-6}$ haloalkyl;

$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;

$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy, or a pharmaceutically acceptable salt or pharmaceutically acceptable tautomer thereof.

Another embodiment provides a compound having the following Formula Id:

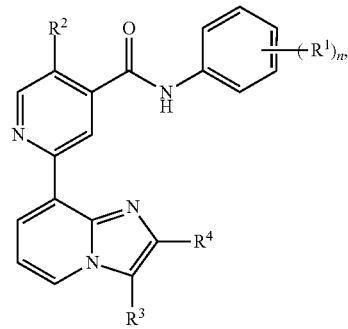

(Id)

wherein:

n is 0, 1, 2, 3, or 4;

each $R^1$ is independently $C_{1-6}$ alkyl or halo;

$R^2$ is halo, $C_{1-6}$ alkyl or $C_{1-6}$ haloalkyl;

$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;

$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy, or a pharmaceutically acceptable salt or pharmaceutically acceptable tautomer thereof.

Another embodiment provides a compound having the following Formula Ie:

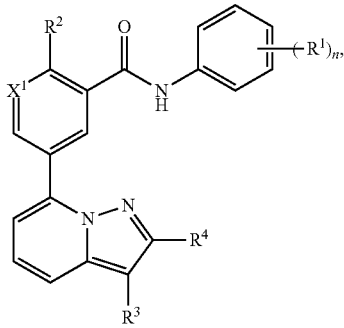

(Ie)

wherein:
$X^1$ is N or CH;
n is 0, 1, 2, 3, or 4;
each $R^1$ is independently $C_{1-6}$ alkyl or halo;
$R^2$ is halo, $C_{1-6}$ alkyl or $C_{1-6}$ haloalkyl;
$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;
$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and
each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy, or a pharmaceutically acceptable salt or pharmaceutically acceptable tautomer thereof.

Another embodiment provides a compound having the following Formula If:

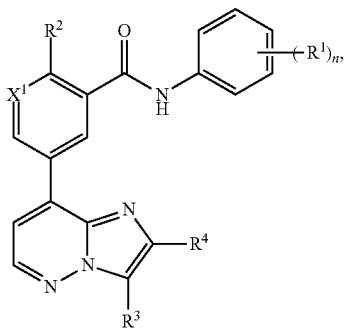

(If)

wherein:
$X^1$ is N or CH;
n is 0, 1, 2, 3, or 4;
each $R^1$ is independently $C_{1-6}$ alkyl or halo;
$R^2$ is halo, $C_{1-6}$ alkyl or $C_{1-6}$ haloalkyl;
$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;
$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy, or a pharmaceutically acceptable salt or pharmaceutically acceptable tautomer thereof.

Another embodiment provides a compound having the following Formula Ig:

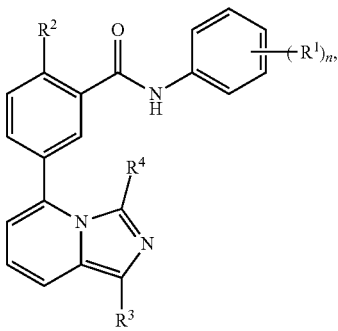

(Ig)

wherein:
n is 0, 1, 2, 3, or 4;
each $R^1$ is independently $C_{1-6}$ alkyl or halo;
$R^2$ is halo, $C_{1-6}$ alkyl or $C_{1-6}$ haloalkyl;
$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;
$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and
each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy, or a pharmaceutically acceptable salt or pharmaceutically acceptable tautomer thereof.

Another embodiment provides a compound having the following Formula Ih:

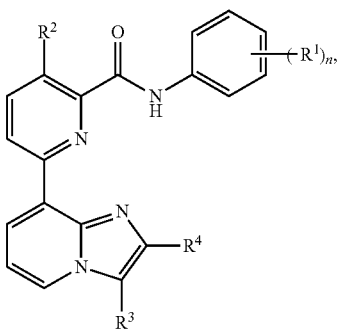

(Ih)

wherein:
n is 0, 1, 2, 3, or 4;
each $R^1$ is independently $C_{1-6}$ alkyl or halo;
$R^2$ is halo, $C_{1-6}$ alkyl or $C_{1-6}$ haloalkyl;
$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;

$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy, or a pharmaceutically acceptable salt or pharmaceutically acceptable tautomer thereof.

In some embodiments, provided is a compound having the structure of Formula Ii:

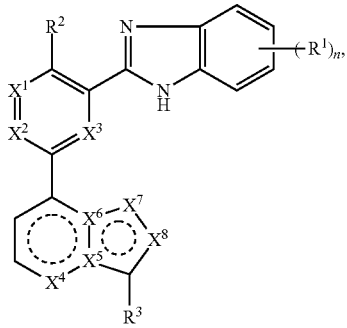

(Ii)

wherein:

$X^1$, $X^2$, $X^3$, and $X^4$ are each independently N or CH;

each

indicates that the ring in which it is contained is aromatic;

one of $X^5$ and $X^6$ is C and one of $X^5$ and $X^6$ is N;

one of $X^7$ and $X^8$ is $CR^4$ and one of $X^7$ and $X^8$ is N, provided that if $X^5$ is N, $X^8$ is $CR^4$;

n is 0, 1, 2, 3, or 4;

each $R^1$ is independently $C_{1-6}$ alkyl or halo;

$R^2$ is halo, $C_{1-6}$ alkyl or $C_{1-6}$ haloalkyl;

$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;

$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy, or a pharmaceutically acceptable salt or pharmaceutically acceptable tautomer thereof.

In some embodiments, provided is a compound having the structure of Formula Ij:

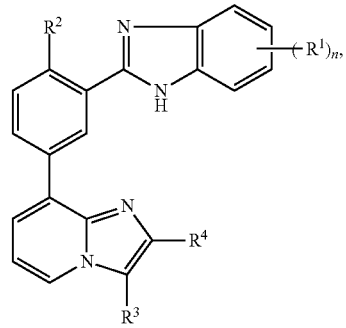

(Ij)

wherein:

n is 0, 1, 2, 3, or 4;

each $R^1$ is independently $C_{1-6}$ alkyl or halo;

$R^2$ is halo, $C_{1-6}$ alkyl or $C_{1-6}$ haloalkyl;

$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;

$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy, or a pharmaceutically acceptable salt or pharmaceutically acceptable tautomer thereof.

In some embodiments, a method of treating a subject having a disease or condition responsive to the inhibition of IDO1 activity with a pharmaceutical composition having a compound of Formula I, Ia, Ib, Ic, Id, Ie, If, Ig, Ih, Ii, or Ij, or a pharmaceutically acceptable salt or pharmaceutically acceptable tautomer thereof is provided.

In some embodiments, a method of inhibiting the activity of an IDO1 protein by contacting the protein with the a compound of Formula I, Ia, Ib, Ic, Id, Ie, If, Ig, Ih, Ii, or Ij, or a pharmaceutically acceptable salt or pharmaceutically acceptable tautomer thereof is provided.

In some embodiments, a method of inhibiting growth or a proliferation of cancer cells, by administering a therapeutically effective amount of a compound of any of Formula I, Ia, Ib, Ic, Id, Ie, If, Ig, Ih, Ii, or Ij, or a pharmaceutically acceptable salt or pharmaceutically acceptable tautomer thereof is provided.

In some embodiments, a method of inhibiting immunosuppression in a subject by administering a therapeutically effective amount of a compound of any of Formula I, Ia, Ib, Ic, Id, Ie, If, Ig, Ih, Ii, or Ij, or a pharmaceutically acceptable salt or pharmaceutically acceptable tautomer thereof is provided.

In some embodiments, a method of treating cancer or viral infection in a subject by administering a therapeutically effective amount of a compound of any of Formula I, Ia, Ib, Ic, Id, Ie, If, Ig, Ih, Ii, or Ij, or a pharmaceutically acceptable salt or pharmaceutically acceptable tautomer thereof is provided. In some embodiments, the viral infection is hepatitis B virus (HBV) or human immunodeficiency virus (HIV). In some embodiments, the cancer is selected from the group consisting of melanoma, non-small cell lung cancer, colorectal cancer, pancreatic cancer, and bladder cancer.

In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of an anti-viral agent, a chemotherapeutic, an immunosuppressant, radiation, an anti-tumor vaccine, an antiviral vaccine, cytokine therapy, a checkpoint inhibitor, or a tyrosine kinase inhibitor.

In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of an HBV inhibitor or an HIV inhibitor.

In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of a checkpoint inhibitor, where the checkpoint inhibitor is a PD1 inhibitor, a PD-L1 inhibitor, a PD1 and a PD-L1 inhibitor, a TIM-3 inhibitor, a TIM-3 and PD1 inhibitor, a LAG-3 inhibitor, or a LAG-3 and PD-1 inhibitor. In some embodiments, the checkpoint inhibitor is a monoclonal antibody. In some embodiments, the checkpoint inhibitor is a small molecule. In some embodiments, the checkpoint inhibitor is nivolumab, pembrolizumab, lambrolizumab, pidilizumab, durvalumab, avelumab, atezolizumab, PDR001, TSR-042, or BMS-986016, or a pharmaceutically acceptable salt or solvate of any of the forgoing.

In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of at least one additional therapeutic agent selected from the following group: Inducible T-cell costimulator (ICOS) agonists, cytotoxic T-lymphocyte antigen 4 (CTLA-4)-blocking antibodies, PD1 and/or PD-L1 inhibitors, Cluster of Differentiation 47 (CD47) inhibitors, Hematopoietic Progenitor Kinase (HPK1) inhibitors, Toll-like receptor 7 (TLR7) agonists, OX40 agonists, GITR agonists, CD40 agonists, CD137 agonists, Indoleamine-pyrrole-2,3-dioxygenase (IDO1) inhibitors, Toll-like receptor 8 (TLR8) agonists, T cell immunoglobulin and mucin domain-3 (TIM-3) inhibitors, lymphocyte activation gene 3 (LAG-3) inhibitors, CEACAM1 inhibitors, T cell immunoreceptor with Ig and ITIM domains (TIGIT) inhibitors, V-domain immunoglobulin (Ig)-containing suppressor of T-cell activation (VISTA) inhibitors, anti-Killer IgG-like receptors (KIR) inhibitors, STING agonists, C—X—C chemokine receptor type 4 (CXCR-4) inhibitors, B7-H3 inhibitors, and CD73 inhibitors.

In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of at least one additional therapeutic agent selected from the following group of PD1 inhibitors: nivolumab, lambrolizumab, pembrolizumab, pidilizumab, PDR001, or TSR-001, or a pharmaceutically acceptable salt or solvate of any of the forgoing.

In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of at least one additional therapeutic agent selected from the following group of PD-L1 inhibitors: atezolizumab, durvalumab, or avelumab, or a pharmaceutically acceptable salt or solvate of any of the forgoing.

In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of Toll-like receptor 7 (TLR7) agonist. In some embodiments, the Toll-like receptor 7 (TLR7) agonist is vesatolimod.

In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of a Toll-like receptor 8 (TLR8) agonist. In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of a Toll-like receptor 8 (TLR8) agonist and a therapeutically effective amount of a Programmed Death 1 (PD-1) inhibitor and/or a Programmed Death Ligand 1 (PD-L1) inhibitor.

In some embodiments, the method of inhibiting IDO1 protein activity, the method of inhibiting growth or proliferation of cancer cells, the method of inhibiting immunosuppression, the method of treating cancer, or the method of treating a viral infection further includes administering to the subject a therapeutically effective amount of an additional therapeutic agent selected from T cell immunomodulators along with the compounds of Formula I, Ia, Ib, Ic, Id, Ie, If, Ig, Ih, Ii, or Ij, or a pharmaceutically acceptable salt or pharmaceutically acceptable tautomer thereof. In some embodiements, the T cell immunomodulator is selected from the group consisting of inhibitory RNA, HPK1 inhibitors, IL2/15/17 fusion proteins, OX40 agonists, CD27 agonists, MKNK1/2 inhibitors, CD40 agonists, CD137 agonists, CD28 agonists, and GITR agonists.

Some embodiments provide a method of using a compound of Formula I, Ia, Ib, Ic, Id, Ie, If, Ig, Ih, Ii, or Ij, or additional Formulas described throughout, or a pharmaceutically acceptable salt or pharmaceutically acceptable tautomer thereof, in the treatment of a disease or condition in a mammal, particularly a human, that is amenable to treatment by an IDO1 inhibitor (e.g., cancer, HBV, etc.).

In some embodiments, the disclosure herein provides pharmaceutical compositions comprising a therapeutically effective amount of a compound of the disclosure (e.g., a compound of Formula I, Ia, Ib, Ic, Id, Ie, If, Ig, Ih, Ii, or Ij, or additional Formulas described throughout), or a pharmaceutically acceptable salt or pharmaceutically acceptable tautomer thereof, and at least one pharmaceutically acceptable excipient.

In some embodiments, the disclosure herein provides an article of manufacture comprising a unit dosage of a compound of the disclosure (e.g., a compound of Formula I, Ia, Ib, Ic, Id, Ie, If, Ig, Ih, Ii, or Ij, or additional Formulas described throughout), or a pharmaceutically acceptable salt or pharmaceutically acceptable tautomer thereof.

In some embodiments, the disclosure herein provides an article of manufacture comprising a unit dosage of a compound of the disclosure (e.g., a compound of Formula I, Ia, Ib, Ic, Id, Ie, If, Ig, Ih, Ii, or Ij, or additional Formulas described throughout, or a pharmaceutically acceptable salt thereof).

In some embodiments, the disclosure herein provides a compound of the disclosure (e.g., a compound of Formula I, Ia, Ib, Ic, Id, Ie, If, Ig, Ih, Ii, or Ij, or additional Formulas described throughout), or a pharmaceutically acceptable salt or pharmaceutically acceptable tautomer thereof, for use in medical therapy.

In some embodiments, the disclosure herein provides a compound of the disclosure (e.g., a compound of Formula I, Ia, Ib, Ic, Id, Ie, If, Ig, Ih, Ii, or Ij, or additional Formulas described throughout), or a pharmaceutically acceptable salt or pharmaceutically acceptable tautomer thereof, for use in medical therapy.

In some embodiments, the disclosure herein provides a compound of the disclosure (e.g., a compound of Formula I, Ia, Ib, Ic, Id, Ie, If, Ig, Ih, Ii, or Ij, or additional Formulas described throughout), or a pharmaceutically acceptable salt or pharmaceutically acceptable tautomer thereof, for the manufacture of a medicament for the treatment of a disease or condition in a mammal, particularly a human, that is amenable to treatment by an IDO1 inhibitor (e.g., cancer, HBV, etc.).

In some embodiments, the disclosure herein provides a compound of the disclosure (e.g., a compound of Formula I, Ia, Ib, Ic, Id, Ie, If, Ig, Ih, Ii, or Ij, or additional Formulas described throughout), or a pharmaceutically acceptable salt or pharmaceutically acceptable tautomer thereof, for the manufacture of a medicament for the treatment of a disease or condition in a mammal, particularly a human, that is amenable to treatment by an IDO1 inhibitor (e.g., cancer, HBV, etc.).

The inventions of this disclosure are described throughout. In addition, specific embodiments of the invention are as disclosed herein.

DETAILED DESCRIPTION

Definitions and General Parameters

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash that is not between two letters or symbols is used to indicate a point of attachment for a substituent. For example, —CONH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —(CH$_2$)$_3$CH$_3$), sec-butyl (i.e. —CH(CH$_3$)CH$_2$CH$_3$), isobutyl (i.e. —CH$_2$CH(CH$_3$)$_2$) and tert-butyl (i.e. —C(CH$_3$)$_3$); and "propyl" includes n-propyl (i.e. —(CH$_2$)$_2$CH$_3$) and isopropyl (i.e. —CH(CH$_3$)$_2$).

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy. "Haloalkoxy" refers to an alkoxy group as defined above, wherein one or more hydrogen atoms are replaced by a halogen.

"Acyl" refers to a group —C(=O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —C(=O)NR$^y$R$^z$ and an "N-amido" group which refers to the group —NR$^y$C(=O)R$^z$, wherein R$^y$ and R$^z$ are independently selected from the group consisting of hydrogen, alkyl, aryl, haloalkyl, or heteroaryl; each of which may be optionally substituted.

"Amino" refers to the group —NR$^y$R$^z$ wherein R$^y$ and R$^z$ are independently selected from the group consisting of hydrogen, alkyl, haloalkyl, aryl, or heteroaryl; each of which may be optionally substituted.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Bridged" refers to a ring fusion wherein non-adjacent atoms on a ring are joined by a divalent substituent, such as an alkylenyl or heteroalkylenyl group or a single heteroatom. Quinuclidinyl and admantanyl are examples of bridged ring systems.

The term "fused" refers to a ring which is bound to an adjacent ring.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocyclyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl include 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocyclyl" or "heterocyclic ring" or "heterocycle" refer to an unsaturated non-aromatic cyclic alkyl group, with one or more ring heteroatoms independently selected from nitrogen, oxygen and sulfur. As used herein, "heterocyclyl" or "heterocyclic ring" or "heterocycle" refer to rings that are saturated or partially saturated unless otherwise indicated, e.g., in some embodiments "heterocyclyl" or "heterocyclic ring" or "heterocycle" refer to rings that are partially saturated where specified. The term "heterocyclyl" or "heterocyclic ring" or "heterocycle" includes heterocycloalkenyl groups (i.e., the heterocyclyl group having at least one double bond). A heterocyclyl may be a single ring or multiple rings wherein the multiple rings may be fused, bridged, or spiro. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, "bridged-heterocyclyl" includes bicyclic and tricyclic ring systems. Also as used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. As used herein, the terms "heterocycle", "heterocyclyl", and "heterocyclic ring" are used interchangeably.

"Hydroxy" or "hydroxyl" refers to the group —OH.

"Oxo" refers to the group (=O) or (O).

"Sulfonyl" refers to the group —S(O)$_2$R, where R is alkyl, haloalkyl, heterocyclyl, cycloalkyl, heteroaryl, or aryl.

Examples of sulfonyl are methylsulfonyl, ethylsulfonyl, phenylsulfonyl, and toluenesulfonyl.

Whenever the graphical representation of a group terminates in a singly bonded nitrogen atom, that group represents an —NH group unless otherwise indicated. Similarly, unless otherwise expressed, hydrogen atom(s) are implied and deemed present where necessary in view of the knowledge of one of skill in the art to complete valency or provide stability.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, the term "substituted alkyl" refers to an alkyl group having one or more substituents including hydroxyl, halo, alkoxy, cycloalkyl, heterocyclyl, aryl, and heteroaryl. In additional embodiments, "substituted cycloalkyl" refers to a cycloalkyl group having one or more substituents including alkyl, haloalkyl, cycloalkyl, heterocyclyl, aryl, heteroaryl, alkoxy, halo, oxo, and hydroxyl; "substituted heterocyclyl" refers to a heterocyclyl group having one or more substituents including alkyl, haloalkyl, heterocyclyl, cycloalkyl, aryl, heteroaryl, alkoxy, halo, oxo, and hydroxyl; "substituted aryl" refers to an aryl group having one or more substituents including halo, alkyl, haloalkyl, cycloalkyl, heterocyclyl, heteroaryl, alkoxy, and cyano; "substituted heteroaryl" refers to an heteroaryl group having one or more substituents including halo, alkyl, haloalkyl, heterocyclyl, heteroaryl, alkoxy, and cyano and "substituted sulfonyl" refers to a group —S(O)$_2$R, in which R is substituted with one or more substituents including alkyl, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds of Formula I, Ia, Ib, Ic, Id, Ie, If, Ig, Ih, Ii, or Ij, in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I, Ia, Ib, Ic, Id, Ie, If, Ig, Ih, Ii, or Ij.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, mono, di or tri cycloalkyl amines, mono, di or tri arylamines or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival).

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or pharmaceutically acceptable salts, isomer, or a mixture thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of IDO1 activity. The therapeutically effective amount may vary depending on the subject, and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process. "Inhibition of activity of IDO1" or variants thereof refers to a decrease in activity in IDO1 as a direct or indirect response to the presence of a compound of the present application relative to the activity IDO1 in the absence of the compound of the present application. "Inhibition of IDO1" refers to a decrease in IDO1 activity as a direct or indirect response to the presence of a compound described herein relative to the activity of IDO1 in the absence of the compound described herein. In some embodiments, the inhibition of IDO1 activity may be compared in the same subject prior to treatment, or other subjects not receiving the treatment.

Compounds

Provided herein are compounds that function as inhibitors of IDO1. In one aspect, provided is a compound having structure of Formula I:

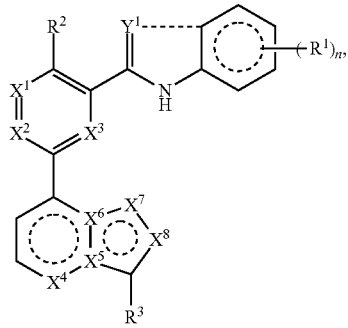

(I)

or a pharmaceutically acceptable salt or pharmaceutically acceptable tautomer thereof.

In some embodiments, compounds of formula I are compounds of formula Ia:

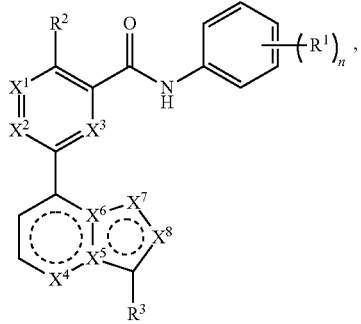

(Ia)

or a pharmaceutically acceptable salt or pharmaceutically acceptable tautomer thereof.

In some embodiments, compounds of formula I are compounds of formula Ib:

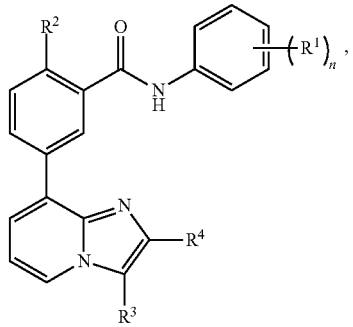

(Ib)

or a pharmaceutically acceptable salt or pharmaceutically acceptable tautomer thereof.

In some embodiments, compounds of formula I are compounds of formula Ic:

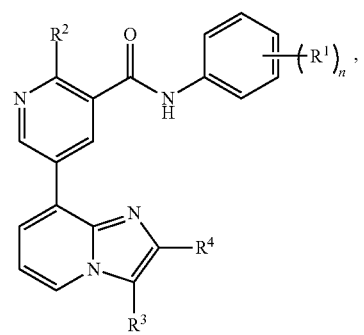

(Ic)

or a pharmaceutically acceptable salt or pharmaceutically acceptable tautomer thereof.

In some embodiments, compounds of formula I are compounds of formula Id:

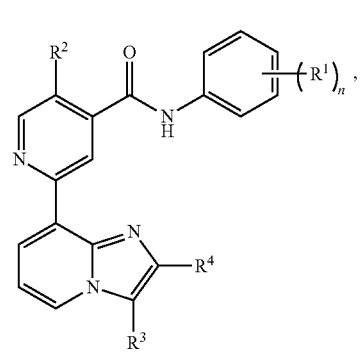

(Id)

or a pharmaceutically acceptable salt or pharmaceutically acceptable tautomer thereof.

In some embodiments, compounds of formula I are compounds of formula Ie:

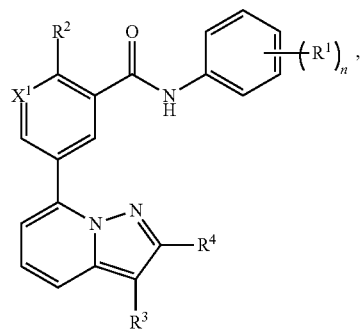

(Ie)

or a pharmaceutically acceptable salt or pharmaceutically acceptable tautomer thereof.

In some embodiments, compounds of formula I are compounds of formula If

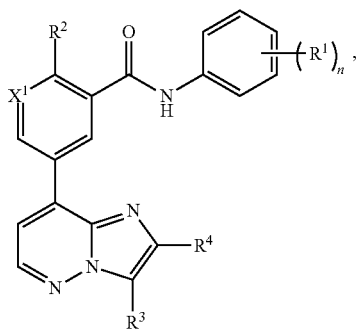

(If)

or a pharmaceutically acceptable salt or pharmaceutically acceptable tautomer thereof.

In some embodiments, compounds of formula I are compounds of formula Ig:

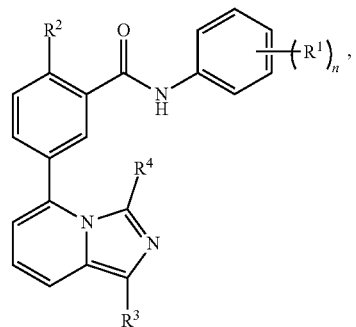

(Ig)

or a pharmaceutically acceptable salt or pharmaceutically acceptable tautomer thereof.

In some embodiments, compounds of formula I are compounds of formula Ih:

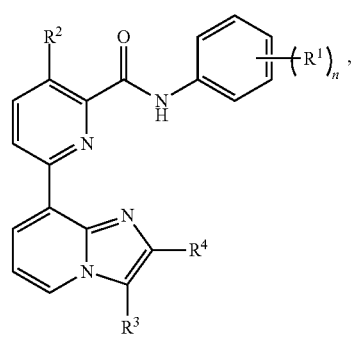

(Ih)

or a pharmaceutically acceptable salt or pharmaceutically acceptable tautomer thereof.

In some embodiments, provided is a compound having the structure of Formula Ii:

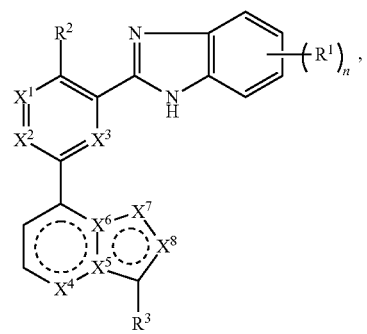

(Ii)

or a pharmaceutically acceptable salt or pharmaceutically acceptable tautomer thereof.

In some embodiments, provided is a compound having the structure of Formula Ij:

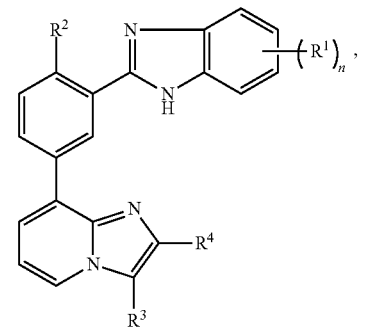

(Ij)

or a pharmaceutically acceptable salt or pharmaceutically acceptable tautomer thereof.

Specific values listed below are values for a compound of Formula I as well as all related formulas (e.g., Ia, Ib, Ic, Id, Ie, If, Ig, Ih, Ii, and Ij), or a pharmaceutically acceptable salt or pharmaceutically acceptable tautomer thereof. It is to be understood that two or more values may combined. Thus, it is to be understood that any variable for compounds of Formula I as well as all related formulas may be combined with any other variable for compounds of Formula I as well as all related formulas the same as if each and every combination of variables were specifically and individually listed. For example, it is understood that any specific value of $R^1$ detailed herein for compounds of Formula I may be combined with any other specific value for one or more of the variables n, $X^1$, $X^2$, $X^4$, $X^5$, $X^6$, $X^7$, $X^8$, $Y^1$, $R^2$, $R^3$, $R^4$, or $R^5$ the same as if each and every combination were specifically and individually listed.

In some embodiments of Formula I, $Y^1$ is O and ------ is absent. In some embodiments of Formula I, $Y^1$ is N and ------ is a present single bond.

In some embodiments of Formula I, Ia, Ie, If, or Ii, $X^1$ is N. In some embodiments of Formula I, Ia, Ie, If, or Ii, $X^1$ is CH.

In some embodiments of Formula I, Ia, or Ii, $X^2$ is N. In some embodiments of Formula I, Ia, or Ii, $X^2$ is CH.

In some embodiments of Formula I, Ia, or Ii, $X^3$ is N. In some embodiments of Formula I, Ia, or Ii, $X^3$ is CH.

In some embodiments of Formula I, Ia or Ii, $X^4$ is N. In some embodiments of Formula I, Ia, or Ii, $X^4$ is CH.

In some embodiments of Formula I, Ia, or Ii, $X^5$ is C and $X^6$ is N. In some embodiments of Formula I, Ia, or Ii, $X^5$ is N and $X^6$ is C.

In some embodiments of Formula I, Ia, or Ii, $X^7$ is N and $X^8$ is $CR^4$. In some embodiments of Formula I, Ia, or Ii, $X^7$ is $CR^4$ and $X^8$ is N.

In some embodiments of Formula I, Ia, or Ii, $X^5$ is C, $X^6$ is N, $X^7$ is N, and $X^8$ is $CR^4$.

In some embodiments of Formula I, Ia, or Ii, $X^5$ is N, $X^6$ is C, $X^7$ is N, and $X^8$ is $CR^4$. In some embodiments of Formula I, Ia, or Ii, $X^5$ is C, $X^6$ is N, $X^7$ is $CR^4$, and $X^8$ is N.

In some embodiments of Formula I, Ia, or Ii, $X^1$ is CH, $X^2$ is CH, $X^3$ is CH, $X^4$ is CH, $X^5$ is N, $X^6$ is C, $X^7$ is N, and $X^8$ is $CR^4$. In some embodiments, $X^1$ is N, $X^2$ is CH, $X^3$ is CH, $X^4$ is CH, $X^5$ is N, $X^6$ is C, $X^7$ is N, and $X^8$ is $CR^4$. In some embodiments, $X^1$ is CH, $X^2$ is N, $X^3$ is CH, $X^4$ is CH, $X^5$ is N, $X^6$ is C, $X^7$ is N, and $X^8$ is $CR^4$. In some embodiments, $X^1$ is N, $X^2$ is CH, $X^3$ is CH, $X^4$ is CH, $X^5$ is C, $X^6$ is N, $X^7$ is N, and $X^8$ is $CR^4$. In some embodiments, $X^1$ is CH, $X^2$ is CH, $X^3$ is CH, $X^4$ is CH, $X^5$ is C, $X^6$ is N, $X^7$ is N, and $X^8$ is $CR^4$. In some embodiments, $X^1$ is N, $X^2$ is CH, $X^3$ is CH, $X^4$ is N, $X^5$ is N, $X^6$ is C, $X^7$ is N, and $X^8$ is $CR^4$. In some embodiments, $X^1$ is CH, $X^2$ is CH, $X^3$ is CH, $X^4$ is N, $X^5$ is N, $X^6$ is C, $X^7$ is N, and $X^8$ is $CR^4$. In some embodiments, $X^1$ is CH, $X^2$ is CH, $X^3$ is CH, $X^4$ is CH, $X^5$ is C, $X^6$ is N, $X^7$ is $CR^4$, and $X^8$ is N. In some embodiments, $X^1$ is CH, $X^2$ is CH, $X^3$ is N, $X^4$ is CH, $X^5$ is N, $X^6$ is C, $X^7$ is N, and $X^8$ is $CR^4$.

In some embodiments of Formula I, Ia, Ib, Ic, Id, Ie, If, Ig, Ih, Ii, or Ij, n is 0, 1, 2, or 3. In some embodiments, n is 0, 1, or 2. In some embodiments, n is 0 or 1. In some embodiments, n is 0. In some embodiments, n is 1. In some embodiments, n is 2. In some embodiments, n is 3. In some embodiments, n is 4. In some embodiments of Formula I, n is 1 and $R^1$ is located at the position para to the —NH—C(=$Y^1$)— moiety. In some embodiments of Formula Ia, Ib, Ic, Id, Ie, If, Ig, or Ih, n is 1 and $R^1$ is located at the position para to the —NH—C(=O)— moiety. In one such emobodiment of Formula I, Ia, Ib, Ic, Id, Ie, If, Ig, or Ih, $R^1$ is halo, such as chloro or flouro. In another such emobodiment of Formula I, Ia, Ib, Ic, Id, Ie, If, Ig, or Ih, $R^1$ is $C_{1-6}$ alkyl, such as methyl or ethyl.

In some embodiments of Formula I, Ia, Ib, Ic, Id, Ie, If, Ig, Ih, Ii, or Ij, n is 1, 2, 3 or 4 and each $R^1$ is independently $C_{1-6}$ alkyl or halo. In some embodiments, each $R^1$ is independently $C_{1-6}$ alkyl, such as methyl, ethyl, n-propyl, isopropyl, butyl, isobutyl, secbutyl, or tertbutyl. In some embodiments, each $R^1$ is independently halo, such as cloro or fluoro. In some embodiments, each $R^1$ is independently methyl, ethyl, n-propyl, isopropyl, butyl, isobutyl, secbutyl, tertbutyl, fluoro, chloro, or bromo. In some embodiments, each $R^1$ is fluoro.

In some embodiments of Formula I, Ia, Ib, Ic, Id, Ie, If, Ig, Ih, Ii, or Ij, $R^2$ is halo, such as cloro or fluoro. In some embodiments of Formula I, Ia, Ib, Ic, Id, Ie, If, Ig, Ih, Ii, or Ij, $R^2$ is $C_{1-6}$ alkyl, such as methyl, ethyl, n-propyl, isopropyl, butyl, isobutyl, secbutyl, or tertbutyl. In some embodiments of Formula I, Ia, Ib, Ic, Id, Ie, If, Ig, Ih, Ii, or Ij, $R^2$ is $C_{1-6}$ haloalkyl, such as fluoromethyl, difluoromethyl, trifluoromethyl, fluoroethyl, difluoroethyl, trifluoroethyl, chloromethyl, dichloromethyl, trichloromethyl, chloroethyl, dichloroethyl, or trichloroethyl. In some embodiments of Formula I, Ia, Ib, Ic, Id, Ie, If, Ig, Ih, Ii, or Ij, $R^2$ is halo, $C_{1-3}$ alkyl or $C_{1-3}$ haloalkyl. In some embodiments of Formula I, Ia, Ib, Ic, Id, Ie, If, Ig, Ih, Ii, or Ij, $R^2$ is methyl, ethyl, n-propyl, isopropyl, butyl, isobutyl, secbutyl, tertbutyl, fluoro, chloro, bromo, iodo, fluoromethyl, difluoromethyl, trifluoromethyl, fluoroethyl, difluoroethyl, trifluoroethyl, chloromethyl, dichloromethyl, trichloromethyl, chloroethyl, dichloroethyl, or trichloroethyl. In some embodiments, $R^2$ is methyl, chloro, or trifluoromethyl. In some embodiments, $R^2$ is methyl. In some embodiments, $R^2$ is chloro. In some embodiments, $R^2$ is trifluoromethyl.

In some embodiments of Formula I, Ia, Ib, Ic, Id, Ie, If, Ig, Ih, Ii, or Ij, $R^3$ is 6-12 membered aryl or 5-12 membered heteroaryl, each of which is unsubstituted. In some embodiments of Formula I, Ia, Ib, Ic, Id, Ie, If, Ig, Ih, Ii, or Ij, $R^3$ is 6-12 membered monocyclic aryl or 5-12 membered monocyclic heteroaryl, each of which is unsubstituted. In some embodiments, $R^3$ is an unsubstituted 6-12 membered aryl, such as phenyl or naphthyl. In some embodiments, $R^3$ is an unsubstituted 5-12 membered heteroaryl, such as pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl. In some embodiments, $R^3$ is 6-12 membered aryl substituted with one, two, or three substituents independently selected from halo, CN, $C_{1-6}$ alkyl, and $C_{1-6}$ haloalkyl. In some embodiments, $R^3$ is 6-12 membered monocyclic aryl substituted with one, two, or three substituents independently selected from halo, CN, $C_{1-6}$ alkyl, and $C_{1-6}$ haloalkyl. In some embodiments, $R^3$ is 5-12 membered heteroaryl substituted with one, two, or three substituents independently selected from halo, CN, $C_{1-6}$ alkyl, and $C_{1-6}$ haloalkyl. In some embodiments, $R^3$ is 5-12 membered monocyclic heteroaryl substituted with one, two, or three substituents independently selected from halo, CN, $C_{1-6}$ alkyl, and $C_{1-6}$ haloalkyl. In some embodiments, $R^3$ is 6-12 membered aryl or 5-12 membered heteroaryl, each of which is unsubstituted or substituted with one, two, or three substituents independently selected from halo and $C_{1-6}$ alkyl. In some embodiments, $R^3$ is 6-12 membered aryl or 5-12 membered heteroaryl, each of which is unsubstituted or substituted with one, two, or three substituents independently selected from fluoro, chloro, bromo, iodo, methyl, ethyl, n-propyl, isopropyl, butyl, isobutyl, secbutyl, and tertbutyl. In some embodiments, $R^3$ is 6-12 membered aryl or 5-12 membered heteroaryl, each of which is unsubstituted or substituted with one, two, or three substituents independently selected from fluoro, chloro, bromo, and iodo. In some embodiments, $R^3$ is 6-12 membered aryl or 5-12 membered heteroaryl, each of which is unsubstituted or substituted with one, two, or three substituents independently selected from methyl, ethyl, n-propyl, isopropyl, butyl, isobutyl, secbutyl, and tertbutyl. In some embodiments, $R^3$ is 6-12 membered aryl or 5-12 membered heteroaryl, each of which is unsubstituted or substituted with one, two, or three substituents independently selected from methyl and fluoro.

In some embodiments of Formula I, Ia, Ib, Ic, Id, Ie, If, Ig, Ih, Ii, or Ij, $R^3$ is phenyl or 5-6 membered heteroaryl, wherein the phenyl or 5-6 membered heteroaryl of $R^3$ is unsubstituted or substituted with one or two substituents independently selected from halo and $C_{1-3}$ alkyl. In some embodiments, $R^3$ is an unsubstituted phenyl. In some embodiments, $R^3$ is an unsubstituted 5-6 membered heteroaryl, such as pyridyl. In some embodiments, $R^3$ is phenyl or a 5-6 membered heteroaryl, each of which is unsubstituted or substituted with one, two, or three substituents independently selected from fluoro, chloro, bromo, iodo, methyl, ethyl, or propyl. In some embodiments, $R^3$ is phenyl or a 5-6 membered heteroaryl, each of which is unsubstituted or substituted with one, two, or three substituents independently selected from fluoro, chloro, bromo, and iodo. In some embodiments, $R^3$ is phenyl or a 5-6 membered heteroaryl, each of which is unsubstituted or substituted with one, two, or three substituents independently selected from methyl, ethyl, or propyl. In some embodiments, $R^3$ is phenyl or a 5-6 membered heteroaryl, each of which is unsubstituted or substituted with one, two, or three substituents independently selected from methyl and fluoro. In some embodiments, the 5-6 membered heteroaryl is pyridinyl, such as pyridin-2-yl, pyridin-3-yl and pyridin-4-yl.

In some embodiments of Formula I, Ia, Ib, Ic, Id, Ie, If, Ig, Ih, Ii, or Ij, $R^3$ is selected from the group consisting of:

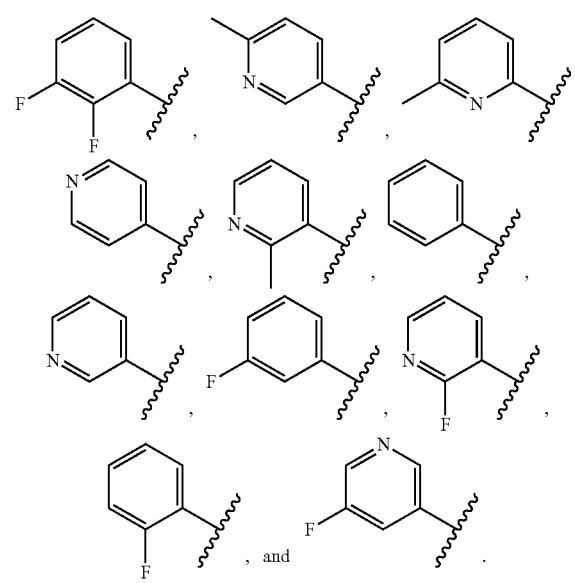

In some embodiments of Formula I, Ia, Ib, Ic, Id, Ie, If, Ig, Ih, Ii, or Ij, $R^2$ is $C_{1-6}$ alkyl, and $R^3$ is 6-12 membered aryl unsubstituted or substituted with one, two, or three substituents independently selected from halo, CN, $C_{1-6}$ alkyl, and $C_{1-6}$ haloalkyl. In some embodiments, $R^2$ is $C_{1-6}$ haloalkyl, and $R^3$ is 6-12 membered aryl unsubstituted or substituted with one, two, or three substituents independently selected from halo, CN, $C_{1-6}$ alkyl, and $C_{1-6}$ haloalkyl. In some embodiments, $R^2$ is halo, and $R^3$ is 6-12 membered aryl unsubstituted or substituted with one, two, or three substituents independently selected from halo, CN, $C_{1-6}$ alkyl, and $C_{1-6}$ haloalkyl. In some embodiments, $R^2$ is $C_{1-6}$ alkyl, and $R^3$ is 5-12 membered heteroaryl unsubstituted or substituted with one, two, or three substituents independently selected from halo, CN, $C_{1-6}$ alkyl, and $C_{1-6}$ haloalkyl. In some embodiments, $R^2$ is $C_{1-6}$ haloalkyl, and $R^3$ is 5-12 membered heteroaryl unsubstituted or substituted with one, two, or three substituents independently selected from halo, CN, $C_{1-6}$ alkyl, and $C_{1-6}$ haloalkyl. In some embodiments, $R^2$ is halo, and $R^3$ is 5-12 membered heteroaryl unsubstituted or substituted with one, two, or three substituents independently selected from halo, CN, $C_{1-6}$ alkyl, and $C_{1-6}$ haloalkyl. In some embodiments, $R^2$ is methyl, ethyl, n-propyl, isopropyl, butyl, isobutyl, secbutyl, tertbutyl, fluoro, chloro, bromo, iodo, fluoromethyl, difluoromethyl, trifluoromethyl, fluoroethyl, difluoroethyl, trifluoroethyl, chloromethyl, dichloromethyl, trichloromethyl, chloroethyl, dichloroethyl, or trichloroethyl; and $R^3$ is phenyl, naphthyl, pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl, each of which is unsubstituted or substituted with one, two, or three substituents independently selected from halo, CN, $C_{1-6}$ alkyl, and $C_{1-6}$ haloalkyl. In some embodiments, $R^2$ is methyl, chloro, or trifluoromethyl; and $R^3$ is selected from the group consisting of:

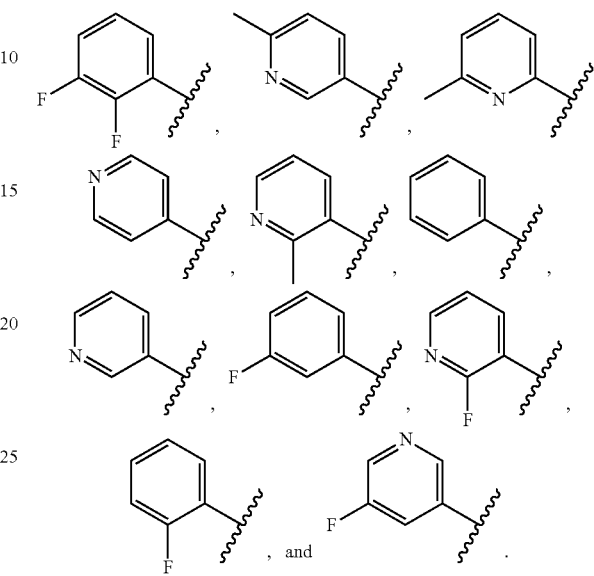

In some embodiments of Formula I, Ia, Ib, Ic, Id, Ie, If, Ig, Ih, Ii, or Ij, $R^4$ is hydrogen. In some embodiments of Formula I, Ia, Ib, Ic, Id, Ie, If, Ig, Ih, Ii, or Ij, $R^4$ is halo, such as cloro or fluoro. In some embodiments of Formula I, Ia, Ib, Ic, Id, Ie, If, Ig, Ih, Ii, or Ij, $R^4$ is $C_{1-6}$ alkyl which is unsubstituted or substituted with one, two, or three $R^5$. In some embodiments of Formula I, Ia, Ib, Ic, Id, Ie, If, Ig, Ih, Ii, or Ij, $R^4$ is $C_{1-6}$ alkoxy which is unsubstituted or substituted with one, two, or three $R^5$. In some embodiments, $R^4$ is hydrogen, fluoro, chloro, bromo, iodo, methyl, ethyl, n-propyl, isopropyl, butyl, pentyl, or hexyl, wherein each of the methyl, ethyl, n-propyl, isopropyl, butyl, pentyl, or hexyl is unsubstituted or substituted with one, two, or three $R^5$. In some embodiments, $R^4$ is hydrogen, fluoro, chloro, methyl, or ethyl, wherein each of the methyl or ethyl is unsubstituted or substituted with one, two, or three $R^5$. In some embodiments, $R^4$ is chloro. In some embodiments, $R^4$ is methyl, or ethyl, wherein each of the methyl or ethyl is unsubstituted or substituted with one, two, or three $R^5$. In some embodiments, $R^4$ is methyl which unsubstituted or substituted with one, two, or three $R^5$. In some embodiments, $R^4$ is ethyl which unsubstituted or substituted with one, two, or three $R^5$.

In some embodiments of Formula I, Ia, Ib, Ic, Id, Ie, If, Ig, Ih, Ii, or Ij, each $R^5$ is independently hydroxyl, amino, $C_{1-2}$ alkyl or $C_{1-2}$ alkoxy, wherein the $C_{1-2}$ alkyl or $C_{1-2}$ alkoxy of $R^5$ is unsubstituted. In some embodiments, at leaset one of $R^5$ is hydroxyl. In some embodiments, at least one of $R^5$ is amino. In some embodiments, at least one of $R^5$ is $C_{1-4}$ alkyl, which is unsubstituted or substituted with $C_{1-3}$ alkyl or $C_{1-3}$ alkoxy. In some embodiments, at least one of $R^5$ is $C_{1-4}$ alkoxy, which is unsubstituted or substituted with $C_{1-3}$ alkyl or $C_{1-3}$ alkoxy. In some embodiments, each $R^5$ is independently hydroxyl, amino, methyl, ethyl, propyl, methoxy, or ethoxy, wherein each of the methyl, ethyl, propyl, methoxy, or ethoxy is unsubstituted or substituted with methyl, ethyl, propyl, methoxy, or ethoxy.

In some embodiments of Formula I, Ia, Ib, Ic, Id, Ie, If, Ig, Ih, Ii, or Ij, R⁴ is selected from the group consisting of: hydrogen, methyl, chloro,

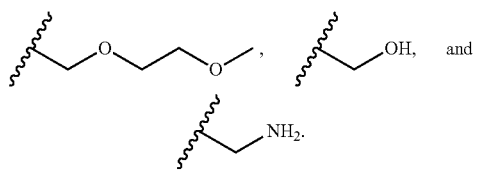

In some embodiments of Formula I, Ia, Ib, Ic, Id, Ie, If, Ig, Ih, Ii, or Ij, the compound of the present disclosure has at least one, two, three, four, five, six, or seven of the following features:

(1) n, where applicable, is 0 or 1;
(2) n, where applicable, is 1 and $R^1$ is located at the position para to the —NH—C(=Y¹)— moiety; (3) each $R^1$ is independently $C_{1-6}$ alkyl, such as methyl, ethyl, n-propyl, isopropyl, butyl, isobutyl, secbutyl, or tertbutyl;
(4) each $R^1$ is independently a halo, such as cloro or fluoro;
(5) each $R^1$ is fluoro;
(6) $R^2$ is $C_{1-6}$ alkyl, such as methyl, ethyl, n-propyl, isopropyl, butyl, isobutyl, secbutyl, or tertbutyl;
(7) $R^2$ is $C_{1-6}$ haloalkyl, such as fluoromethyl, difluoromethyl, trifluoromethyl, fluoroethyl, difluoroethyl, trifluoroethyl, chloromethyl, dichloromethyl, trichloromethyl, chloroethyl, dichloroethyl, or trichloroethyl;
(8) $R^2$ is halo, such as cloro or fluoro;
(9) $R^2$ is methyl, ethyl, n-propyl, isopropyl, butyl, isobutyl, secbutyl, tertbutyl, fluoro, chloro, bromo, iodo, fluoromethyl, difluoromethyl, trifluoromethyl, fluoroethyl, difluoroethyl, trifluoroethyl, chloromethyl, dichloromethyl, trichloromethyl, chloroethyl, dichloroethyl, or trichloroethyl;
(10) $R^2$ is methyl, chloro, or trifluoromethyl;
(11) $R^3$ is an unsubstituted 6-12 membered aryl, such as phenyl or naphthyl;
(12) $R^3$ is an unsubstituted 5-12 membered heteroaryl, such as pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl;
(13) $R^3$ is a 6-12 membered aryl substituted with one, two, or three substituents independently selected from halo, CN, $C_{1-6}$ alkyl, and $C_{1-6}$ haloalkyl;
(14) $R^3$ is a 5-12 membered heteroaryl substituted with one, two, or three substituents independently selected from halo, CN, $C_{1-6}$ alkyl, and $C_{1-6}$ haloalkyl;
(15) $R^3$ is phenyl, naphthyl, pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl, each of which is unsubstituted or substituted with one, two, or three substituents independently selected from halo, CN, $C_{1-6}$ alkyl, and $C_{1-6}$ haloalkyl;
(16) $R^3$ is phenyl or a 5-6 membered heteroaryl, wherein the phenyl or 5-6 membered heteroaryl of $R^3$ is unsubstituted or substituted with one or two substituents independently selected from halo and $C_{1-3}$ alkyl;
(17) $R^3$ is phenyl or pyridinyl, each of which is unsubstituted or substituted with one, two, or three substituents independently selected from methyl and fluoro;

(18) $R^3$ is selected from the group consisting of:

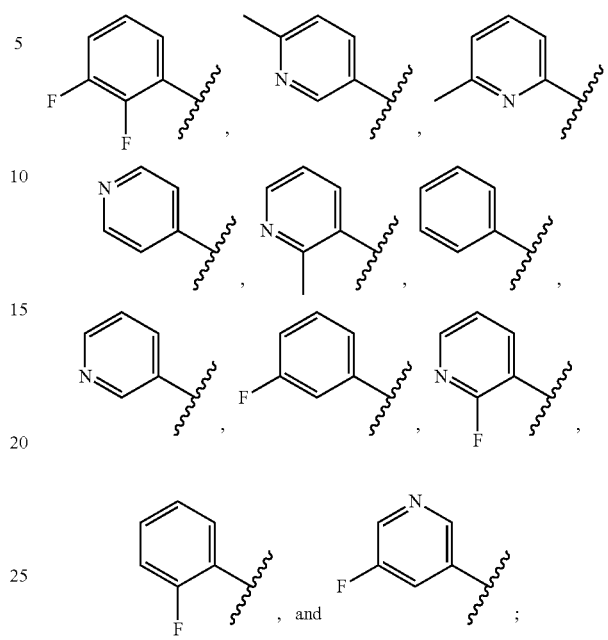

(19) $R^4$ is $C_{1-6}$ alkyl which is unsubstituted or substituted with one, two, or three $R^5$;
(20) $R^4$ is $C_{1-6}$ alkoxy which is unsubstituted or substituted with one, two, or three $R^5$;
(21) $R^4$ is hydrogen;
(22) $R^4$ is hydrogen, fluoro, chloro, methyl, or ethyl, wherein each of the methyl or ethyl is unsubstituted or substituted with one, two, or three $R^5$;
(23) each $R^5$ is independently hydroxyl, amino, $C_{1-2}$ alkyl or $C_{1-2}$ alkoxy, wherein the $C_{1-2}$ alkyl or $C_{1-2}$ alkoxy of $R^5$ is unsubstituted;
(24) at least one of $R^5$ is hydroxyl;
(25) at least one of $R^5$ is amino;
(26) at least one of $R^5$ is $C_{1-4}$ alkyl, which is unsubstituted or substituted with $C_{1-3}$ alkyl or $C_{1-3}$ alkoxy;
(27) each $R^5$ is independently hydroxyl, amino, methyl, ethyl, propyl, methoxy, or ethoxy, wherein each of the methyl, ethyl, propyl, methoxy, or ethoxy is unsubstituted or substituted with methyl, ethyl, propyl, methoxy, or ethoxy; and
(28) $R^4$ is selected from the group consisting of: hydrogen, methyl, chloro,

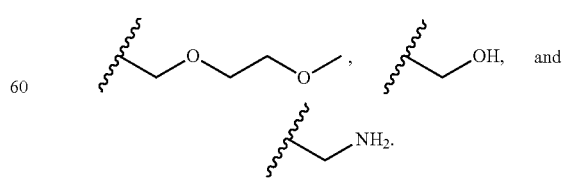

In one embodiment, the compound of the present disclosure is selected from the group consisting of:

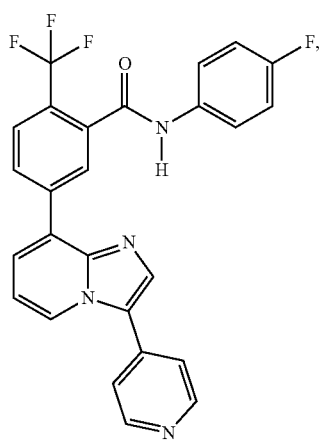
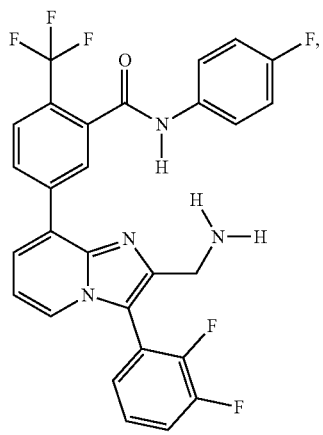
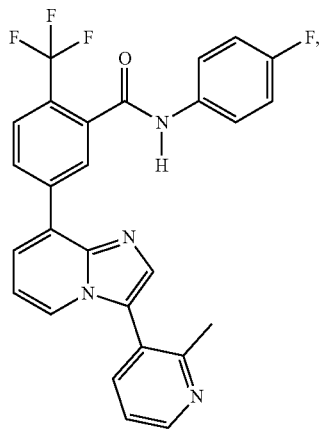
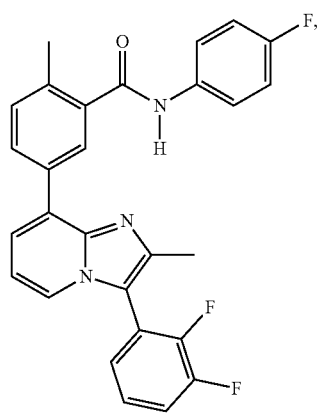
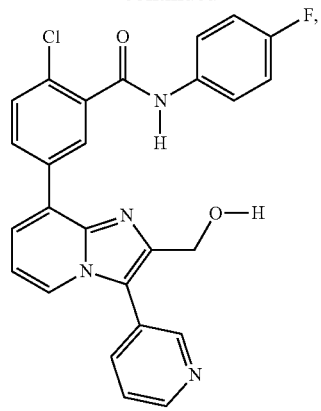
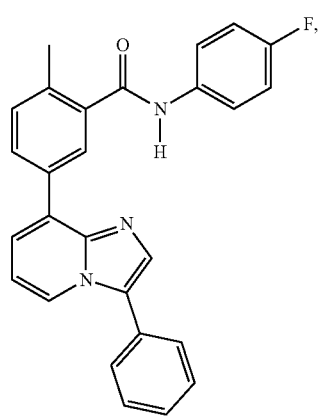
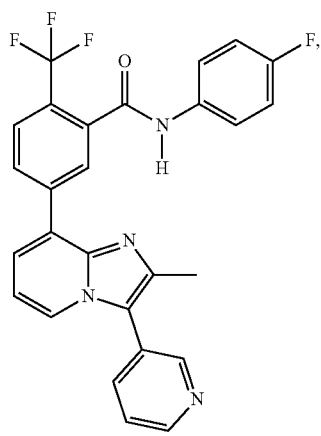
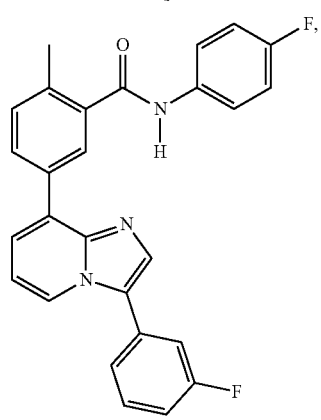

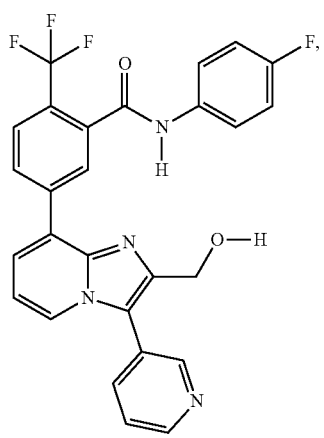
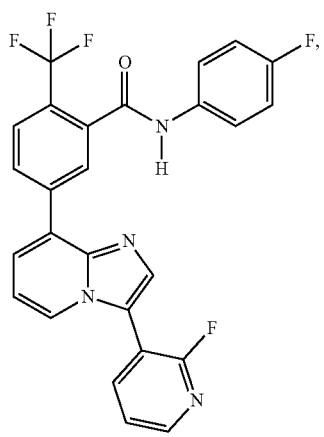
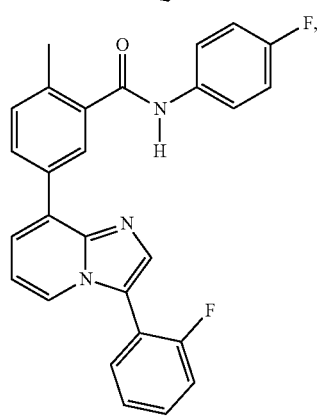
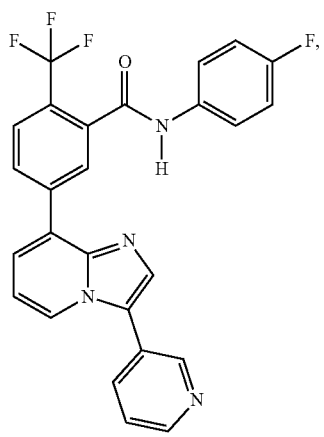
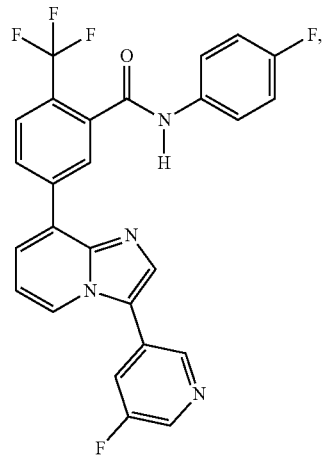
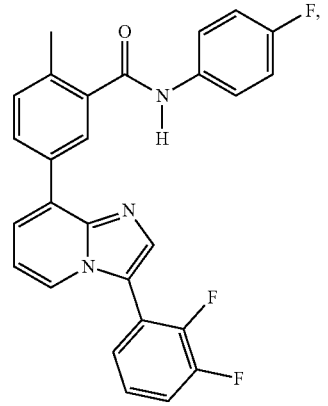
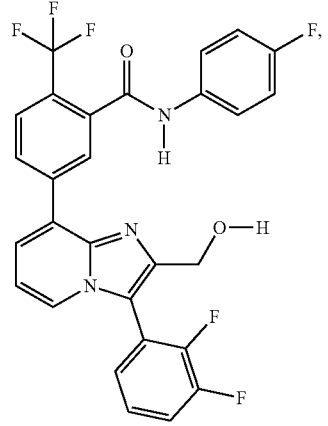
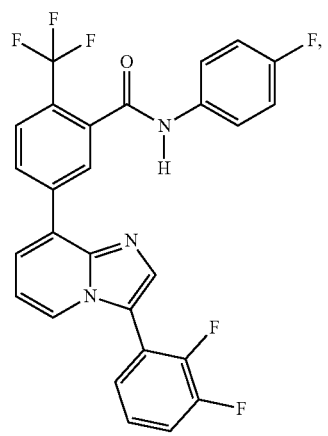

-continued
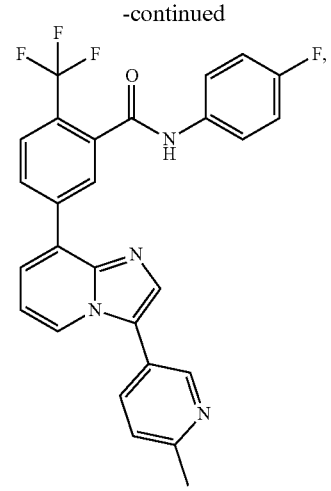
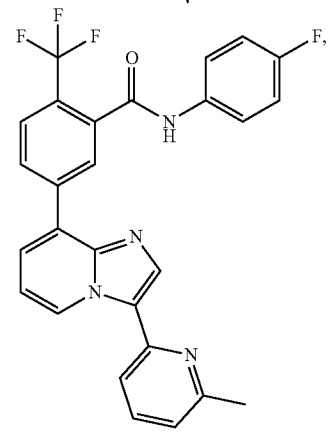
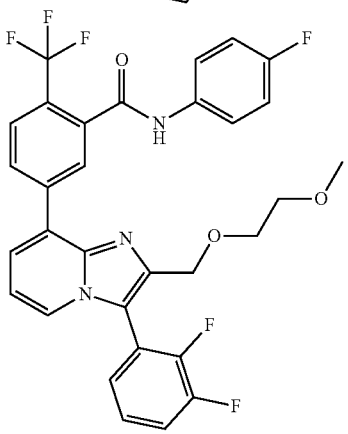
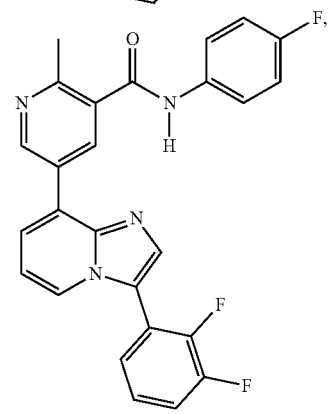
,
-continued
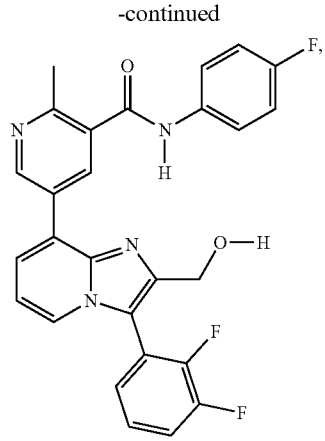
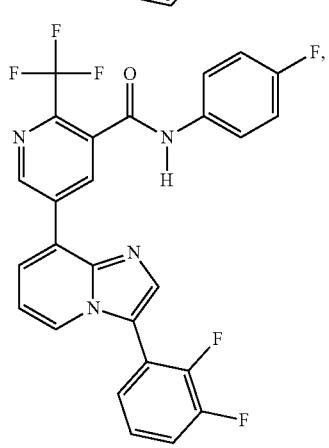
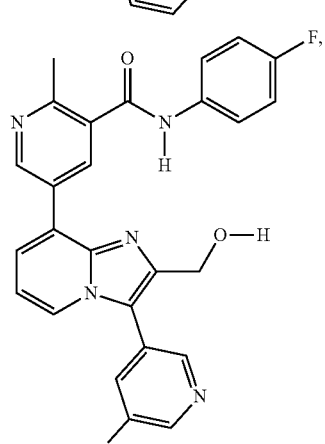
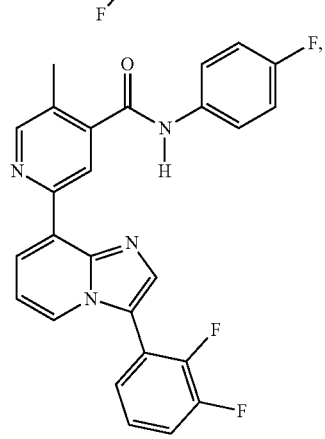

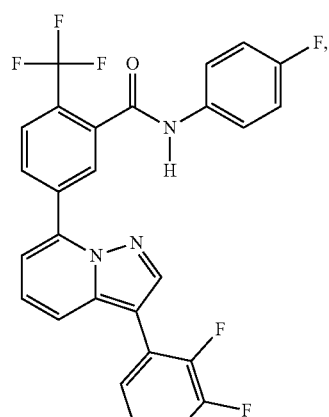
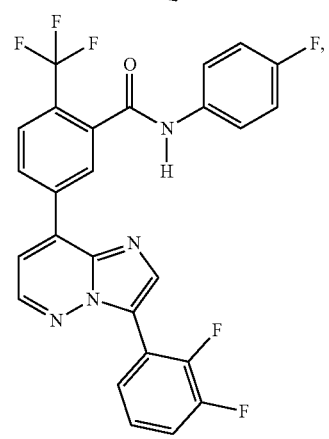
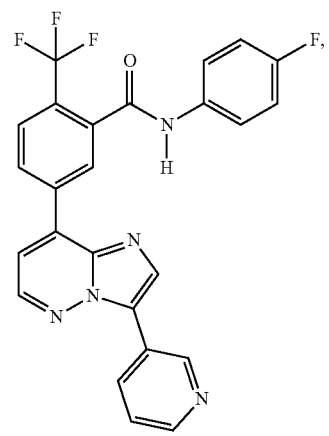
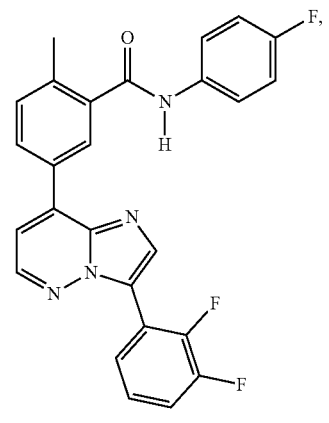
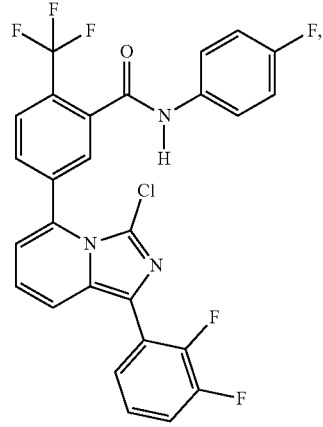
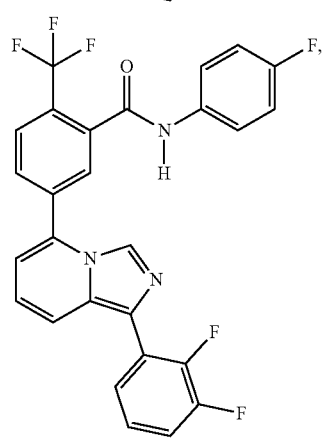
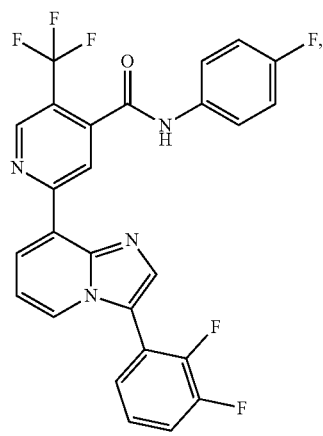 [SMILES: O=C(Nc1ccc(F)cc1)c1cc(-c2cccn3c(-c4cccc(F)c4F)cnc23)ccc1C(F)(F)F]
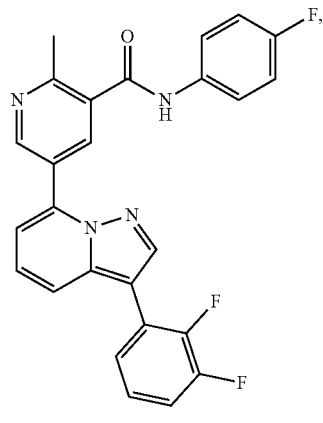

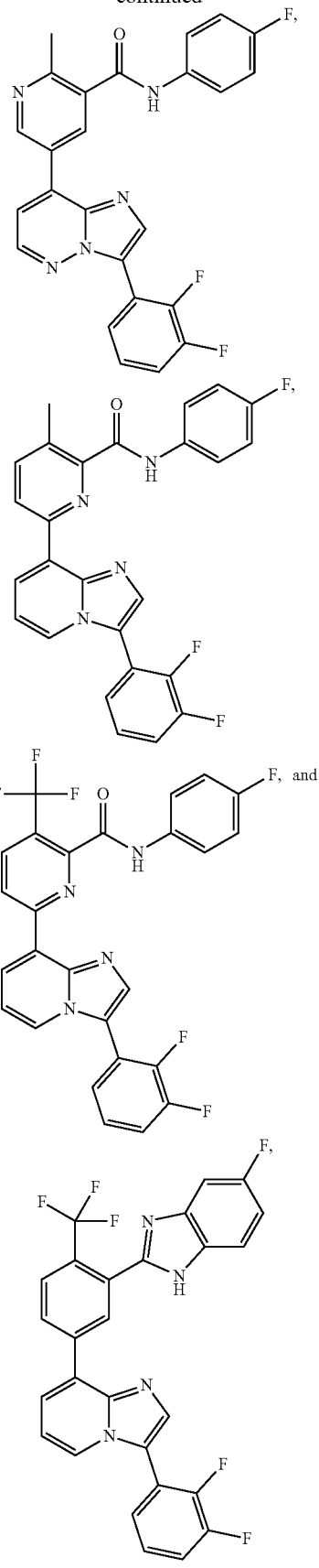
or a pharmaceutically acceptable salt or pharmaceutically acceptable tautomer thereof.
In one embodiment, the compound of the present disclosure is selected from the group consisting of:
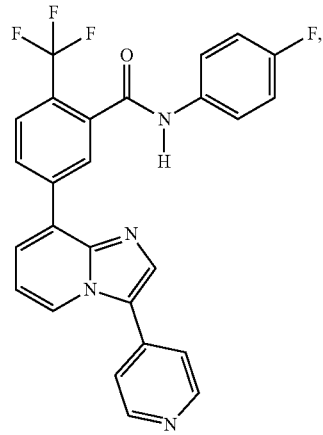
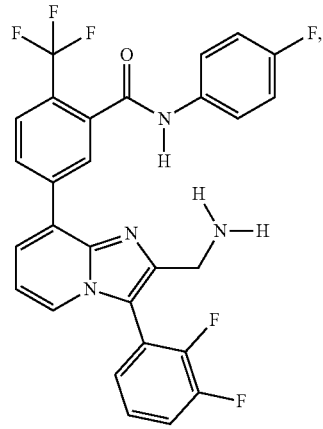
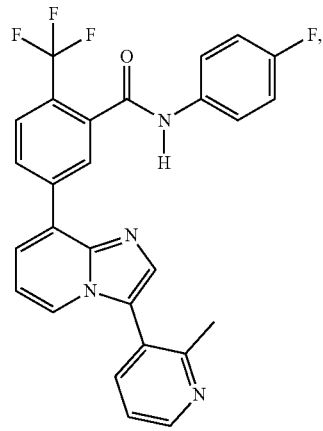

-continued
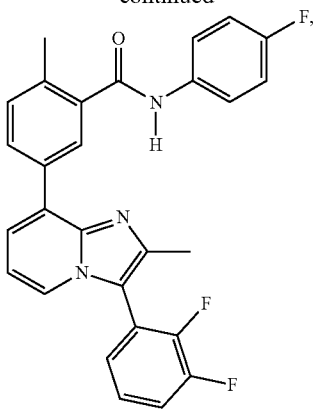
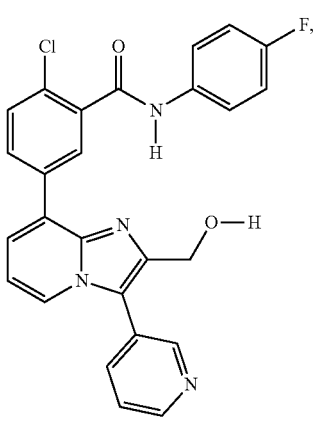
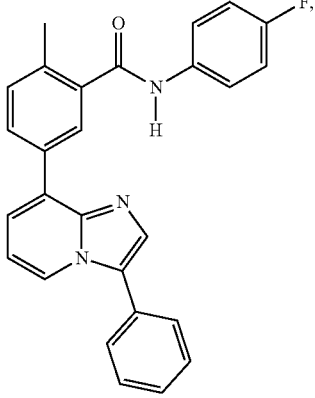
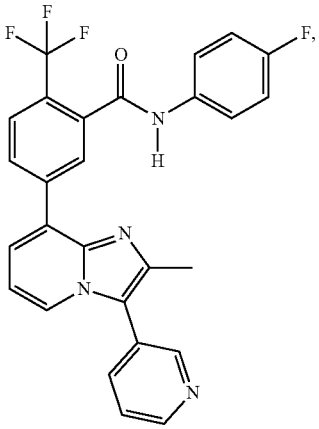
-continued
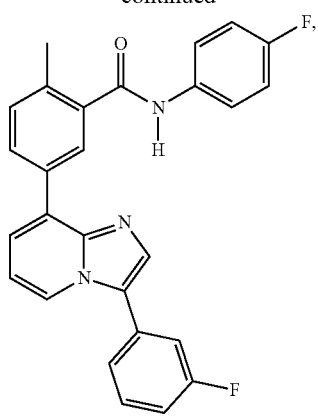
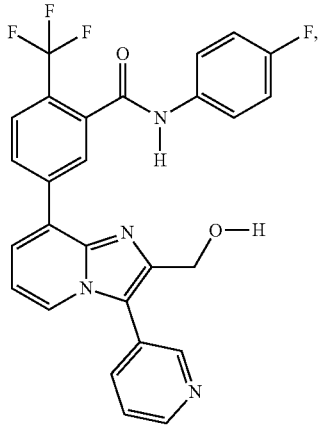
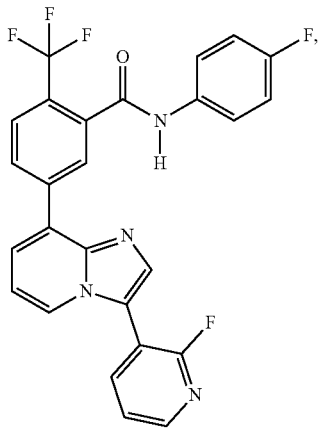
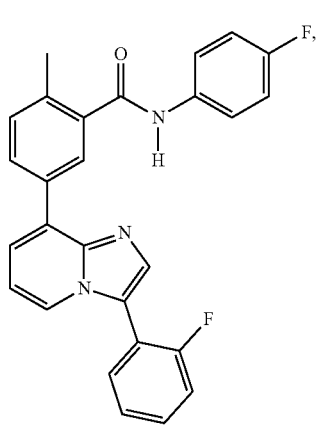

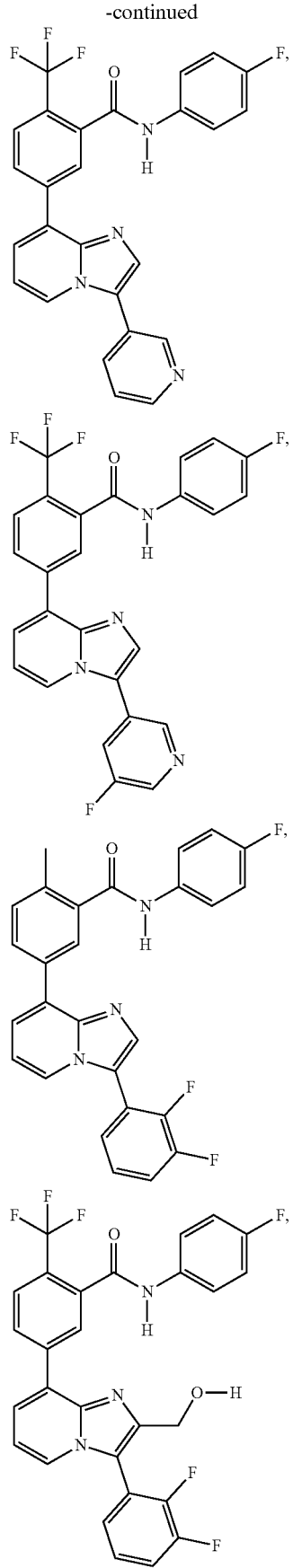
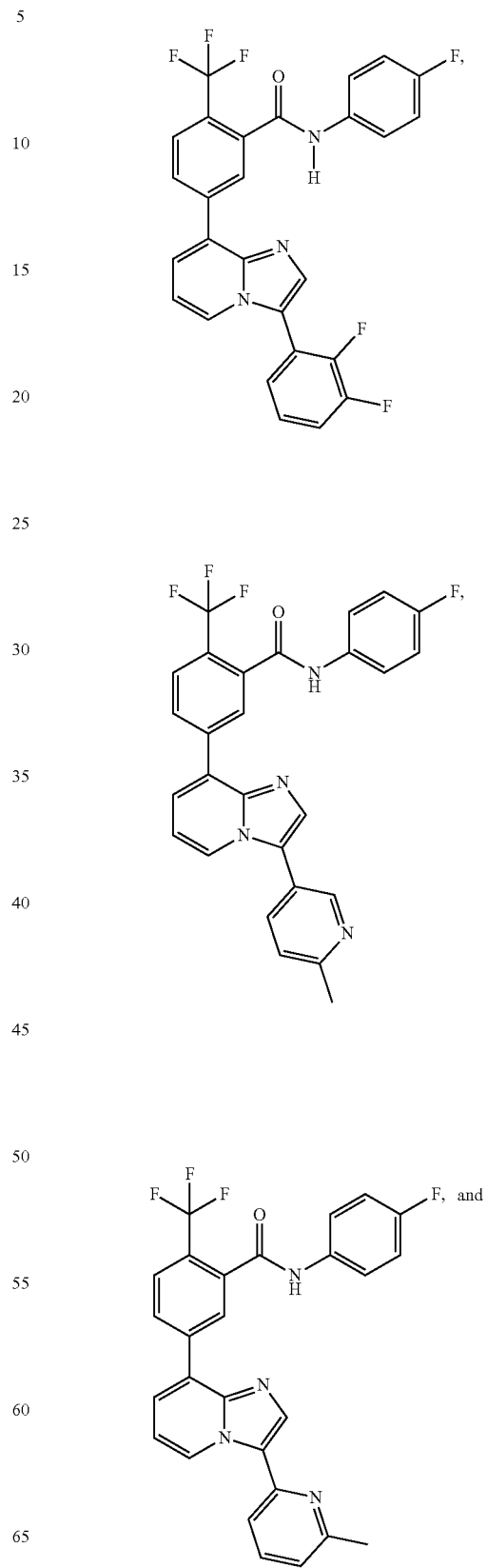

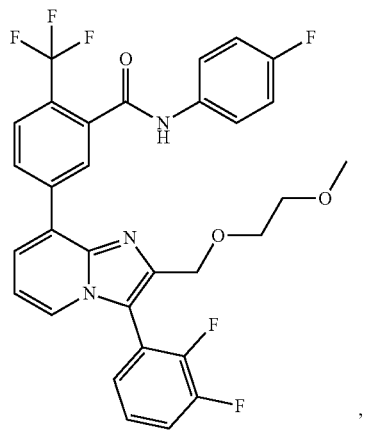

, or a pharmaceutically acceptable salt or pharmaceutically acceptable tautomer thereof. Such a compound or pharmaceutically acceptable salt or pharmaceutically acceptable tautomer thereof may also be included in any of the compositions or kits described herein or used in any of the methods described herein.

In one embodiment, the compound of the present disclosure is selected from the group consisting of:

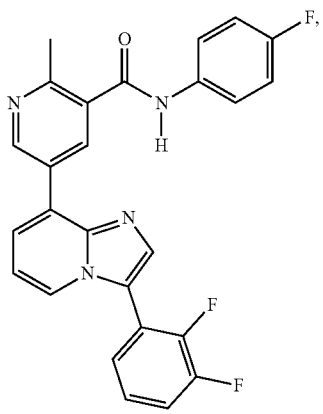

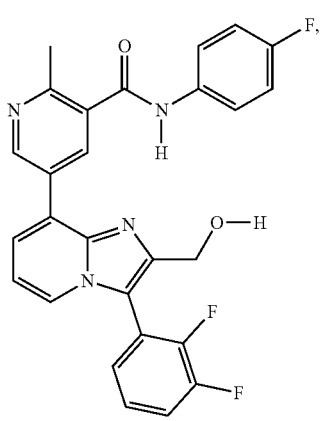

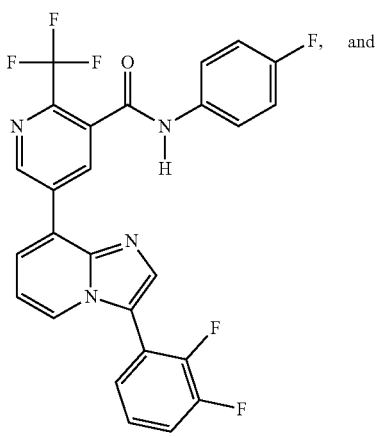

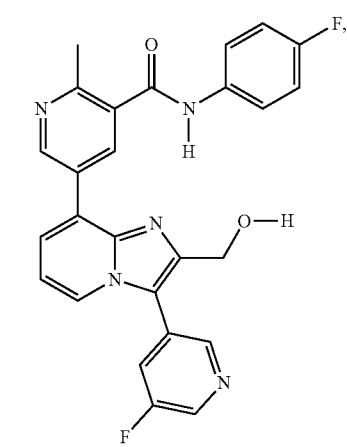

or a pharmaceutically acceptable salt or pharmaceutically acceptable tautomer thereof. Such a compound or pharmaceutically acceptable salt or pharmaceutically acceptable tautomer thereof may also be included in any of the compositions or kits described herein or used in any of the methods described herein.

In one embodiment, the compound of the present disclosure is selected from the group consisting of:

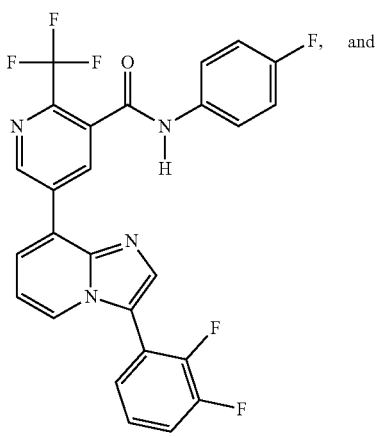

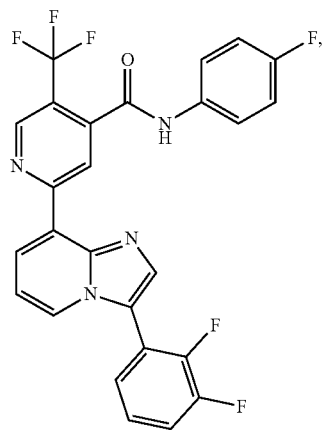 [SMILES: O=C(Nc1ccc(F)cc1)c1cc(-c2cccn3c(-c4cccc(F)c4F)cnc23)ccc1C(F)(F)F]

or a pharmaceutically acceptable salt or pharmaceutically acceptable tautomer thereof. Such a compound or pharmaceutically acceptable salt or pharmaceutically acceptable tautomer thereof may also be included in any of the compositions or kits described herein or used in any of the methods described herein.

In one embodiment, the compound of the present disclosure is selected from the group consisting of:

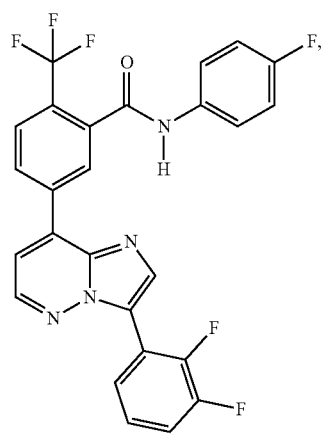

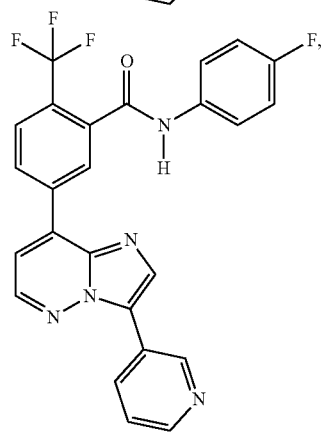

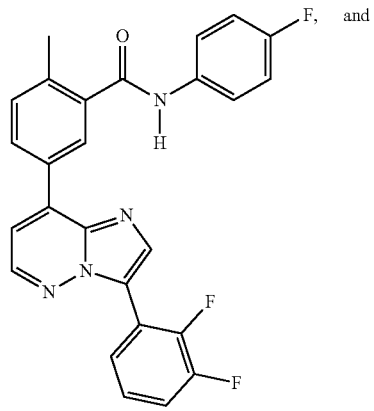

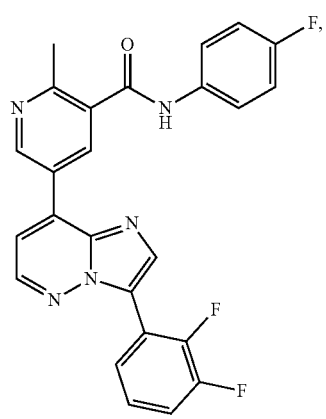

or a pharmaceutically acceptable salt or pharmaceutically acceptable tautomer thereof. Such a compound or pharmaceutically acceptable salt or pharmaceutically acceptable tautomer thereof may also be included in any of the compositions or kits described herein or used in any of the methods described herein.

In one embodiment, the compound of the present disclosure is selected from the group consisting of:

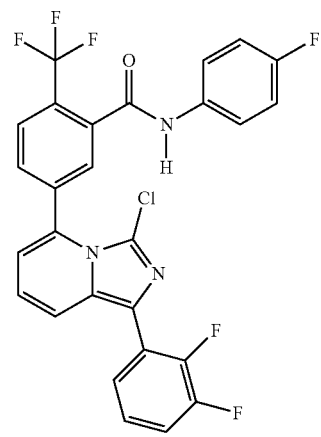

and

-continued

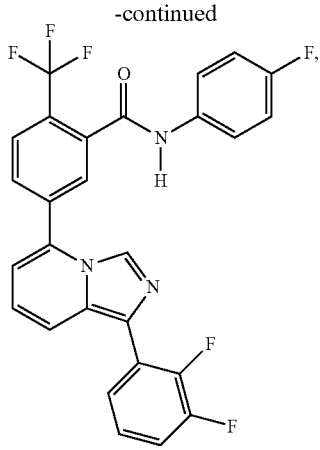

or a pharmaceutically acceptable salt or pharmaceutically acceptable tautomer thereof. Such a compound or pharmaceutically acceptable salt or pharmaceutically acceptable tautomer thereof may also be included in any of the compositions or kits described herein or used in any of the methods described herein.

In one embodiment, the compound of the present disclosure is selected from the group consisting of:

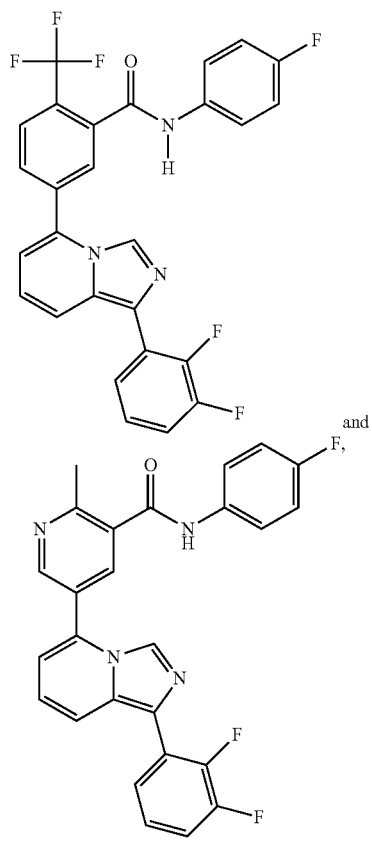

or a pharmaceutically acceptable salt or pharmaceutically acceptable tautomer thereof. Such a compound or pharmaceutically acceptable salt or pharmaceutically acceptable tautomer thereof may also be included in any of the compositions or kits described herein or used in any of the methods described herein.

In one embodiment, the compound of the present disclosure is selected from the group consisting of:

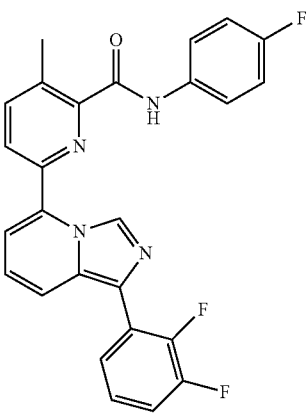

and

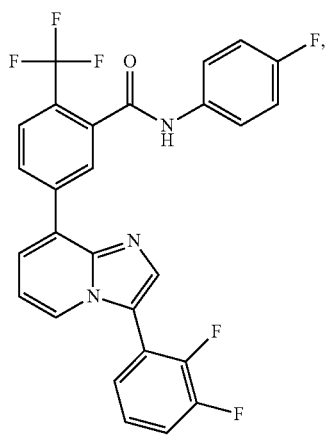

or a pharmaceutically acceptable salt or pharmaceutically acceptable tautomer thereof. Such a compound or pharmaceutically acceptable salt or pharmaceutically acceptable tautomer thereof may also be included in any of the compositions or kits described herein or used in any of the methods described herein.

In one embodiment, the compound of the present disclosure is selected from the group consisting of:

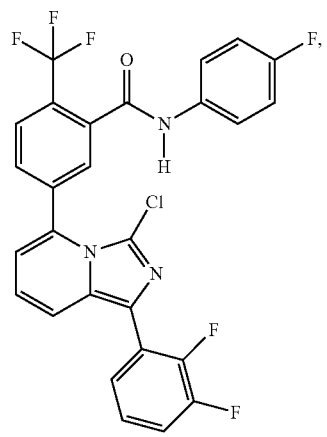

49
-continued

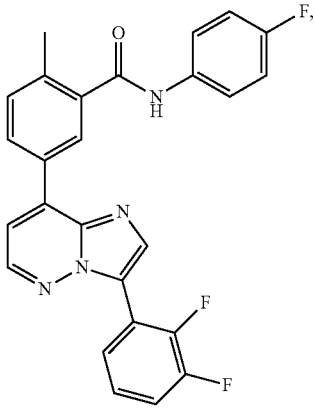

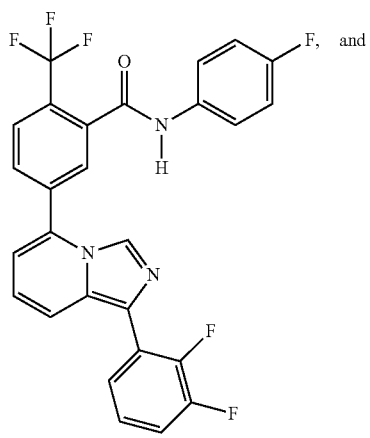

, and

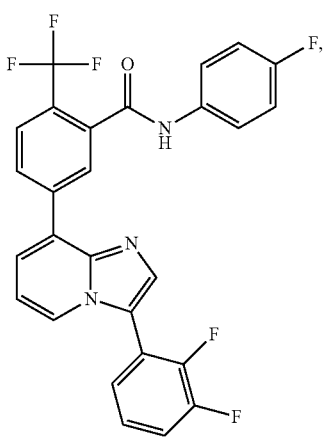

or a pharmaceutically acceptable salt or pharmaceutically acceptable tautomer thereof. Such a compound or pharmaceutically acceptable salt or pharmaceutically acceptable tautomer thereof may also be included in any of the compositions or kits described herein or used in any of the methods described herein.

50

In some embodiments, provided herein is

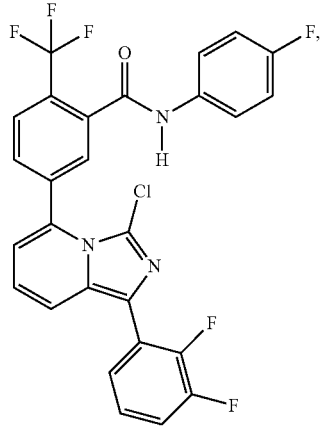 [SMILES: O=C(Nc1ccc(F)cc1)c1cc(-c2cccc3c(-c4cccc(F)c4F)nc(Cl)n23)ccc1C(F)(F)F]

or a pharmaceutically acceptable salt or pharmaceutically acceptable tautomer thereof. Such a compound or pharmaceutically acceptable salt or pharmaceutically acceptable tautomer thereof may also be included in any of the compositions or kits described herein or used in any of the methods described herein.

In some embodiments, provided herein is

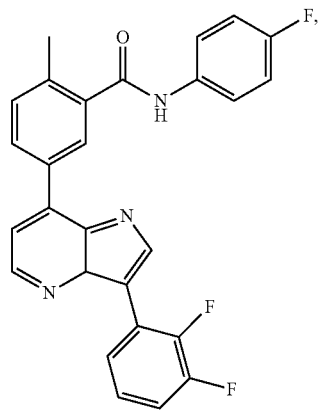

or a pharmaceutically acceptable salt or pharmaceutically acceptable tautomer thereof. Such a compound or pharmaceutically acceptable salt or pharmaceutically acceptable tautomer thereof may also be included in any of the compositions or kits described herein or used in any of the methods described herein.

In some embodiments, provided herein is

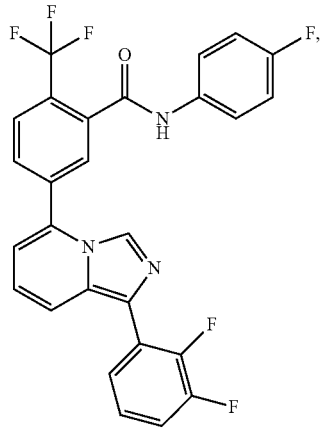 [SMILES: O=C(Nc1ccc(F)cc1)c1cc(-c2cccc3c(-c4cccc(F)c4F)ncn23)ccc1C(F)(F)F]

or a pharmaceutically acceptable salt or pharmaceutically acceptable tautomer thereof. Such a compound or pharmaceutically acceptable salt or pharmaceutically acceptable tautomer thereof may also be included in any of the compositions or kits described herein or used in any of the methods described herein.

In some embodiments, provided herein is

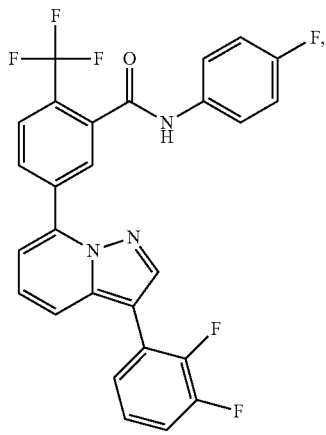 [SMILES: O=C(Nc1ccc(F)cc1)c1cc(-c2cccc3c(-c4cccc(F)c4F)cnn23)ccc1C(F)(F)F]

or a pharmaceutically acceptable salt or pharmaceutically acceptable tautomer thereof. Such a compound or pharmaceutically acceptable salt or pharmaceutically acceptable tautomer thereof may also be included in any of the compositions or kits described herein or used in any of the methods described herein.

Provided are also compounds described herein or pharmaceutically acceptable salts, isomer, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

A "solvate" is formed by the interaction of a solvent and a compound. Solvates of salts of the compounds described herein are also provided. Hydrates of the compounds described herein are also provided.

A "prodrug" is a biologically inactive derivative of a drug that upon administration to the human body is converted to the biologically active parent drug according to some chemical or enzymatic pathway.

In certain embodiments, provided are optical isomers, racemates, or other mixtures thereof of the compounds described herein or pharmaceutically acceptable salts or a mixture thereof. In those situations, the single enantiomer or diastereomer, i.e., optically active form, can be obtained by asymmetric synthesis or by resolution of the racemate. Resolution of racemates can be accomplished, for example, by conventional methods such as crystallization in the presence of a resolving agent, or chromatography, using, for example a chiral high pressure liquid chromatography (HPLC) column. In addition, provided are also Z- and E-forms (or cis- and trans-forms) of the hydroxyamidine compounds described herein. Specifically, Z- and E-forms are included even if only one designation is named for both carbon-carbon double bonds as well as the hydroxyamidine bond.

Where chirality is not specified but is present, it is understood that the embodiment is directed to either the specific diastereomerically or enantiomerically enriched form; or a racemic or scalemic mixture of such compound(s).

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" are stereoisomers that have at least two asymmetric atoms, but which are not mirror-images of each other.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

In certain embodiments, provided herein are also crystalline and amorphous forms of the compounds described herein or pharmaceutically acceptable salts, isomer, or a mixture thereof.

In certain embodiments, provided are also chelates, non-covalent complexes, and mixtures thereof, of the compounds described herein or pharmaceutically acceptable salts, isomer, or a mixture thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

Therapeutic Uses of the Compounds

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the invention may be used for a variety of purposes, including therapeutic and experimental purposes. For example, the invention may be used ex vivo to determine the optimal schedule and/or dosing of administration of an IDO1 inhibitor for a given indication, cell type, individual, and other parameters. Information gleaned from such use may be used for experimental purposes or in the clinic to set protocols for in vivo treatment. Other ex vivo uses for which the invention may be suited are described below or will become apparent to those skilled in the art. The selected compounds may be further characterized to examine the safety or tolerance dosage in human or non-human subjects. Such properties may be examined using commonly known methods to those skilled in the art.

In some embodiments, the compounds described herein may be used to treat subjects who have or are suspected of having disease states, disorders, and conditions (also collectively referred to as "indications") responsive or believed to be responsive to the inhibition of IDO1 activity. In some embodiments, the compounds described herein may be used to inhibit the activity of an IDO1 polypeptide. In some embodiments, the compounds described herein may be used to inhibit excessive or destructive immune reactions or growth or a proliferation of a cell, such as a cancer cell, or inhibit immunosuppression.

Example indications suitable for treatment with compounds described here include, without limitation cancer, viral infection such as HIV infection, HBV infection, HCV infection, other infections (e.g., skin infections, GI infection, urinary tract infections, genito-urinary infections, and systemic infections), depression, neurodegenerative disorders such as Alzheimer's disease and Huntington's disease, trauma, age-related cataracts, organ transplantation (e.g., organ transplant rejection), and autoimmune diseases.

Examples of autoimmune diseases include, but are not limited to, asthma, collagen diseases such as rheumatoid arthritis, systemic lupus erythematosus. Sharp's syndrome, CREST syndrome (calcinosis, Raynaud's syndrome, esophageal dysmotility, sclerodactyly, telangiectasia), dermatomyositis, vasculitis (Morbus Wegener's) and Sjögren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, allergic inflammation, inflammatory bowel disease, psoriasis and systemic lupus erythematosusor, malaria and Chagas disease.

In some embodiments, the compounds described herein may be used for treating cancer, viral infection, depression, a neurodegenerative disorder, trauma, age-related cataracts, organ transplant rejection, or an autoimmune disease.

In other embodiments, the disease to be treated is a solid tumor. In particular embodiments, the solid tumor is from pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancers, CNS cancers, brain tumors (e.g., glioma, anaplastic oligodendroglioma, adult glioblastoma multiforme, and adult anaplastic astrocytoma), bone cancer, or soft tissue sarcoma.

In some embodiments, the solid tumor is from non-small cell lung cancer, small-cell lung cancer, colon cancer, CNS cancer, melanoma, ovarian cancer, renal cancer, prostate cancer, or breast cancer.

In some embodiments, the disease to be treated is leukemia or lymphoma. In some embodiments, the disease to be treated is large B-cell lymphoma, diffuse large B-cell lymphoma (DLBCL), mediastinal B-cell lymphoma, high grade B-cell lymphoma, follicular lymphoma, acute lymphoblastic leukemia (ALL), such as B-cell acute lymphoblastic leukemia (BALL), acute myeloid leukemia (AML), chronic lymphocytic leukemia (CLL), chronic myeloid leukemia (CML), or hairy cell leukemia (HCL).

In some embodiments, the disease is an autoimmune disease. In particular embodiments, the autoimmune disease is lupus (e.g., systemic lupus erythematosus (SLE)), myestenia gravis, rheumatoid arthritis (RA), acute disseminated encephalomyelitis, idiopathic thrombocytopenic purpura, multiple sclerosis (MS), psoriasis, Sjoegren's syndrome, psoriasis, autoimmune hemolytic anemia, asthma, or chronic obstructive pulmonary disease (COPD). In other embodiments, the disease is inflammation. In yet other embodiments, the disease is excessive or destructive immune reactions, such as asthma, rheumatoid arthritis, multiple sclerosis, chronic obstructive pulmonary disease (COPD), and lupus.

Provided is a method for treating a subject, who has or is suspected of having a disease or condition responsive or believed to be responsive to the inhibition of IDO1 activity by administering to the subject the compound described herein or pharmaceutically acceptable salts, isomer, or a mixture thereof. Provided is also a method of inhibiting kinase activity of a IDO1 polypeptide by contacting the polypeptide with the compound described herein or pharmaceutically acceptable salts, isomer, or a mixture thereof. Provided is also a method of inhibiting a growth or a proliferation of cancer cells of hematopoietic origin comprising contacting the cancer cells with an effective amount of a compound described herein or pharmaceutically acceptable salts, isomer, or a mixture thereof.

In one embodiment, the compounds of the present application may be used in combination with one or more additional therapeutic agent that are being used and/or developed to treat cancers or inflammatory disorders. The one or more additional therapeutic agent may be a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof.

The one or more additional therapeutic agent may be an inhibitor to PI3K such as PI3Kγ, PI3Kβ, PI3Kδ, and/or PI3Kα, Janus kinase (JAK) such as JAK1, JAK2 and/or JAK3, spleen tyrosine kinase (SYK), Bruton's tyrosine kinase (BTK), bromodomain containing protein inhibitor (BRD) such as BRD4, a lysyl oxidase protein (LOX), lysyl oxidase-like protein (LOXL) such as LOXL1-5, matrix metalloprotease (MMP) such as MMP 1-10, adenosine A2B receptor (A2B), isocitrate dehydrogenase (IDH) such as IDH1, apoptosis signal-regulating kinase (ASK) such as ASK1, serine/threonine kinase TPL2, discoidin domain receptor (DDR) such as DDR1 and DDR2, histone deacetylase (HDAC), protein kinase C (PKC), or any combination thereof.

The compounds described herein may be used or combined with one or more of a chemotherapeutic agent, an anti-cancer agent, an anti-angiogenic agent, an anti-fibrotic agent, an immunotherapeutic agent, a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a radiotherapeutic agent, an anti-neoplastic agent, an anti-proliferation agent, an oncolytic virus, gene modifiers or editors such as CRISPR (including CRISPR Cas9), zinc finger nucleases or synthetic nucleases (TALENs), a CAR (chimeric antigen receptor) T-cell immunotherapeutic agent, T-cell receptor (TCR) immunotherapeutic agent, an immune checkpoint inhibitor, an immune checkpoint stimulatory protein agonist, or any combination thereof. These therapeutic agents may be in the forms of compounds, antibodies, polypeptides, or polynucleotides. In one embodiment, the application provides a product comprising a compound described herein and an additional therapeutic agent as a combined preparation for simultaneous, separate, or sequential use in therapy.

In some embodiments, the compounds disclosed herein may be used or combined with one or more of a chemotherapeutic agent, an anti-cancer agent, an anti-angiogenic agent, an anti-fibrotic agent, an immunotherapeutic agent, a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a radiotherapeutic agent, an anti-neoplastic agent, an anti-proliferation agent, an oncolytic virus, gene modifiers or editors such as CRISPR (including CRISPR Cas9), zinc finger nucleases or synthetic nucleases (TALENs), a CAR (chimeric antigen receptor) T-cell immunotherapeutic agent, T-cell receptor (TCR) immunotherapeutic agent, or any combination thereof. These therapeutic agents may be in the forms of compounds, antibodies, polypeptides, live cells (e.g., cell therapy), or polynucleotides. In some embodiments, the application provides a product comprising a compound described herein and an additional therapeutic agent as a combined preparation for simultaneous, separate, or sequential use in therapy.

In some embodiments, the CAR (chimeric antigen receptor) T-cell immunotherapeutic agent is selected from YESCARTA™ (axicabtagene ciloleucel) and KYMRIAH™ (tisagenlecleucel).

In some embodiments, the CAR (chimeric antigen receptor) T-cell immunotherapeutic agent is YESCARTA™ (axicabtagene ciloleucel).

In some embodiments, the compound is administered to the subject prior to, subsequent to, or simultaneous to administration of one or more additional therapeutic agents.

In some embodiments, the compound is administered to the subject about 30 minutes or more, about 1 hour or more, about 2 hours or more, about 4 hours or more, about 6 hours or more, about 12 hours or more, about 24 hours or more, about 48 hours or more, or about 72 hour or more prior to or subsequent to administration of the one or more additional therapeutic agents.

In some embodiments, the compound is administered to the subject about 30 minutes or less, about 1 hour or less, about 2 hours or less, about 4 hours or less, about 6 hours or less, about 12 hours or less, about 24 hours or less, about 48 hours or less, or about 72 hour or less prior to or subsequent to administration of the one or more additional therapeutic agents.

In some embodiments, a method of treating a disease in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with one or more additional therapeutic agents. In some embodiments, the one or more additional therapeutic agents includes an immunotherapeutic agent, such as an immune checkpoint inhibitor, an hematopoietic progenitor kinase 1 (HPK1) inhibitor, an immune checkpoint stimulatory protein agonist, or an engineered immune cell (for example a T cell with an chimeric antigen receptor (i.e., a CAR T cell) or a T cell with an engineered T cell receptor (TCR). In some embodiments, the compound is administered to the subject prior to, subsequent to, or simultaneous to administration of one or more immunotherapeutic agents. In some embodiments, the compound is administered to the subject about 30 minutes or more, about 1 hour or more, about 2 hours or more, about 4 hours or more, about 6 hours or more, about 12 hours or more, about 24 hours or more, about 48 hours or more, or about 72 hour or more prior to or subsequent to administration of the one or more immunotherapeutic agents. In some embodiments, the compound is administered to the subject about 30 minutes or less, about 1 hour or less, about 2 hours or less, about 4 hours or less, about 6 hours or less, about 12 hours or less, about 24 hours or less, about 48 hours or less, or about 72 hour or less prior to or subsequent to administration of the one or more immunotherapeutic agents.

In some embodiments, a method of treating a disease in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with a therapeutically effective amount of one or more immune checkpoint inhibitors. In some embodiments, the compound is administered to the subject prior to, subsequent to, or simultaneous to administration of the immune checkpoint inhibitor. In some embodiments, the immune checkpoint inhibitor is a small-molecule inhibitor. In some embodiments, the immune checkpoint inhibitor is an antibody or a fragment thereof. In some embodiments, the immune checkpoint inhibitor inhibits the Adenosine $A_{2A}$ Receptor (A2aR), B7-H3, V-Set Domain-Containing T-cell Activation Inhibitor 1 (VTCN1, also known as B7-H4), the B- and T-Lymphocyte Attenuator (BTLA), cytotoxic T-Lypmphocyte-Associated protein 4 (CTLA-4), Killer-cell Immunoglobulin-like Receptor (KIR), Lymphocyte Activation Gene 3 (LAG3), Programmed Death 1 (PD-1), Programmed Death Ligand 1 (PD-L1), Programmed Death Ligand 2 (PD-L2), T-cell Immunoreceptor with Ig and ITIM Domains (TIGIT), T-cell Immunoglobulin and Mucin-Domain Containing 3 (TIM-3), or V-Domain Ig Suppresor of T-cell Activation (VISTA). Exemplary immune checkpoint inhibitors include, but are not limited to, avelumab, atezolizumab, durvalumab, nivolumab, pembrolizumab, ipilimumab, PDR001, TSR-042, and BMS-986016.

In some embodiments, a method of treating a disease in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with a therapeutically effective amount of one or more immune checkpoint stimulatory protein agonists. In some embodiments, the compound is administered to the subject prior to, subsequent to, or simultaneous to administration of the immune checkpoint stimulatory protein agonist. In some embodiments, the immune checkpoint stimulatory protein agonist is an antibody or a fragment thereof. In some embodiments, the immune checkpoint stimulatory protein agonist is an agonist of CD27, CD28, CD40, CD122, 4-1BB, OX40, Gluocorticoid-Induced TNFR family related protein (GITR), or Inducible T-Cell Costimulator (ICOS).

In some embodiments, a method of treating a disease in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with a therapeutically effective amount of engineered immune cells, such as CAR T cells or T cells with an engineered TCR. In some embodiments, the compound is administered to the subject prior to, subsequent to, or simultaneous to administration of the engineered immune cells. In some embodiments, the engineered immune cells are heterologous engineered immune cells, such as heterologous engineered T cells (e.g., CAR T cells or T cells with an engineered TCR). In some embodiments, the engineered immune cells are autologous engineered immune cells, such as autologous engineered T cells (e.g., CAR T cells or T cells with an engineered TCR).

In some embodiments, a method of treating a disease in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with a therapeutically effective amount of axicabtagene ciloleucel, sold under the trade name YESCARTA™. In some embodiments, a method of treating a disease in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with a therapeutically effective amount of tisagenlecleucel, sold under the trade name KYMRIAH™.

In some embodiments, a method of treating a disease in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with (1) a therapeutically effective amount of engineered immune cells, such as CAR T cells or T cells with an engineered TCR, and (2) a therapeutically effective amount of an immune checkpoint inhibitor or an immune checkpoint stimulatory protein agonist.

In some embodiments, a method of treating cancer or a proliferative disorder in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with one or more additional therapeutic agents. In some embodiments, the one or more additional therapeutic agents includes an immunotherapeutic agent, such as an immune checkpoint inhibitor, an hematopoietic progenitor kinase 1 (HPK1) inhibitor, an immune checkpoint stimulatory protein agonist, or an engineered immune cell (for example a T cell with an chimeric antigen receptor (i.e., a CAR T cell) or a T cell with an engineered T cell receptor (TCR). In some embodiments, the compound is administered to the subject prior to, subsequent to, or simultaneous to administration of one or more immunotherapeutic agents. In some embodiments, the compound is administered to the subject about 30 minutes or more, about 1 hour or more, about 2 hours or more, about 4 hours or more, about 6 hours or more, about 12 hours or more, about 24 hours or more, about 48 hours or more, or about 72 hour or more prior to or subsequent to administration of the one or more immunotherapeutic agents. In some embodiments, the compound is administered to the subject about 30 minutes or less, about 1 hour or less, about 2 hours or less, about 4 hours or less, about 6 hours or less, about 12 hours or less, about 24 hours or less, about 48 hours or less, or about 72 hour or less prior to or subsequent to administration of the one or more immunotherapeutic agents.

In some embodiments, a method of treating cancer or a proliferative disease in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with a therapeutically effective amount of one or more immune checkpoint inhibitors. In some embodiments, the compound is administered to the subject prior to, subsequent to, or simultaneous to administration of the immune checkpoint inhibitor. In some embodiments, the immune checkpoint inhibitor is a small-molecule inhibitor. In some embodiments, the immune checkpoint inhibitor is an antibody or a fragment thereof. In some embodimetns, the immune checkpoint inhibitor inhibits the Adenosine $A_2A$ Receptor (A2aR), B7-H3, V-Set Domain-Containing T-cell Activation Inhibitor 1 (VTCN1, also known as B7-H4), the B- and T-Lymphocyte Attenuator (BTLA), cytotoxic T-Lypmphocyte-Associated protein 4 (CTLA-4), Killer-cell Immunoglobulin-like Receptor (KIR), Lymphocyte Activation Gene 3 (LAG3), Programmed Death 1 (PD-1), Programmed Death Ligand 1 (PD-L1), Programmed Death Ligand 2 (PD-L2), T-cell Immunoreceptor with Ig and ITIM Domains (TIGIT), T-cell Immunoglobulin and Mucin-Domain Containing 3 (TIM-3), or V-Domain Ig Suppresor of T-cell Activation (VISTA). Exemplary immune checkpoint inhibitors include, but are not limited to, avelumab, atezolizumab, durvalumab, nivolumab, pembrolizumab, ipilimumab, PDR001, TSR-042, and BMS-986016.

In some embodiments, a method of treating cancer or a proliferative disease in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with a therapeutically effective amount of one or more immune checkpoint stimulatory protein agonists. In some embodiments, the compound is administered to the subject prior to, subsequent to, or simultaneous to administration of the immune checkpoint stimulatory protein agonist. In some embodiments, the immune checkpoint stimulatory protein agonist is an antibody or a fragment thereof. In some embodimetns, the immune checkpoint stimulatory protein agonist is an agonist of CD27, CD28, CD40, CD122, 4-1BB, OX40, Gluocorticoid-Induced TNFR family related protein (GITR), or Inducible T-Cell Costimulator (ICOS).

In some embodiments, a method of treating cancer or a proliferative disease in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with a therapeutically effective amount of engineered immune cells, such as CAR T cells or T cells with an engineered TCR. In some embodiments, the compound is administered to the subject prior to, subsequent to, or simultaneous to administration of the engineered immune cells. In some embodiments, the engineered immune cells are heterologous engineered immune cells, such as heterologous engineered T cells (e.g., CAR T cells or T cells with an engineered TCR). In some embodiments, the engineered immune cells are autologous engineered immune cells, such as autologous engineered T cells (e.g., CAR T cells or T cells with an engineered TCR). In some embodiments, the engineered immune cells (e.g., engineered T cells) target a tumor antigen. In some embodiments, the engineered immune cells (e.g., engineered T cells) target CD7, CD19, CD22, CD30, CD33, CD70, CD123, GD2, HER2, EpCAM, PSA, MUC1, CEA, B-cell maturation antigen (BCMA), glypican 3, mesothelin, or EGFRvIII.

In some embodiments, a method of treating cancer or a proliferative disease in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with a therapeutically effective amount of axicabtagene ciloleucel, sold under the trade name YESCARTA™. In some embodiments, a method of treating cancer or a proliferative disease in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with a therapeutically effective amount of tisagenlecleucel, sold under the trade name KYMRIAH™.

In some embodiments, a method of treating cancer or a proliferative disease in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with (1) a therapeutically effective amount of engineered immune cells, such as CAR T cells or T cells with an engineered TCR, and (2) a therapeutically effective amount of an immune checkpoint inhibitor or an immune checkpoint stimulatory protein agonist. In some embodiments, a method of treating cancer or a proliferative disease in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with (1) a therapeutically effective amount of engineered immune cells, such as CAR T cells or T cells with an engineered TCR, and (2) a therapeutically effective amount of a chemotherapeutic agent. In some embodiments, a method of treating cancer or a proliferative disease in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with (1) a therapeutically effective amount of an immune checkpoint inhibitor or an immune checkpoint stimulatory protein agonist, and (2) a therapeutically effective amount of a chemotherapeutic agent. In some embodiments, a method of treating cancer or a proliferative disease in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with (1) a therapeutically effective amount of engineered immune cells, such as CAR T cells or T cells with an engineered TCR, (2) a therapeutically effective amount of an immune checkpoint inhibitor or an immune checkpoint stimulatory protein agonist, and (3) a therapeutically effective amount of a chemotherapeutic agent.

A phosphoinositide 3-kinase inhibitor (PI3K inhibitor) functions by inhibiting one or more of the phosphoinositide 3-kinase enzymes, including but not limited to PI3Kγ, PI3Kβ, PI3Kδ, and PI3Kα. Non-limiting examples of PI3K inhibitors include wortmannin, demethoxyviridin, LY294002, idelalisib, perifosine, PX-866, IPI-145, BAY 80-6946, BEZ235, RP6530, TGR 1202, INK1117, GDC-0941, BKM120, XL147 (also known as SAR245408), XL765 (also known as SAR245409), Palomid 529, GSK1059615, ZSTK474, PWT33597, IC87114, CAL263, RP6503, PI-103, GNE-477, CUDC-907 and AEZS-136. In some embodiments, the PI3K inhibitor is a PI3Kδ inhibitors, such as idelalisib, IPI-145, RP6530, and RP6503, as well as those disclosed in U.S. Pat. No. 8,569,296, and PCX publications WO 2014/006572 and WO 2015/001491.

In some embodiments, the one or more additional therapeutic agent may be an MMP9 inhibitor, or an agent that inhibits the expression and/or activity of MMP9. A representative protein sequence for MMP9 is GenBank Accession No. NP_004985. The inhibitor can be small molecule or biologic. For instance, Gu et al., *The Journal of Neuroscience,* 25(27): 6401-6408 (2005), discloses a specific MMP9 inhibitor, SB-3CT (CAS 292605-14-2). Further, siRNA, antisense RNA and antibodies have also been demonstrated to inhibit the expression or activity of MMP9 and are within the scope of the present disclosure. In one embodiment, an MMP9 inhibitor is a monoclonal anti-MMP9 antibody. In some embodiment, the one or more additional therapeutic agent includes an MMP9 inhibitor and a nucleoside analog such as gemcitabine.

One, two, three, or more of the therapeutic agents (e.g. a PI3K inhibitor, a JAK inhibitor, a SYK inhibitor, a BTK inhibitor, a BRIM inhibitor, a LOXL2 inhibitor, a MMP9 inhibitor, a A2B inhibitor, an IDH inhibitor, an ASK inhibitor, a TPL2 inhibitor, a DDR1 inhibitor, a TBK inhibitor, a HDAC inhibitor, a PKC inhibitor) may be further used or combined with a chemotherapeutic agent, an immunotherapeutic agent, a radiotherapeutic agent, an anti-neoplastic agent, an anti-cancer agent, an anti-fibrotic agent, an anti-angiogenic agent, a therapeutic antibody, or any combination thereof.

Chemotherapeutic agents may be categorized by their mechanism of action into, for example, the following groups: anti-metabolites/anti-cancer agents, such as pyrimidine analogs (floxuridine, capecitabine, and cytarabine); purine analogs, folate antagonists and related inhibitors, antiproliferative/antimitotic agents including natural products such as vinca alkaloid (vinblastine, vincristine) and microtubule such as taxane (paclitaxel, docetaxel), vinblastin, nocodazole, epothilones and navelbine, epidipodophyllotoxins (etoposide, teniposide); DNA damaging agents (actinomycin, amsacrine, busulfan, carboplatin, chlorambucil, cisplatin, cyclophosphamide, Cytoxan, dactinomycin, daunorubicin, doxorubicin, epirubicin, iphosphamide, melphalan, merchlorehtamine, mitomycin, mitoxantrone, nitrosourea, procarbazine, taxol, taxotere, teniposide, etoposide, triethylenethiophosphoramide); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards cyclophosphamide and analogs, melphalan, chlorambucil), and (hexamethylmelamine and thiotepa), alkyl nitrosoureas (BCNU) and analogs, streptozocin), trazenes-dacarbazinine (DTIC); antiproliferative/antimitotic antimetabolites such as folic acid analogs (methotrexate); platinum coordination complexes (cisplatin, oxiloplatinim, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel; antimigratory agents; antisecretory agents (breveldin); immunosuppressives tacrolimus sirolimus azathioprine, mycophenolate; compounds (TNP-470, genistein) and growth factor inhibitors (vascular endothelial growth factor inhibitors, fibroblast growth factor inhibitors); angiotensin receptor blocker, nitric oxide donors; anti-sense oligonucleotides; antibodies (trastuzumab, rituximab); cell cycle inhibitors and differentiation inducers (tretinoin); inhibitors, topoisomerase inhibitors (doxorubicin (adriamycin), daunorubicin, dactinomycin, eniposide, epirubicin, etoposide, idarubicin, irinotecan and mitoxantrone, topotecan, irinotecan, camptothesin), corticosteroids (cortisone, dexamethasone, hydrocortisone, methylpednisolone, prednisone, and prenisolone); growth factor signal transduction kinase inhibitors; dysfunction inducers, toxins such as Cholera toxin, ricin, Pseudomonas exotoxin, Bordetella pertussis adenylate cyclase toxin, or diphtheria toxin, and caspase activators; and chromatin.

As used herein the term "chemotherapeutic agent" or "chemotherapeutic" (or "chemotherapy," in the case of treatment with a chemotherapeutic agent) is meant to encompass any non-proteinaceous (i.e., non-peptidic) chemical compound useful in the treatment of cancer. Examples of chemotherapeutic agents include alkylating agents such as thiotepa and cyclophosphamide (CYTOXAN); alkyl sulfonates such as busulfan, improsulfan and piposulfan; aziridines such as benzodopa, carboquone, meturedopa, and uredopa; emylerumines and memylamelamines including alfretamine, triemylenemelamine, triethylenephosphoramide, triethylenethiophosphoramide and trimemylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (articularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g., calicheamicin, especially calicheamicin gammaII and calicheamicin phill, see, e.g., Agnew, Chem. Inti. Ed. Engl, 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofiir, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replinisher such as frolinic acid; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; PSK®; razoxane; rhizoxin; sizofiran; spirogermanium; tenuazonic acid; triaziquone; 2,2',2"-tricUorotriemylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiopeta; taxoids, e.g., paclitaxel (TAXOL® and docetaxel (TAXOTERE®); chlorambucil; gemcitabine (Gemzar®); 6-thioguanine; mercaptopurine; methotrexate; platinum analogs such as cisplatin and carboplatin; vinblastine; platinum; etoposide (VP-16); ifosfamide; mitroxantrone; vancristine; vinorelbine (Navelbine®); novantrone; teniposide; edatrexate; daunomycin; aminopterin; xeoloda; ibandronate; CPT-11; topoisomerase inhibitor RFS 2000; difluoromethylomithine (DMFO); retinoids such as retinoic acid; capecitabine; FOLFIRI (fluorouracil, leucovorin, and irinotecan) and pharmaceutically acceptable salts, acids or derivatives of any of the above. One or more chemotherapeutic agent are used or included in the present application. For example, gemcitabine, nab-paclitaxel, and gemcitabine/nab-paclitaxel are used with the JAK inhibitor and/or PI3Kδ inhibitor for treating hyperproliferative disorders.

Also included in the definition of "chemotherapeutic agent" are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, FY117018, onapristone, and toremifene (Fareston®); inhibitors of the enzyme aromatase, which regulates estrogen production in the adrenal glands, such as, for example, 4(5)-imidazoles, aminoglutethimide, megestrol acetate (Megace®), exemestane, formestane, fadrozole, vorozole (Rivisor®), letrozole (Femara®), and anastrozole (Arimidex®); and anti-androgens such as flutamide, nilutamide, bicalutamide, leuprohde, and goserelin; and pharmaceutically acceptable salts, acids or derivatives of any of the above.

The anti-angiogenic agents include, but are not limited to, retinoid acid and derivatives thereof, 2-methoxyestradiol, ANGIOSTATIN®, ENDOSTATIN®, suramin, squalamine, tissue inhibitor of metalloproteinase-1, tissue inhibitor of metalloprotemase-2, plasminogen activator inhibitor-1, plasminogen activator inhibitor-2, cartilage-derived inhibitor, paclitaxel (nab-paclitaxel), platelet factor 4, protamine sulphate (clupeine), sulfated chitin derivatives (prepared from queen crab shells), sulfated polysaccharide peptidoglycan complex (sp-pg), staurosporine, modulators of matrix metabolism, including for example, proline analogs ((l-azetidine-2-carboxylic acid (LACA), cishydroxyproline, D,L-3,4-dehydroproline, thiaproline, .alpha.-dipyridyl, beta-aminopropionitrile fumarate, 4-propyl-5-(4-pyridinyl)-2 (3H)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpba-2-antiplasmin, bisantrene, lobenzarit disodium, n-2-carboxyphenyl-4-chloroanthronilic acid disodium or "CCA", thalidomide; angiostatic steroid, cargboxynaminolmidazole; metalloproteinase inhibitors such as BB94. Other anti-angiogenesis agents include antibodies, preferably monoclonal antibodies against these angiogenic growth factors: beta-FGF, alpha-FGF, FGF-5, VEGF isoforms, VEGF-C, HGF/SF and Ang-1/Ang-2. See Ferrara N. and Alitalo, K. "Clinical application of angiogenic growth factors and their inhibitors" (1999) Nature Medicine 5:1359-1364.

The anti-fibrotic agents include, but are not limited to, the compounds such as beta-aminoproprionitrile (BAPN), as well as the compounds disclosed in U.S. Pat. No. 4,965,288 to Palfreyman, et al., issued Oct. 23, 1990, entitled "Inhibitors of lysyl oxidase," relating to inhibitors of lysyl oxidase and their use in the treatment of diseases and conditions associated with the abnormal deposition of collagen; U.S. Pat. No. 4,997,854 to Kagan, et al., issued Mar. 5, 1991, entitled "Anti-fibrotic agents and methods for inhibiting the activity of lysyl oxidase in situ using adjacently positioned diamine analogue substrate," relating to compounds which inhibit LOX for the treatment of various pathological fibrotic states, which are herein incorporated by reference. Further exemplary inhibitors are described in U.S. Pat. No. 4,943,593 to Palfreyman, et al., issued Jul. 24, 1990, entitled "Inhibitors of lysyl oxidase," relating to compounds such as 2-isobutyl-3-fluoro-, chloro-, or bromo-allylamine; as well as, e.g., U.S. Pat. Nos. 5,021,456; 5,5059,714; 5,120,764; 5,182,297; 5,252,608 (relating to 2-(1-naphthyloxymemyl)-3-fluoroallylamine); and U.S. Patent Application No. 2004/0248871, which are herein incorporated by reference. Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives, semicarbazide, and urea derivatives, aminonitriles, such as beta-aminopropionitrile (BAPN), or 2-nitroethylamine, unsaturated or saturated haloamines, such as 2-bromo-ethylamine, 2-chloroethylamine, 2-trifluoroethylamine, 3-bromopropylamine, p-halobenzylamines, selenohomocysteine lactone. Also, the anti-fibrotic agents are copper chelating agents, penetrating or not penetrating the cells. Exemplary compounds include indirect inhibitors such compounds blocking the aldehyde derivatives originating from the oxidative deamination of the lysyl and hydroxylysyl residues by the lysyl oxidases, such as the thiolamines, in particular D-penicillamine, or its analogues such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, sodium-4-mercaptobutanesulphinate trihydrate.

The immunotherapeutic agents include and are not limited to therapeutic antibodies suitable for treating patients; such as abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, namatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8. The exemplified therapeutic antibodies may be further labeled or combined with a radioisotope particle, such as indium In 111, yttrium Y 90, iodine I-131.

The application also provides method for treating a subject who is undergoing one or more standard therapies, such as chemotherapy, radiotherapy, immunotherapy, surgery, or combination thereof. Accordingly, one or more therapeutic agent or inhibitors may be administered before, during, or after administration of chemotherapy, radiotherapy, immunotherapy, surgery or combination thereof.

In certain embodiments, the subject may be a human who is (i) substantially refractory to at least one chemotherapy treatment, or (ii) in relapse after treatment with chemotherapy, or both (i) and (ii). In some of embodiments, the subject is refractory to at least two, at least three, or at least four chemotherapy treatments (including standard or experimental chemotherapies).

In certain embodiments, the subject is refractory to at least one, at least two, at least three, or at least four chemotherapy treatment (including standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D. T. PACE (dexamethasone, thalidomide, cisplatin, Adriamycin®, cyclophosphamide, etoposide).

Other examples of chemotherapy treatments (including standard or experimental chemotherapies) are described below. In addition, treatment of certain lymphomas is reviewed in Che son, B. D., Leonard, J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CEL" *Hematology* 2006, p. 285-294. Lymphoma incidence patterns in the United States is profiled in Morton, L. M., et al. "Lymphoma Incidence Patterns by WHO Subtype in the United States, 1992-2001" *Blood* 2006, 107(1), p. 265-276.

Examples of immunotherapeutic agents treating lymphoma or leukemia include, but are not limited to, rituximab (such as Rituxan), alemtuzumab (such as Campath, MabCampath), anti-CD19 antibodies, anti-CD20 antibodies, anti-MN-14 antibodies, anti-TRAIL, Anti-TRAIL DR4 and DR5 antibodies, anti-CD74 antibodies, apolizumab, bevacizumab, CHIR-12.12, epratuzumab (hLL2-anti-CD22 humanized antibody), galiximab, ha20, ibritumomab tiuxetan, lumiliximab, milatuzumab, ofatumumab, PR0131921, SGN-40, WT-1 analog peptide vaccine, WT1 126-134 peptide vaccine, tositumomab, autologous human tumor-derived HSPPC-96, and veltuzumab. Additional immunotherapy agents includes using cancer vaccines based upon the genetic makeup of an individual patient's tumor, such as lymphoma vaccine example is GTOP-99 (MyVax®).

Examples of chemotherapy agents for treating lymphoma or leukemia include aldesleukin, alvocidib, antineoplaston AS2-1, antineoplaston A10, anti-thymocyte globulin, amifostine trihydrate, aminocamptothecin, arsenic trioxide, beta alethine, Bcl-2 family protein inhibitor ABT-263, BMS-345541, bortezomib (Velcade®), bryostatin 1, busulfan, carboplatin, campath-1H, CC-5103, carmustine, caspofungin acetate, clofarabine, cisplatin, Cladribine (Leustarin), Chlorambucil (Leukeran), Curcumin, cyclosporine, Cyclophosphamide (Cyloxan, Endoxan, Endoxana, Cyclostin), cytarabine, denileukin diftitox, dexamethasone, DT PACE, docetaxel, dolastatin 10, Doxorubicin (Adriamycin®, Adriblastine), doxorubicin hydrochloride, enzastaurin, epoetin alfa, etoposide, Everolimus (RAD001), fenretinide, filgrastim, melphalan, mesna, Flavopiridol, Fludarabine (Fludara), Geldanamycin (17-AAG), ifosfamide, irinotecan hydrochloride, ixabepilone, Lenalidomide (Revlimid®, CC-5013), lymphokine-activated killer cells, melphalan, methotrexate, mitoxantrone hydrochloride, motexafin gadolinium, mycophenolate mofetil, nelarabine, oblimersen (Genasense) Obatoclax (GX15-070), oblimersen, octreotide acetate, omega-3 fatty acids, oxaliplatin, paclitaxel, PD0332991, PEGylated liposomal doxorubicin hydrochloride, pegfdgrastim, Pentstatin (Nipent), perifosine, Prednisolone, Prednisone, R-roscovitine (Selicilib, CYC202), recombinant interferon alfa, recombinant interleukin-12, recombinant interleukin-11, recombinant flt3 ligand, recombinant human thrombopoietin, rituximab, sargramostim, sildenafil citrate, simvastatin, sirolimus, Styryl sulphones, tacrolimus, tanespimycin, Temsirolimus (CC1-779), Thalidomide, therapeutic allogeneic lymphocytes, thiotepa, tipifamib, Velcade® (bortezomib or PS-341), Vincristine (Oncovin), vincristine sulfate, vinorelbine ditartrate, Vorinostat (SAHA), vorinostat, and FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R-CHOP (rituximab plus CHOP), R-CVP (rituximab plus CVP), R-FCM (rituximab plus FCM), R-ICE (rituximab-ICE), and R-MCP (Rituximab-MCP).

In some embodiments, the cancer is melanoma. Suitable agents for use in combination with the compounds described herein include, without limitation, dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY™. Compounds according to the invention may also be combined with immunotherapy drugs, including cytokines such as interferon alpha, interleukin 2, and tumor necrosis factor (TNF) in the treatment of melanoma.

Compounds described here may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds described herein, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F.

Melphalan is the drug most often used in this chemotherapy procedure. This can be given with another agent called tumor necrosis factor (TNF).

The therapeutic treatments can be supplemented or combined with any of the abovementioned therapies with stem cell transplantation or treatment. One example of modified approach is radioimmunotherapy, wherein a monoclonal antibody is combined with a radioisotope particle, such as indium In 111, yttrium Y 90, iodine I-131. Examples of combination therapies include, but are not limited to, Iodine-131 tositumomab (Bexxar®), Yttrium-90 ibritumomab tiuxetan (Zevalin®), Bexxar® with CHOP.

Other therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

Anti-HBV Combination Therapy

In certain embodiments, a method for treating or preventing an HBV infection in a human having or at risk of having the infection is provided, comprising administering to the human a therapeutically effective amount of a compound disclosed herein (such as a compound of Formula I, Ia, Ib, Ic, Id, Ie, If, Ig, Ih, Ii, or Ij), or a pharmaceutically acceptable salt thereof, in combination with a therapeutically effective amount of one or more (e.g., one, two, three, four, one or two, or one to three, or one to four) additional therapeutic agents. In one embodiment, a method for treating an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, or one to three, or one to four) additional therapeutic agents.

In certain embodiments, the present disclosure provides a method for treating an HBV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HBV infection.

In one embodiment, pharmaceutical compositions comprising a compound disclosed herein, or a pharmaceutically acceptable salt thereof, in combination with one or more (e.g., one, two, three, four, one or two, or one to three, or one to four) additional therapeutic agents, and a pharmaceutically acceptable carrier, diluent or excipient are provided.

In one embodiment, kits comprising a compound disclosed herein (such as a compound of Formula I, Ia, Ib, Ic, Id, Ie, If, Ig, Ih, Ii, or Ij), or a pharmaceutically acceptable salt thereof, in combination with one or more (e.g., one, two, three, four, one or two, or one to three, or one to four) additional therapeutic agents are provided.

In the above embodiments, the additional therapeutic agent may be an anti-HBV agent. For example, in some embodiments, the additional therapeutic agent is selected from the group consisting of HBV combination drugs, HBV DNA polymerase inhibitors, immunomodulators, toll-like receptor modulators (modulators of tlr1, tlr2, tlr3, tlr4, tlr5, tlr6, tlr7, tlr8, tlr9, tlr10, tlr11, tlr12 and tlr13), interferon alpha receptor ligands, hyaluronidase inhibitors, recombinant IL-7, hepatitis B surface antigen (HBsAg) inhibitors, compounds targeting hepatitis B core antigen (HbcAg), cyclophilin inhibitors, HBV therapeutic vaccines, HBV prophylactic vaccines, HBV viral entry inhibitors, NTCP (Na+-taurocholate cotransporting polypeptide) inhibitors, antisense oligonucleotide targeting viral mRNA, short interfering RNAs (siRNA), miRNA gene therapy agents, endonuclease modulators, inhibitors of ribonucleotide reductase, hepatitis B virus E antigen inhibitors, recombinant scavenger receptor A (SRA) proteins, Src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), CCR2 chemokine antagonists, thymosin agonists, cytokines, nucleoprotein inhibitors (HBV core or capsid protein inhibitors), stimulators of retinoic acid-inducible gene 1, stimulators of NOD2, stimulators of NOD1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), Hepatitis B virus replication inhibitors compounds such as those disclosed in US20100143301 (Gilead Sciences), US20110098248 (Gilead Sciences), US20090047249 (Gilead Sciences), U.S. Pat. No. 8,722,054 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (VentirxPharma), US20140275167 (Noviratherapeutics), US20130251673 (Noviratherapeutics), US8513184 (Gilead Sciences), US20140030221 (Gilead Sciences), US20130344030 (Gilead Sciences), US20130344029 (Gilead Sciences), US20140343032 (Roche), WO2014037480 (Roche), US20130267517 (Roche), WO2014131847 (Janssen), WO2014033176 (Janssen), WO2014033170 (Janssen), WO2014033167 (Janssen), US20140330015 (Ono pharmaceutical), US20130079327 (Ono pharmaceutical), US20130217880 (Ono pharmaceutical), and other drugs for treating HBV, and combinations thereof.

In certain embodiments, the one or more additional therapeutic agents include a Toll-like receptor 8 (TLR8) modulator. In some embodiments, the Toll-like receptor 8 (TLR8) modulator is a Toll-like receptor 8 (TLR8) agonist. In some embodiments, the Toll-like receptor 8 (TLR8) agonist is a comopund disclosed in U.S. Pat. No. 9,670,205, which is incorporated herein by reference in its entirety and specifically with respect to the compounds disclosed (such as, but not limited to, compounds of Examples 59, 61, 62, 63, 65, 66, 80, 98, 101, 114, and 116, or a pharmaceutically acceptable salt thereof) and methods of making and using the same. In some embodiments, the Toll-like receptor 8 (TLR8) agonist is selected from the group consisting of:

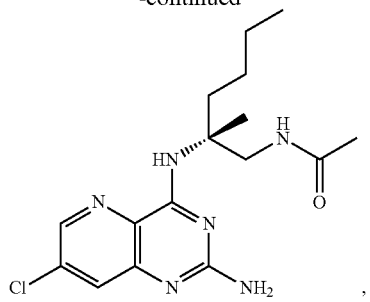

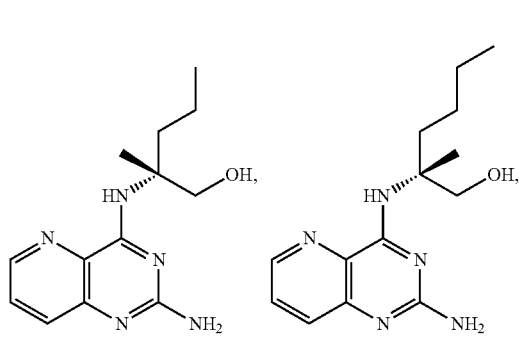

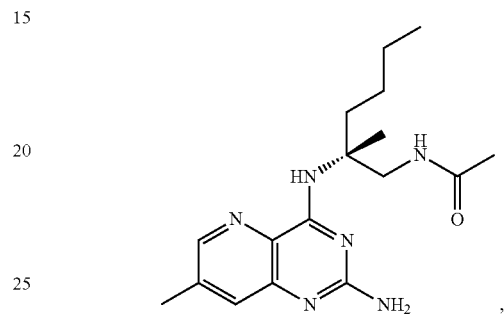

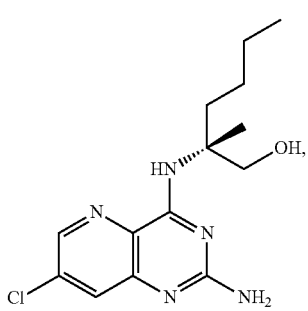

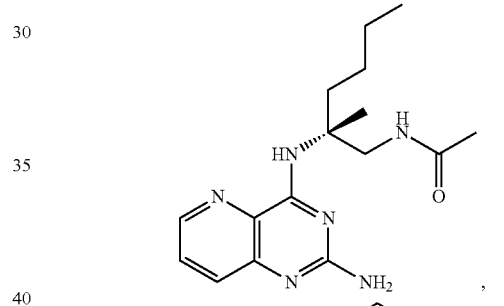

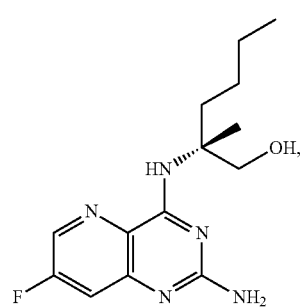

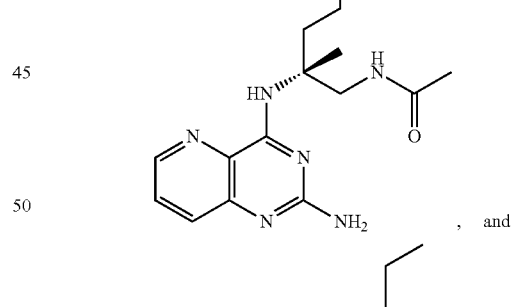

or a pharmaceutically acceptable salt thereof. In some embodiments, the Toll-like receptor 8 (TLR8) agonist is selected from the group consisting of:

71

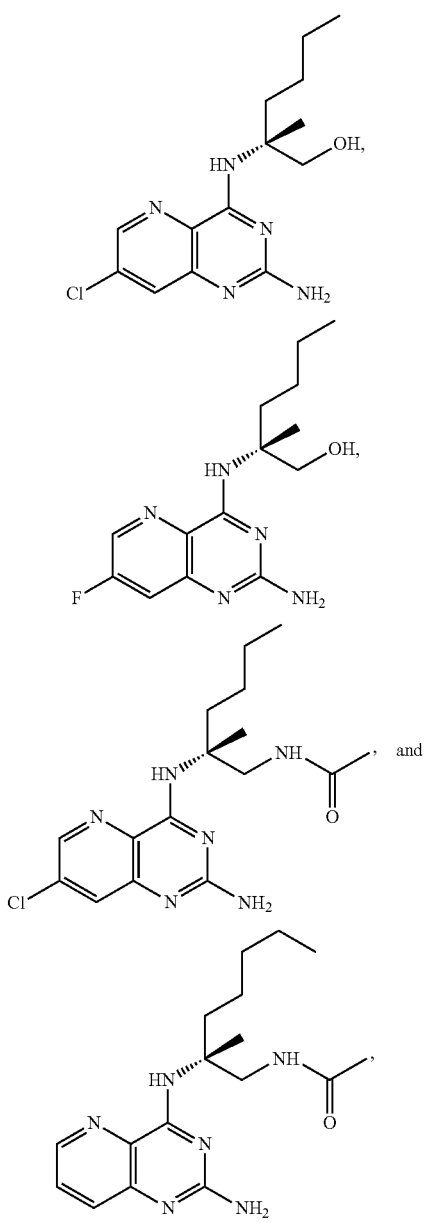

or a pharmaceutically acceptable salt thereof.

In some embodiments, the Toll-like receptor 8 (TLR8) agonist is selected from the group consisting of:

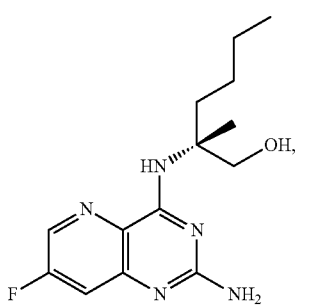

72

-continued

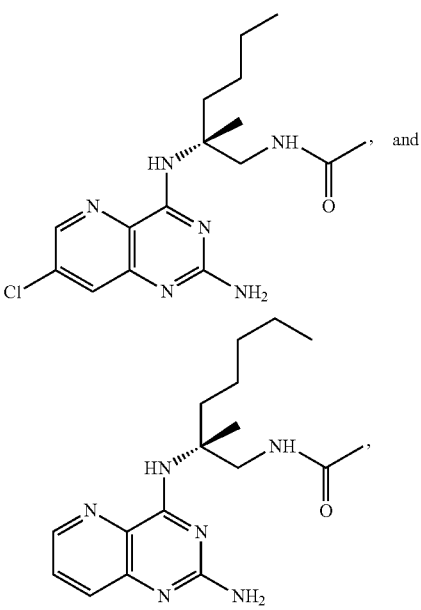

or a pharmaceutically acceptable salt thereof.

In some embodiments, the Toll-like receptor 8 (TLR8) agonist is:

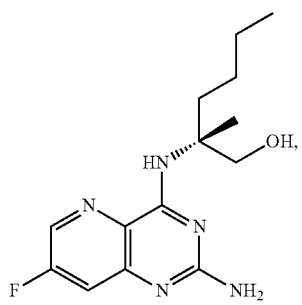

or a pharmaceutically acceptable salt thereof.

In some embodiments, the Toll-like receptor 8 (TLR8) agonist is:

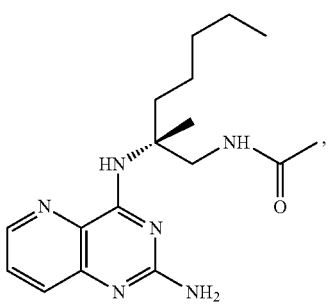

or a pharmaceutically acceptable salt thereof.

In some embodiments, the one or more additional therapeutic agents further include a Programmed Death 1 (PD-1) inhibitor and/or a Programmed Death Ligand 1 (PD-L1) inhibitor. In some embodiments, the Programmed Death 1 (PD-1) inhibitor is selected from the group consisting of nivolumab, lambrolizumab, pembrolizumab, pidilizumab, PDR001, and TSR-001, or a pharmaceutically acceptable salt or solvate of any of the forgoing. In some embodiments, the Programmed Death Ligand 1 (PD-L1) inhibitor is selected from the group consisting of atezolizumab, durvalumab, or avelumab, or a pharmaceutically acceptable salt or solvate of any of the forgoing.

In certain embodiments, a method for treating an HBV infection in a human having the infection is provided, comprising administering to the human:
(i) a therapeutically effective amount of a compound disclosed herein, which is selected from the group consisting of:

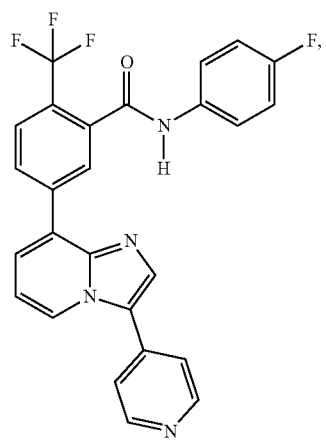

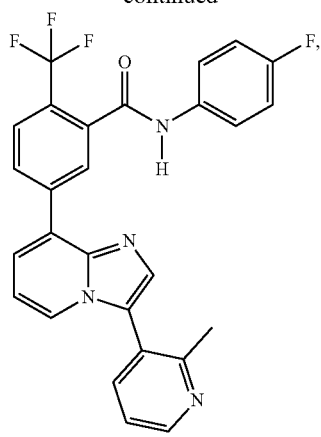

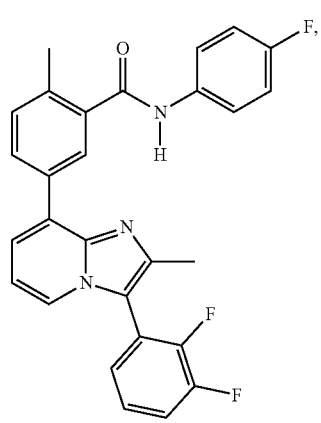

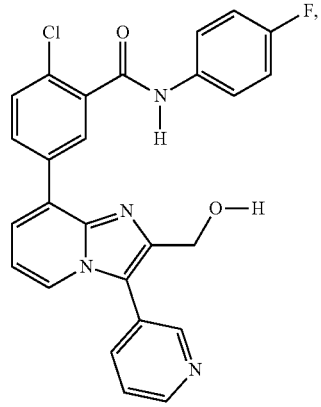

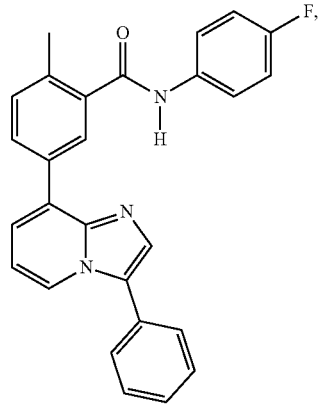

75
-continued
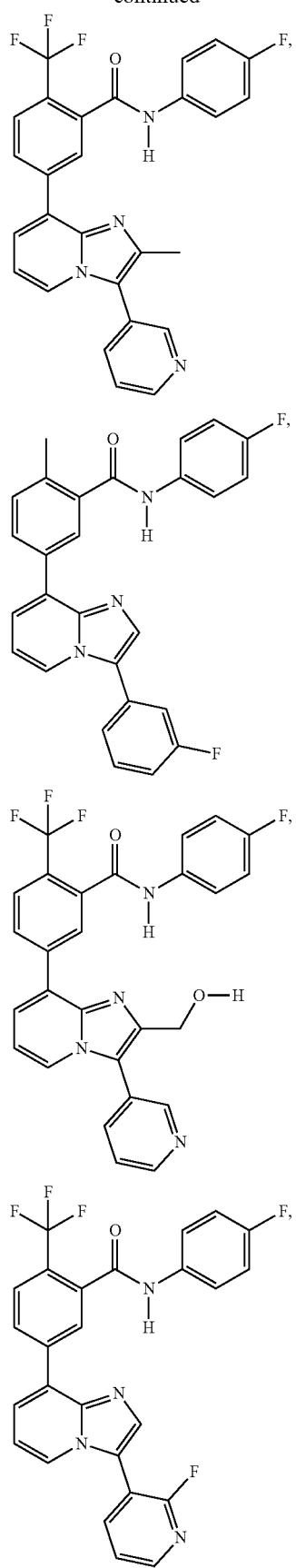
76
-continued
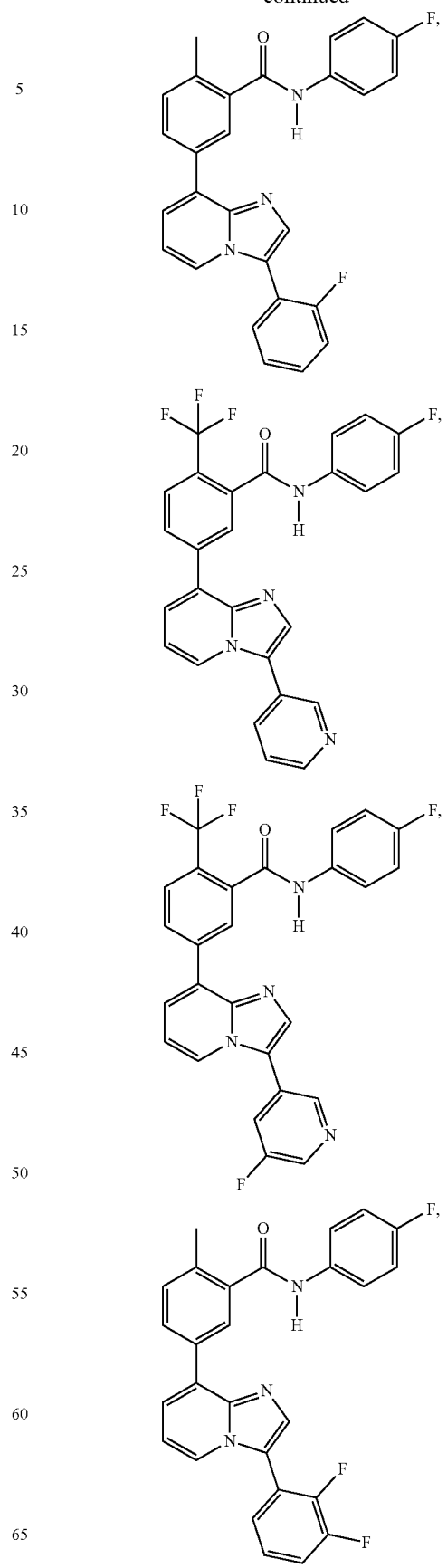

77
-continued
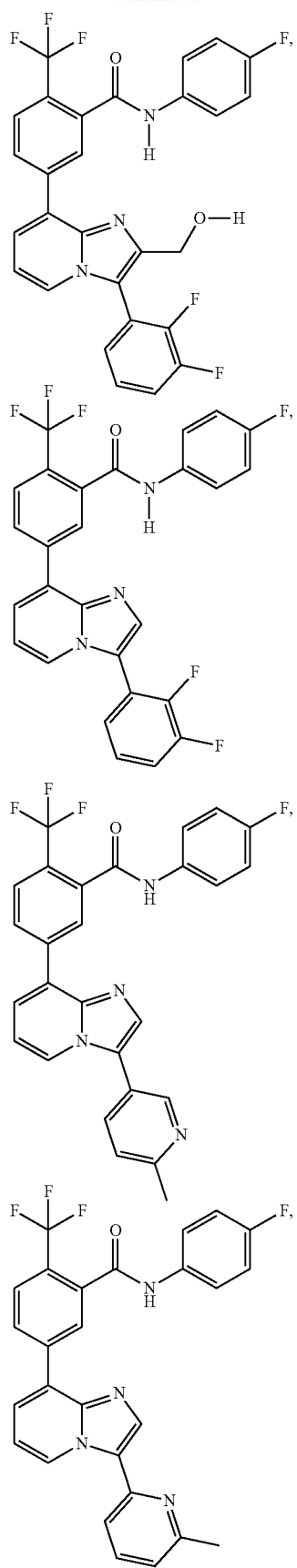
78
-continued
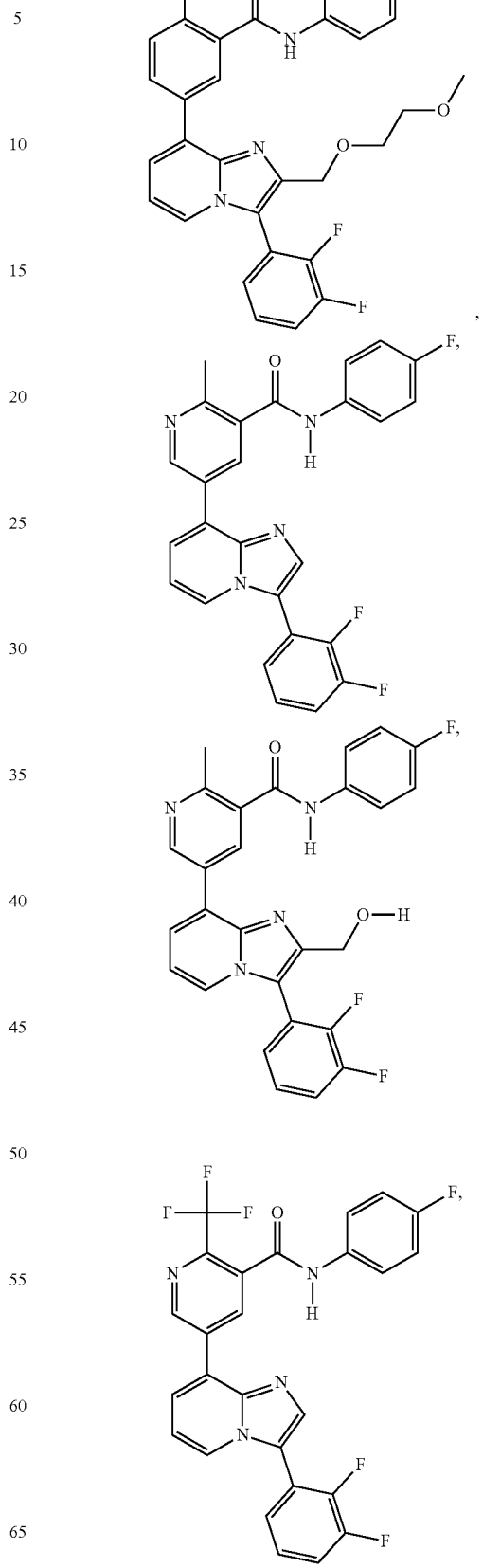

-continued
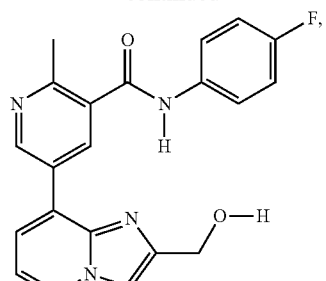
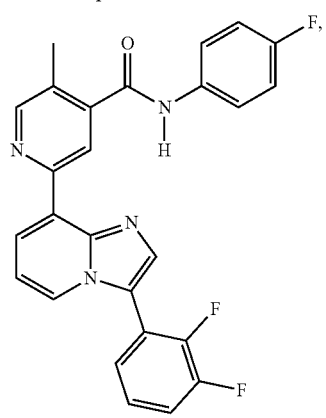
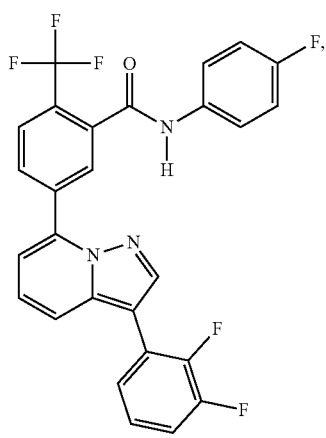
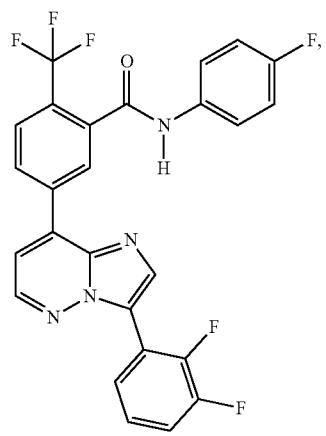
-continued
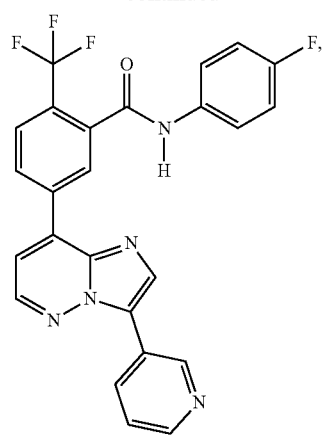
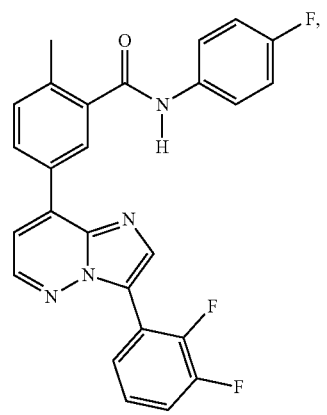
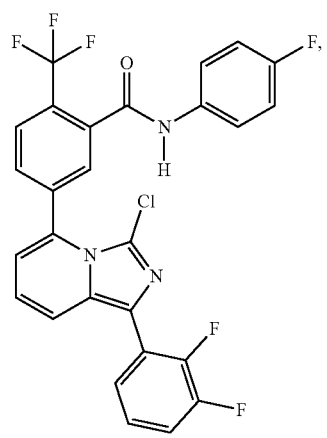
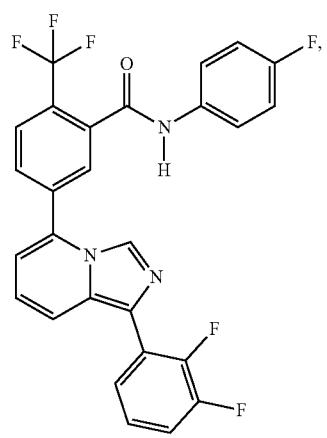

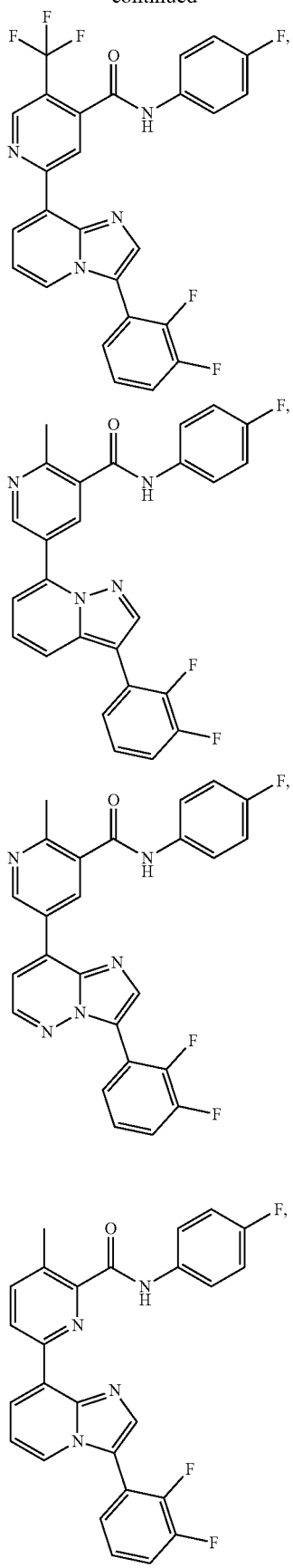
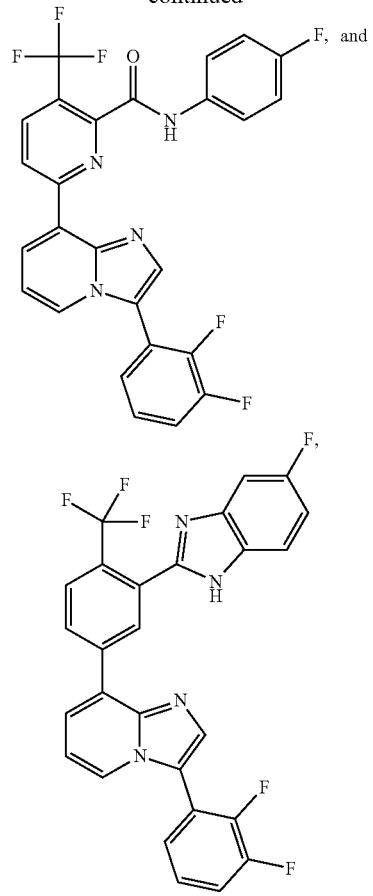
or a pharmaceutically acceptable salt or pharmaceutically acceptable tautomer thereof; in combination with
(ii) a therapeutically effective amount of a Toll-like receptor 8 (TLR8) agonist which is selected from the group consisting of:
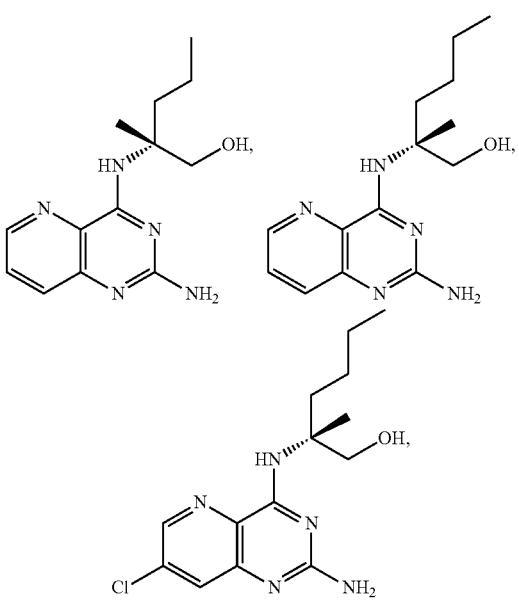

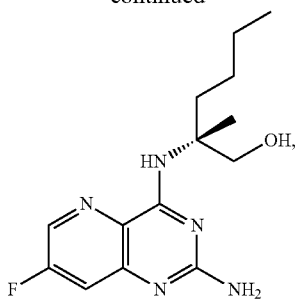

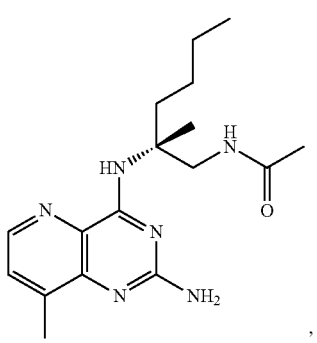

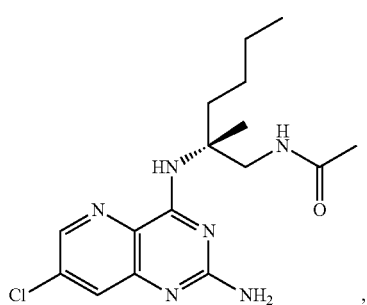

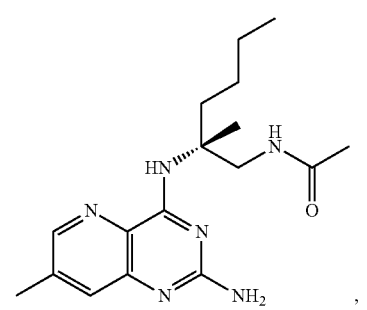

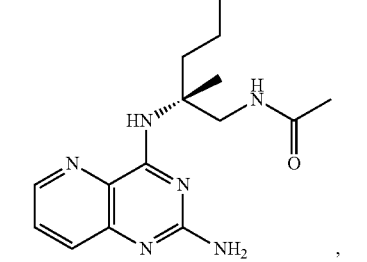

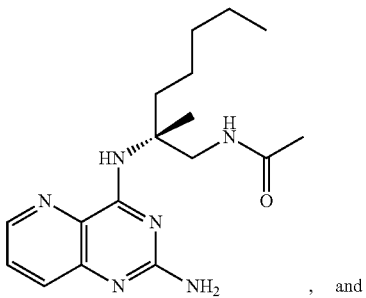

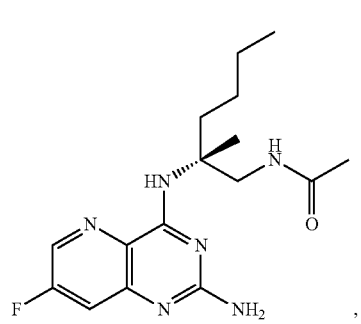

or a pharmaceutically acceptable salt thereof, and (iii) optionally, a PD-1 inhibitor and/or a PD-L1 inhibitor. In one such method, the optional PD-1 inhibitor and/or a PD-L1 inhibitor is not administered. In another such method, the optional PD-1 inhibitor and/or PD-L1 inhibitor is administered. In one such method, a PD-1 inhibitor is administered. In another such method, a PD-L1 inhibitor is administered. In another such method, a PD-1 inhibitor and a PD-L1 inhibitor are administered.

In certain embodiments, a method for treating an HBV infection in a human having the infection is provided, comprising administering to the human:

(i) a therapeutically effective amount of a compound which is selected from the group consisting of:

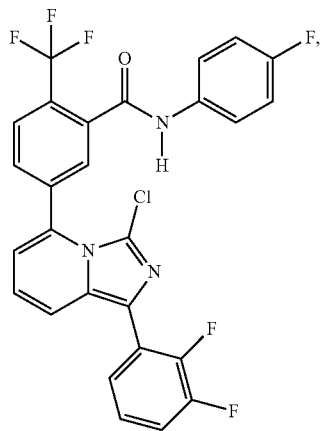 [SMILES: O=C(Nc1ccc(F)cc1)c1cc(-c2cccc3c(-c4cccc(F)c4F)nc(Cl)n23)ccc1C(F)(F)F]

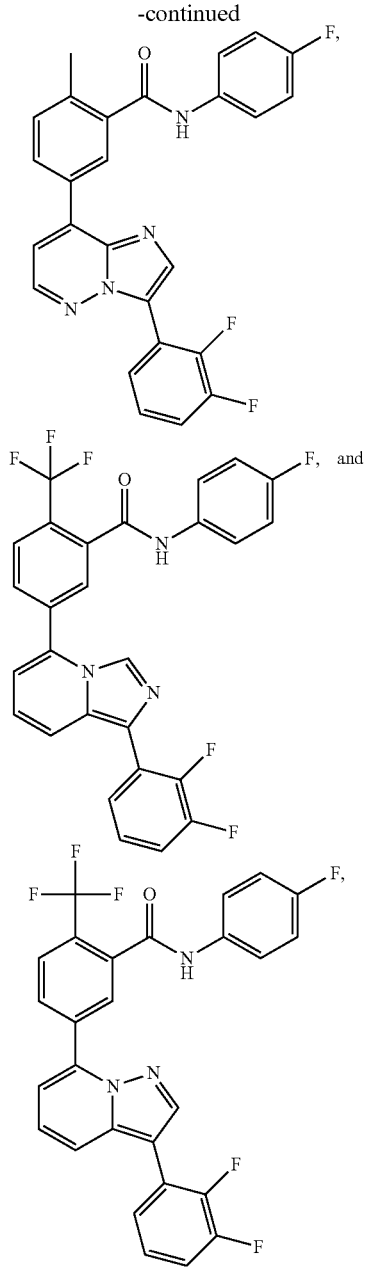

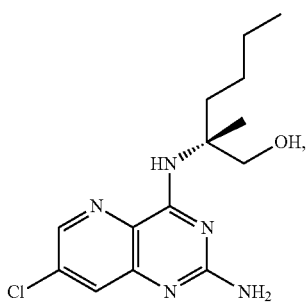

or a pharmaceutically acceptable salt or pharmaceutically acceptable tautomer thereof; in combination with
(ii) a therapeutically effective amount of a Toll-like receptor 8 (TLR8) agonist which is selected from the group consisting of:

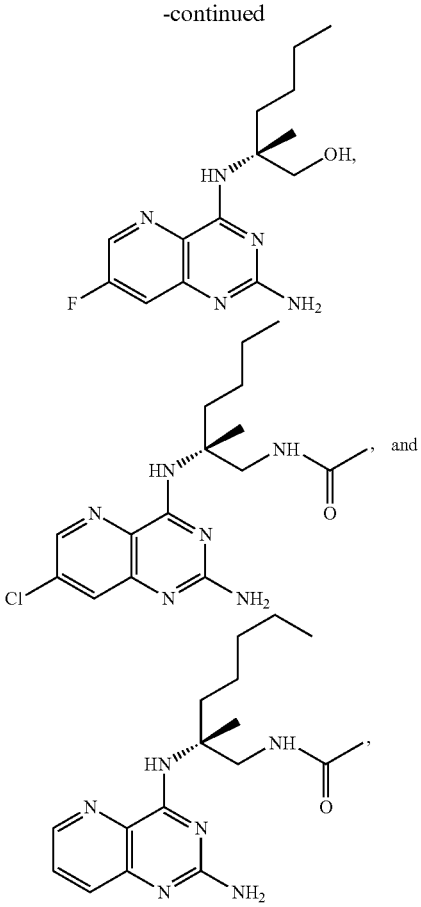

or a pharmaceutically acceptable salt thereof; and
(iii) optionally, a PD-1 inhibitor and/or a PD-L1 inhibitor. In one such method, the optional PD-1 inhibitor and/or a PD-L1 inhibitor is not administered. In another such method, the optional PD-1 inhibitor and/or PD-L1 inhibitor is administered. In one such method, a PD-1 inhibitor is administered. In another such method, a PD-L1 inhibitor is administered. In another such method, a PD-1 inhibitor and a PD-L1 inhibitor are administered.

In certain embodiments, a method for treating an HBV infection in a human having the infection is provided, comprising administering to the human:
(i) a therapeutically effective amount of a compound which is:

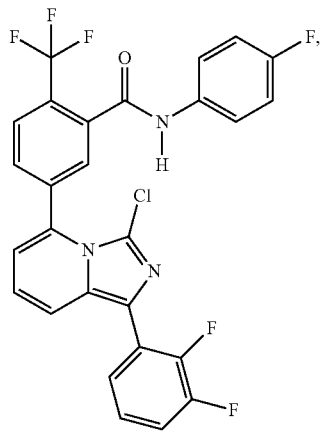

or a pharmaceutically acceptable salt or pharmaceutically acceptable tautomer thereof; in combination with
(ii) a therapeutically effective amount of a Toll-like receptor 8 (TLR8) agonist which is:

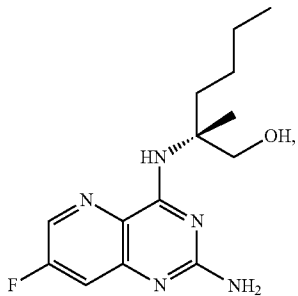

or a pharmaceutically acceptable salt thereof; and
(iii) optionally, a PD-1 inhibitor and/or a PD-L1 inhibitor. In one such method, the optional PD-1 inhibitor and/or a PD-L1 inhibitor is not administered. In another such method, the optional PD-1 inhibitor and/or PD-L1 inhibitor is administered. In one such method, a PD-1 inhibitor is administered. In another such method, a PD-L1 inhibitor is administered. In another such method, a PD-1 inhibitor and a PD-L1 inhibitor are administered.

In certain embodiments, a method for treating an HBV infection in a human having the infection is provided, comprising administering to the human:
(i) a therapeutically effective amount of a compound which is:

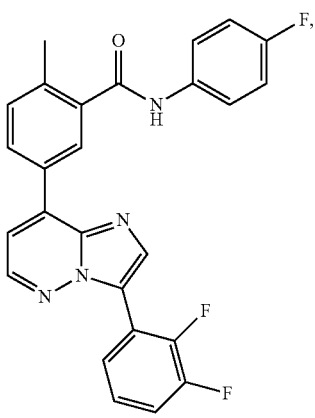

or a pharmaceutically acceptable salt or pharmaceutically acceptable tautomer thereof; in combination with
(ii) a therapeutically effective amount of a Toll-like receptor 8 (TLR8) agonist which is:

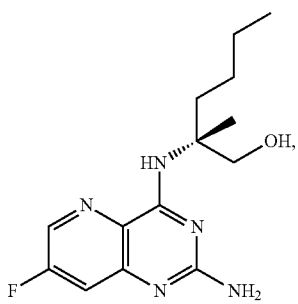

or a pharmaceutically acceptable salt thereof: and
(iii) optionally, a PD-1 inhibitor and/or a PD-L1 inhibitor. In one such method, the optional PD-1 inhibitor and/or a PD-L1 inhibitor is not administered. In another such method, the optional PD-1 inhibitor and/or PD-L1 inhibitor is administered. In one such method, a PD-1 inhibitor is administered. In another such method, a PD-L1 inhibitor is administered. In another such method, a PD-1 inhibitor and a PD-L1 inhibitor are administered.

In certain embodiments, a method for treating an HBV infection in a human having the infection is provided, comprising administering to the human:
(i) a therapeutically effective amount of a compound which is:

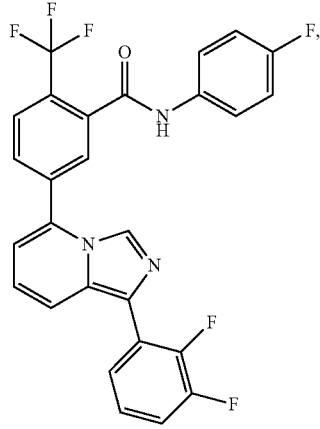 [SMILES: O=C(Nc1ccc(F)cc1)c1cc(-c2cccc3c(-c4cccc(F)c4F)ncn23)ccc1C(F)(F)F]

or a pharmaceutically acceptable salt or pharmaceutically acceptable tautomer thereof; in combination with
(ii) a therapeutically effective amount of a Toll-like receptor 8 (TLR8) agonist which is:

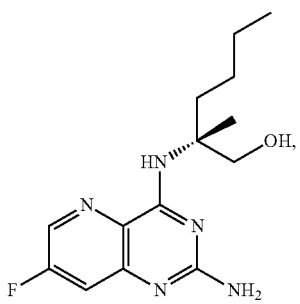

or a pharmaceutically acceptable salt thereof: and
(iii) optionally, a PD-1 inhibitor and/or a PD-L1 inhibitor. In one such method, the optional PD-1 inhibitor and/or a PD-L1 inhibitor is not administered. In another such method, the optional PD-1 inhibitor and/or PD-L1 inhibitor is administered. In one such method, a PD-1 inhibitor is administered. In another such method, a PD-L1 inhibitor is administered. In another such method, a PD-1 inhibitor and a PD-L1 inhibitor are administered.

In certain embodiments, a method for treating an HBV infection in a human having the infection is provided, comprising administering to the human:

(i) a therapeutically effective amount of a compound which is:

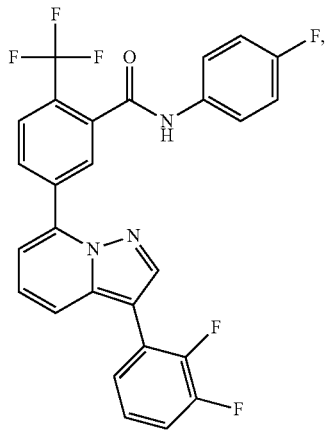 [SMILES: O=C(Nc1ccc(F)cc1)c1cc(-c2cccc3c(-c4cccc(F)c4F)cnn23)ccc1C(F)(F)F]

or a pharmaceutically acceptable salt or pharmaceutically acceptable tautomer thereof; in combination with
(ii) a therapeutically effective amount of a Toll-like receptor 8 (TLR8) agonist which is:

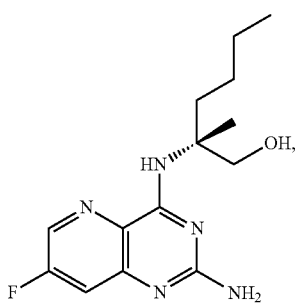

or a pharmaceutically acceptable salt thereof: and
(iii) optionally, a PD-1 inhibitor and/or a PD-L1 inhibitor. In one such method, the optional PD-1 inhibitor and/or a PD-L1 inhibitor is not administered. In another such method, the optional PD-1 inhibitor and/or PD-L1 inhibitor is administered. In one such method, a PD-1 inhibitor is administered. In another such method, a PD-L1 inhibitor is administered. In another such method, a PD-1 inhibitor and a PD-L1 inhibitor are administered.

Compositions and kits for combination therapy are also provided. In some embodiments, provided herein is a composition comprising:
(i) a compound disclosed herein, which is selected from the group consisting of:

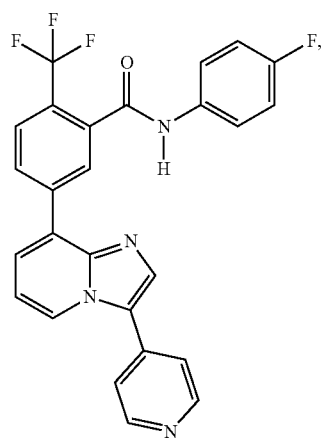

-continued

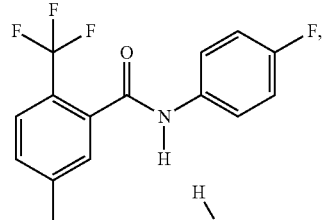

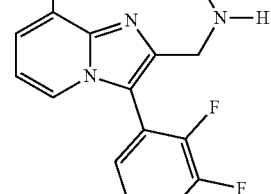

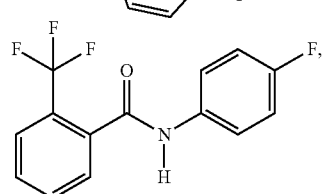

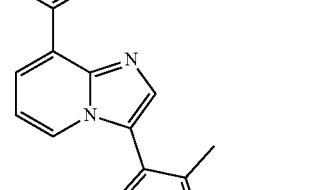

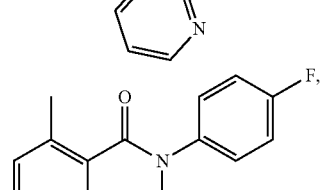

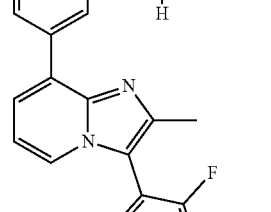

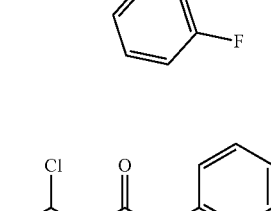

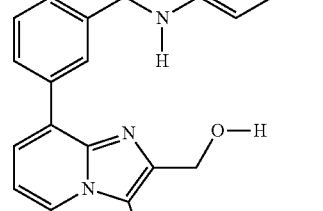

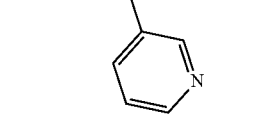

-continued
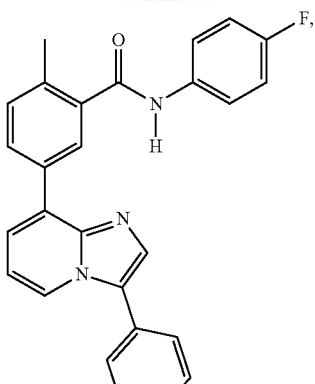
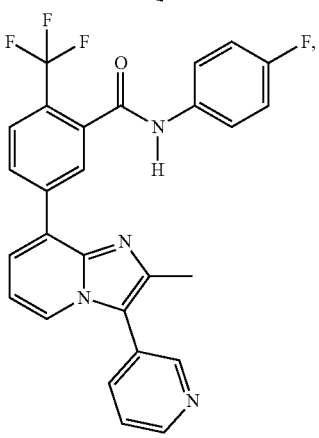
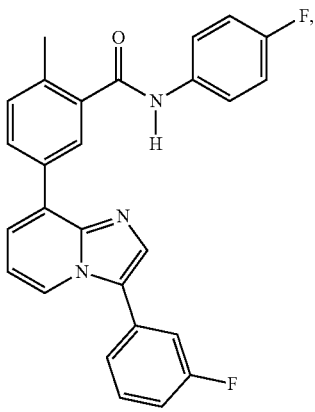
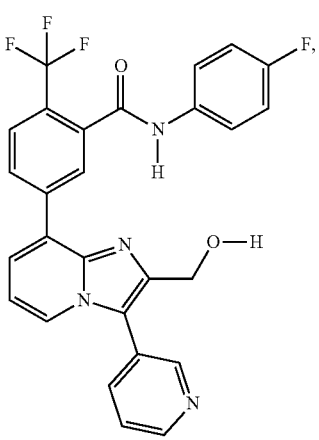
-continued
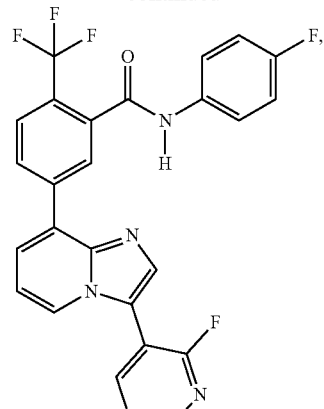
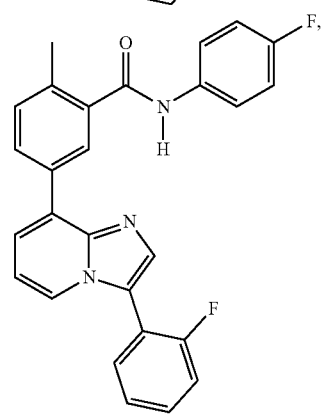
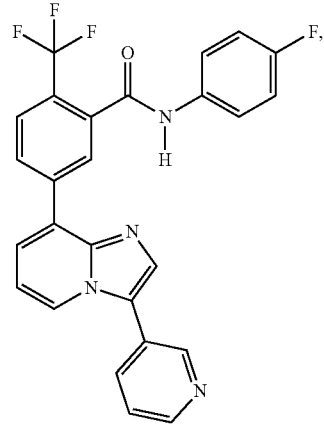
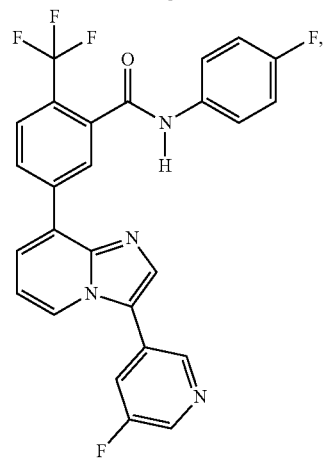

93
-continued
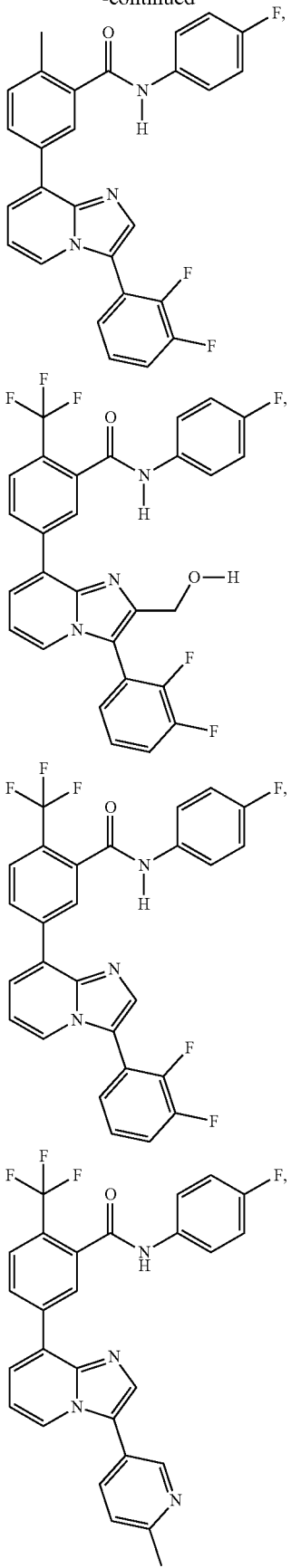
94
-continued
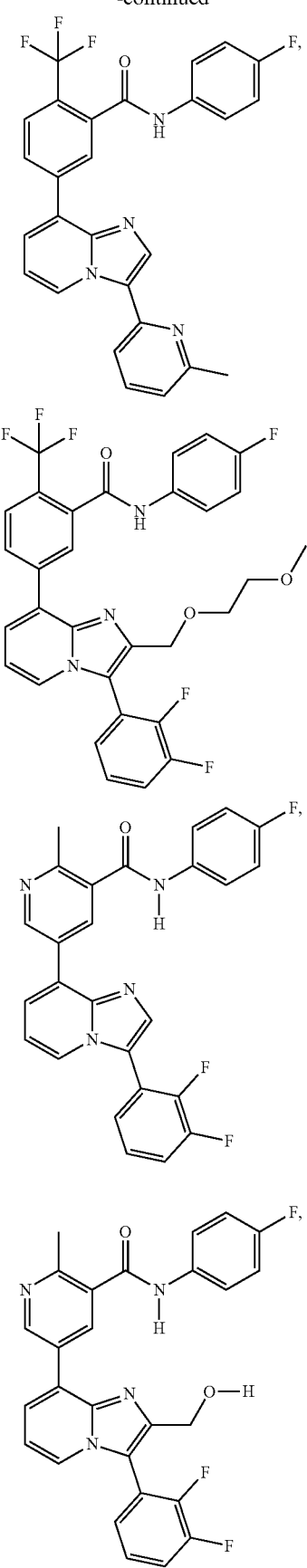

-continued
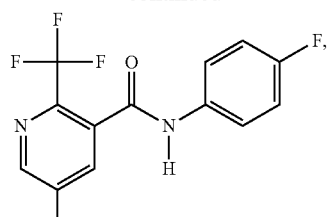
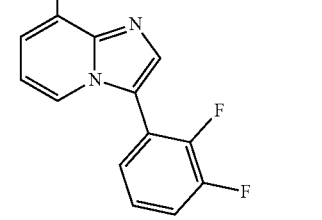
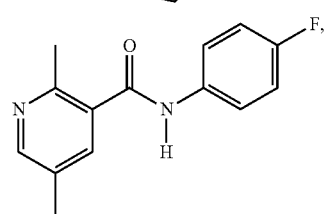
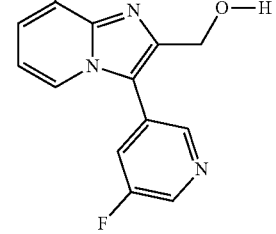
-continued
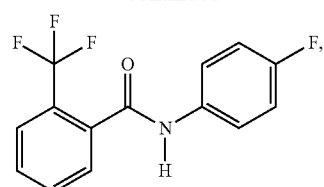
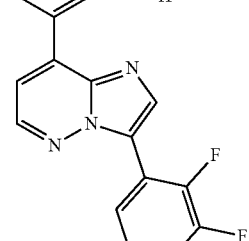
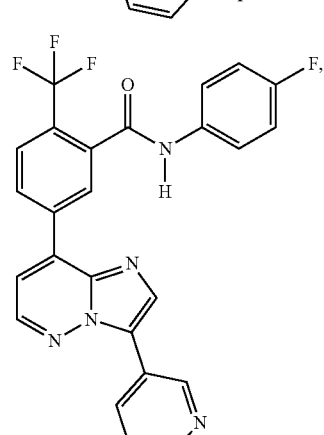
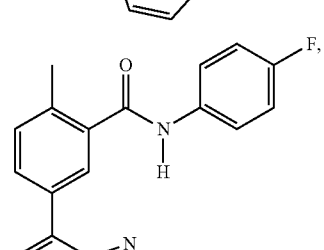
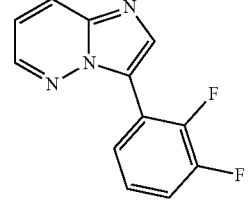
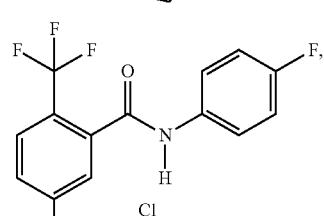
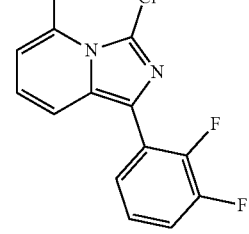
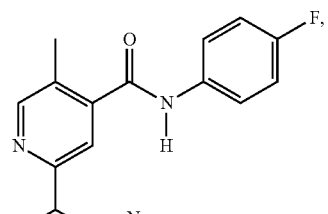
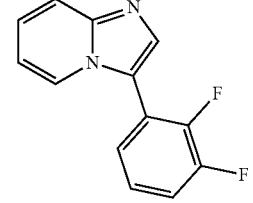
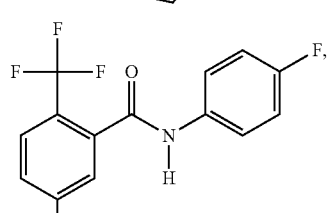
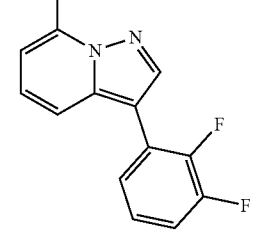

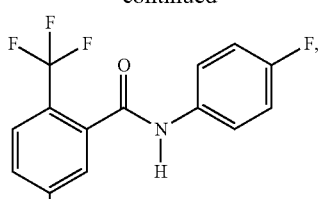
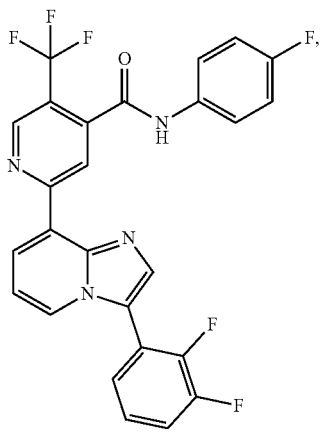 [SMILES: O=C(Nc1ccc(F)cc1)c1cc(-c2cccn3c(-c4cccc(F)c4F)cnc23)ccc1C(F)(F)F]
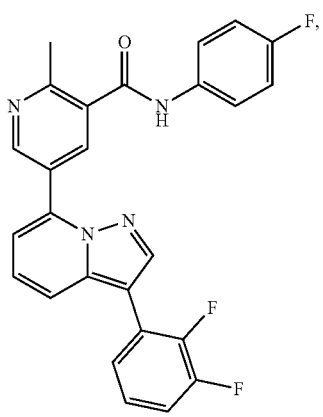
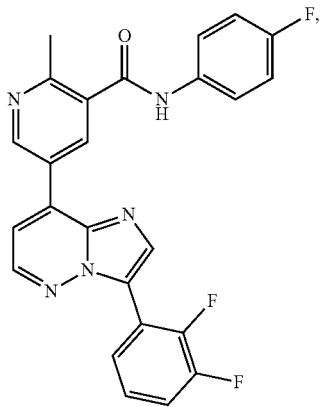
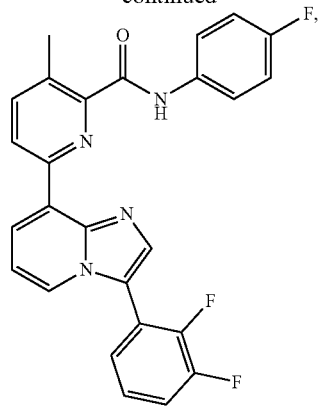
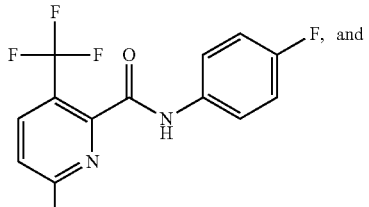
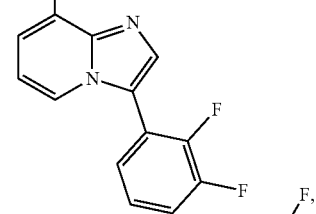
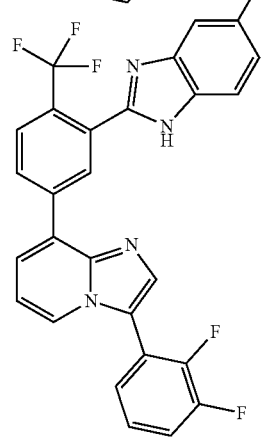
or a pharmaceutically acceptable salt or pharmaceutically acceptable tautomer thereof; and
(ii) a Toll-like receptor 8 (TLR8) agonist which is selected from the group consisting of:
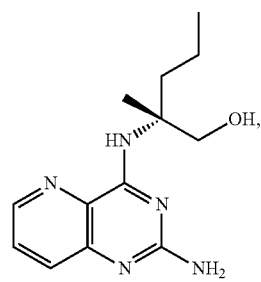

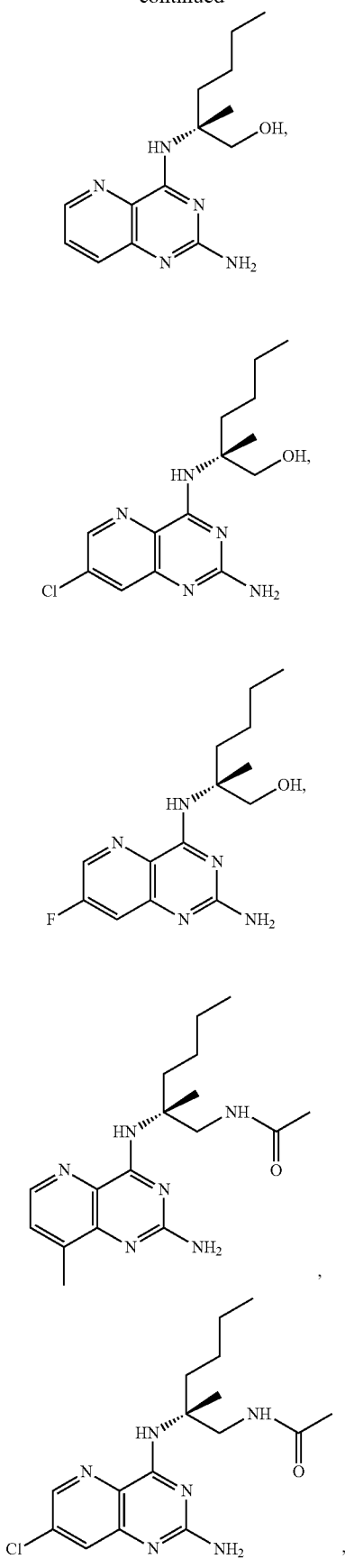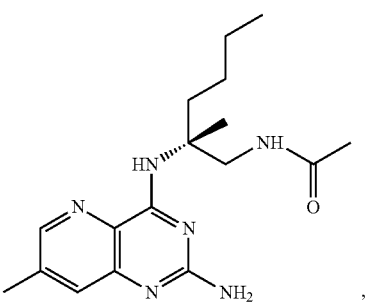
or a pharmaceutically acceptable salt thereof. In some embodiments, the composition further comprises a PD-1 inhibitor and/or a PD-L1 inhibitor.
In certain embodiments, a composition is provided, comprising:

(i) a compound disclosed herein, which is selected from the group consisting of:

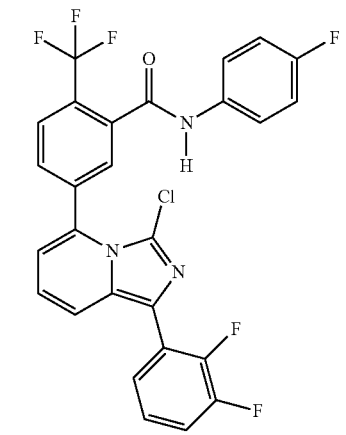

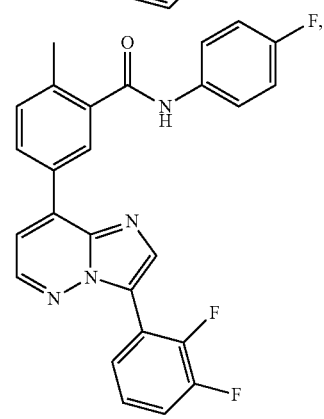

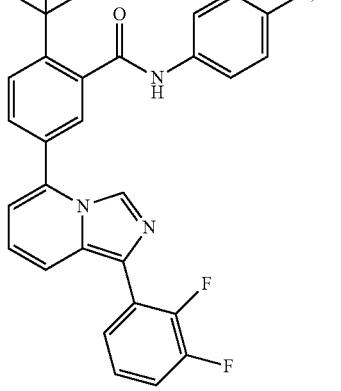

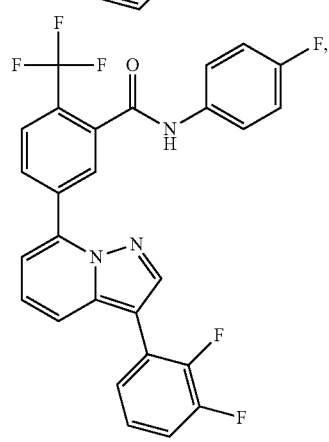

or a pharmaceutically acceptable salt or pharmaceutically acceptable tautomer thereof; and (ii) a Toll-like receptor 8 (TLR8) agonist which is selected from the group consisting of:

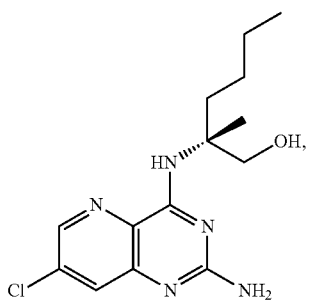

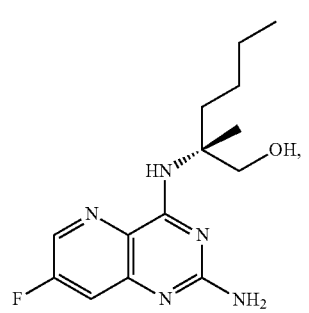

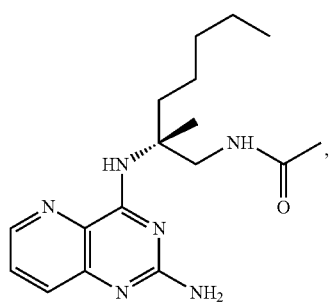

or a pharmaceutically acceptable salt thereof. In some embodiments, the composition further comprises a PD-1 inhibitor and/or a PD-L1 inhibitor.

In some embodiments, a composition is provided, comprising:

(i) a compound disclosed herein, which is:

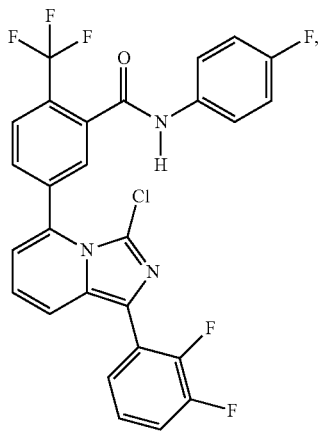 [SMILES: O=C(Nc1ccc(F)cc1)c1cc(-c2cccc3c(-c4cccc(F)c4F)nc(Cl)n23)ccc1C(F)(F)F]

or a pharmaceutically acceptable salt or pharmaceutically acceptable tautomer thereof; and
(ii) a Toll-like receptor 8 (TLR8) agonist which is:

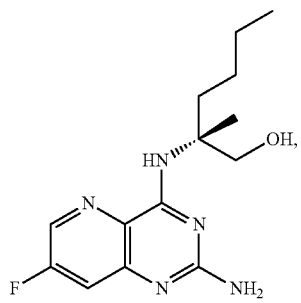

or a pharmaceutically acceptable salt thereof. In some embodiments, the composition further comprises a PD-1 inhibitor and/or a PD-L1 inhibitor.

In some embodiments, a composition is provided, comprising:
(i) a compound disclosed herein, which is:

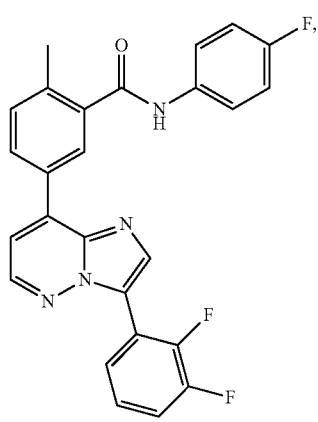 [SMILES: Cc1ccc(-c2ccnn3c(-c4cccc(F)c4F)cnc23)cc1C(=O)Nc1ccc(F)cc1]

or a pharmaceutically acceptable salt or pharmaceutically acceptable tautomer thereof; and (ii) a Toll-like receptor 8 (TLR8) agonist which is:

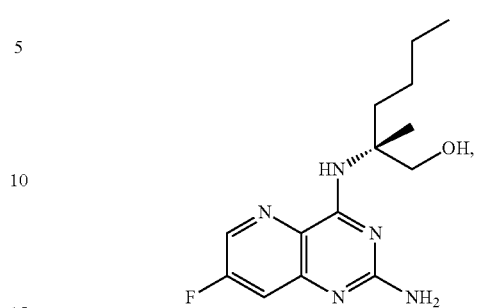

or a pharmaceutically acceptable salt thereof. In some embodiments, the composition further comprises a PD-1 inhibitor and/or a PD-L1 inhibitor.

In certain embodiments, a composition is provided, comprising:
(i) a compound disclosed herein, which is:

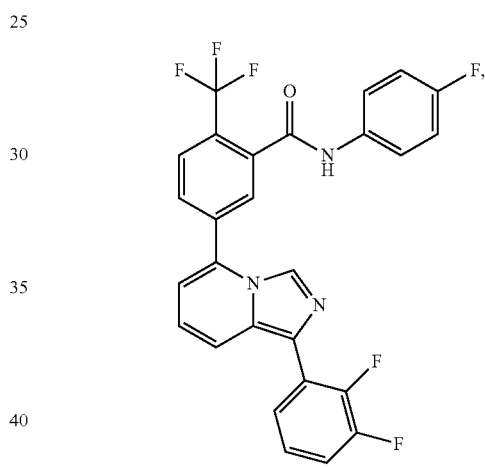

or a pharmaceutically acceptable salt or pharmaceutically acceptable tautomer thereof; and
(ii) a Toll-like receptor 8 (TLR8) agonist which is:

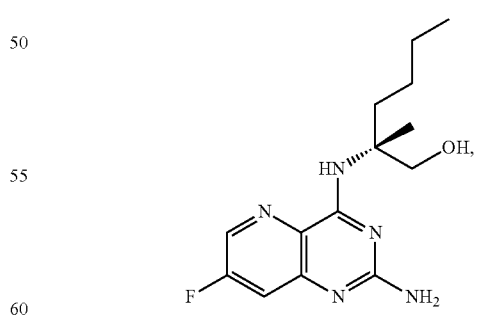

or a pharmaceutically acceptable salt thereof. In some embodiments, the composition further comprises a PD-1 inhibitor and/or a PD-L1 inhibitor.

In certain embodiments, a composition is provided, comprising:

105

(i) a compound disclosed herein, which is:

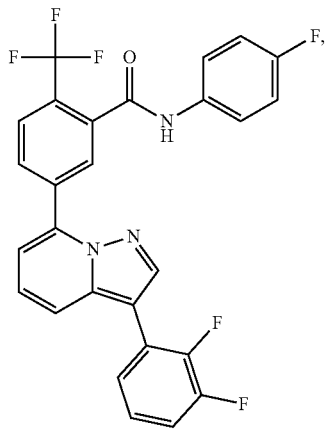 [SMILES: O=C(Nc1ccc(F)cc1)c1cc(-c2cccc3c(-c4cccc(F)c4F)cnn23)ccc1C(F)(F)F]

or a pharmaceutically acceptable salt or pharmaceutically acceptable tautomer thereof; and (ii) a Toll-like receptor 8 (TLR8) agonist which is:

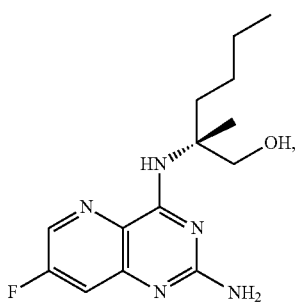

or a pharmaceutically acceptable salt thereof. In some embodiments, the composition further comprises a PD-1 inhibitor and/or a PD-L1 inhibitor.

In some embodiments, provided herein is a kit comprising:

(i) a compound disclosed herein, which is selected from the group consisting of:

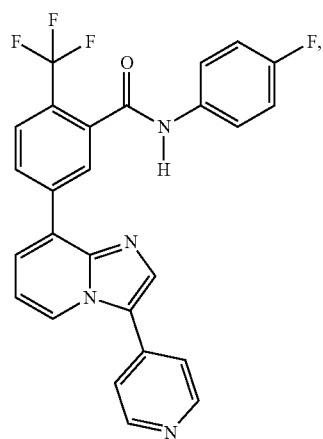

106

-continued

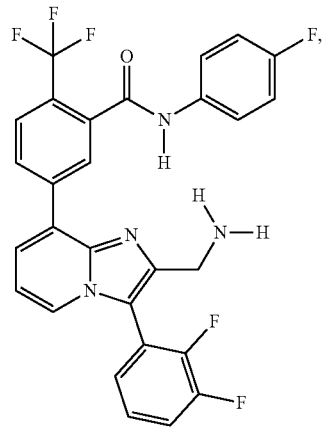

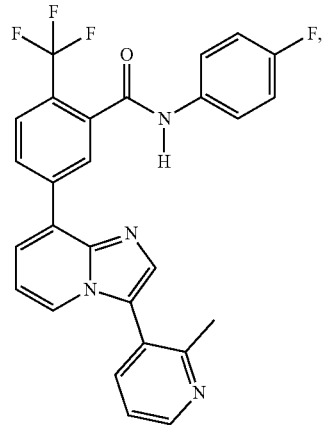

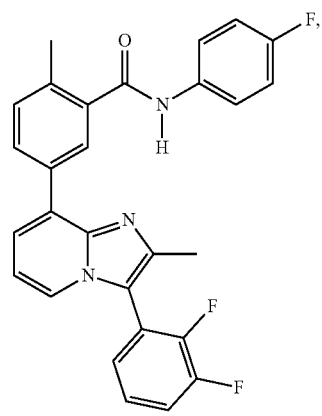

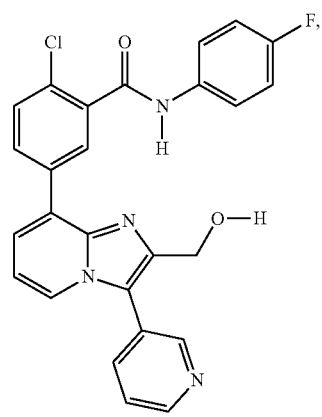

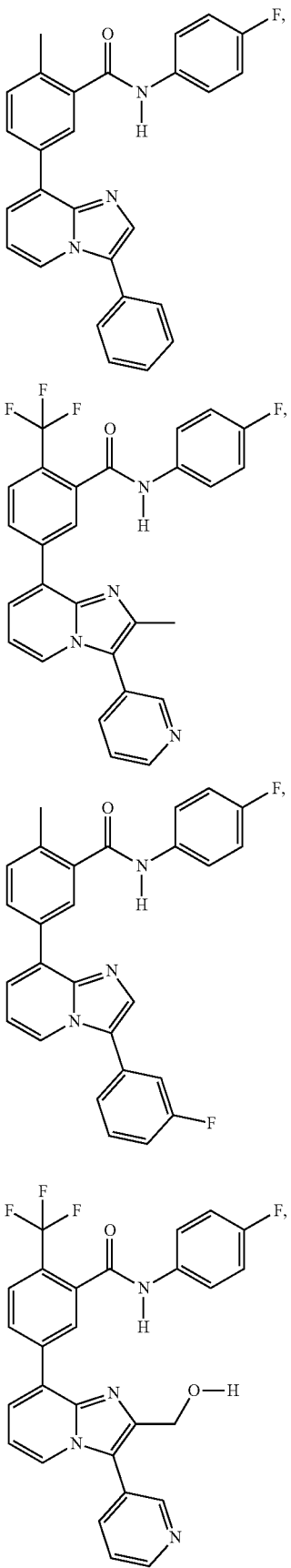
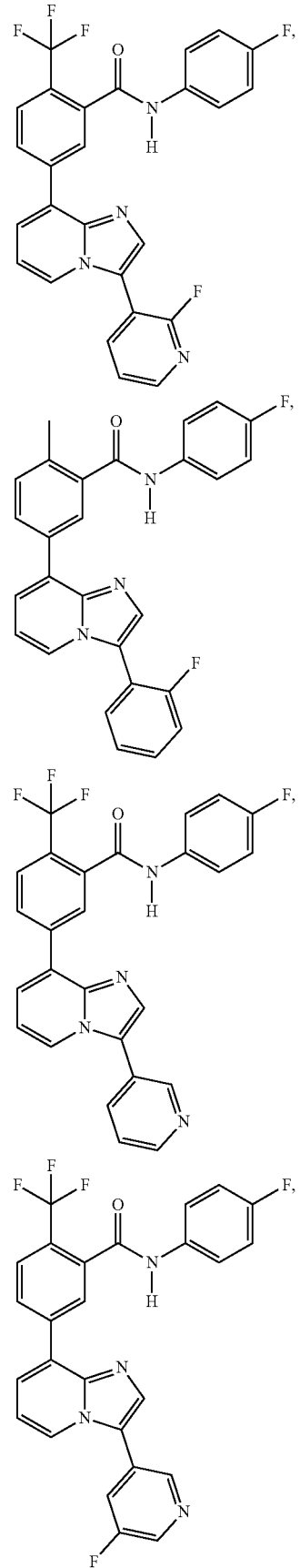

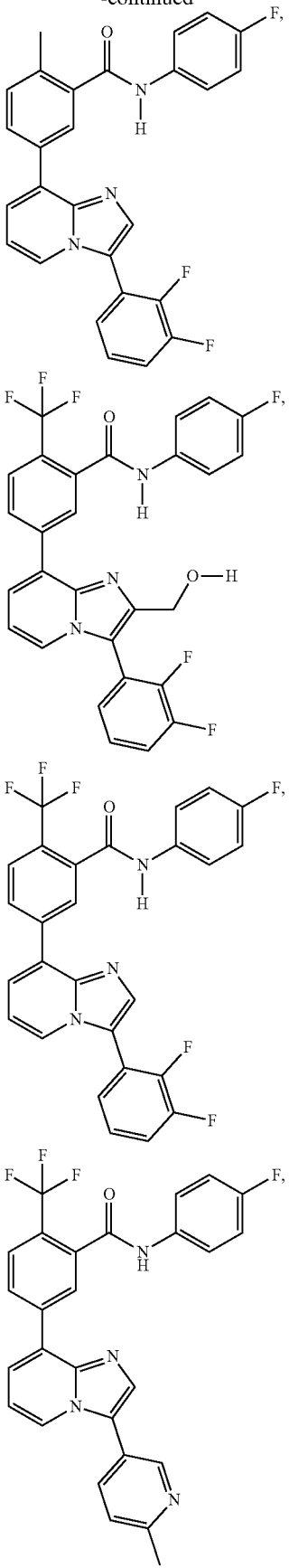
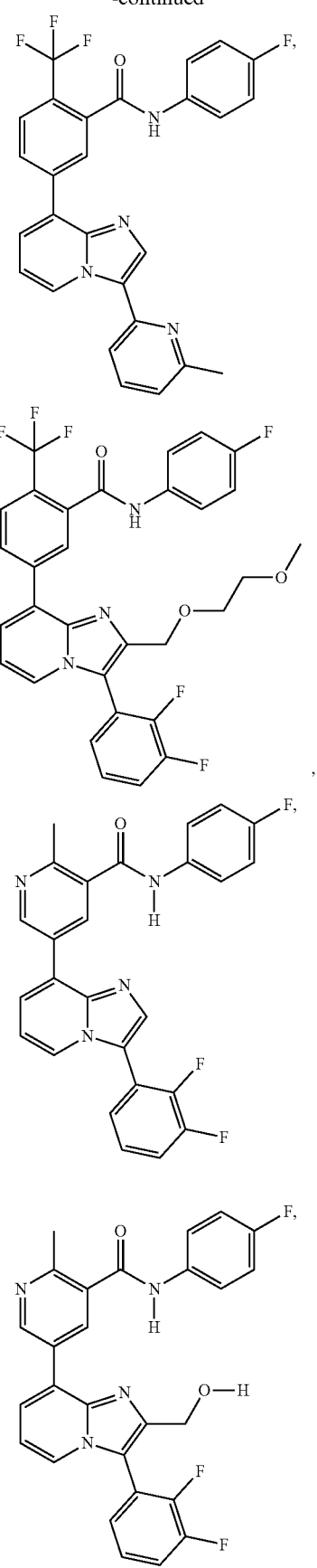

-continued
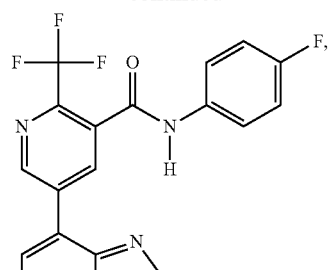
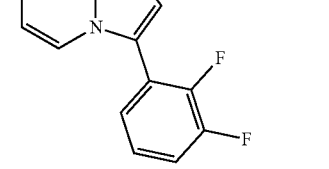
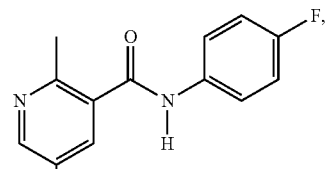
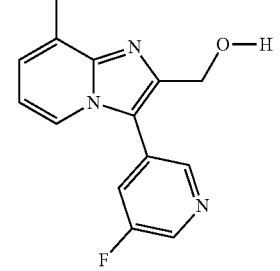
-continued
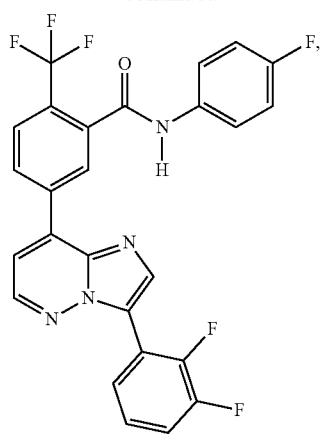
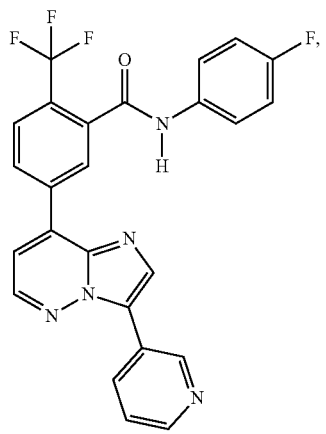
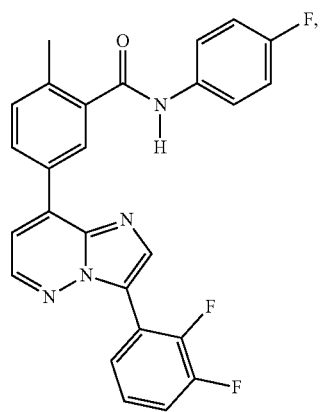
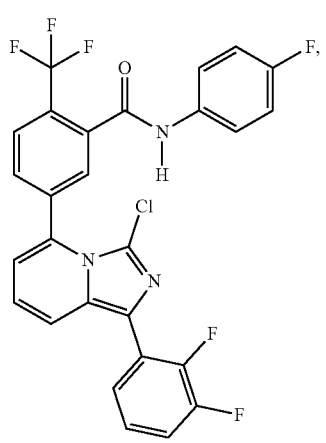

113
-continued
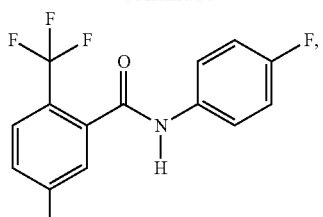
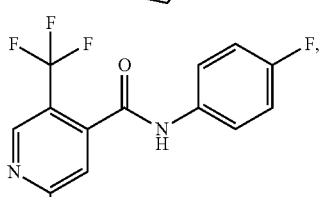
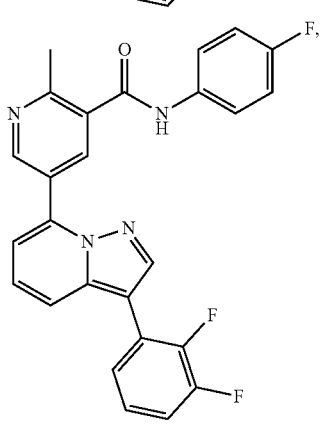
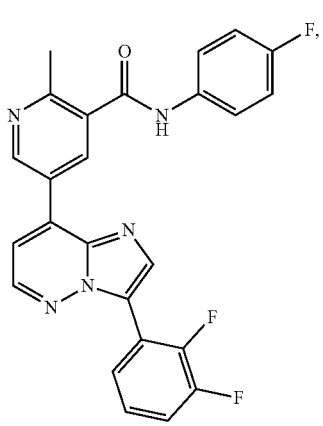
114
-continued
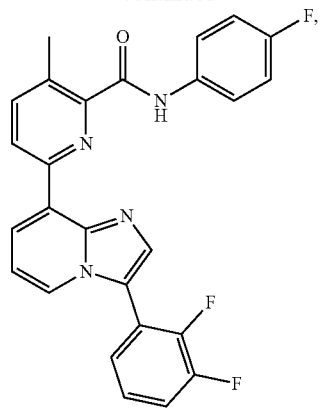
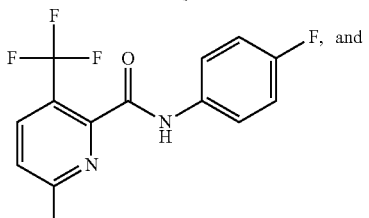
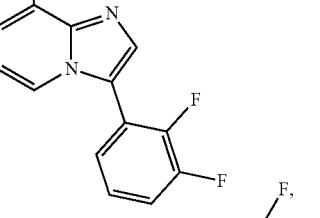
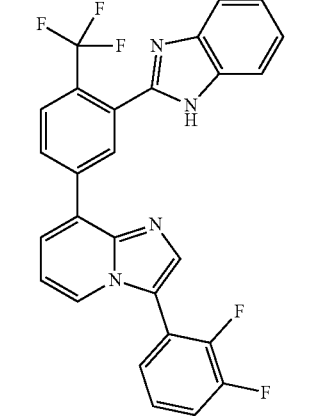
or a pharmaceutically acceptable salt or pharmaceutically acceptable tautomer thereof; and
(ii) a Toll-like receptor 8 (TLR8) agonist which is selected from the group consisting of:
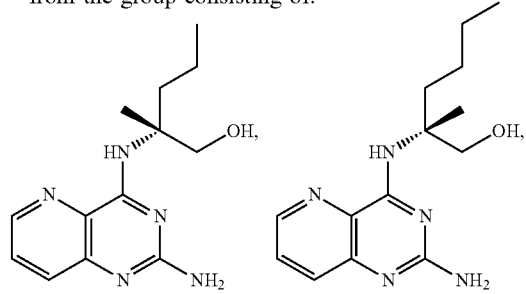

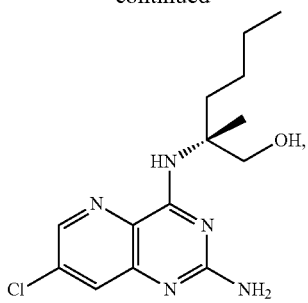

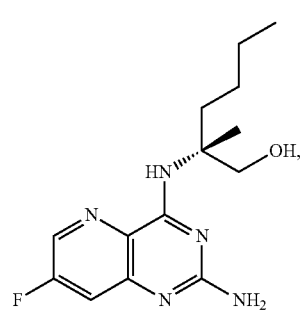

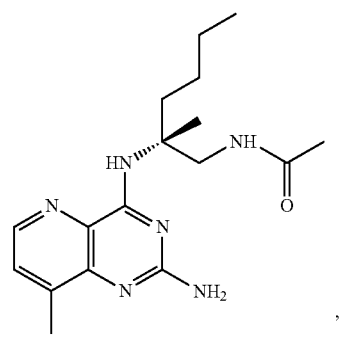

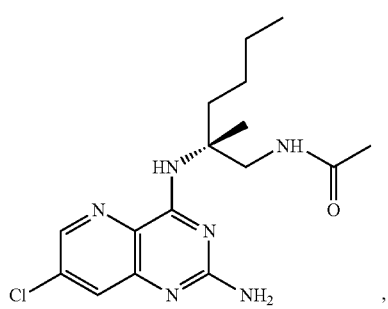

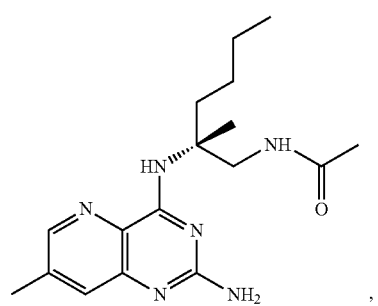

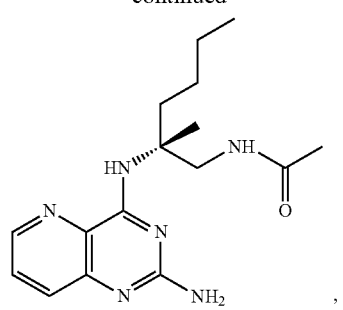

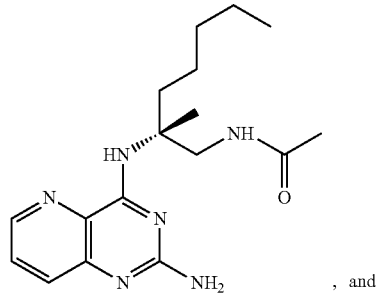

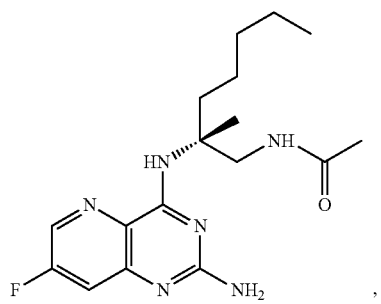

or a pharmaceutically acceptable salt thereof. In some embodiments, the kit further comprises a PD-1 inhibitor and/or a PD-L1 inhibitor. In some embodiments, the kit further comprises instructions for use in the treatment of an HBV infection in a human.

In certain embodiments, a kit is provided, comprising:

(i) a compound disclosed herein, which is selected from the group consisting of:

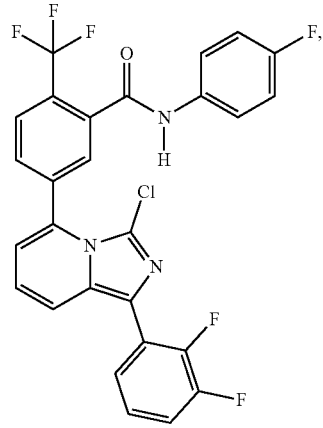

-continued

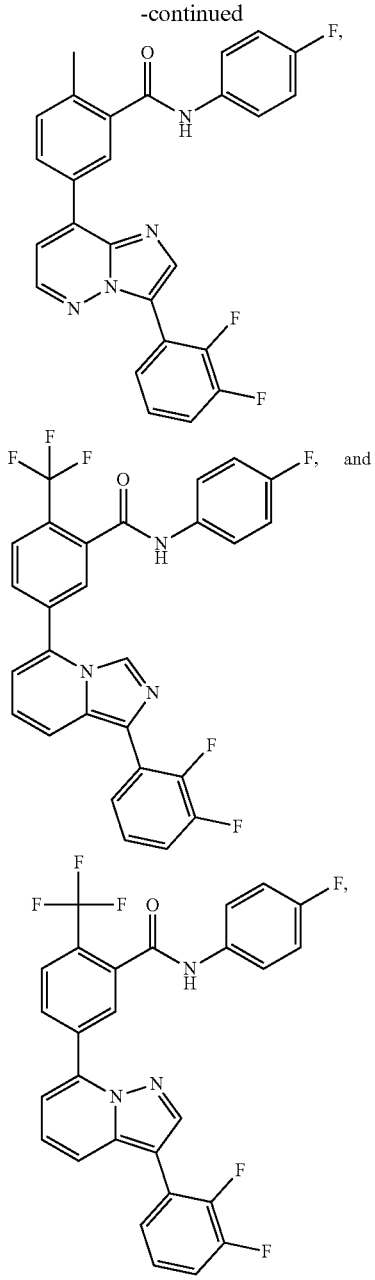

or a pharmaceutically acceptable salt or pharmaceutically acceptable tautomer thereof; and
(ii) a Toll-like receptor 8 (TLR8) agonist which is selected from the group consisting of:

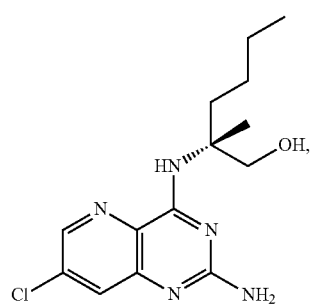

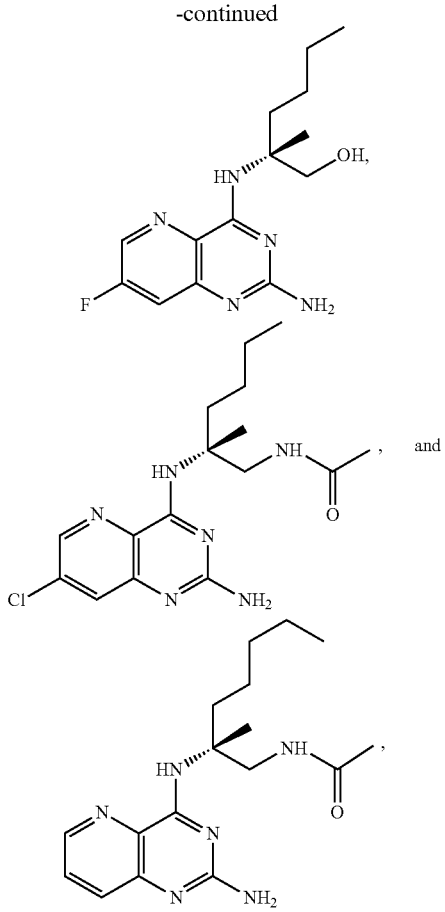

or a pharmaceutically acceptable salt thereof. In some embodiments, the kit further comprises a PD-1 inhibitor and/or a PD-L1 inhibitor. In some embodiments, the kit further comprises instructions for use in the treatment of an HBV infection in a human.

In certain embodiments, the additional therapeutic is selected from the group consisting of HBV combination drugs, HBV DNA polymerase inhibitors, toll-like receptor 7 modulators, toll-like receptor 8 modulators, Toll-like receptor 7 and 8 modulators, Toll-like receptor 3 modulators, interferon alpha receptor ligands, HBsAg inhibitors, compounds targeting HbcAg, cyclophilin inhibitors, HBV therapeutic vaccines, HBV prophylactic vaccines, HBV viral entry inhibitors, NTCP inhibitors, antisense oligonucleotide targeting viral mRNA, short interfering RNAs (siRNA), hepatitis B virus E antigen inhibitors, HBx inhibitors, cccDNA inhibitors, HBV antibodies including HBV antibodies targeting the surface antigens of the hepatitis B virus, thymosin agonists, cytokines, nucleoprotein inhibitors (HBV core or capsid protein inhibitors), stimulators of retinoic acid-inducible gene 1, stimulators of NOD2, stimulators of NOD1, recombinant thymosin alpha-1, BTK inhibitors, and hepatitis B virus replication inhibitors, and combinations thereof.

In certain embodiments a compound disclosed herein is formulated as a tablet, which may optionally contain one or more other compounds useful for treating HBV. In certain embodiments, the tablet can contain another active ingredient for treating HBV, such as HBV DNA polymerase inhibitors, immunomodulators, toll-like receptor modulators (modulators of tlr1, tlr2, tlr3, tlr4, tlr5, tlr6, tlr7, tlr8, tlr9, tlr10, tlr11, tlr12 and tlr13), modulators of tlr7, modulators of tlr8, modulators of tlr7 and tlr8, interferon alpha receptor ligands, hyaluronidase inhibitors, hepatitis B surface antigen (HBsAg) inhibitors, compounds targeting hepatitis B core antigen (HbcAg), cyclophilin inhibitors, HBV viral entry inhibitors, NTCP (Na+-taurocholate cotransporting polypeptide) inhibitors, endonuclease modulators, inhibitors of ribonucleotide reductase, hepatitis B virus E antigen inhibitors, Src kinase inhibitors, HBx inhibitors, cccDNA inhibitors, CCR2 chemokine antagonists, thymosin agonists, nucleoprotein inhibitors (HBV core or capsid protein inhibitors), stimulators of retinoic acid-inducible gene 1, stimulators of NOD2, stimulators of NOD1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, BTK inhibitors, modulators of TIGIT, modulators of CD47, modulators of SIRP alpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, and Hepatitis B virus replication inhibitors, and combinations thereof.

In some embodiments, a method of treating HBV in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with an immunotherapeutic agent, such as an immune checkpoint inhibitor, an hematopoietic progenitor kinase 1 (HPK1) inhibitor, an immune checkpoint stimulatory protein agonist, or an engineered immune cell (for example a T cell with an chimeric antigen receptor (i.e., a CAR T cell) or a T cell with an engineered T cell receptor (TCR). In some embodiments, the compound is administered to the subject prior to, subsequent to, or simultaneous to administration of one or more immunotherapeutic agents. In some embodiments, the compound is administered to the subject about 30 minutes or more, about 1 hour or more, about 2 hours or more, about 4 hours or more, about 6 hours or more, about 12 hours or more, about 24 hours or more, about 48 hours or more, or about 72 hour or more prior to or subsequent to administration of the one or more immunotherapeutic agents. In some embodiments, the compound is administered to the subject about 30 minutes or less, about 1 hour or less, about 2 hours or less, about 4 hours or less, about 6 hours or less, about 12 hours or less, about 24 hours or less, about 48 hours or less, or about 72 hour or less prior to or subsequent to administration of the one or more immunotherapeutic agents.

In some embodiments, a method of treating HBV in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with a therapeutically effective amount of one or more immune checkpoint inhibitors. In some embodiments, the compound is administered to the subject prior to, subsequent to, or simultaneous to administration of the immune checkpoint inhibitor. In some embodiments, the immune checkpoint inhibitor is a small-molecule inhibitor. In some embodiments, the immune checkpoint inhibitor is an antibody or a fragment thereof. In some embodiments, the immune checkpoint inhibitor inhibits the Adenosine $A_2A$ Receptor (A2aR), B7-H3, V-Set Domain-Containing T-cell Activation Inhibitor 1 (VTCN1, also known as B7-H4), the B- and T-Lymphocyte Attenuator (BTLA), cytotoxic T-Lypmphocyte-Associated protein 4 (CTLA-4), Killer-cell Immunoglobulin-like Receptor (KIR), Lymphocyte Activation Gene 3 (LAG3), Programmed Death 1 (PD-1), Programmed Death Ligand 1 (PD-L1), Programmed Death Ligand 2 (PD-L2), T-cell Immunoreceptor with Ig and ITIM Domains (TIGIT), T-cell Immunoglobulin and Mucin-Domain Containing 3 (TIM-3), or V-Domain Ig Suppresor of T-cell Activation (VISTA). Exemplary immune checkpoint inhibitors include, but are not limited to, avelumab, atezolizumab, durvalumab, nivolumab, pembrolizumab, ipilimumab, PDR001, TSR-042, and BMS-986016.

In some embodiments, a method of treating HBV in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with a therapeutically effective amount of one or more immune checkpoint stimulatory protein agonists. In some embodiments, the compound is administered to the subject prior to, subsequent to, or simultaneous to administration of the immune checkpoint stimulatory protein agonist. In some embodiments, the immune checkpoint stimulatory protein agonist is an antibody or a fragment thereof. In some embodiments, the immune checkpoint stimulatory protein agonist is an agonist of CD27, CD28, CD40, CD122, 4-1BB, OX40, Gluocorticoid-Induced TNFR family related protein (GITR), or Inducible T-Cell Costimulator (ICOS).

In some embodiments, a method of treating HBV in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with a therapeutically effective amount of engineered immune cells, such as CAR T cells or T cells with an engineered TCR. In some embodiments, the compound is administered to the subject prior to, subsequent to, or simultaneous to administration of the engineered immune cells. In some embodiments, the engineered immune cells are heterologous engineered immune cells, such as heterologous engineered T cells (e.g., CAR T cells or T cells with an engineered TCR). In some embodiments, the engineered immune cells are autologous engineered immune cells, such as autologous engineered T cells (e.g., CAR T cells or T cells with an engineered TCR). In some embodiments, the engineered immune cells (e.g., engineered T cells) target an HBV antigen, such as a hepatitis B surface antigen (HBsAg) or hepatitis B core antigen (HBcAg).

In some embodiments, a method of treating HBV in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with (1) a therapeutically effective amount of engineered immune cells, such as CAR T cells or T cells with an engineered TCR, and (2) a therapeutically effective amount of an immune checkpoint inhibitor or an immune checkpoint stimulatory protein agonist. In some embodiments, a method of treating HBV in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with (1) a therapeutically effective amount of engineered immune cells, such as CAR T cells or T cells with an engineered TCR, and (2) a therapeutically effective amount of an antiviral agent (such as an anti-HBV agent). In some embodiments, a method of treating HBV in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with (1) a therapeutically effective amount of an immune checkpoint inhibitor or an immune checkpoint stimulatory protein agonist, and (2) a therapeutically effective amount of an antiviral agent (such as an anti-HBV agent). In some embodiments, a method of treating HBV in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with (1) a therapeutically effective amount of engineered immune cells, such as CAR T cells or T cells with an engineered TCR, (2) a therapeutically effective amount of an immune checkpoint inhibitor or an immune checkpoint stimulatory protein agonist, and (3) a therapeutically effective amount of an antiviral agent (such as an anti-HBV agent).

In certain embodiments, such tablets are suitable for once daily dosing.

In certain embodiments, the additional therapeutic agent is selected from one or more of:
(1) Combination drugs selected from the group consisting of tenofovir disoproxil fumarate+emtricitabine (TRU-VADA®); adefovir+clevudine, ABX-203+lamivudine+PEG-IFNalpha, ABX-203+adefovir+PEG-IFNalpha and GBV-015;
(2) HBV DNA polymerase inhibitors selected from the group consisting of besifovir, entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, telbivudine (Tyzeka®), pradefovir, Clevudine, emtricitabine (Emtriva®), ribavirin, lamivudine (Epivir-HBV®), phosphazide, famciclovir, SNC-019754, FMCA, fusolin, AGX-1009 and metacavir;
(3) Immunomodulators selected from the group consisting of rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), WF-10, ribavirin, IE-12, polymer polyethyleneimine (PEI), Gepon, VGV-1, MOR-22, BMS-936559 and IR-103;
(4) Toll-like receptor 7 modulators selected from the group consisting of GS-9620, GSK-2245035, imiquimod, resiquimod, DSR-6434, DSP-3025, IMO-4200, MCT-465, 3M-051, SB-9922, 3M-052, Limtop, TMX-30X, TMX-202 RG-7863 and RG-7795;
(5) Toll-like receptor 8 modulators selected from the group consisting of motolimod, resiquimod, 3M-051, 3M-052, MCT-465, IMO-4200, VTX-763, VTX-1463;
(6) Toll-like receptor 3 modulators selected from the group consisting of rintatolimod, poly-ICLC, MCT-465, MCT-475, Riboxxon, Riboxxim and ND-1.1;
(7) Interferon alpha receptor ligands selected from the group consisting of interferon alpha-21) (Intron A®), pegylated interferon alpha-2a (Pegasys®), interferon alpha 1b (Hapgen®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-Intron®), Bioferon, Novaferon, Inmutag (Inferon), Multiferon®, interferon alfa-n1 (Humoferon®), interferon beta-1a (Avonex®), Shaferon, interferon alfa-2b (AXXO), Alfaferone, interferon alfa-2b (BioGeneric Pharma), interferon-alpha 2 (CJ), Laferonum, VIPEG, BLAUFERON-B, BLAUFERON-A, Intermax Alpha, Realdiron, Lanstion, Pegaferon, PDferon-B PDferon-B, interferon alfa-2b (IFN, Laboratories Bioprofarma), alfainterferona 2b, Kalferon, Pegnano, Feronsure, Pegi-Hep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b and Interapo (Interapa);
(8) Hyaluronidase inhibitors selected from the group consisting of astodrimer;
(9) Modulators of IE-10;
(10) HBsAg inhibitors selected from the group consisting of HBF-0259, PBHBV-001, PBHBV-2-15, PBHBV-2-1, REP 9AC, REP-9C and REP 9AC';
(11) Toll like receptor 9 modulators selected from CYT003;
(12) Cyclophilin inhibitors selected from the group consisting of OCB-030, SCY-635 and NVP-018;
(13) HBV Prophylactic vaccines selected from the group consisting of Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, Engerix B®, recombinant hepatitis B vaccine (intramuscular, Kangtai Biological Products), recombinant hepatitis B vaccine (Hansenual *polymorpha* yeast, intramuscular, Hualan Biological Engineering), Bimmugen, Euforavac, Eutravac, anrix-DTaP-IPV-Hep B, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan6, rhHBsAG vaccine, and DTaP-rHB-Hib vaccine;
(14) HBV Therapeutic vaccines selected from the group consisting of HB sAG-HBIG complex, Bio-Hep-B, NAS-VAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, TG-1050, NU-500, HBVax, im/TriGrid/antigen vaccine, Mega-CD40L-adjuvanted vaccine, HepB-v, NO-1800, recombinant VLP-based therapeutic vaccine (HBV infection, VLP Biotech), AdTG-17909, AdTG-17910 AdTG-18202, ChronVac-B, and Em HBV;
(15) HBV viral entry inhibitor selected from the group consisting of Myrcludex B;
(16) Antisense oligonucleotide targeting viral mRNA selected from the group consisting of ISIS-HBVRx;
(17) Short interfering RNAs (siRNA) selected from the group consisting of TKM-HBV (TKM-HepB), ALN-HBV, SR-008, ddRNAi and ARC-520;
(18) Endonuclease modulators selected from the group consisting of PGN-514;
(19) Inhibitors of ribonucleotide reductase selected from the group consisting of Trimidox;
(20) Hepatitis B virus E antigen inhibitors selected from the group consisting of wogonin;
(21) HBV antibodies targeting the surface antigens of the hepatitis B virus selected from the group consisting of GC-1102, XTL-17, XTL-19, XTL-001, KN-003 and fully human monoclonal antibody therapy (hepatitis B virus infection, Humabs BioMed);
(22) HBV antibodies including monoclonal antibodies and polyclonal antibodies selected from the group consisting of Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products) and Fovepta (BT-088);
(23) CCR2 chemokine antagonists selected from the group consisting of propagermanium;
(24) Thymosin agonists selected from the group consisting of Thymalfasin;
(25) Cytokines selected from the group consisting of recombinant IL-7, CYT-107, interleukin-2 (IL-2, Immunex); recombinant human interleukin-2 (Shenzhen Neptunus) and celmoleukin;
(26) Nucleoprotein inhibitors (HBV core or capsid protein inhibitors) selected from the group consisting of NVR-1221, NVR-3778, BAY 41-4109, morphothiadine mesilate and DVR-23;
(27) Stimulators of retinoic acid-inducible gene 1 selected from the group consisting of SB-9200, SB-40, SB-44, ORI-7246, ORI-9350, ORI-7537, ORI-9020, ORI-9198 and ORI-7170;
(28) Stimulators of NOD2 selected from the group consisting of SB-9200;
(29) Recombinant thymosin alpha-1 selected from the group consisting of NL-004 and PEGylated thymosin alpha 1;
(30) Hepatitis B virus replication inhibitors selected from the group consisting of isothiafludine, IQP-HBV, RM-5038 and Xingantie;
(31) PI3K inhibitors selected from the group consisting of idelalisib, AZD-8186, buparlisib, CLR-457, pictilisib, neratinib, rigosertib, rigosertib sodium, EN-3342, TGR-1202, alpelisib, duvelisib, UCB-5857, taselisib, XL-765, gedatolisib, VS-5584, copanlisib, CAI orotate, perifosine, RG-7666, GSK-2636771, DS-7423, panulisib, GSK-2269557, GSK-2126458, CUDC-907, PQR-309, INCB-040093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301 and CLR-1401;
(32) cccDNA inhibitors selected from the group consisting of BSBI-25;
(33) PD-L1 inhibitors selected from the group consisting of MEDI-0680, RG-7446, durvalumab, KY-1003, KD-033, MSB-0010718C, TSR-042, ALN-PDL, STI-A1014 and BMS-936559;
(34) PD-1 inhibitors selected from the group consisting of nivolumab, pembrolizumab, pidilizumab, BGB-108 and mDX-400;
(35) BTK inhibitors selected from the group consisting of ACP-196, dasatinib, ibrutinib, PRN-1008, SNS-062, ONO-4059, BGB-3111, MSC-2364447, X-022, spebrutinib, TP-4207, HM-71224, KBP-7536 and AC-0025;
(36) Other drugs for treating HBV selected from the group consisting of gentiopicrin (gentiopicroside), nitazoxanide, birinapant, NOV-205 (Molixan; BAM-205), Oligotide, Mivotilate, Feron, levamisole, Ka Shu Ning, Alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbama, IBPB-006IA, Hepuyinfen, DasKloster 0014-01, Jiangantai (Ganxikang), picroside, GA5 NM-HBV, DasKloster-0039, hepulantai, IMB-2613, TCM-800B, reduced glutathione and ZH-2N; and
(37) The compounds disclosed in US20100143301 (Gilead Sciences), US20110098248 (Gilead Sciences), US20090047249 (Gilead Sciences), U.S. Pat. No. 8,722,054 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (VentirxPharma), US20140275167 (Novira therapeutics), US20130251673 (Novira therapeutics), U.S. Pat. No. 8,513,184 (Gilead Sciences), US20140030221 (Gilead Sciences), US20130344030 (Gilead Sciences), US20130344029 (Gilead Sciences), US20140343032 (Roche), WO2014037480 (Roche), US20130267517 (Roche), WO2014131847 (Janssen), WO2014033176 (Janssen), WO2014033170 (Janssen), WO2014033167 (Janssen), US20140330015 (Ono pharmaceutical), US20130079327 (Ono pharmaceutical), and US20130217880 (Ono pharmaceutical).

In certain embodiments, a compound disclosed herein, or a pharmaceutically acceptable salt thereof, is combined with one, two, three, four or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In a specific embodiment, a compound disclosed herein, or a pharmaceutically acceptable salt thereof, is combined with an HBV DNA polymerase inhibitor. In another specific embodiment, a compound disclosed herein, or a pharmaceutically acceptable salt thereof, is combined with an HBV DNA polymerase inhibitor and at least one additional therapeutic agent selected from the group consisting of: immunomodulators, toll-like receptor modulators (modulators of tlr1, tlr2, tlr3, tlr4, tlr5, tlr6, tlr7, tlr8, tlr9, tlr10, tlr11, tlr12 and tlr13), interferon alpha receptor ligands, hyaluronidase inhibitors, recombinant IL-7, HBsAg inhibitors, compounds targeting HbcAg, cyclophilin inhibitors, HBV therapeutic vaccines, HBV prophylactic vaccines HBV viral entry inhibitors, NTCP inhibitors, antisense oligonucleotide targeting viral mRNA, short interfering RNAs (siRNA), miRNA gene therapy agents, endonuclease modulators, inhibitors of ribonucleotide reductase, Hepatitis B virus E antigen inhibitors, recombinant scavenger receptor A (SRA) proteins, src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), CCR2 chemokine antagonists, thymosin agonists, cytokines, nucleoprotein inhibitors (HBV core or capsid protein inhibitors), stimulators of retinoic acid-inducible gene 1, stimulators of NOD2, stimulators of NOD1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), and Hepatitis B virus replication inhibitors.

In another specific embodiment, a compound disclosed herein, or a pharmaceutically acceptable salt thereof, is combined with an HBV DNA polymerase inhibitor and at least a second additional therapeutic agent selected from the group consisting of: immunomodulators, toll-like receptor modulators (modulators of tlr1, tlr2, tlr3, tlr4, tlr5, tlr6, tlr7, tlr8, tlr9, tlr10, tlr11, tlr12 and tlr13), HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), cyclophilin inhibitors, stimulators of retinoic acid-inducible gene 1, PD-1 inhibitors, PD-L1 inhibitors, Arginase-1 inhibitors, PI3K inhibitors and stimulators of NOD2.

In another specific embodiment, a compound disclosed herein, or a pharmaceutically acceptable salt thereof, is combined with an HBV DNA polymerase inhibitor and at least a second additional therapeutic agent selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In another specific embodiment, a compound disclosed herein, or a pharmaceutically acceptable salt thereof, is combined with an HBV DNA polymerase inhibitor, one or two additional therapeutic agents selected from the group consisting of: immunomodulators, toll-like receptor modulators (modulators of tlr1, tlr2, tlr3, tlr4, tlr5, tlr6, tlr7, tlr8, tlr9, tlr10, tlr11, tlr12 and tlr13), HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), cyclophilin inhibitors, stimulators of retinoic acid-inducible gene 1, PD-1 inhibitors, PD-L1 inhibitors, Arginase-1 inhibitors, PI3K inhibitors and stimulators of NOD2, and one or two additional therapeutic agents selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In a particular embodiment, a compound disclosed herein, or a pharmaceutically acceptable salt thereof, is combined with one, two, three, four or more additional therapeutic agents selected from adefovir (Hepsera®), tenofovir disoproxil fumarate+emtricitabine (TRUVADA®), tenofovir disoproxil fumarate (Viread®), entecavir (Baraclude®), lamivudine (Epivir-HBV®), tenofovir alafenamide, tenofovir, tenofovir disoproxil, tenofovir alafenamide fumarate, tenofovir alafenamide hemifumarate, telbivudine (Tyzeka®), Clevudine®, emtricitabine (Emtriva®), peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1 (Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (AXXO), Alfaferone, interferon alfa-2b (BioGeneric Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon and celmoleukin;

In a particular embodiment, a compound disclosed herein, or a pharmaceutically acceptable salt thereof, is combined with entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®).

In a particular embodiment, a compound disclosed herein, or a pharmaceutically acceptable salt thereof, is combined with entecavir (Baraclude®), adefovir (Hepsera®), tenofovir disoproxil fumarate (Viread®), tenofovir alafenamide hemifumarate, telbivudine (Tyzeka®) or lamivudine (Epivir-HBV®).

In a particular embodiment, a compound disclosed herein, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least a second additional therapeutic agent selected from the group consisting of immunomodulators, toll-like receptor modulators (modulators of tlr1, tlr2, tlr3, tlr4, tlr5, tlr6, tlr7, tlr8, tlr9, tlr10, tlr11, tlr12 and tlr13), interferon alpha receptor ligands, hyaluronidase inhibitors, recombinant IL-7, HBsAg inhibitors, compounds targeting HbcAg, cyclophilin inhibitors, HBV Therapeutic vaccines, HBV prophylactic vaccines, HBV viral entry inhibitors, NTCP inhibitors, antisense oligonucleotide targeting viral mRNA, short interfering RNAs (siRNA), miRNA gene therapy agents, endonuclease modulators, inhibitors of ribonucleotide reductase, Hepatitis B virus E antigen inhibitors, recombinant scavenger receptor A (SRA) proteins, src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), CCR2 chemokine antagonists, thymosin agonists, cytokines, nucleoprotein inhibitors (HBV core or capsid protein inhibitors), stimulators of retinoic acid-inducible gene 1, stimulators of NOD2, stimulators of NOD1, recombinant thymosin alpha-1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambd, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), a and Hepatitis B virus replication inhibitors.

In a particular embodiment, a compound disclosed herein, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least a second additional therapeutic agent selected from the group consisting of peginterferon alfa-2b (PEG-Intron®), Multiferon®, interferon alpha Ib (Hapgen®), interferon alpha-2b (Intron A®), pegylated interferon alpha-2a (Pegasys®), interferon alfa-n1 (Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (AXXO), Alfaferone, interferon alfa-2b (BioGeneric Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratories Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon and celmoleukin;

In a particular embodiment, a compound disclosed herein, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least a second additional therapeutic agent selected from the group consisting of immunomodulators, toll-like receptor modulators (modulators of tlr1, tlr2, tlr3, tlr4, tlr5, tlr6, tlr7, tlr8, tlr9, tlr10, tlr11, tlr12 and tlr13), HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), cyclophilin inhibitors, stimulators of retinoic acid-inducible gene 1, Arginase-1 inhibitors, PI3K inhibitors, PD-1 inhibitors, PD-L1 inhibitors and stimulators of NOD2.

In a particular embodiment, a compound disclosed herein, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least a second additional therapeutic agent selected from the group consisting of HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In a particular embodiment, a compound disclosed herein, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®), one or two additional therapeutic agents selected from the group consisting of: immunomodulators, toll-like receptor modulators (modulators of tlr1, tlr2, tlr3, tlr4, tlr5, tlr6, tlr7, tlr8, tlr9, tlr10, tlr11, tlr12 and tlr13), HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), cyclophilin inhibitors, stimulators of retinoic acid-inducible gene 1, PD-1 inhibitors, PD-L1 inhibitors, Arginase-1 inhibitors, PI3K inhibitors and stimulators of NOD2, and one or two additional therapeutic agents selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide.

In certain embodiments, a compound disclosed herein, or a pharmaceutically acceptable salt thereof, is combined with 25 mg tenofovir alafenamide fumarate, tenofovir alafenamide hemifumarate, or tenofovir alafenamide. A compound as disclosed herein (e.g., a compound of formula (I) and/or a compound of formula (II)) may be combined with the agents provided herein in any dosage amount of the compound (e.g., from 50 mg to 500 mg of compound) the same as if each combination of dosages were specifically and individually listed.

In certain embodiments, a compound disclosed herein, or a pharmaceutically acceptable salt thereof, is combined with 100-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil. In certain embodiments, a compound disclosed herein, or a pharmaceutically acceptable salt thereof, is combined with 250 mg tenofovir disoproxil fumarate, tenofovir disoproxil hemifumarate, or tenofovir disoproxil. In certain embodiments, a compound disclosed herein, or a pharmaceutically acceptable salt thereof, is combined with 150 mg tenofovir disoproxil fumarate, tenofovir disoproxil hemifumarate, or tenofovir disoproxil. A compound as disclosed herein (e.g., a compound of formula (I) and/or a compound of formula (II)) may be combined with the agents provided herein in any dosage amount of the compound (e.g., from 50 mg to 500 mg of compound) the same as if each combination of dosages were specifically and individually listed.

In certain embodiments, when a compound disclosed herein is combined with one or more additional therapeutic agents as described above, the components of the composition are administered as a simultaneous or sequential regimen. When administered sequentially, the combination may be administered in two or more administrations.

In certain embodiments, a compound disclosed herein is combined with one or more additional therapeutic agents in a unitary dosage form for simultaneous administration to a patient, for example as a solid dosage form for oral administration.

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and one or more additional therapeutic agents are both present in the body of the patient.

Co-administration includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

Anti-HIV Combination Therapy

In certain embodiments, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, or one to three, or one to four) additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, or one to three, or one to four) additional therapeutic agents.

In certain embodiments, the present disclosure provides a method for treating an HIV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HIV infection.

In one embodiment, pharmaceutical compositions comprising a compound disclosed herein, or a pharmaceutically acceptable salt thereof, in combination with one or more (e.g., one, two, three, four, one or two, or one to three, or one to four) additional therapeutic agents, and a pharmaceutically acceptable carrier, diluent or excipient are provided.

In one embodiment, kits comprising a compound disclosed herein, or a pharmaceutically acceptable salt thereof, in combination with one or more (e.g., one, two, three, four, one or two, or one to three, or one to four) additional therapeutic agents are provided.

In the above embodiments, the additional therapeutic agent may be an anti-HIV agent. For example, in some embodiments, the additional therapeutic agent is selected from the group consisting of HIV protease inhibitors, HIV non-nucleoside inhibitors of reverse transcriptase, HIV nucleoside or nucleotide inhibitors of reverse transcriptase, HIV integrase inhibitors, HIV non-catalytic site (or allosteric) integrase inhibitors, entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, compounds that target the HIV capsid ("capsid inhibitors"; e.g., capsid polymerization inhibitors or capsid disrupting compounds such as those disclosed in WO 2013/006738 (Gilead Sciences), US 2013/0165489 (University of Pennsylvania), and WO 2013/006792 (Pharma Resources), pharmacokinetic enhancers, and other drugs for treating HIV, and combinations thereof.

In further embodiments, the additional therapeutic agent is selected from one or more of:
(38) HIV protease inhibitors selected from the group consisting of amprenavir, atazanavir, fosamprenavir, indinavir, lopinavir, ritonavir, nelfmavir, saquinavir, tipranavir, brecanavir, darunavir, TMC-126, TMC-114, mozenavir (DMP-450), JE-2147 (AG 1776), U-756423, RO0334649, KNI-272, DPC-681, DPC-684, GW640385X, DG17, PPU-100, DG35, and AG 1859;
(39) HIV non-nucleoside or non-nucleotide inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, TMC-120, rilpivirene, BIUR 355 BS, VRX 840773, lersivirine (UK-453061), RDEA806, KM023 and MK-1439;
(40) HIV nucleoside or nucleotide inhibitors of reverse transcriptase selected from the group consisting of zidovudine, emtricitabine, didanosine, stavudine, zalcitabine, lamivudine, abacavir, abavavir sulfate, amdoxovir, elvucitabine, alovudine, MIV-210, ±-FTC, D-d4FC, emtricitabine, phosphazide, fozivudine tidoxil, apricitibine (AVX754), KP-1461, GS-9131 (Gilead Sciences) and fosalvudine tidoxil (formerly HDP 99.0003), tenofovir, tenofovir disoproxil fumarate, tenofovir alafenamide (Gilead Sciences), tenofovir alafenamide hemifumarate (Gilead Sciences), GS-9148 (Gilead Sciences), adefovir, adefovir dipivoxil, CMX-001 (Chimerix) or CMX-157 (Chimerix);
(41) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA Oil, elvitegravir, dolutegravir and GSK-744;
(42) HIV non-catalytic site, or allosteric, integrase inhibitors (NCINI) including, but not limited to, BI-224436, CX0516, CX05045, CXI4442, compounds disclosed in WO 2009/062285 (Boehringer Ingelheim), WO 2010/130034 (Boehringer Ingelheim), WO 2013/159064 (Gilead Sciences), WO 2012/145728 (Gilead Sciences), WO 2012/003497 (Gilead Sciences), WO 2012/003498 (Gilead Sciences) each of which is incorporated by references in its entirety herein;
(43) gp41 inhibitors selected from the group consisting of enfuvirtide, sifuvirtide, albuvirtide, FB006M, and TRI-1144;
(44) the CXCR4 inhibitor AMD-070;
(45) the entry inhibitor SP01A;
(46) the gp120 inhibitor BMS-488043;
(47) the G6PD and NADH-oxidase inhibitor immunitin;
(48) CCR5 inhibitors selected from the group consisting of aplaviroc, vicriviroc, maraviroc, cenicriviroc, PRO-140, INCB15050, PF-232798 (Pfizer), and CCR5mAb004;
(49) CD4 attachment inhibitors selected from the group consisting of ibalizumab (TMB-355) and BMS-068 (BMS-663068);
(50) pharmacokinetic enhancers selected from the group consisting of cobicistat and SPI-452; and
(51) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, AEG 889, and PA-1050040 (PA-040), and combinations thereof.

In certain embodiments, the additional therapeutic agent is a Toll-like receptor 8 modulator selected from the group consisting of motolimod, resiquimod, 3M-051, 3M-052, MCT-465, IMO-4200, VTX-763, VTX-1463 and those disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (VentirxPharma), US20140275167 (Novira therapeutics), US20130251673 (Noviratherapeutics), U.S. Pat. No. 9,670,205 (Gilead Sciences Inc.), US20160289229 (Gilead Sciences Inc.), U.S. patent application Ser. No. 15/692,161 (Gilead Sciences Inc.), and U.S. patent application Ser. No. 15/692,093 (Gilead Sciences Inc.).

In certain embodiments, the one or more additional therapeutic agents include a Toll-like receptor 8 (TLR8) modulator. In some embodiments, the Toll-like receptor 8 (TLR8) modulator is a Toll-like receptor 8 (TLR8) agonist. In some embodiments, the Toll-like receptor 8 (TLR8) agonist is a comopund disclosed in U.S. Pat. No. 9,670,205, or a pharmaceutically acceptable salt thereof.

In certain embodiments, a compound disclosed herein, or a pharmaceutically acceptable salt thereof, is combined with one, two, three, four or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The two, three, four or more additional therapeutic agents can be different therapeutic agents selected from the same class of therapeutic agents, or they can be selected from different classes of therapeutic agents. In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In a further embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In another embodiment, a compound disclosed herein, or a pharmaceutically acceptable salt thereof, is combined with two HIV nucleoside or nucleotide inhibitor of reverse transcriptase.

In a particular embodiment, a compound disclosed herein, or a pharmaceutically acceptable salt thereof, is combined with abacavir sulfate, tenofovir, tenofovir disoproxil fumarate, tenofovir alafenamide, or tenofovir alafenamide hemifumarate.

In a particular embodiment, a compound disclosed herein, or a pharmaceutically acceptable salt thereof, is combined with tenofovir, tenofovir disoproxil fumarate, tenofovir alafenamide, or tenofovir alafenamide hemifumarate.

In a particular embodiment, a compound disclosed herein, or a pharmaceutically acceptable salt thereof, is combined with a first additional therapeutic agent selected from the group consisting of: abacavir sulfate, tenofovir, tenofovir disoproxil fumarate, tenofovir alafenamide, and tenofovir alafenamide hemifumarate and a second additional therapeutic agent selected from the group consisting of emtricitibine and lamivudine. In a particular embodiment, a compound disclosed herein, or a pharmaceutically acceptable salt thereof, is combined with a first additional therapeutic agent selected from the group consisting of: tenofovir, tenofovir disoproxil fumarate, tenofovir alafenamide, and tenofovir alafenamide hemifumarate and a second additional therapeutic agent, wherein the second additional therapeutic agent is emtricitibine.

In some embodiments, a method of treating HIV in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with an immunotherapeutic agent, such as an immune checkpoint inhibitor, an hematopoietic progenitor kinase 1 (HPK1) inhibitor, an immune checkpoint stimulatory protein agonist, or an engineered immune cell (for example a T cell with an chimeric antigen receptor (i.e., a CAR T cell) or a T cell with an engineered T cell receptor (TCR). In some embodiments, the compound is administered to the subject prior to, subsequent to, or simultaneous to administration of one or more immunotherapeutic agents. In some embodiments, the compound is administered to the subject about 30 minutes or more, about 1 hour or more, about 2 hours or more, about 4 hours or more, about 6 hours or more, about 12 hours or more, about 24 hours or more, about 48 hours or more, or about 72 hour or more prior to or subsequent to administration of the one or more immunotherapeutic agents. In some embodiments, the compound is administered to the subject about 30 minutes or less, about 1 hour or less, about 2 hours or less, about 4 hours or less, about 6 hours or less, about 12 hours or less, about 24 hours or less, about 48 hours or less, or about 72 hour or less prior to or subsequent to administration of the one or more immunotherapeutic agents.

In some embodiments, a method of treating HIV in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with a therapeutically effective amount of one or more immune checkpoint inhibitors. In some embodiments, the compound is administered to the subject prior to, subsequent to, or simultaneous to administration of the immune checkpoint inhibitor. In some embodiments, the immune checkpoint inhibitor is a small-molecule inhibitor. In some embodiments, the immune checkpoint inhibitor is an antibody or a fragment thereof. In some embodiments, the immune checkpoint inhibitor inhibits the Adenosine $A_2A$ Receptor (A2aR), B7-H3, V-Set Domain-Containing T-cell Activation Inhibitor 1 (VTCN1, also known as B7-H4), the B- and T-Lymphocyte Attenuator (BTLA), cytotoxic T-Lypmphocyte-Associated protein 4 (CTLA-4), Killer-cell Immunoglobulin-like Receptor (KIR), Lymphocyte Activation Gene 3 (LAG3), Programmed Death 1 (PD-1), Programmed Death Ligand 1 (PD-L1), Programmed Death Ligand 2 (PD-L2), T-cell Immunoreceptor with Ig and ITIM Domains (TIGIT), T-cell Immunoglobulin and Mucin-Domain Containing 3 (TIM-3), or V-Domain Ig Suppresor of T-cell Activation (VISTA). Exemplary immune checkpoint inhibitors include, but are not limited to, avelumab, atezolizumab, durvalumab, nivolumab, pembrolizumab, ipilimumab, PDR001, TSR-042, and BMS-986016.

In some embodiments, a method of treating HIV in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with a therapeutically effective amount of one or more immune checkpoint stimulatory protein agonists. In some embodiments, the compound is administered to the subject prior to, subsequent to, or simultaneous to administration of the immune checkpoint stimulatory protein agonist. In some embodiments, the immune checkpoint stimulatory protein agonist is an antibody or a fragment thereof. In some embodiments, the immune checkpoint stimulatory protein agonist is an agonist of CD27, CD28, CD40, CD122, 4-1BB, OX40, Gluocorticoid-Induced TNFR family related protein (GITR), or Inducible T-Cell Costimulator (ICOS).

In some embodiments, a method of treating HIV in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with a therapeutically effective amount of engineered immune cells, such as CAR T cells or T cells with an engineered TCR. In some embodiments, the compound is administered to the subject prior to, subsequent to, or simultaneous to administration of the engineered immune cells. In some embodiments, the engineered immune cells are heterologous engineered immune cells, such as heterologous engineered T cells (e.g., CAR T cells or T cells with an engineered TCR). In some embodiments, the engineered immune cells are autologous engineered immune cells, such as autologous engineered T cells (e.g., CAR T cells or T cells with an engineered TCR).

In some embodiments, a method of treating HIV in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with (1) a therapeutically effective amount of engineered immune cells, such as CAR T cells or T cells with an engineered TCR, and (2) a therapeutically effective amount of an immune checkpoint inhibitor or an immune checkpoint stimulatory protein agonist. In some embodiments, a method of treating HIV in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with (1) a therapeutically effective amount of engineered immune cells, such as CAR T cells or T cells with an engineered TCR, and (2) a therapeutically effective amount of an antiviral agent (such as an anti-HIV agent). In some embodiments, a method of treating HIV in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with (1) a therapeutically effective amount of an immune checkpoint inhibitor or an immune checkpoint stimulatory protein agonist, and (2) a therapeutically effective amount of an antiviral agent (such as an anti-HIV agent). In some embodiments, a method of treating HIV in a subject comprises administering to the subject a therapeutically effective amount of any of the compounds described herein (e.g., a compound of Formula I, Ia, Ib, Ic, Id, Ie, If, Ig, Ih, Ii, or Ij, or a pharmaceutically acceptable salt or pharmaceutically acceptable tautomer thereof) in combination with (1) a therapeutically effective amount of engineered immune cells, such as CAR T cells or T cells with an engineered TCR, (2) a therapeutically effective amount of an immune checkpoint inhibitor or an immune checkpoint stimulatory protein agonist, and (3) a therapeutically effective amount of an antiviral agent (such as an anti-HIV agent).

In certain embodiments, when a compound disclosed herein is combined with one or more additional therapeutic agents as described above, the components of the composition are administered as a simultaneous or sequential regimen. When administered sequentially, the combination may be administered in two or more administrations.

In certain embodiments, a compound disclosed herein is combined with one or more additional therapeutic agents in a unitary dosage form for simultaneous administration to a patient, for example as a solid dosage form for oral administration.

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and one or more additional therapeutic agents are both present in the body of the patient.

Co-administration includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

Kits

Provided herein are also kits that include a compound of Formula I, Ia, Ib, Ic, Id, Ie, If, Ig, Ih, Ii, or Ij, or a pharmaceutically acceptable salt, pharmaceutically acceptable tautomer, stereoisomer, prodrug, or solvate thereof, and suitable packaging. In one embodiment, a kit further includes instructions for use. In one aspect, a kit includes a compound of Formula I, Ia, Ib, Ic, Id, Ie, If, Ig, Ih, Ii, or Ij, or a pharmaceutically acceptable salt, pharmaceutically acceptable tautomer, stereoisomer, prodrug, or solvate thereof, or a pharmaceutically acceptable salt, stereoisomer, prodrug, or solvate thereof, and a label and/or instructions for use of the compounds in the treatment of the indications, including the diseases or conditions, described herein.

Provided herein are also articles of manufacture that include a compound described herein or a pharmaceutically acceptable salt, pharmaceutically acceptable tautomer, stereoisomer, prodrug, or solvate, or a mixture thereof in a suitable container. The container may be a vial, jar, ampoule, preloaded syringe, and intravenous bag.

Pharmaceutical Compositions and Modes of Administration

Compounds provided herein are usually administered in the form of pharmaceutical compositions. Thus, provides herein are also pharmaceutical compositions that contain one or more of the compounds described herein or pharmaceutically acceptable salts, isomer, or a mixture thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or pharmaceutically acceptable salts, isomer, or a mixture thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or pharmaceutically acceptable salts, isomer, or a mixture thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or pharmaceutically acceptable salts, isomer, or a mixture thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula I, Ia, Ib, Ic, Id, Ie, If, Ig, Ih, Ii, or Ij, or a pharmaceutically acceptable salt or pharmaceutically acceptable tautomer thereof, may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human subject may be between 1 mg and 1,000 mg, between about 10-500 mg/day, between about 50-300 mg/day, between about 75-200 mg/day, or between about 100-150 mg/day.

In some embodiments, daily dosage (which may be an oral dosage) of a compound of Formula I, Ia, Ib, Ic, Id, Ie, If, Ig, Ih, Ii, or Ij, or a pharmaceutically acceptable salt or pharmaceutically acceptable tautomer thereof, is between about 40 mg/day and about 120 mg/day, between about 60 mg/day and about 100 mg/day, or about 80 mg/day.

The compounds of the present application or the compositions thereof may be administered once, twice, three, or four times daily, using any suitable mode described above.

Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 500 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Synthesis of the Compounds of Formula I

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

Each of the intermediates in the below schemes may be isolated and/or purified prior to the subsequent step, or used in the next step without purification and/or isolation. It will also be appreciated that the addition of any substituent may result in the production of a number of isomeric products any or all of which may be isolated and purified using conventional techniques.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, and the like). Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

EXAMPLES

The following examples are included to demonstrate specific embodiments of the disclosure. It should be appreciated by those of skill in the art that the techniques disclosed in the examples which follow represent techniques discovered by the inventor to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

| List of Abbreviations and Acronyms | |
|---|---|
| Abbreviation | Meaning |
| % | Percent |
| ° C. | Degree Celsius |
| A2B | Adenosine A2B receptor |
| Ac | Acetyl |
| ACN/CH$_3$CN/MeCN | Acetonitrile |
| ADME | Absorption, distribution, metabolism and excretion |
| APECED | Autoimmune polyendocrinopathy-candidiasis-ectodermal dystrophy |
| ASK | Apoptosis signal-regulating kinase |
| BAPN | Beta-aminoproprionitrile |
| BCNU | Carmustine |
| Bicarb | Bicarbonate |
| Bpin | Pinacolborane |
| br | Broad |
| BRD | Bromodomain containing protein inhibitor |
| BTK | Bruton's tyrosine kinase |
| CAS | Chemical Abstract Service |
| CD | Cluster of differentiation |
| CHOP | Cyclophosphamide |
| CNS | Central nervous system |
| COPD | Chronic obstructive pulmonary disease |
| CREST | Calcinosis, Raynaud's syndrome, esophageal dysmotility, sclerodactyly and telangiectasia |
| CRISPR | Clustered regularly interspaced short palindromic repeats |
| CVP | Cyclophosphamide, vincristine, prednisone |
| d | Doublet |
| D | Deuterium |
| D.T. PACE | Dexamethasone, thalidomide, cisplatin, Adriamycin ®, cyclophosphamide, etoposide |
| D/d | Deuterium |
| DABCO ® | 1,4-Diazabicyclo[2.2.2]octane |
| DCE | Dichloroethane |
| DCM/CH$_2$Cl$_2$ | Dichloromethane/methylene chloride |
| dd | Doublet of doublets |
| DDR | Discoidin domain receptor |
| DIPEA/DIEA | N,N-Diisopropylethylamine |
| DMF | Dimethylformamide |
| DMFO | Difluoromethylornithine |
| DMPK | Drug metabolism and pharmacokinetics |
| DMSO | Dimethylsulfoxide |
| DTIC | Dacarbazine |
| EC$_{50}$ | The half maximal effective concentration |
| equiv/eq | Equivalents |
| Et | Ethyl |
| EtOAc/AcOEt | Ethylacetate |
| EtOH | Ethanol |
| F | Fahrenheit |
| Fab | Fragment antigen-binding |
| FBS | Fetal bovine serum |
| FCM | Fludarabine, cyclophosphamide, mitoxantrone |
| FCR | Fludarabine, cyclophosphamide, rituximab |
| FOLFIRI | Fluorouracil, leucovorin, and irinotecan |
| FR | Fludarabine, rituximab |
| g | Grams |
| GITR | Glucocorticoid-induced TNFR-related protein |
| Gp | Glycoprotein |
| h/hr | Hours |

-continued

| List of Abbreviations and Acronyms | |
|---|---|
| Abbreviation | Meaning |
| HATU | (1-[Bis(dimethylamino)methylene]-1H-1,2,3-triazolo[4,5-b]pyridinium 3-oxid hexafluorophosphate) |
| HbcAg | Hepatitis B core antigen |
| HBsAg | Hepatitis B surface antigen |
| HBV | Hepatitis B virus |
| HBx | Hepatitis B viral protein |
| HDAC | Histone deacetylase |
| hex | Hexanes |
| HPLC | High pressure liquid chromatography |
| hyperCVAD | Hyperfractionated cyclophosphamide, vincristine, doxorubicin, dexamethasone, methotrexate, cytarabine |
| Hz | Hertz |
| ICE | Iphosphamide, carboplatin, etoposide |
| ICOS | Inducible T-cell COStimulator |
| IDH | Isocitrate dehydrogenase |
| IDO1 | Indoleamine 2,3-dioxygenase 1 |
| IL | Interleukin |
| INCB24360 | Epacadostat |
| IUPAC | International Union of Pure and Applied Chemistry |
| J | Coupling constant (MHz) |
| JAK | Janus kinase |
| Kg/kg | Kilogram |
| LACA | 1-Azetidine-2-carboxylic acid |
| LCMS/LC-MS | Liquid chromatography—mass spectrometry |
| LOX | Lysyl oxidase protein |
| LOXL | Lysyl oxidase-like protein |
| M | Molar |
| m | multiplet |
| M+ | Mass peak |
| M + H | Mass peak plus hydrogen |
| MCP | Mitoxantrone, chlorambucil, and prednisolone |
| Me | Methyl |
| mg | Milligram |
| MHz | Megahertz |
| min/m | Minute |
| miRNA | MicroRNA |
| ml/mL | Milliliter |
| mM | Millimolar |
| MMF | Ester derivative mycophenolate mofetil |
| mmol | Millimole |
| MMP | Matrix metalloprotease |
| mol | Mole |
| MS | Mass spectroscopy |
| MS | Multiple sclerosis |
| N | Normal |
| NADH | Nicotinamide adenine dinucleotide in reduced form |
| NCINI | Non-catalytic site, or allosteric, integrase inhibitors |
| ng | Nanograms |
| nM | NanoMolar |
| NMR | Nuclear magnetic resonance |
| NTCP | Na+-taurocholate cotransporting polypeptide |
| Palau'Clor ® | 2-Chloro-1,3-bis(methoxycarbonyl)guanidine or Baran CBMG Reagent |
| PD-L | Programmed death-ligand |
| PEG | Polyethylene glycol |
| PEI | Polymer polyethyleneimine |
| PET | Positron emission tomography |
| Ph | Phenyl |
| PI3K | Phosphoinositide 3-kinase |
| PKC | Protein kinase C |
| prep | Preparative |
| q.s. | Quantity sufficient to achieve a stated function |
| RA | Rheumatoid arthritis |
| R-CHOP | Rituximab-CHOP (Rituximab plus CHOP) |
| R-CVP | Rituximab-CVP (Rituximab plus CVP) |
| Rf | Retention factor |
| R-FCM | Rituximab plus FCM |
| R-hyperCVAD | Rituximab-hyperCVAD |
| R-ICE | Rituximab-ICE |
| R-MCP | Rituximab-MCP |

List of Abbreviations and Acronyms

| Abbreviation | Meaning |
| --- | --- |
| RPM | Revolutions per minute |
| rSIFN-co | Recombinant super compound interferon |
| RT/rt | Room temperature |
| s | Second |
| s | Singlet |
| SAHA | Vorinostat |
| sat. | Saturated |
| SERMs | Selective estrogen receptor modulators |
| siRNA | Short interfering RNAs |
| SIRP | Signal-regulatory protein |
| SLE | Systemic lupus erythematosus |
| SPECT | Single-photon emission computed tomography |
| SRA | Scavenger receptor A |
| Src | Proto-oncogene tyrosine-protein kinase |
| sshRNAs | Short synthetic hairpin RNAs |
| STING | Sequence To and withIN Graphics |
| SYK | Spleen tyrosine kinase |
| t | Triplet |
| TALENs | Transcription activator-like effector nucleases |
| TCA | Trichloroacetic acid |
| TEA | Triethylamine |
| temp. | Temperature |
| TFA | Trifluoroacetic acid |
| THF | Tetrahydrofuran |
| TIGIT | T cell immunoreceptor with Ig and ITIM domains |
| TIM | T-cell immunoglobulin and mucin domain |
| TKM-HBV | TKM-HepB |
| Tlr | Toll-like receptor modulators |
| TNF | Tumor necrosis factor |
| TPL2 | Serine/threonine kinase |
| Vac | Vacuum |
| w/v | Weight/volume |
| w/w | Weight/weight |
| YPEG-rhIFNalpha-2a | PEG-interferon alfa-2a |
| YPEG-rhIFNalpha-2b | Ypeginterferon alfa-2b |
| δ | Chemical shift (ppm) |
| μg | Microgram |
| μL/μl | Microliter |
| μM | Micromolar |
| μm | Micrometer |
| μmol | Micromole |

General Synthesis of Formula I

In some embodiments, compounds of the Formula (I) may be synthesized according to Scheme 1:

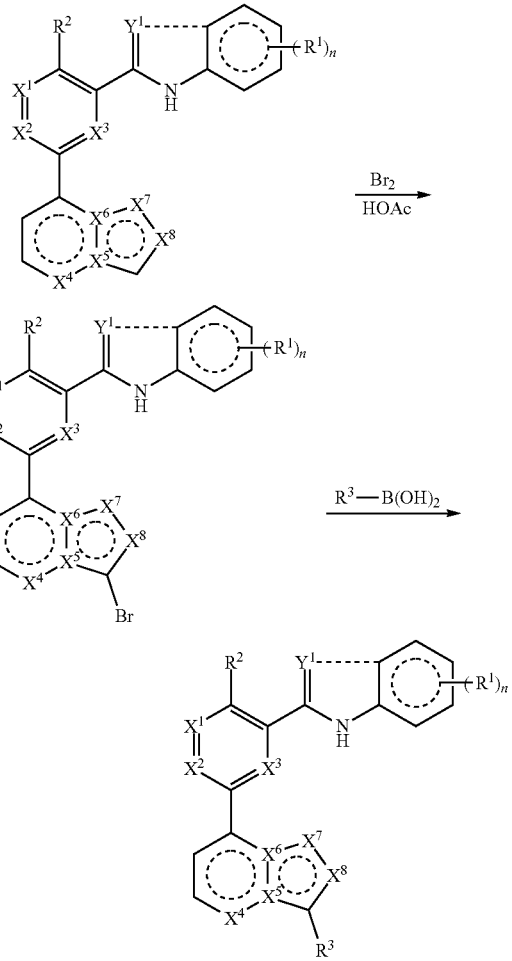

wherein n, $X^1$, $X^2$, $X^3$, $X^4$, $X^5$, $X^6$, $X^7$, $X^8$, $Y^1$, -----, $R^1$, $R^2$, and $R^3$ are as defined herein, and X is a halogen.

In some embodiments, compounds of the Formula (I) may be synthesized according to Scheme 2:

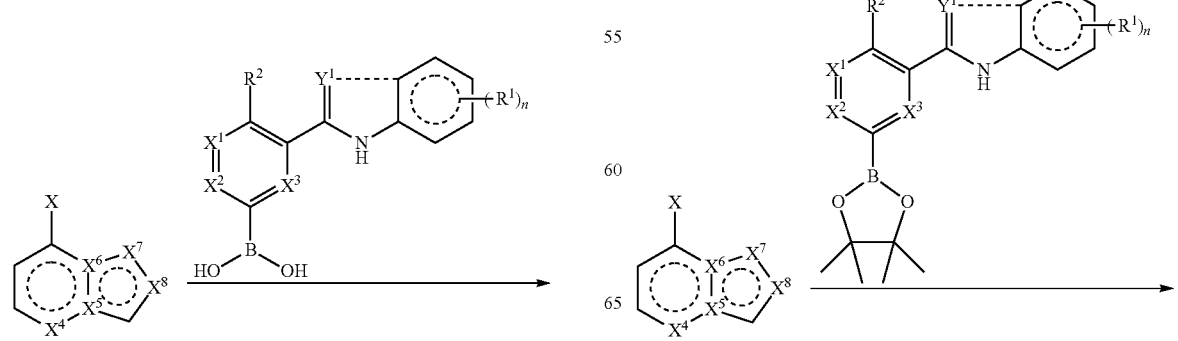

145

-continued

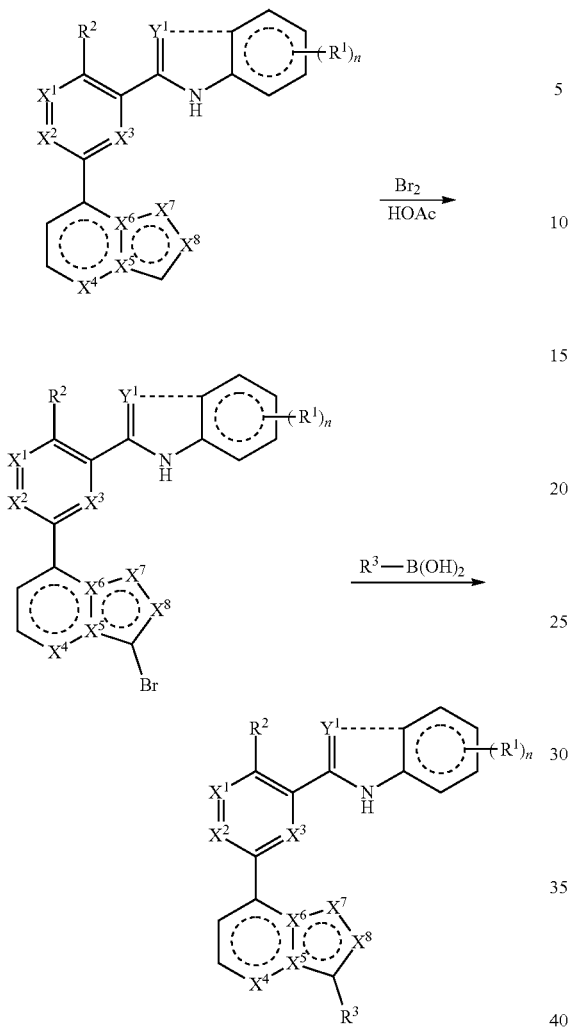

wherein n, $X^1$, $X^2$, $X^3$, $X^4$, $X^5$, $X^6$, $X^7$, $X^8$, $Y^1$, -----, $R^1$, $R^2$, and $R^3$ are as defined herein, and X is a halogen.

In some embodiments, compounds of the Formula (I) may be synthesized according to Scheme 3:

146

-continued

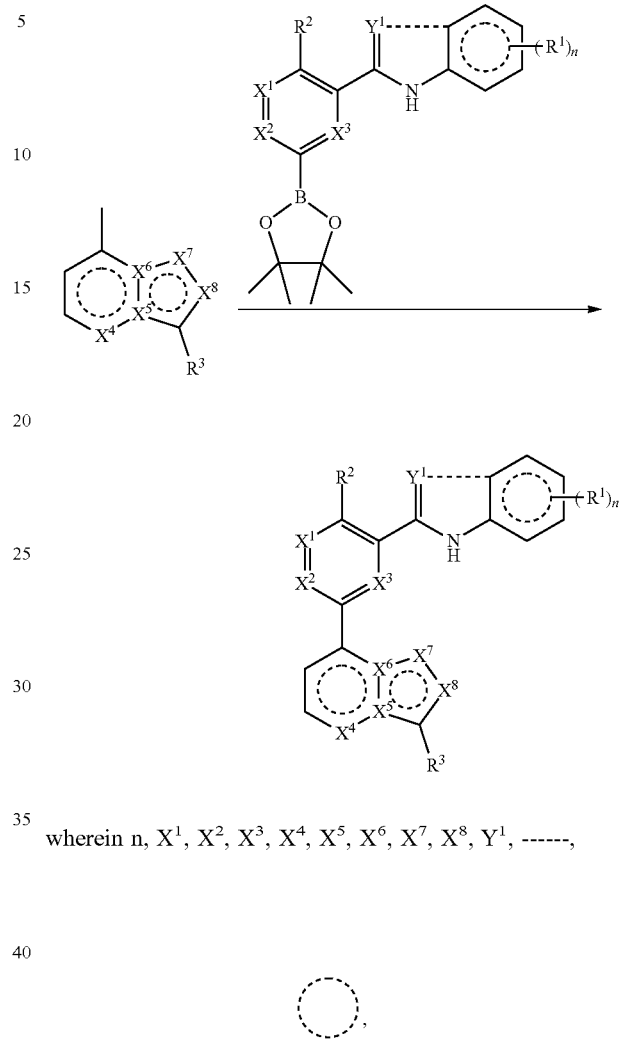

wherein n, $X^1$, $X^2$, $X^3$, $X^4$, $X^5$, $X^6$, $X^7$, $X^8$, $Y^1$, -----, $R^1$, $R^2$, and $R^3$ are as defined herein, and X is a halogen.

In some embodiments, compounds of the Formula (I) may be synthesized according to Scheme 4:

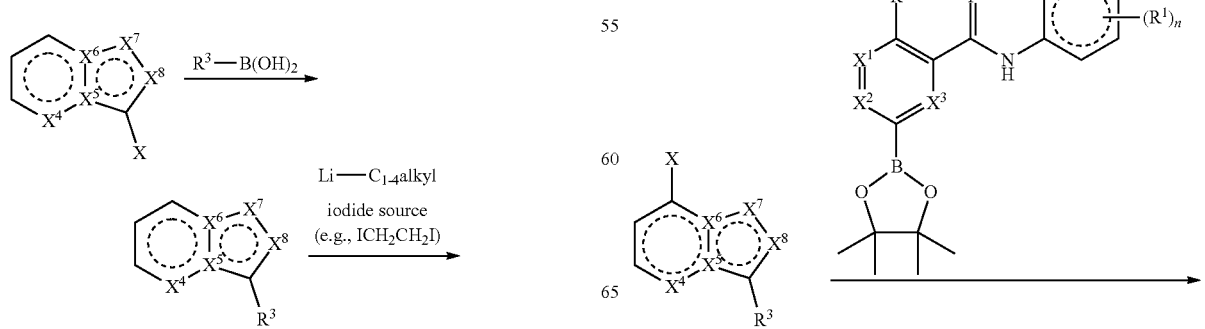

-continued

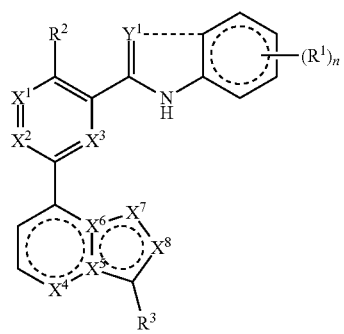

wherein n, $X^1$, $X^2$, $X^3$, $X^4$, $X^5$, $X^6$, $X^7$, $X^8$, $Y^1$, -----,

$R^1$, $R^2$, and $R^3$ are as defined herein, and X is a halogen.

In some embodiments, compounds of the Formula (I) may be synthesized according to Scheme 5:

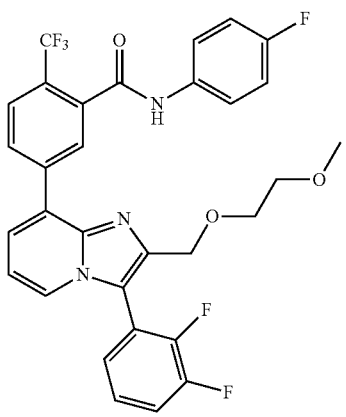

$X^6 = N$
$X^7 = CH$
$X^8 = N$ wherein n, $X^1$, $X^2$, $X^3$, $X^4$, $X^5$, $X^6$, $X^7$, $X^8$, $Y^1$, -----,

$R^1$, $R^2$, and $R^3$ are as defined herein.

Example 1: 5-(3-(2,3-difluorophenyl)-2-((2-methoxyethoxy)methyl)imidazo[1,2-a]pyridin-8-yl)-N-(4-fluorophenyl)-2-(trifluoromethyl)benzamide

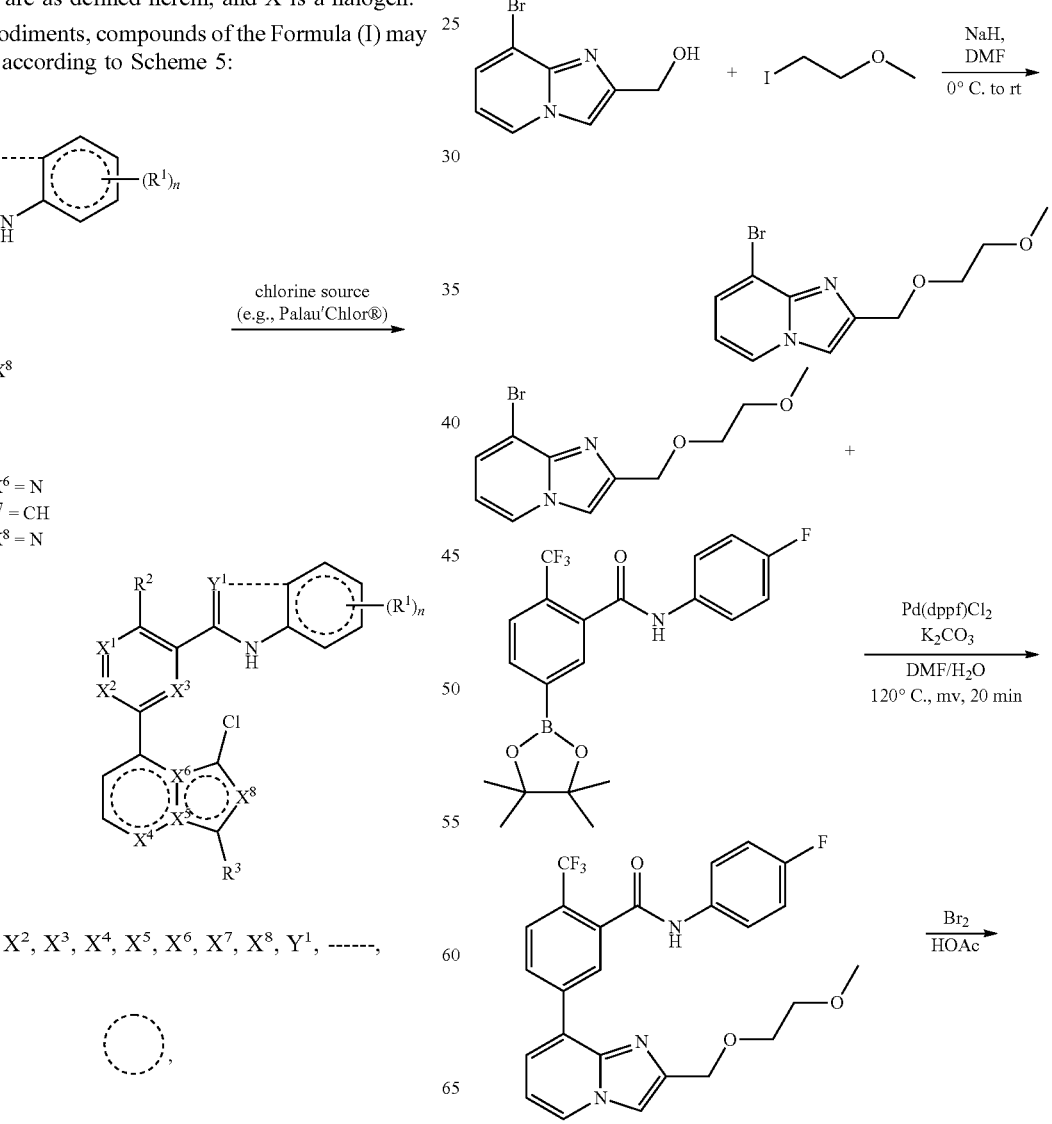

-continued

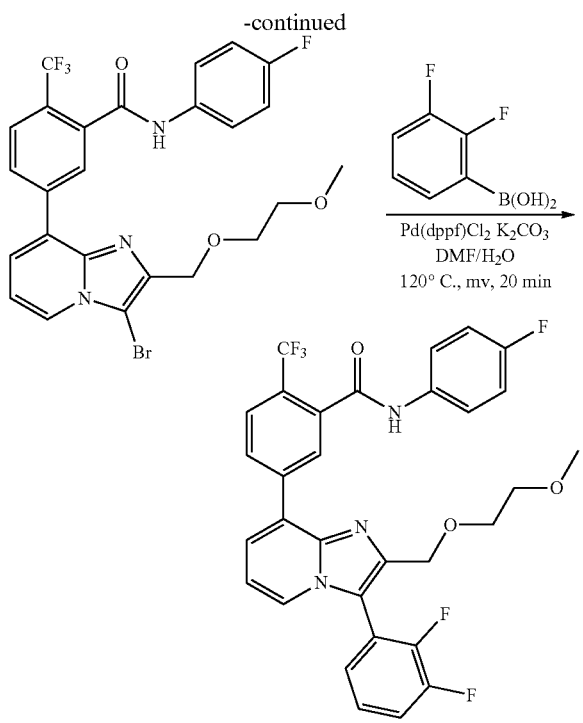

Example 1 was synthesized according to the scheme disclosed above. To a solution of (8-bromoimidazo[1,2-a]pyridin-2-yl)methanol (100 mg, 0.44 mmol) in dimethylformamide (3 mL) was added sodium hydride (60% 60% dispersion in mineral oil) (44 mg, 1.1 mmol) followed by 1-iodo-2-methoxyethane (164 mg, 0.88 mmol). The resulting reaction mixture was stirred at room temperature for 12 hrs, and quenched with water and extracted with dichloromethane. The combined organic extracts were concentrated down to dryness and purified by reversed phase HPLC to give the intermediate 8-bromo-2-((2-methoxyethoxy)methyl)imidazo[1,2-a]pyridine. 285 (M+H).

Example 1 was made analogously to Examples 28 and 11 using the intermediate (8-bromo-2-((2-methoxyethoxy)methyl)imidazo[1,2-a]pyridine). $C_{33}H_{23}F_6N_3O_3$. 600 (M+1). $^1$H NMR (400 MHz, Chloroform-d) δ 10.19 (s, 1H), 8.37 (s, 1H), 7.94-7.79 (m, 3H), 7.79-7.67 (m, 2H), 7.44-7.28 (m, 4H), 7.09-6.96 (m, 3H), 4.64 (s, 2H), 3.74-3.68 (m, 2H), 3.55-3.46 (m, 2H), 3.31 (s, 3H).

Example 2: N-(4-fluorophenyl)-5-(3-(5-fluoropyridin-3-yl)-2-(hydroxymethyl)imidazo[1,2-a]pyridin-8-yl)-2-methylnicotinamide

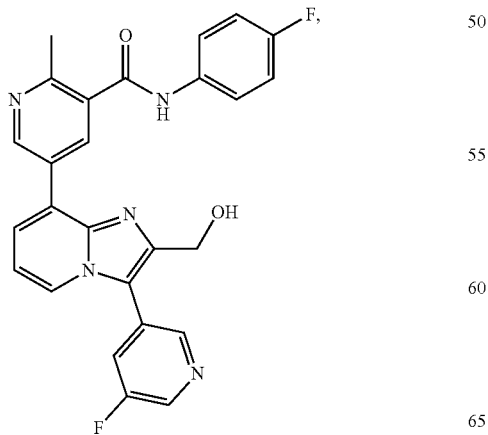

Example 2 was made analogously to Examples 11 and 14 using (5-fluoropyridin-3-yl)boronic acid in place of (2,3-difluorophenyl)boronic acid. $C_{26}H_{19}F_2N_5O_2$. 471 (M+1). $^1$H NMR (400 MHz, Chloroform-d) δ 10.29 (s, 1H), 8.92 (d, J=2.2 Hz, 1H), 8.83-8.74 (m, 2H), 8.60 (d, J=2.7 Hz, 1H), 8.41 (d, J=6.8 Hz, 1H), 8.33-8.31 (m, 1H), 7.97 (d, J=7.3 Hz, 1H), 7.71-7.68 (m, 2H), 7.60-7.55 (m, 1H), 7.11-7.03 (m, 2H), 4.87 (s, 2H), 2.91 (s, 3H).

Example 3: 2-(3-(2,3-difluorophenyl)imidazo[1,2-a]pyridin-8-yl)-N-(4-fluorophenyl)-5-(trifluoromethyl)isonicotinamide

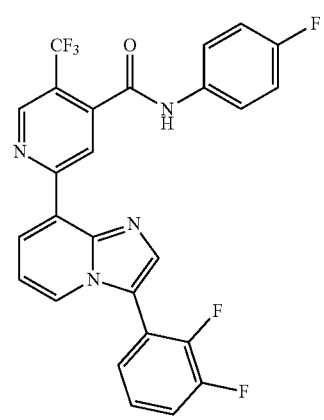

Example 3 was made analogously to Example 24 starting with 2-bromo-N-(4-fluorophenyl)-5-(trifluoromethyl)isonicotinamide in place 6-bromo-N-(4-fluorophenyl)-3-(trifluoromethyl)picolinamide. $C_{26}H_{14}F_6N_4O$. 513 (M+1). $^1$H NMR (400 MHz, Chloroform-d) δ 9.87 (s, 1H), 9.13 (s, 1H), 8.52 (s, 1H), 8.31 (d, J=7.2 Hz, 1H), 8.27-8.21 (m, 1H), 8.07 (s, 1H), 7.77-7.68 (m, 2H), 7.48-7.33 (m, 4H), 7.11-7.03 (m, 2H).

Example 4: N-(4-fluorophenyl)-5-(3-(6-methylpyridin-3-yl)imidazo[1,2-a]pyridin-8-yl)-2-(trifluoromethyl)benzamide

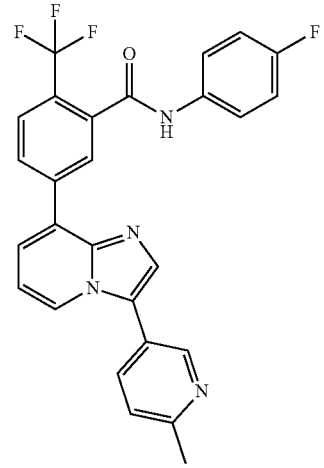 [SMILES: Cc1ccc(-c2cnc3c(-c4ccc(C(F)(F)F)c(C(=O)Nc5ccc(F)cc5)c4)cccn23)cn1]

Example 4 was made analogously to Example 27 using (6-methylpyridin-3-yl)boronic acid in place of (2,3-difluorophenyl)boronic acid. $C_{27}H_{18}F_4N_4O$. 491 (M+1). $_1$H NMR (400 MHz, DMSO-d6) δ 10.73 (s, 1H), 8.90 (d, J=2.2 Hz, 1H), 8.71 (d, J=6.9 Hz, 1H), 8.52-8.34 (m, 2H), 8.34-8.21 (m, 1H), 8.10 (s, 1H), 8.02 (d, J=8.4 Hz, 1H), 7.88 (d, J=7.1 Hz, 1H), 7.78-7.58 (m, 3H), 7.31-7.11 (m, 3H), 2.64 (s, 3H).

Example 5: N-(4-fluorophenyl)-2-methyl-5-(3-(2-methylpyridin-3-yl)-[1,2,4]triazolo[4,3-a]pyridin-8-yl)benzamide

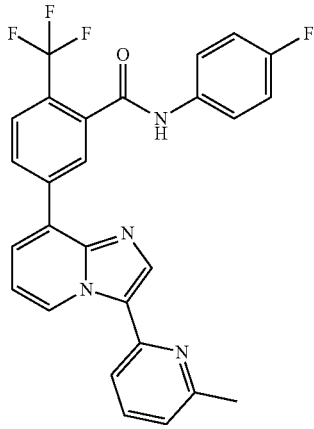 [SMILES: Cc1cccc(-c2cnc3c(-c4ccc(C(F)(F)F)c(C(=O)Nc5ccc(F)cc5)c4)cccn23)n1]

Example 5 was made analogously to Example 27 using (6-methylpyridin-2-yl)boronic acid in place of (2,3-difluorophenyl)boronic acid. $C_{27}H_{18}F_4N_4O$. 491 M(+1). $^1$H NMR (400 MHz, DMSO-d6) δ 10.72 (s, 1H), 10.14 (dd, J=7.0, 1.1 Hz, 1H), 8.56 (s, 1H), 8.46-8.32 (m, 2H), 8.01 (d, J=8.2 Hz, 1H), 7.97-7.61 (m, 6H), 7.36 (t, J=7.1 Hz, 1H), 7.27-7.13 (m, 3H), 2.61 (s, 3H).

Example 6: N-(4-fluorophenyl)-5-(3-(pyridin-4-yl)imidazo[1,2-a]pyridin-8-yl)-2-(trifluoromethyl)benzamide

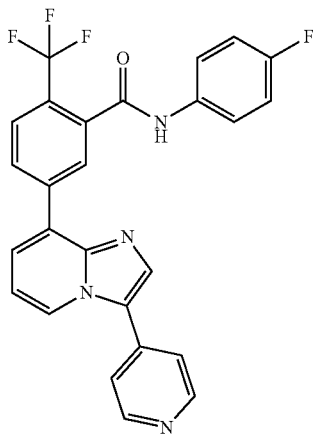 [SMILES: O=C(Nc1ccc(F)cc1)c1cc(-c2cccn3c(-c4ccncc4)cnc23)ccc1C(F)(F)F]

Example 6 was made analogously to Example 27 using pyridin-4-ylboronic acid in place of (2,3-difluorophenyl)boronic acid. $C_{26}H_{16}F_4N_4O$. 477 (M+1). $^1$H NMR (400 MHz, DMSO-d6) δ 10.73 (s, 1H), 9.00 (d, J=6.9 Hz, 1H), 8.89-8.82 (m, 2H), 8.51-8.37 (m, 3H), 8.20 (d, J=6.0 Hz, 2H), 8.01 (d, J=8.4 Hz, 1H), 7.98-7.92 (m, 1H), 7.76-7.66 (m, 2H), 7.34 (t, J=7.1 Hz, 1H), 7.24-7.14 (m, 2H).

Example 7: 5-(2-(aminomethyl)-3-(2,3-difluorophenyl)imidazo[1,2-a]pyridin-8-yl)-N-(4-fluorophenyl)-2-(trifluoromethyl)benzamide

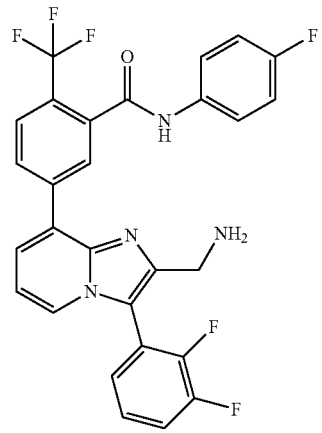

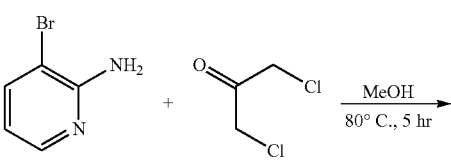

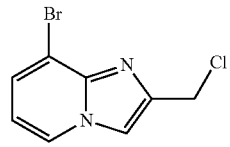

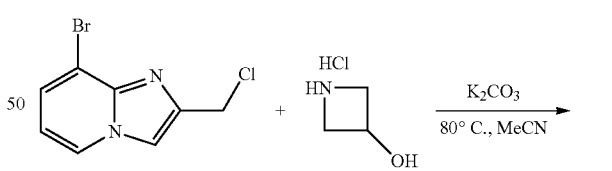

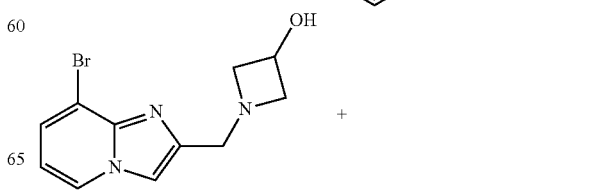

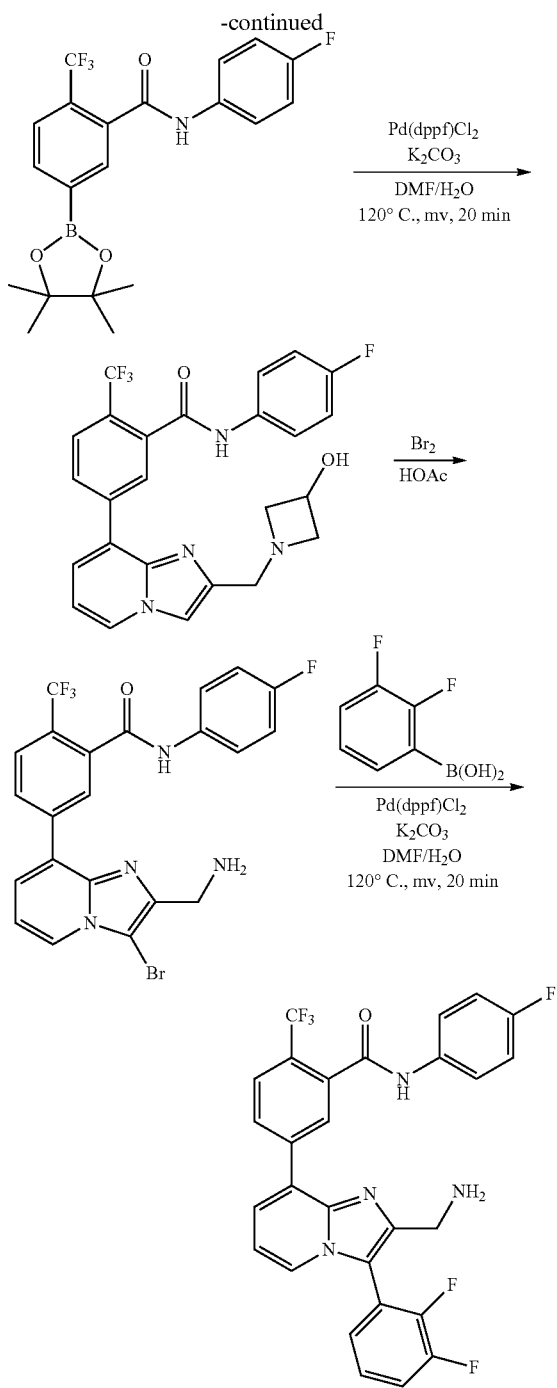

to dryness and purified by reversed phase HPLC to give 1-((8-bromoimidazo[1,2-a]pyridin-2-yl)methyl)azetidin-3-ol. 282 (M+H).

1-((8-bromoimidazo[1,2-a]pyridin-2-yl)methyl)azetidin-3-ol (138 mg, 0.49 mmole) was combined with N-(4-fluorophenyl)-5-(4,4,5,5-tetramethyl-1,3,2-dioxaborolan-2-yl)-2-(trifluoromethyl)benzamide (150 mg, 0.37 mmole), [1,1'-Bis(diphenylphosphino)ferrocene]palladium(II) dichloride (0.05 equiv), and potassium carbonate (127 mg, 0.92 mmol) in microwave seal tube. To this mixture was added dimethylformamide (3 mL) and water (0.3 mL). The resulting mixture was stirred at 120° C. for 20 min. Reaction was cooled and diluted with EtOAc and filtered through celite. The filtrate was concentrated and purified by reversed phase HPLC to give N-(4-fluorophenyl)-5-(2-((3-hydroxyazetidin-1-yl)methyl)imidazo[1,2-a]pyridin-8-yl)-2-(trifluoromethyl)benzamide. 485 (M+H).

To a solution of N-(4-fluorophenyl)-5-(2-((3-hydroxyazetidin-1-yl)methyl)imidazo[1,2-a]pyridin-8-yl)-2-(trifluoromethyl)benzamide (100 mg, 0.21 mmol) in acetic acid was added bromine (1 equiv) dropwise. The resulting mixture was stirred at room temperature for 1 hour then concentrated and purified by reversed phase HPLC to give 5-(2-(aminomethyl)-3-bromoimidazo[1,2-a]pyridin-8-yl)-N-(4-fluorophenyl)-2-(trifluoromethyl)benzamide. 508 (M+H).

5-(2-(aminomethyl)-3-bromoimidazo[1,2-a]pyridin-8-yl)-N-(4-fluorophenyl)-2-(trifluoromethyl)benzamide (15 mg, 0.03 mmole) was combined with (2,3-difluorophenyl) boronic acid (7 mg, 0.04 mmole), [1,1'-Bis(diphenylphosphino)ferrocene]palladium(II) dichloride (0.05 equiv), and potassium carbonate (8.2 mg, 0.06 mmol) in microwave seal tube. To this mixture was added dimethylformamide (3 mL) and water (0.3 mL). The resulting mixture was stirred at 120° C. for 20 min. Reaction was cooled and diluted with EtOAc and filtered through celite. The filtrate was concentrated and purified by reversed phase HPLC to give 5-(2-(aminomethyl)-3-(2,3-difluorophenyl)imidazo[1,2-a]pyridin-8-yl)-N-(4-fluorophenyl)-2-(trifluoromethyl) benzamide. 540 (M+1). $C_{28}H_{18}F_6N_4O$. 1H NMR (400 MHz, Chloroform-d) δ 10.12 (s, 1H), 8.35 (s, 1H), 8.11 (d, J=8.2 Hz, 1H), 7.99-7.94 (m, 1H), 7.91 (d, J=8.2 Hz, 1H), 7.69-7.62 (m, 2H), 7.54 (dd, J=7.1, 1.1 Hz, 1H), 7.47-7.38 (m, 1H), 7.38-7.29 (m, 2H), 7.13-7.03 (m, 3H), 2.22 (s, 2H).

Example 8: 2-(3-(2,3-difluorophenyl)imidazo[1,2-a]pyridin-8-yl)-N-(4-fluorophenyl)-5-methylisonicotinamide

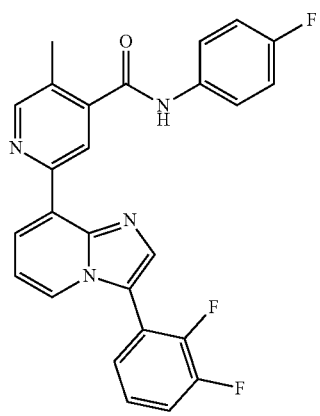 [SMILES: Cc1cnc(-c2cccn3c(-c4cccc(F)c4F)cnc23)cc1C(=O)Nc1ccc(F)cc1]

Example 7 was synthesized via the following scheme. To a solution of 3-bromopyridin-2-amine (1 gram, 5.8 mmol) in methanol (10 mL) was added 1,3-dichloropropan-2-one (954 mg, 7.5 mmol). The reaction was refluxed for 5 hr. The reaction was concentrated and triturated with a small amount of methanol to give 8-bromo-2-(chloromethyl)imidazo[1,2-a]pyridine. 245 (M+H).

To a solution of 8-bromo-2-(chloromethyl)imidazo[1,2-a]pyridine (390 mg, 1.6 mmol) in acetonitrile was added potassium carbonate (296 mg, 4.8 mmol) followed by azetidin-3-ol hydrochloride (209 mg, 1.9 mmole). The resulting mixture was heated at 80° C. for 48 hours. Filtered off potassium carbonate, and the filtrate was concentrated down Example 8 was made analogously to Example 24 starting with 2-bromo-N-(4-fluorophenyl)-5-methylisonicotinamide in place 6-bromo-N-(4-fluorophenyl)-3-(trifluoromethyl)picolinamide. C₂₆H₁₇F₃N₄O. 459 (M+1). $^1$H NMR (400 MHz, DMSO-d6) δ 10.60 (d, J=2.2 Hz, 2H), 9.31 (d, J=2.2 Hz, 1H), 8.68 (s, 1H), 8.60 (d, J=2.2 Hz, 1H), 8.24 (s, 1H), 7.78-7.71 (m, 4H), 7.25-7.15 (m, 4H), 2.62 (s, 3H).

Example 9: N-(4-fluorophenyl)-5-(3-(2-methylpyridin-3-yl)imidazo[1,2-a]pyridin-8-yl)-2-(trifluoromethyl)benzamide

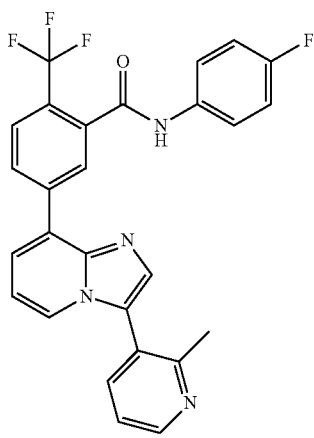 [SMILES: Cc1ncccc1-c1cnc2c(-c3ccc(C(F)(F)F)c(C(=O)Nc4ccc(F)cc4)c3)cccn12]

Example 9 was made analogously to Example 27 using (2-methylpyridin-3-yl)boronic acid in place of (2,3-difluorophenyl)boronic acid. C₂₇H₁₈F₄N₄O. 491 (M+1). $^1$H NMR (400 MHz, DMSO-d6) δ 10.72 (s, 1H), 8.78 (dd, J=5.3, 1.6 Hz, 1H), 8.46-8.39 (m, 2H), 8.31 (d, J=6.8 Hz, 1H), 8.21 (d, J=8.0 Hz, 1H), 8.16-7.96 (m, 2H), 7.91 (d, J=8.0, 1H), 7.76-7.66 (m, 3H), 7.34-7.08 (m, 3H), 2.46 (s, 3H)

Example 10: 5-(3-(2,3-difluorophenyl)pyrazolo[1,5-a]pyridin-7-yl)-N-(4-fluorophenyl)-2-methylnicotinamide

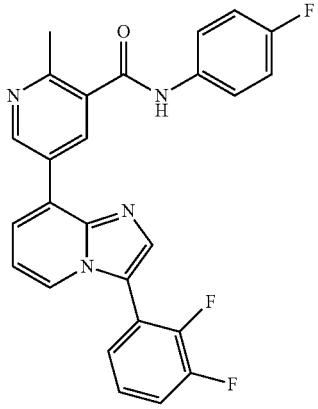 [SMILES: Cc1ncc(-c2cccn3c(-c4cccc(F)c4F)cnc23)cc1C(=O)Nc1ccc(F)cc1]

Example 10 was made analogously to Example 35 using (5-((4-fluorophenyl)carbamoyl)-6-methylpyridin-3-yl)boronic acid in place of N-(4-fluorophenyl)-5-(4,4,5,5-tetramethyl-1,3,2-dioxaborolan-2-yl)-2-(trifluoromethyl)benzamide. C₂₆H₁₇F₃N₄O. 459.3 (M+1). $^1$H NMR (400 MHz, DMSO-d₆) δ 10.61 (s, 1H), 9.16 (d, J=2.2 Hz, 1H), 8.50 (d, J 2.2 Hz, 1H), 8.37 (d, J=1.6 Hz, 1H), 7.88 (dt, J=9.0, 1.6 Hz, 1H), 7.81-7.72 (m, 2H), 7.56-7.49 (m, 2H), 7.41 (ddd, J=10.3, 7.6, 1.8 Hz, 1H), 7.38-7.30 (m, 2H), 7.27-7.17 (m, 2H), 2.68 (s, 3H).

Example 11: 5-(3-(2,3-difluorophenyl)-2-methylimidazo[1,2-a]pyridin-8-yl)-N-(4-fluorophenyl)-2-methylbenzamide

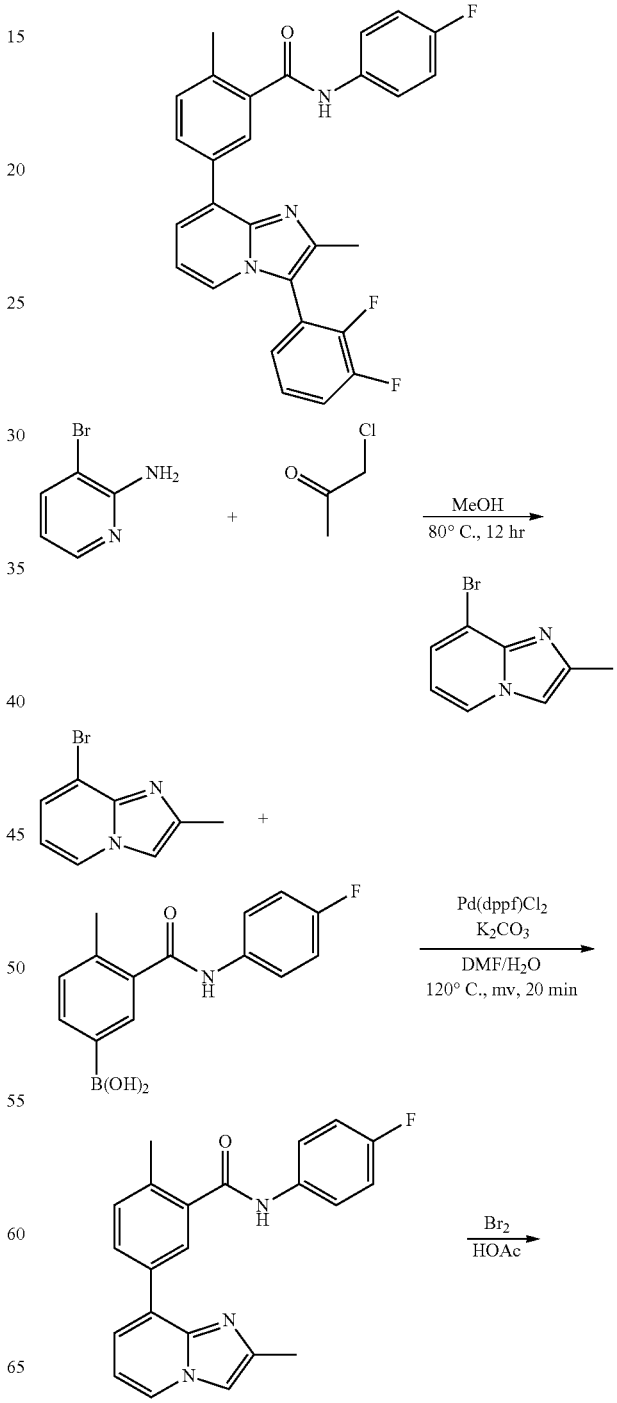

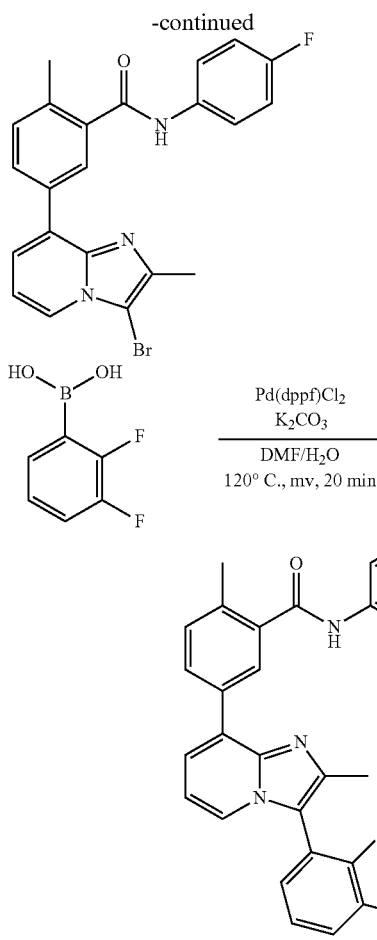

Example 11 was synthesized following the following scheme. To a solution of 3-bromopyridin-2-amine (200 mg, 1.2 mmol) in methanol (6 mL) was added 1-chloropropan-2-one (139 mg, 1.5 mmol). The reaction was refluxed for 12 hr. The reaction was concentrated down to dryness and purified by reversed phase HPLC to give 8-bromo-2-methylimidazo[1,2-a]pyridine. 210 (M+H).

8-Bromo-2-methylimidazo[1,2-a]pyridine (171 mg, 0.81 mmole) was combined with (3-((4-fluorophenyl)carbamoyl)-4-methylphenyl)boronic acid (256 mg, 0.97 mmole), [1,1'-Bis(diphenylphosphino)ferrocene]palladium(II) dichloride (0.05 equiv), and potassium carbonate (280 mg, 2.0 mmol) in microwave seal tube. To this mixture was added dimethylformamide (3 mL) and water (0.3 mL). The resulting mixture was stirred at 90° C. for 3 hours. Reaction was cooled and diluted with EtOAc and filtered through celite. The filtrate was concentrated, and solid was precipitated out of DMF/H₂O mixture to give N-(4-fluorophenyl)-2-methyl-5-(2-methylimidazo[1,2-a]pyridin-8-yl)benzamide. 360 (M+H).

To a solution of N-(4-fluorophenyl)-2-methyl-5-(2-methylimidazo[1,2-a]pyridin-8-yl)benzamide (50 mg, 0.14 mmol) in acetic acid (1 mL) was added bromine (1 equiv) dropwise. Yellow solid formed immediately. Filtered off solid and washed with water. Air dried overnight to give 5-(3-bromo-2-methylimidazo[1,2-a]pyridin-8-yl)-N-(4-fluorophenyl)-2-methylbenzamide. 438 (M+H).

5-(3-bromo-2-methylimidazo[1,2-a]pyridin-8-yl)-N-(4-fluorophenyl)-2-methylbenzamide (40 mg, 0.09 mmole) was combined with (2,3-difluorophenyl)boronic acid (17 mg, 0.11 mmole), [1,1'-Bis(diphenylphosphino)ferrocene]palladium(II) dichloride (0.05 equiv), and potassium carbonate (31 mg, 0.23 mmol) in microwave seal tube. To this mixture was added dimethylformamide (3 mL) and water (0.3 mL). The resulting mixture was stirred heated in the microwave reactor at 120° C. for 20 min. Reaction was cooled and diluted with EtOAc and filtered through celite. The filtrate was concentrated to dryness and purified by reverse-phase HPLC to give 5-(3-(2,3-difluorophenyl)-2-methylimidazo[1,2-a]pyridin-8-yl)-N-(4-fluorophenyl)-2-methylbenzamide. $C_{28}H_{20}F_3N_3O$. 472 (M+H). ¹H NMR (400 MHz, DMSO-d6) δ 10.43 (s, 1H), 8.23-8.06 (m, 3H), 7.81-7.72 (m, 2H), 7.65-7.54 (m, 2H), 7.48-7.38 (m, 3H), 7.22-7.11 (m, 2H), 7.07-6.97 (m, 1H), 2.44 (s, 3H), 2.33 (s, 3H).

Example 12: 5-(3-(2,3-difluorophenyl)imidazo[1,2-a]pyridin-8-yl)-N-(4-fluorophenyl)-2-methylnicotinamide

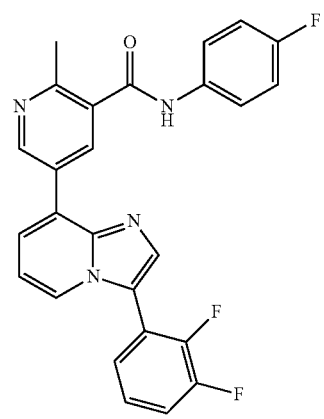 [SMILES: Cc1ncc(-c2cccn3c(-c4cccc(F)c4F)cnc23)cc1C(=O)Nc1ccc(F)cc1]

Example 12 was made analogously to Example 27 using (2,3-difluorophenyl)boronic acid in place of (2,3-difluorophenyl)boronic acid and also using (5-((4-fluorophenyl)carbamoyl)-6-methylpyridin-3-yl)boronic acid in place of N-(4-fluorophenyl)-5-(4,4,5,5-tetramethyl-1,3,2-dioxaborolan-2-yl)-2-(trifluoromethyl)benzamide. $C_{26}H_{17}F_3N_4O$. 459 (M+1). ¹H NMR (400 MHz, DMSO-d6) δ 10.60 (s, 1H), 9.33 (d, J=2.2 Hz, 1H), 8.65 (d, J=2.3 Hz, 1H), 8.43-8.34 (m, 1H), 7.90 (s, 1H), 7.83-7.70 (m, 3H), 7.65-7.38 (m, 3H), 7.23-7.07 (m, 3H), 2.63 (s, 3H).

Example 13: 5-(3-(4-cyanopyridin-2-yl)imidazo[1,5-a]pyridin-8-yl)-N-(4-fluorophenyl)-2-(trifluoromethyl)benzamide

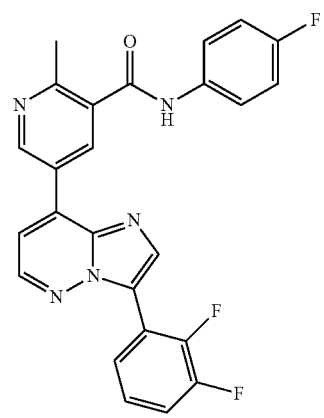 [SMILES: Cc1ncc(-c2ccnn3c(-c4cccc(F)c4F)cnc23)cc1C(=O)Nc1ccc(F)cc1]

Example 13 was made analogously to Example 33 using (5-((4-fluorophenyl)carbamoyl)-6-methylpyridin-3-yl)boronic acid in place of (3-((4-fluorophenyl)carbamoyl)-4-methylphenyl)boronic acid. $C_{25}H_{16}F_3N_5O$. 460.1 (M+1). $^1$H NMR (400 MHz, Chloroform-d) δ 9.07 (s, 1H), 8.79 (s, 1H), 8.55 (s, 1H), 8.17 (s, 1H), 7.97-7.95 (m, 1H), 7.74-7.65 (m, 3H), 7.52-7.42 (m, 2H), 7.12-7.08 (m, 2H), 2.86 (s, 3H).

Example 14: 5-(3-(2,3-difluorophenyl)-2-(hydroxymethyl)imidazo[1,2-a]pyridin-8-yl)-N-(4-fluorophenyl)-2-methylnicotinamide

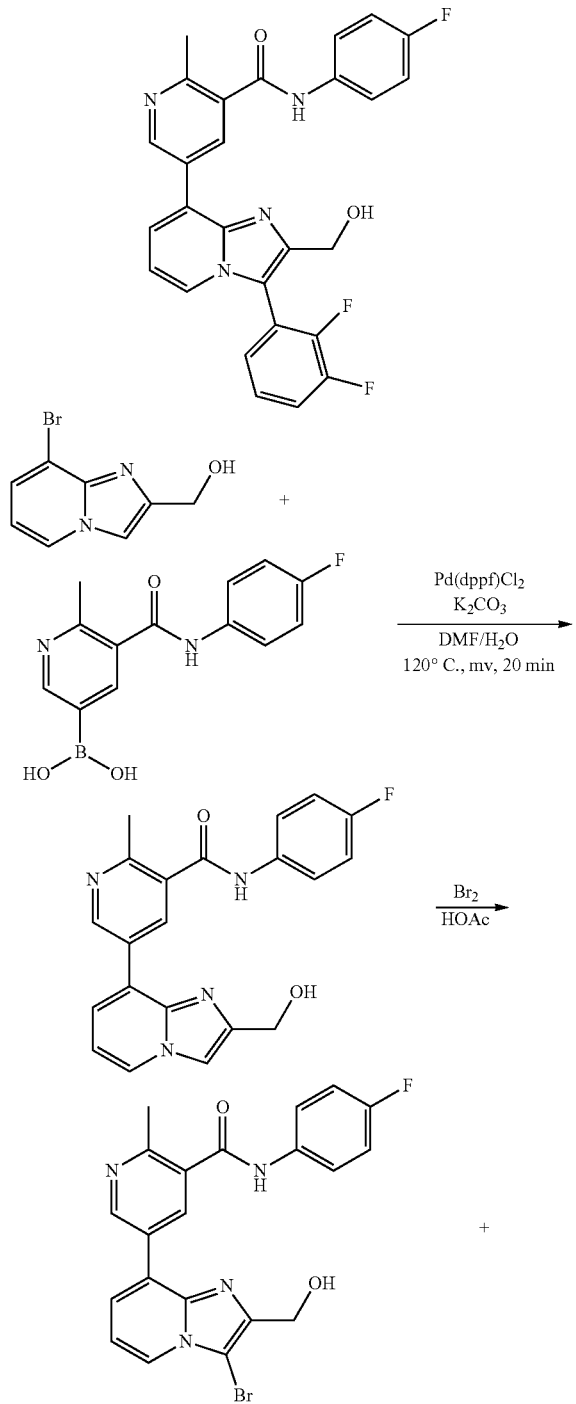

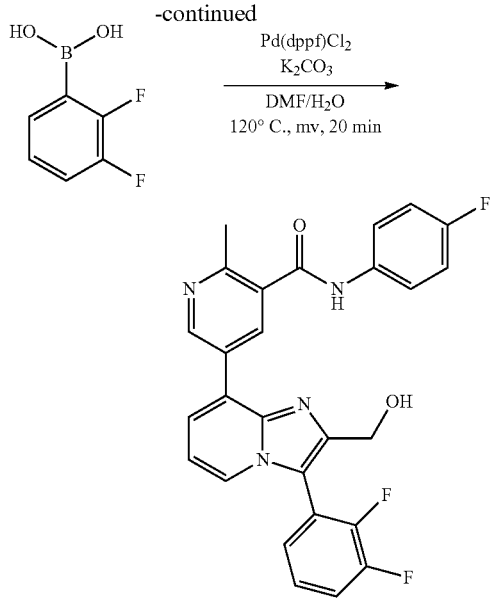

Example 14 was made according to the scheme above and analogously to Example 11 using the intermediate (8-bromoimidazo[1,2-a]pyridin-2-yl)methanol with (5-((4-fluorophenyl)carbamoyl)-6-methylpyridin-3-yl)boronic acid in place of (3-((4-fluorophenyl)carbamoyl)-4-methylphenyl)boronic acid. $C_{27}H_{19}F_3N_4O_2$. 489 (M+1). $^1$H NMR (400 MHz, DMSO-d6) δ 10.63 (s, 1H), 9.32 (d, J=2.2 Hz, 1H), 8.59 (d, J=2.2 Hz, 1H), 8.31 (dd, J=6.9, 3.2 Hz, 1H), 7.86 (d, J=7.1 Hz, 1H), 7.81-7.70 (m, 2H), 7.70-7.56 (m, 1H), 7.53-7.39 (2H), 7.29-7.11 (m, 3H), 4.55 (s, 2H), 2.68 (s, 3H).

Example 15: 2-chloro-N-(4-fluorophenyl)-5-(2-(hydroxymethyl)-3-(pyridin-3-yl)imidazo[1,2-a]pyridin-8-yl)benzamide

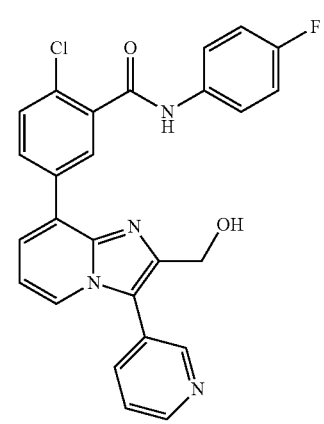 [SMILES: O=C(Nc1ccc(F)cc1)c1cc(-c2cccn3c(-c4cccnc4)c(CO)nc23)ccc1Cl]

Example 15 was made analogously to Examples 11 and 14 using pyridin-3-ylboronic acid in place of (2,3-difluorophenyl)boronic acid and also using (4-chloro-3-((4-fluorophenyl)carbamoyl)phenyl)boronic acid in place of (5-((4-fluorophenyl)carbamoyl)-6-methylpyridin-3-yl)boronic acid. $C_{26}H_{18}ClFN_4O_2$. 473 (M+1). $^1$H NMR (400 MHz, DMSO-d6) δ 10.69 (s, 1H), 8.85 (d, J=2.2 Hz, 1H), 8.67 (dd, J=4.8, 1.6 Hz, 1H), 8.44-8.23 (m, 3H), 8.12-8.07 (m, 1H), 7.76-7.56 (m, 4H), 7.23-7.16 (m, 2H), 7.04 (t, J=7.0 Hz, 1H), 5.23 (s, 1H), 4.51 (d, J=4.8 Hz, 2H).

Example 16: 6-(3-(2,3-difluorophenyl)imidazo[1,2-a]pyridin-8-yl)-N-(4-fluorophenyl)-3-methylpicolinamide

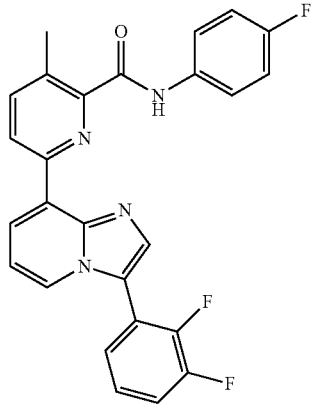 [SMILES: Cc1ccc(-c2cccn3c(-c4cccc(F)c4F)cnc23)nc1C(=O)Nc1ccc(F)cc1]

Example 16 was made analogously to Example 24 starting with 6-bromo-N-(4-fluorophenyl)-3-methylpicolinamide in place of 6-bromo-N-(4-fluorophenyl)-3-(trifluoromethyl)picolinamide. $C_{26}H_{17}F_3N_4O$. 459 (M+1). $^1$H NMR (400 MHz, DMSO-d6) δ 10.67 (s, 1H), 9.03 (s, 1H), 8.61-8.44 (m, 2H), 8.09 (s, 1H), 8.01 (d, J=8.2 Hz, 1H), 7.92-7.79 (m, 2H), 7.69-7.58 (m, 1H), 7.56-7.50 (m, 1H), 7.47-7.38 (m, 1H), 7.30 (t, J=7.0 Hz, 1H), 7.25-7.11 (m, 2H), 2.61 (s, 3H).

Example 17: N-(4-fluorophenyl)-2-methyl-5-(3-phenylimidazo[1,2-a]pyridin-8-yl)benzamide

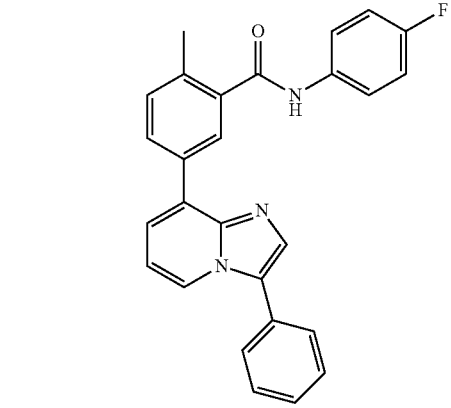

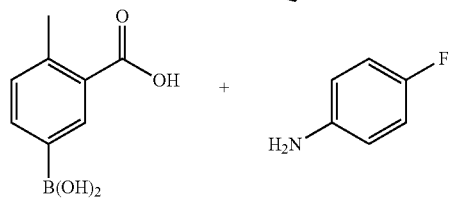

-continued

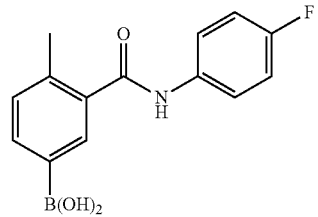

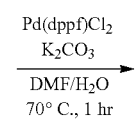
+
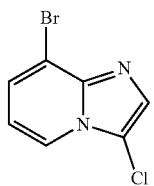

Pd(dppf)Cl$_2$
K$_2$CO$_3$
DMF/H$_2$O
70° C., 1 hr

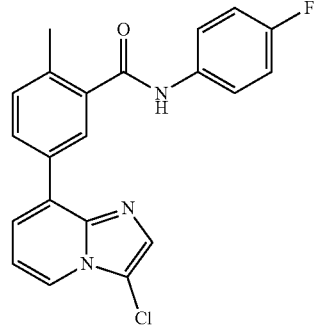
+

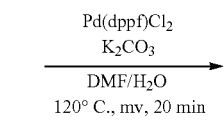

Pd(dppf)Cl$_2$
K$_2$CO$_3$
DMF/H$_2$O
120° C., mv, 20 min

-continued

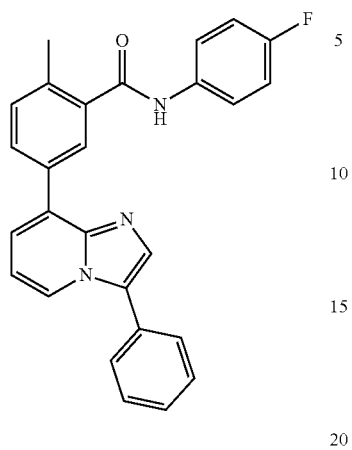

Example 17 was synthesized using the above scheme. To a solution of 5-borono-2-methylbenzoic acid (4.0 g, 22.2 mmol) and HATU (9.3 g, 24.4 mmol) in DMF (10 mL), 4-fluoroaniline (2.7 g, 24.4 mmol) and DIPEA (2 mL) were added and stirred at room temperature for 2 h. To the reaction mixture, water was added and filtered the precipitate, washed with hexanes and dried to get (3-((4-fluorophenyl)carbamoyl)-4-methylphenyl)boronic acid. 274 (M+H).

(3-((4-Fluorophenyl)carbamoyl)-4-methylphenyl)boronic acid (283 mg, 0.86 mmole) was combined with 8-bromo-3-chloroimidazo[1,2-a]pyridine (200 mg, 1.0 mmole), [1,1'-Bis(diphenylphosphino)ferrocene]palladium(II) dichloride (0.05 equiv), and potassium carbonate (298 mg, 2.5 mmol) in microwave seal tube. To this mixture was added dimethylformamide (3 mL) and water (0.3 mL). The resulting mixture was stirred at 90° C. for 1.5 hours. Reaction was cooled and diluted with EtOAc and filtered through celite. The filtrate was concentrated, and solid was precipitated out of DMF/H$_2$O mixture to give 5-(3-chloroimidazo[1,2-a]pyridin-8-yl)-N-(4-fluorophenyl)-2-methylbenzamide. 380 (M+1).

5-(3-chloroimidazo[1,2-a]pyridin-8-yl)-N-(4-fluorophenyl)-2-methylbenzamide (40 mg, 0.11 mmole) was combined with phenylboronic acid (15 mg, 0.13 mmole), [1,1'-Bis(diphenylphosphino)ferrocene]palladiumn(II) dichloride (0.05 equiv), and potassium carbonate (298 mg, 2.5 mmol) in microwave seal tube. To this mixture was added dimethylformamide (3 mL) and water (0.3 mL). The resulting mixture was heated in the microwave reactor at 140° C. for 20 min. Reaction was cooled and diluted with EtOAc and filtered through celite. The filtrate was concentrated to dryness and purified by reverse-phase HPLC to give N-(4-fluorophenyl)-2-methyl-5-(3-phenylimidazo[1,2-a]pyridin-8-yl)benzamide. C$_{27}$H$_{20}$FN$_3$O. 422 (M+1). $^1$H NMR (400 MHz, Methanol-d4) δ 8.76 (dd, J=6.8, 1.0 Hz, 1H), 8.19 (s, 1H), 8.05 (dd, J=7.4, 1.0 Hz, 1H), 7.90 (d, J=2.0 Hz, 1H), 7.84-7.66 (m, 8H), 7.65-7.58 (m, 2H), 7.18-7.11 (m, 2H), 2.62 (s, 3H).

Example 18: N-(4-fluorophenyl)-5-(2-methyl-3-(pyridin-3-yl)imidazo[1,2-a]pyridin-8-yl)-2-(trifluoromethyl)benzamide

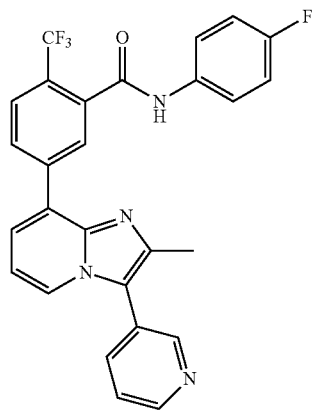 [SMILES: Cc1nc2c(-c3ccc(C(F)(F)F)c(C(=O)Nc4ccc(F)cc4)c3)cccn2c1-c1cccnc1]

Example 18 was made analogously to Examples 1 land 14 using pyridin-3-ylboronic acid in place of (2,3-difluorophenyl)boronic acid. C$_{27}$H$_{18}$F$_4$N$_4$O. 491 (M+H). $^1$H NMR (400 MHz, DMSO-d6) δ 10.73 (s, 1H), 8.87 (s, 1H), 8.78 (d, J=4.8 Hz, 1H), 8.52 (d, J=6.8 Hz, 1H), 8.32 (d, J=8.2 Hz, 1H), 8.25 (s, 1H), 8.17 (dt, J=8.0, 1.8 Hz, 1H), 8.06 (d, J=8.3 Hz, 1H), 7.89 (d, J=7.2 Hz, 1H), 7.79-7.66 (m, 3H), 7.30 (t, J=7.1 Hz, 1H), 7.23-7.16 (m, 2H), 2.43 (s, 3H).

Example 19: N-(4-fluorophenyl)-5-(3-(3-fluorophenyl)imidazo[1,2-a]pyridin-8-yl)-2-methylbenzamide

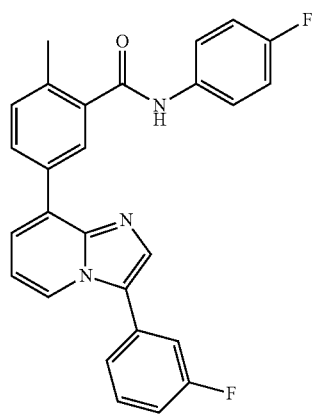 [SMILES: Cc1ccc(-c2cccn3c(-c4cccc(F)c4)cnc23)cc1C(=O)Nc1ccc(F)cc1]

Example 19 was made analogously to Example 17 using (3-fluorophenyl) boronic acid in place of phenylboronic acid. C$_{27}$H$_{19}$F$_2$N$_3$O. 440 (M+1). $^1$H NMR (400 MHz, DMSO-d6) δ 10.43 (s, 1H), 8.70 (d, J=7.2 Hz, 1H), 8.18-8.01 (m, 3H), 7.81-7.34 (m, 8H), 7.20-7.13 (m, 3H), 2.47 (s, 3H).

Example 20: 5-(3-(2,3-difluorophenyl)imidazo[1,2-a]pyridin-8-yl)-N-(4-fluorophenyl)-2-(trifluoromethyl)nicotinamide

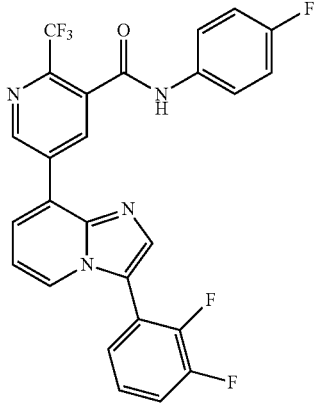

Example 20 was made analogously to Example 24 starting with 5-bromo-N-(4-fluorophenyl)-2-(trifluoromethyl)nicotinamide in place 6-bromo-N-(4-fluorophenyl)-3-(trifluoromethyl)picolinamide. $C_{26}H_{14}F_6N_4O$. 513 (M+1). $^1$H NMR (400 MHz, DMSO-d6) δ 10.88 (s, 1H), 9.64 (d, J=2.0 Hz, 1H), 9.01 (d, J=2.0 Hz, 1H), 8.52-8.43 (m, 1H), 7.97-7.88 (m, 2H), 7.73-7.66 (m, 2H), 7.65-7.55 (m, 1H), 7.54-7.47 (m, 1H), 7.46-7.36 (m, 1H), 7.27-7.11 (m, 3H), 3.32 (s, 3H).

Example 21: N-(4-fluorophenyl)-5-(2-(hydroxymethyl)-3-(pyridin-3-yl)imidazo[1,2-a]pyridin-8-yl)-2-(trifluoromethyl)benzamide

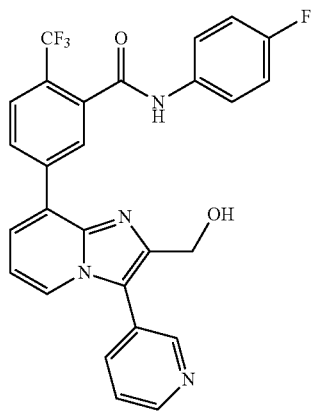 [SMILES: O=C(Nc1ccc(F)cc1)c1cc(-c2cccn3c(-c4cccnc4)c(CO)nc23)ccc1C(F)(F)F]

Example 21 was made analogously to Examples 11 and 14 using the intermediate 5-(3-bromo-2-(hydroxymethyl)imidazo[1,2-a]pyridin-8-yl)-N-(4-fluorophenyl)-2-(trifluoromethyl)benzamide and using pyridin-3-ylboronic acid in place of (2,3-difluorophenyl) boronic acid. $C_{27}H_{18}F_4N_4O_2$. 507 (M+1). $^1$H NMR (400 MHz, Chloroform-d) δ 10.27 (s, 1H), 8.70 (dd, J=4.9, 1.6 Hz, 1H), 8.66-8.61 (m, 1H), 8.23 (s, 1H), 8.09 (dd, J=6.9, 1.1 Hz, 1H), 7.89 (d, J=8.1 Hz, 1H), 7.81 (d, J=8.1 Hz, 1H), 7.59-7.54 (m, 1H), 7.50-7.40 (m, 3H), 7.40-7.32 (m, 1H), 7.03 (t, J=6.9 Hz, 1H), 6.80 (t, J=8.6 Hz, 2H), 4.56 (s, 2H).

Example 22: N-(4-fluorophenyl)-5-(3-(2-fluoropyridin-3-yl)imidazo[1,2-a]pyridin-8-yl)-2-(trifluoromethyl)benzamide

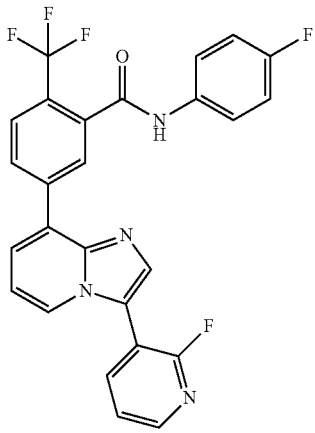 [SMILES: O=C(Nc1ccc(F)cc1)c1cc(-c2cccn3c(-c4cccnc4F)cnc23)ccc1C(F)(F)F]

Example 22 was made analogously to Example 27 using (2-fluoropyridin-3-yl)boronic acid in place of (2,3-difluorophenyl)boronic acid. $C_{26}H_{15}F_5N_4O$. 495 (M+1). $^1$H NMR (400 MHz, DMSO-d6) δ 10.72 (s, 1H), 8.61-8.32 (m, 4H), 8.32-8.24 (mz, 1H), 8.07-7.97 (m, 2H), 7.88 (dd, J=7.2, 1.0 Hz, 1H), 7.76-7.67 (m, 2H), 7.63-7.56 (m, 1H), 7.32-7.07 (m, 3H).

Example 23: N-(4-fluorophenyl)-5-(3-(2-fluorophenyl)imidazo[1,2-a]pyridin-8-yl)-2-methylbenzamide

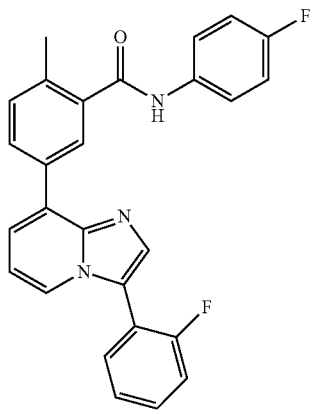 [SMILES: Cc1ccc(-c2cccn3c(-c4ccccc4F)cnc23)cc1C(=O)Nc1ccc(F)cc1]

Example 23 was made analogously to Example 17 using (2-fluorophenyl)boronic acid in place of phenylboronic acid. $C_{27}H_{19}F_2N_3O$. 440 (M+1). $^1$H NMR (400 MHz, DMSO-d6) δ 10.43 (s, 1H), 8.32 (d, J=6.6 Hz, 1H), 8.19-7.99 (m, 3H), 7.83-7.36 (m, 8H), 7.29-7.11 (m, 3H), 2.47 (s, 3H).

Example 24: 6-(3-(2,3-difluorophenyl)imidazo[1,2-a]pyridin-8-yl)-N-(4-fluorophenyl)-3-(trifluoromethyl)picolinamide

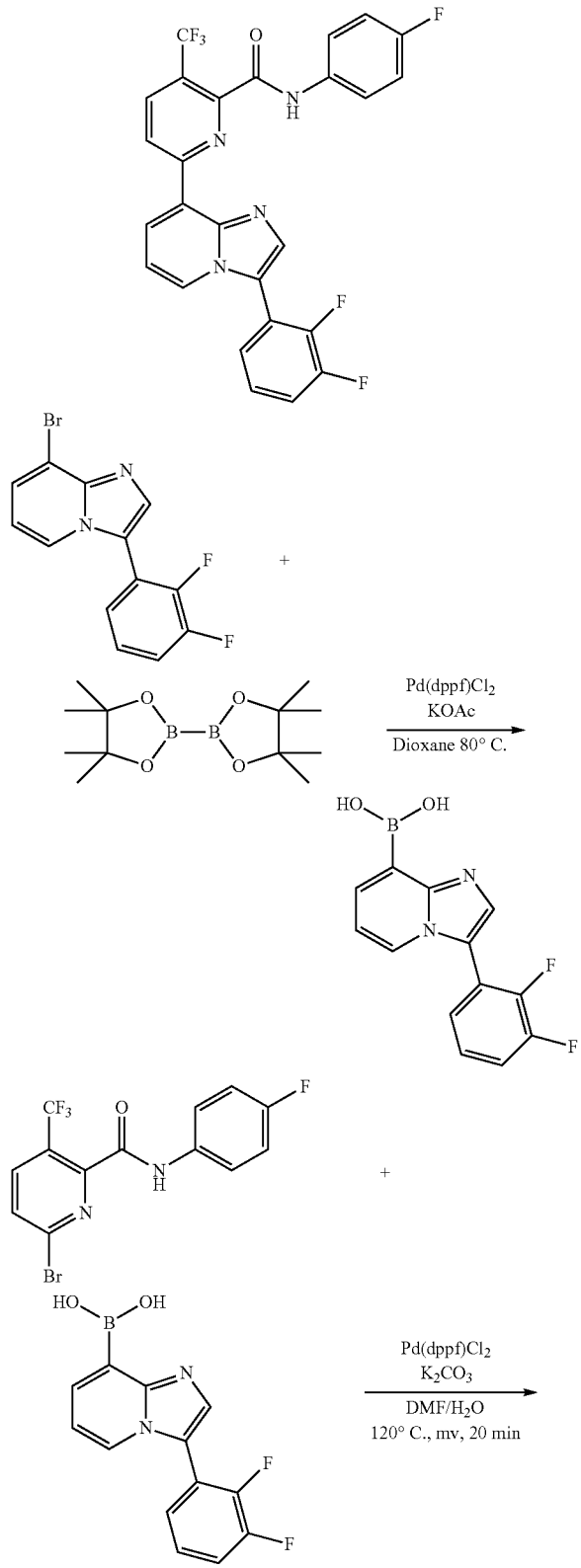

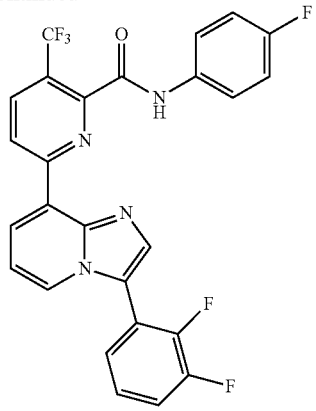 [SMILES: O=C(Nc1ccc(F)cc1)c1nc(-c2cccn3c(-c4cccc(F)c4F)cnc23)ccc1C(F)(F)F]

Example 24 was synthesized using the above disclosed scheme. To a round bottom flask was added 8-bromo-3-(2,3-difluorophenyl)imidazo[1,2-a]pyridine (300 mg, 0.97 mmol), bis(pinacolato)diboron (394 mg, 1.5 mmol), dichloro 1,1-bis(diphenylphosphino)ferrocene palladium(II) (100 mol %), and potassium acetate (285 mg, 2.9 mmol) were added, followed anhydrous dixoane (5 mL). The tube was flushed with Ar, then sealed and heated to reflux for 2 h. After the completion of the reaction, the reaction mixture was diluted with ethyl acetate, filtered through celite, concentrated and the boronic acid thus obtained was used for the next step. 275.0 (M+1).

To a suspension of 6-bromo-N-(4-fluorophenyl)-3-(trifluoromethyl)picolinamide (70 mg, 0.19 mmol), (3-(2,3-difluorophenyl)imidazo[1,5-a]pyridin-8-yl)boronic acid (40 mg, 0.14 mmol), potassium carbonate (40 mg, 0.29 mmol)) in DMF/Water (9:1) palladium catalyst (5 mol %) was added. The reaction mixture was subjected to microwave irradiation at 120° C. for 20 min. The reaction was diluted with ethyl acetate, filtered through celite and concentrated. The residue was purified by prep HPLC using Gilson reverse phase column eluting with ACN and water with 0.1% TFA using Luna column, to give the title compound as a TFA salt. $C_{26}H_{14}F_6N_4O$. 513 (M+1). $^1$H NMR (400 MHz, DMSO-d6) δ 10.90 (s, 1H), 9.41 (d, J=8.5 Hz, 1H), 8.66-8.46 (m, 3H), 8.10 (s, 1H), 7.83-7.70 (m, 2H), 7.70-7.38 (m, 3H), 7.38-7.16 (m, 3H).

Example 25: N-(4-fluorophenyl)-5-(3-(pyridin-3-yl)imidazo[1,2-a]pyridin-8-yl)-2-(trifluoromethyl)benzamide

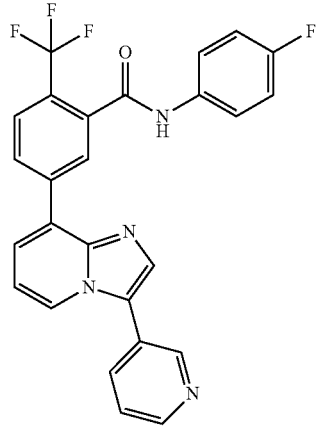

Example 25 was made analogously to Example 27 using pyridin-3-ylboronic acid in place of (2,3-difluorophenyl)

boronic acid. $C_{26}H_{16}F_4N_4O$. 477 (M+1). $^1$H NMR (400 MHz, DMSO-d6) δ 10.71 (s, 1H), 8.98 (s, 1H), 8.79-8.65 (m, 2H), 8.46-8.37 (m, 2H), 8.32-8.27 (m, 1H), 8.14 (s, 1H), 8.02 (d, J=8.3 Hz, 1H), 7.89 (d, J=7.1 Hz, 1H), 7.79-7.63 (m, 3H), 7.32-7.08 (m, 3H).

Example 26: N-(4-fluorophenyl)-5-(3-(5-fluoropyridin-3-yl)imidazo[1,2-a]pyridin-8-yl)-2-(trifluoromethyl)benzamide

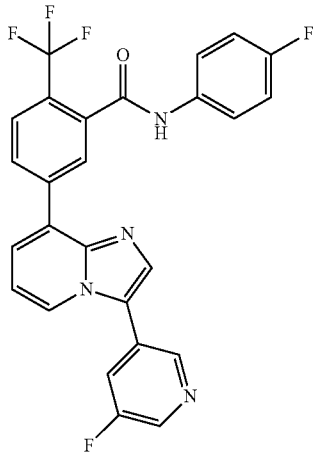 [SMILES: O=C(Nc1ccc(F)cc1)c1cc(-c2cccn3c(-c4cncc(F)c4)cnc23)ccc1C(F)(F)F]

Example 26 was made analogously to Example 27 using (5-fluoropyridin-3-yl)boronic acid in place of (2,3-difluorophenyl)boronic acid. $C_{26}H_{15}F_5N_4O$. 495 (M+1). $^1$H NMR (400 MHz, DMSO-d6) δ 10.72 (s, 1H), 8.80 (t, J=1.8 Hz, 1H), 8.75-8.73 (m, 1H), 8.65 (d, J=2.7 Hz, 1H), 8.57-8.49 (m, 1H), 8.46 (s, 1H), 8.20-8.14 (m, 1H), 8.04 (s, 1H), 7.99 (d, J=8.4, 1H), 7.85-7.81 (m, 1H), 7.76-7.66 (m, 2H), 7.24-7.10 (m, 3H).

Example 27: 5-(3-(2,3-difluorophenyl)imidazo[1,2-a]pyridin-8-yl)-N-(4-fluorophenyl)-2-methylbenzamide

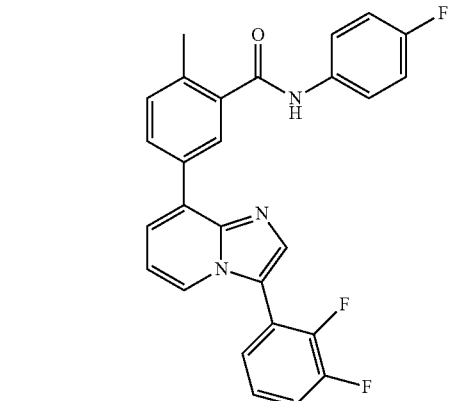

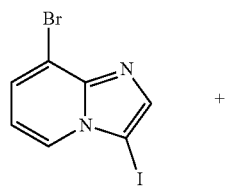

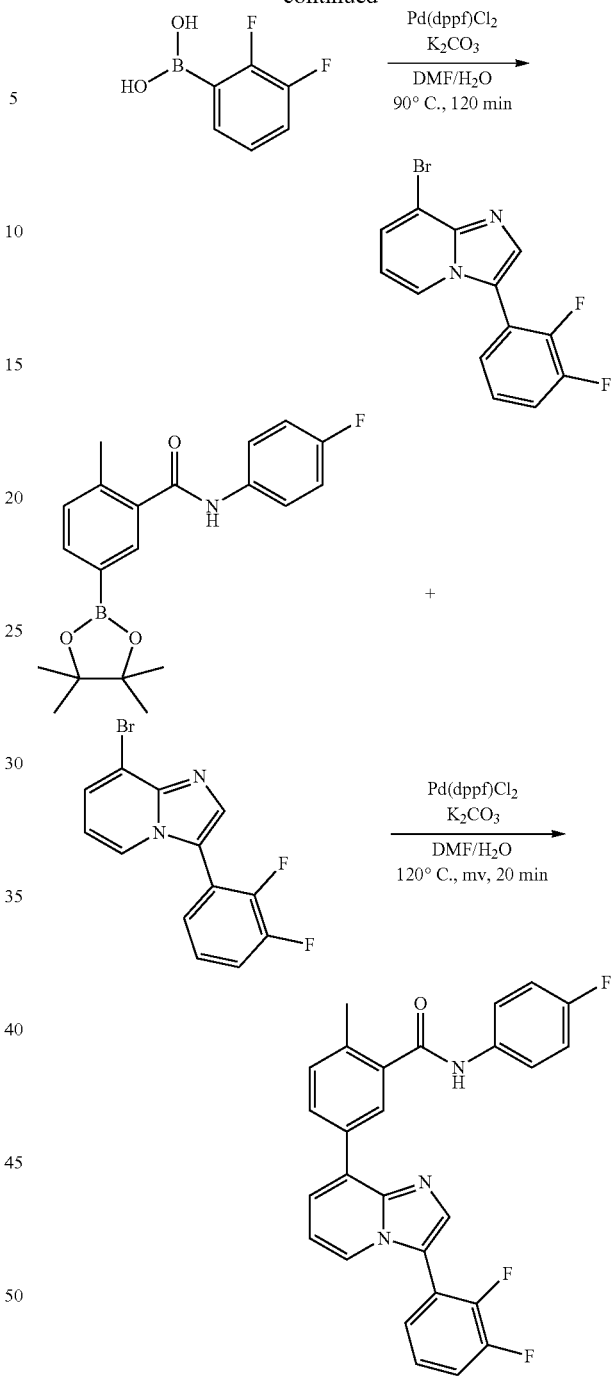

8-bromo-3-iodoimidazo[1,2-a]pyridine (100 mg, 0.31 mmole) was combinded with (2,3-difluorophenyl)boronic acid (49 mg, 0.31 mmole), [1,1'-Bis(diphenylphosphino)ferrocene]palladium(II) dichloride (0.05 equiv), and potassium carbonate (42 mg, 0.31 mmol) in microwave seal tube. To this mixture was added dimethylformamide (2 mL) and water (0.2 mL). The resulting mixture was stirred at 90° C. for 120 min. Reaction was cooled and diluted with EtOAc and filtered through celite. The filtrate was concentrated, and solid was precipitated out of DMF/H$_2$O mixture to give 8-bromo-3-(2,3-difluorophenyl)imidazo[1,2-a]pyridine. 309.0 (M). The precipitate used as such for the next step.

8-bromo-3-(2,3-difluorophenyl)imidazo[1,2-a]pyridine (53 mg, 0.19 mmole) was combinded with N-(4-fluorophenyl)-2-methyl-5-(4,4,5,5-tetramethyl-1,3,2-dioxaborolan-2-yl)benzamide (50 mg, 0.16 mmole), [1,1'-Bis(diphenylphosphino)ferrocene]palladium(II) dichloride (0.05 equiv), and potassium carbonate (22 mg, 0.16 mmol) in microwave seal tube. To this mixture was added dimethylformamide (2 mL) and water (0.2 mL). The resulting mixture was irradiated in a microwave at 120° C. for 20 min. Reaction was cooled and diluted with EtOAc and filtered through celite. The filtrate was concentrated, and solid was precipitated out of DMF/H$_2$O mixture to give 5-(3-(2,3-difluorophenyl)imidazo[1,2-a]pyridin-8-yl)-N-(4-fluorophenyl)-2-methylbenzamide The precipitate was purified by prep HPLC using Gilson reverse phase eluting with ACN and water with 0.1% TFA. Luna column. C$_{27}$H$_{18}$F$_3$N$_3$O; 458.1 (M+1); $^1$H NMR (400 MHz, DMSO-d6) δ 10.45 (s, 1H), 8.47 (d, J=6.9 Hz, 1H), 8.26-7.99 (m, 3H), 7.91-7.70 (m, 3H), 7.74-7.57 (m, 1H), 7.58-7.41 (m, 3H), 7.29 (t, J=7.0 Hz, 1H), 7.20 (t, J=8.9 Hz, 2H), 2.49 (s, 3).

Example 28: 5-(3-(2,3-difluorophenyl)-2-(hydroxymethyl)imidazo[1,2-a]pyridin-8-yl)-N-(4-fluorophenyl)-2-(trifluoromethyl)benzamide

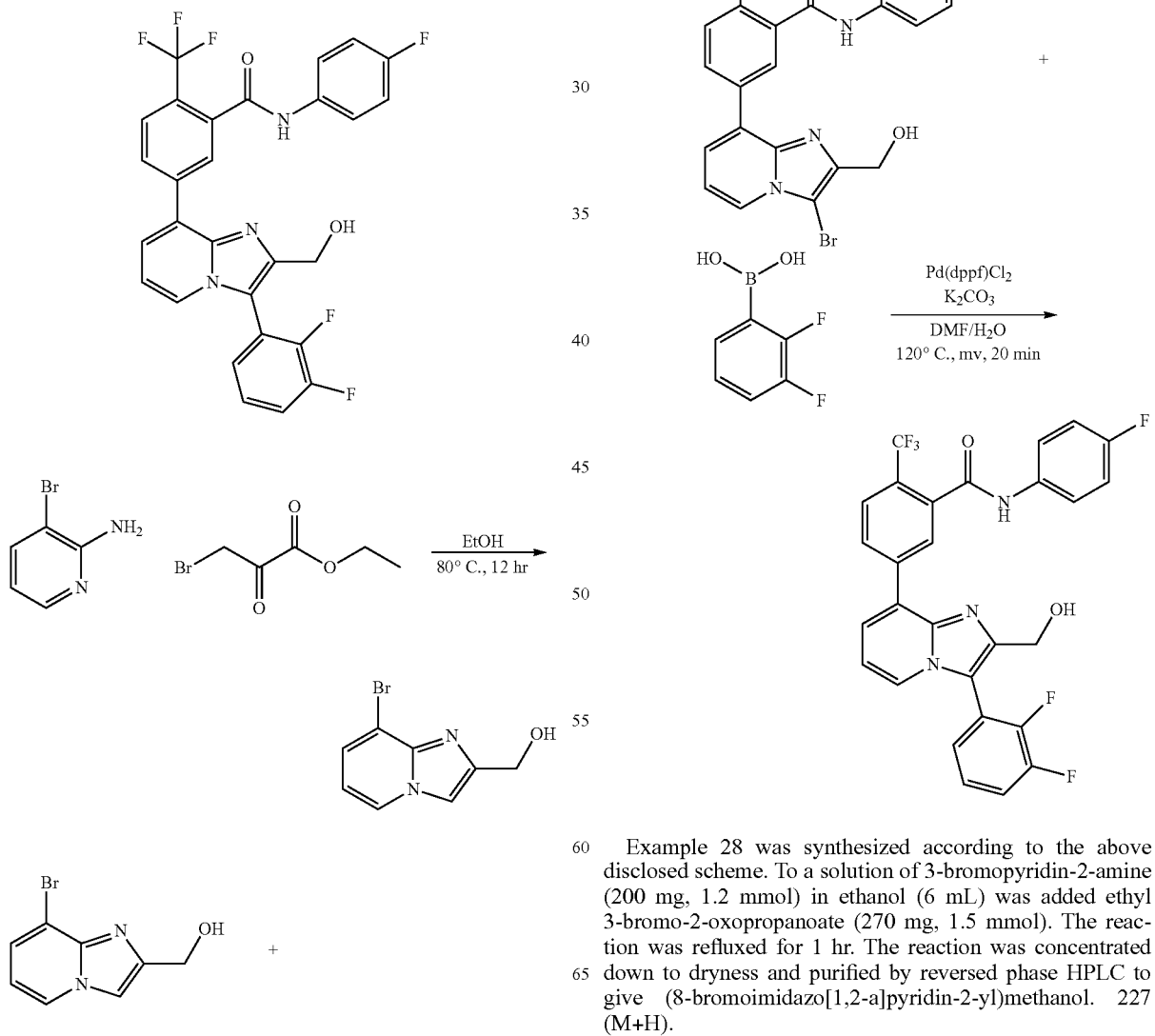

Example 28 was synthesized according to the above disclosed scheme. To a solution of 3-bromopyridin-2-amine (200 mg, 1.2 mmol) in ethanol (6 mL) was added ethyl 3-bromo-2-oxopropanoate (270 mg, 1.5 mmol). The reaction was refluxed for 1 hr. The reaction was concentrated down to dryness and purified by reversed phase HPLC to give (8-bromoimidazo[1,2-a]pyridin-2-yl)methanol. 227 (M+H).

Example 28 was made analogously to Example 11 using the intermediate (8-bromoimidazo[1,2-a]pyridin-2-yl)methanol and using N-(4-fluorophenyl)-5-(4,4,5,5-tetramethyl-1,3,2-dioxaborolan-2-yl)-2-(trifluoromethyl)benzamide in place of (3-((4-fluorophenyl)carbamoyl)-4-methylphenyl)boronic acid. $C_{28}H_{17}F_6N_3O_2$. 542 (M+). $^1$H NMR (400 MHz, DMSO-d6) δ 10.71 (s, 1H), 8.55 (d, J=8.4 Hz, 1H), 8.38 (s, 1H), 8.23 (dd, J=6.8, 3.2 Hz, 1H), 8.01 (d, J=8.4 Hz, 1H), 7.81-7.66 (m, 3H), 7.66-7.54 (m, 1H), 7.54-7.34 (m, 2H), 7.27-7.14 (m, 2H), 7.10 (t, J=7.0 Hz, 1H), 5.13 (t, J=5.6 Hz, 1H), 4.52 (s, 2H)

Example 29: 5-(3-(2,3-difluorophenyl)imidazo[1,2-a]pyridin-8-yl)-N-(4-fluorophenyl)-2-(trifluoromethyl)benzamide

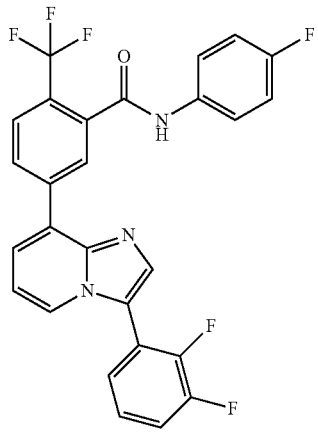 [SMILES: O=C(Nc1ccc(F)cc1)c1cc(-c2cccn3c(-c4cccc(F)c4F)cnc23)ccc1C(F)(F)F]

Example 29 was made analogously to Example 27 using N-(4-fluorophenyl)-5-(4,4,5,5-tetramethyl-1,3,2-dioxaborolan-2-yl)-2-(trifluoromethyl)benzamide in place of (3-((4-fluorophenyl)carbamoyl)-4-methylphenyl)boronic acid. $C_{27}H_{15}F_6N_3O$; 512.1 (M+1); $^1$H NMR (400 MHz, DMSO-d6) δ 10.74 (s, 1H), 8.50 (dd, J=6.9, 3.0 Hz, 2H), 8.45 (d, J=1.7 Hz, 1H), 8.03 (d, J=7.9 Hz, 2H), 7.89 (dd, J=7.2, 1.1 Hz, 1H), 7.79-7.70 (m, 2H), 7.64 (dtd, J=10.1, 8.2, 1.7 Hz, 1H), 7.53 (ddd, J=7.0, 5.4, 1.7 Hz, 1H), 7.45 (dd, J=8.1, 4.3 Hz, 1H), 7.34-7.11 (m, 3H).

Example: 30: 5-(3-(2,3-difluorophenyl)imidazo[1,2-b]pyridazin-8-yl)-N-(4-fluorophenyl)-2-(trifluoromethyl)benzamide

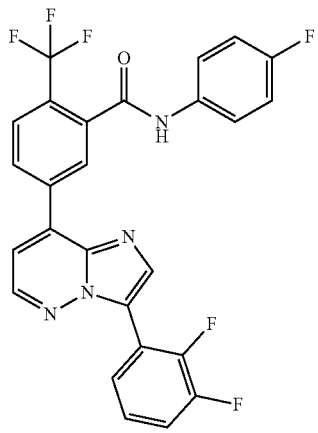 [SMILES: O=C(Nc1ccc(F)cc1)c1cc(-c2ccnn3c(-c4cccc(F)c4F)cnc23)ccc1C(F)(F)F]

Example 30 was made analogously to Example 33 using N-(4-fluorophenyl)-5-(4,4,5,5-tetramethyl-1,3,2-dioxaborolan-2-yl)-2-(trifluoromethyl)benzamide in place of (3-((4-fluorophenyl)carbamoyl)-4-methylphenyl)boronic acid. $C_{26}H_{14}F_6N_4O$. 513.1 (M+1). $^1$H NMR (400 MHz, Chloroform-d) δ 8.55 (d, J=4.8 Hz, 1H), 8.44 (s, 1H), 8.30 (d, J=8.4 Hz, 1H), 8.19-8.14 (m, 2H), 7.98-7.94 (m, 2H), 7.66-7.62 (m, 2H), 7.31-7.26 (m, 3H), 7.11-7.06 (m, 2H).

Example 31: N-(4-fluorophenyl)-5-(3-(pyridin-3-yl)imidazo[1,2-b]pyridazin-8-yl)-2-(trifluoromethyl)benzamide

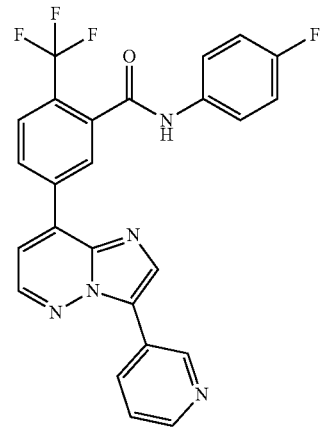 [SMILES: O=C(Nc1ccc(F)cc1)c1cc(-c2ccnn3c(-c4cccnc4)cnc23)ccc1C(F)(F)F]

Example 31 was made analogously to Example 33 using N-(4-fluorophenyl)-5-(4,4,5,5-tetramethyl-1,3,2-dioxaborolan-2-yl)-2-(trifluoromethyl)benzamide in place of (3-((4-fluorophenyl)carbamoyl)-4-methylphenyl)boronic acid, and using pyridin-3-ylboronic acid in place of (2,3-difluorophenyl)boronic acid. $C_{25}H_{15}F_4N_5O$. 478.1 (M+1). 1H NMR (400 MHz, Chloroform-d) δ 9.72 (s, 1H), 8.87-8.12 (m, 2H), 8.75-8.73 (m, 1H), 8.37 (d, J=18.8 Hz, 2H), 8.29 (w, 1H), 8.19 (d, J=8.0 Hz, 1H), 7.99 (d, J=8.0 Hz, 1H), 7.92-7.88 (m, 1H), 7.66-7.63 (m, 2H), 7.51-7.46 (m, 1H), 7.09 (t, J=8.4 Hz, 2H).

Example 32: 5-(3-chloro-1-(2,3-difluorophenyl)imidazo[1,5-a]pyridin-5-yl)-N-(4-fluorophenyl)-2-(trifluoromethyl)benzamide

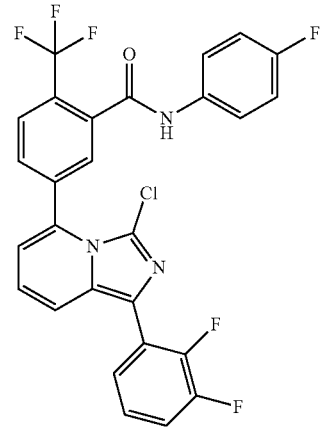

175
-continued

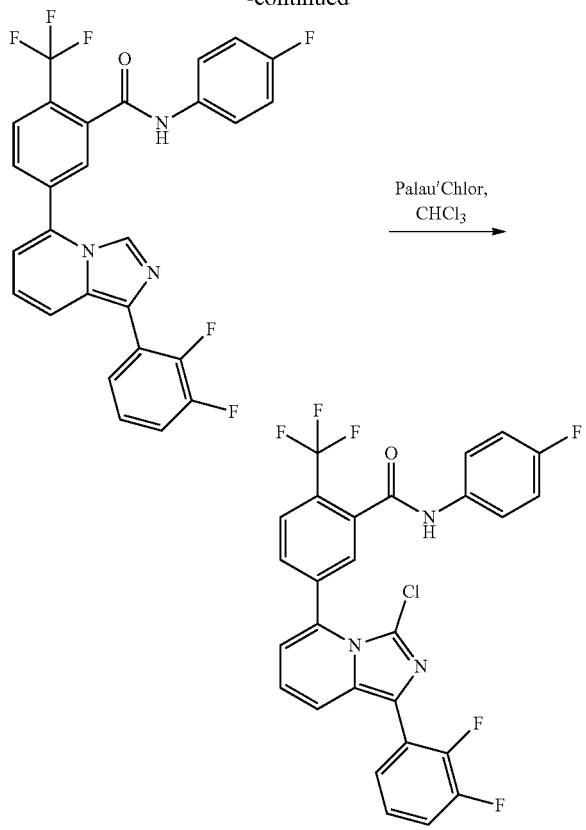

5-(1-(2,3-difluorophenyl)imidazo[1,5-a]pyridin-5-yl)-N-(4-fluorophenyl)-2-(trifluoromethyl)benzamide (13.0 mg, 0.025 mmol) was dissolved in $CHCl_3$ (1.0 mL) and Palau'Chlor (1.2 eq) was added and the reaction was allowed to stir at room temperature for 2 hours and 20 mins. The reaction was diluted with water (1.0 mL) and extracted with DCM (3×1 mL). Combined organic layers were concentrated to dryness and purified by reverse-phase prep HPLC to give 5-(3-chloro-1-(2,3-difluorophenyl)imidazo[1,5-a]pyridin-5-yl)-N-(4-fluorophenyl)-2-(trifluoromethyl)benzamide. $C_{27}H_{14}ClF_6N_3O$. 545.6/547.7 (M+1). $^1$H NMR (400 MHz, DMSO-$d_6$) δ 10.61 (s, 1H), 8.06-7.91 (m, 3H), 7.80-7.73 (m, 1H), 7.74-7.65 (m, 2H), 7.56 (tt, J=6.3, 1.6 Hz, 1H), 7.50-7.41 (m, 1H), 7.39-7.30 (m, 1H), 7.26-7.16 (m, 2H), 7.13 (dd, J=9.3, 6.7 Hz, 1H), 6.86 (dd, J=6.7, 1.1 Hz, 1H).

Example 33: 5-(3-(2,3-difluorophenyl)imidazo[1,2-b]pyridazin-8-yl)-N-(4-fluorophenyl)-2-methylbenzamide

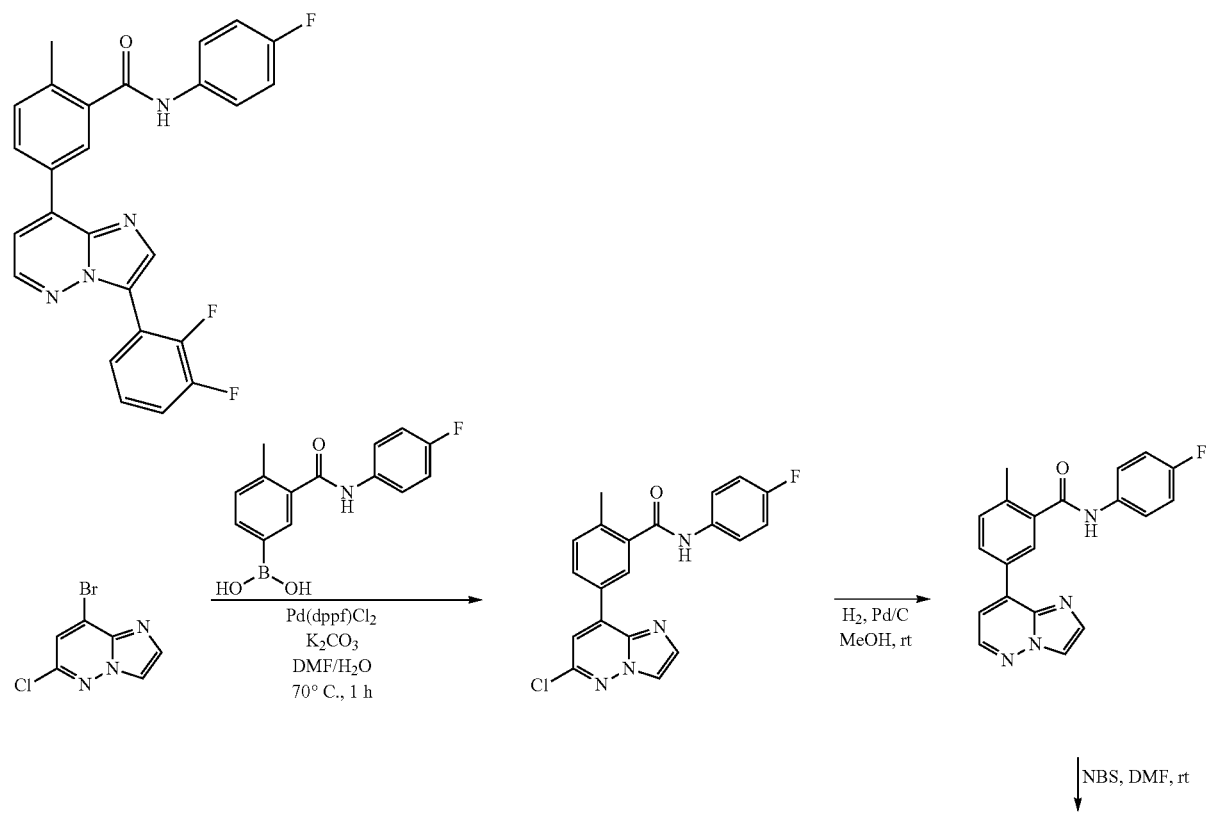

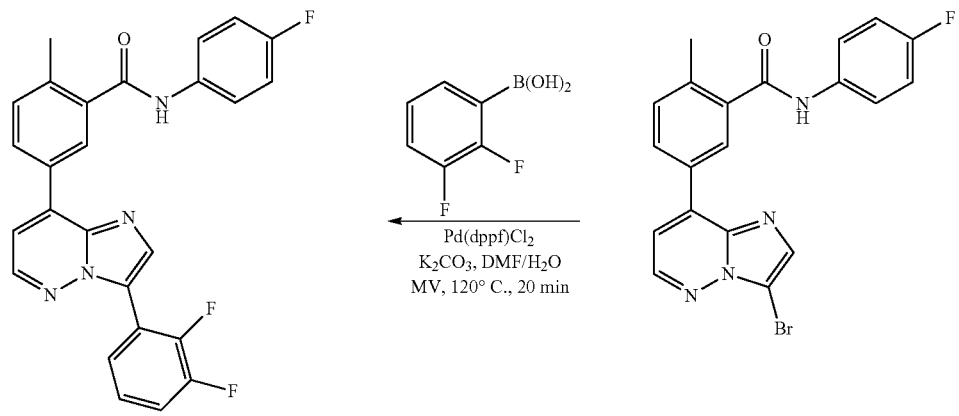

Example 33 was synthesized according to the above disclosed synthesis scheme. 8-Bromo-6-chloroimidazo[1,2-b]pyridazine (160 mg, 0.688 mmol), (3-((4-fluorophenyl)carbamoyl)-4-methylphenyl)boronic acid (225.5 mg, 0.826 mmol), Pd(dppf)Cl$_2$ (56.2 mg, 0.069 mmol), and K$_2$CO$_3$ (285.4 mg, 2.065 mmol) were dissolved in degassed DMF (3.0 mL) and water (0.5 mL) and heated in microwave at 120° C. for 20 minutes. The reaction mixture was filtered through ceilite and washed with EtOAc. The filtrate was concentrated and purified by prep-TLC with 1:1 ratio of EtOAc and Hexanes to give 5-(6-chloroimidazo[1,2-b]pyridazin-8-yl)-N-(4-fluorophenyl)-2-methylbenzamide.

To a stirred solution of 5-(6-chloroimidazo[1,2-b]pyridazin-8-yl)-N-(4-fluorophenyl)-2-methylbenzamide (30 mg, 0.079 mmol) in MeOH (5 mL) was added Pd/C (10% weight), and the mixture was stirred at rt under H$_2$ for 1 h. Filtered the reaction mixture through ceilite and washed with MeOH. The filtrate was concentrated and purified with prep-HPLC to afford N-(4-fluorophenyl)-5-(imidazo[1,2-b]pyridazin-8-yl)-2-methylbenzamide.

To a stirred solution of N-(4-fluorophenyl)-5-(imidazo[1,2-b]pyridazin-8-yl)-2-methylbenzamide (5.2 mg, 0.015 mmol) in DMF (2 mL) was added N-bromosuccinimide (2.9 mg, 0.017 mmol), and the resulting mixture was stirred at rt for 1 h. The mixture was purified by prep-HPLC to give 5-(3-bromoimidazo[1,2-b]pyridazin-8-yl)-N-(4-fluorophenyl)-2-methylbenzamide.

The intermediate 5-(3-bromoimidazo[1,2-b]pyridazin-8-yl)-N-(4-fluorophenyl)-2-methylbenzamide was treated with (2,3-difluorophenyl)boronic acid under Suzuki conditions to provide the final compound 5-(3-(2,3-difluorophenyl)imidazo[1,2-b]pyridazin-8-yl)-N-(4-fluorophenyl)-2-methylbenzamide. C$_{26}$H$_{17}$F$_3$N$_4$O. 459.1 (M+1). $^1$H NMR (400 MHz, Chloroform-d) δ 8.50 (d, J=4.8 Hz, 1H), 8.37 (s, 1H), 8.17 (d, J=2.0 Hz, 1H), 8.02-7.95 (m, 2H), 7.71-7.68 (m, 2H), 7.47 (d, J=8.0 Hz, 1H), 7.27-7.23 (m, 3H), 7.10-7.05 (m, 2H), 2.61 (s, 3H).

Example 34: 5-(1-(2,3-difluorophenyl)imidazo[1,5-a]pyridin-5-yl)-N-(4-fluorophenyl)-2-(trifluoromethyl)benzamide

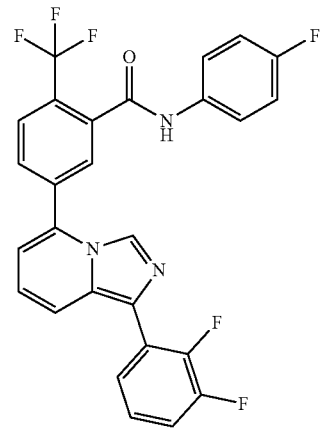 [SMILES: O=C(Nc1ccc(F)cc1)c1cc(-c2cccc3c(-c4cccc(F)c4F)ncn23)ccc1C(F)(F)F]

Example 34 was made analogously to Example 35 using 1-bromoimidazo[1,5-a]pyridine in place of 3-bromopyrazolo[1,5-a]pyridine. C$_{27}$H$_{15}$F$_6$N$_3$O $^1$H NMR (400 MHz, DMSO-d$_6$) δ 10.72 (s, 1H), 8.64 (s, 1H), 8.22 (d, J=1.7 Hz, 1H), 8.17-8.06 (m, 2H), 7.76-7.67 (m, 3H), 7.61 (ddd, J=8.0, 4.9, 1.6 Hz, 1H), 7.46-7.28 (m, 2H), 7.22 (t, J=8.9 Hz, 2H), 7.12 (dd, J=9.3, 6.7 Hz, 1H), 6.95 (dd, J=6.7, 1.0 Hz, 1H). 511.9 (M+1).

Example 35: 5-(3-(2,3-difluorophenyl)pyrazolo[1,5-a]pyridin-7-yl)-N-(4-fluorophenyl)-2-(trifluoromethyl)benzamide

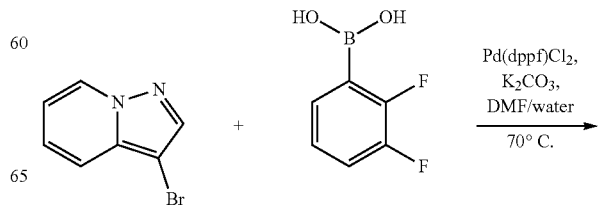

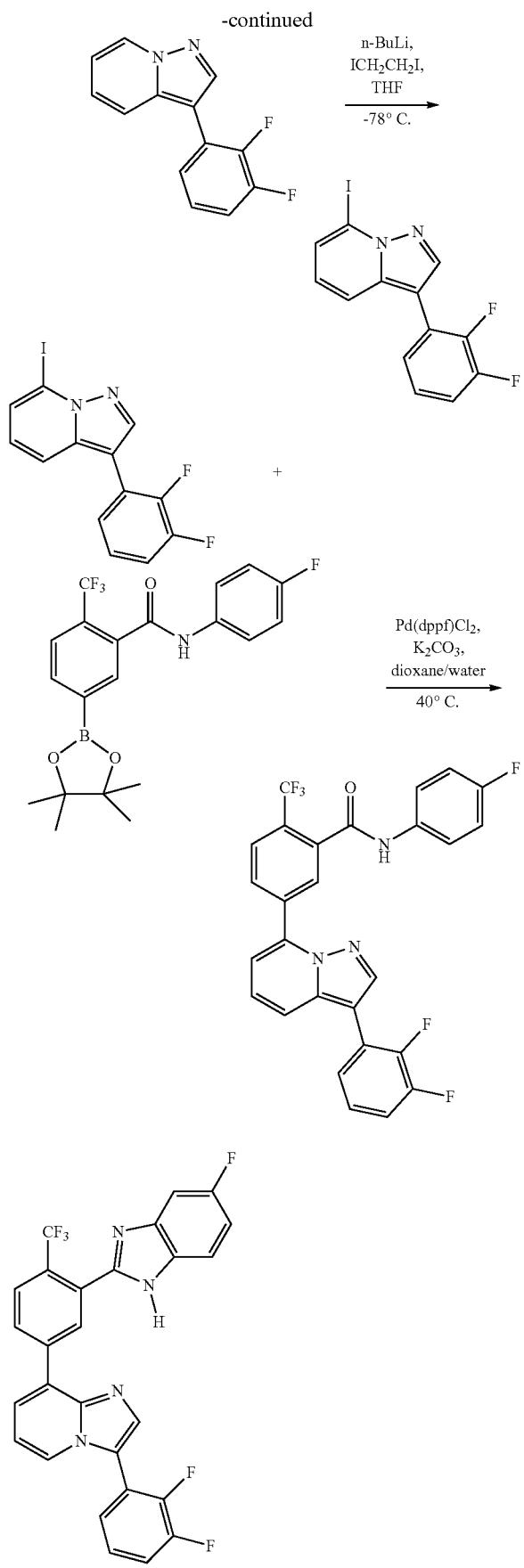

3-bromopyrazolo[1,5-a]pyridine (500 mg, 3.0 mmol), (2,3-difluorophenyl)boronic acid (1.1 eq), Pd(dppf)Cl$_2$ (0.1 eq), and K$_2$CO$_3$ (3.0 eq) were dissolved in degassed DMF (6.0 mL) and water (2.0 mL) and heated for 2 hours at 70° C. The reaction was cooled to room temperature, diluted with water, and extracted with EtOAc (3×5 mL). Combined organic layers were concentrated to dryness under reduced pressure and purified by silica-gel column chromatography (Rf 40% EtOAc/hexanes: 0.58) to give 3-(2,3-difluorophenyl)pyrazolo[1,5-a]pyridine. 3-(2,3-difluorophenyl)pyrazolo[1,5-a]pyridine (200 mg, 0.869 mmol) was dissolved in THF (4.50 mL) under argon and cooled to −78° C. n-BuLi (2.5M, 1.3 eq) was added dropwise and the reaction was allowed to stir at −78° C. for 1 hour. 1,2-diiodoethane (1.2 eq in 1 mL THF) was added dropwise and the reaction was allowed to stir at −78° C. for 2 hours. The reaction was quenched with saturated sodium bicarbonate solution (5 mL) and extracted with EtOAc (3×4 mL). Combined organic layers were concentrated under reduced pressure and purified by silica-gel column chromatography to give 3-(2,3-difluorophenyl)-7-iodopyrazolo[1,5-a]pyridine. 3-(2,3-difluorophenyl)-7-iodopyrazolo[1,5-a]pyridine (100 mg, 0.28 mol), N-(4-fluorophenyl)-5-(4,4,5,5-tetramethyl-1,3,2-dioxaborolan-2-yl)-2-(trifluoromethyl)benzamide (1.1 eq), Pd(ddpf)Cl$_2$ (0.1 eq), and K$_2$CO$_3$ (3.0 eq) were dissolved in degassed 1,4-dioxane (2.0 mL) and water (1.0 mL) and heated overnight at 40° C. The reaction was cooled to room temperature, diluted with water (5 mL) and extracted with EtOAc (3×4 mL). Combined organic layers were concentrated under reduced pressure and purified by reverse-phase prep HPLC to give 5-(3-(2,3-difluorophenyl)pyrazolo[1,5-a]pyridin-7-yl)-N-(4-fluorophenyl)-2-(trifluoromethyl)benzamide. C$_{27}$H$_{15}$F$_6$N$_3$O. 511.6 (M+1). $^1$H NMR (400 MHz, DMSO-d$_6$) δ 10.75 (s, 1H), 8.40-8.33 (m, 2H), 8.28 (d, J=1.7 Hz, 1H), 8.06 (d, J=8.3 Hz, 1H), 7.91 (dt, J=8.9, 1.6 Hz, 1H), 7.76-7.67 (m, 2H), 7.56-7.50 (m, 2H), 7.47-7.38 (m, 1H), 7.38-7.31 (m, 2H), 7.21 (t, J=8.9 Hz, 2H).

Example 36: 2-(5-(3-(2,3-difluorophenyl)imidazo[1,2-a]pyridin-8-yl)-2-(trifluoromethyl)phenyl)-5-fluoro-1H-benzo[d]imidazole

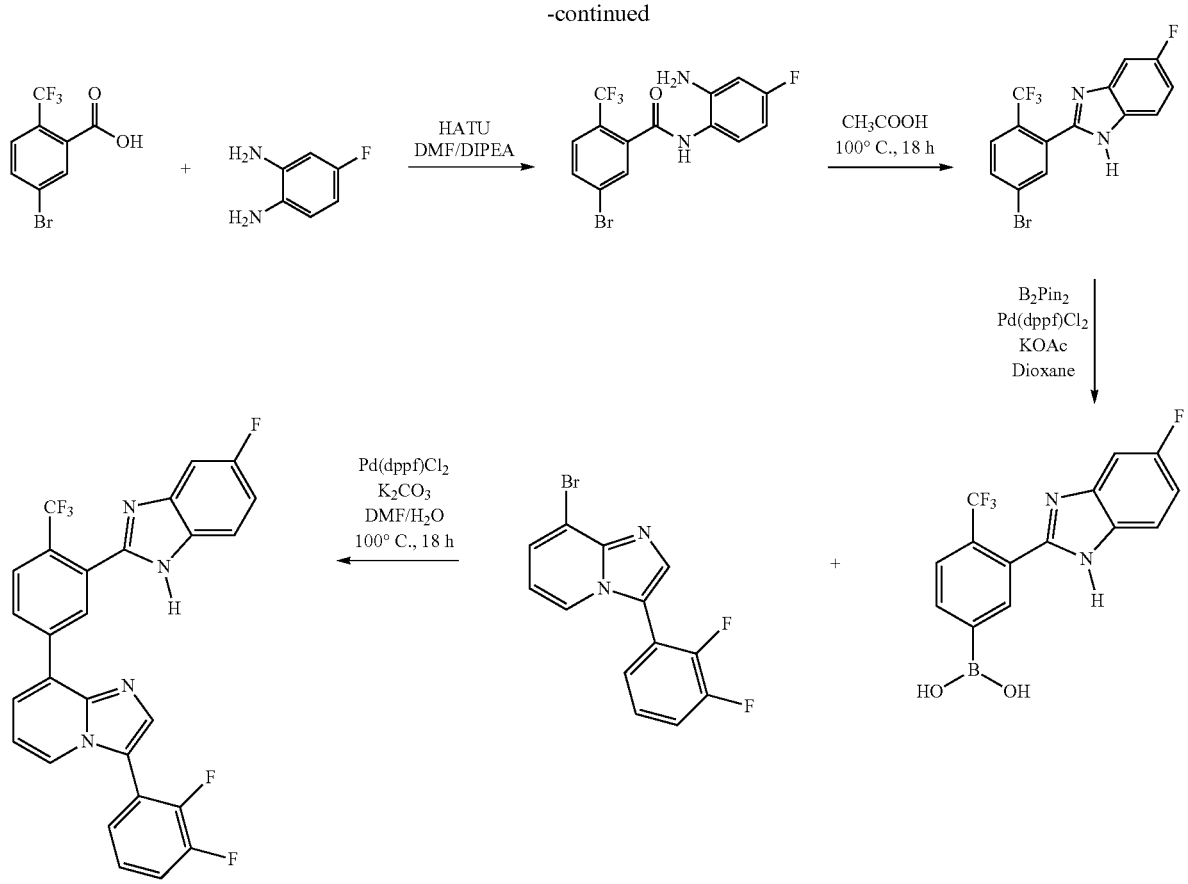

A solution of N-(2-amino-4-fluorophenyl)-5-bromo-2 (trifluoromethyl)benzamide was prepared analogously to (3-((4-fluorophenyl)carbamoyl)-4-methylphenyl)boronic acid in Example 17, using 5-bromo-2-(trifluoromethyl)benzoic acid (427 mg, 1.586 mmol, 1 equiv) in place of 5-borono-2-methylbenzoic acid and 4-fluorobenzene-1,2-diamine in place of 4-fluoroaniline. N-(2-amino-4-fluorophenyl)-5-bromo-2 (trifluoromethyl)benzamide was purified by silica gel chromatography (0-80% EtOAc/hexanes) and isolated.

A solution of N-(2-amino-4-fluorophenyl)-5-bromo-2-(trifluoromethyl)benzamide (190 mg, 0.504 mmol, 1 equiv) in AcOH (1 mL) was stirred overnight at 100° C. The reaction mixture was subsequently concentrated in vacuo, diluted with DMF/water and purified by HPLC. 2-(5-bromo-2-(trifluoromethyl)phenyl)-5-fluoro-1H-benzo[d]imidazole was purified by silica gel chromatography (0-100% EtOAc/hexanes) and isolated. LC-MS m/z: 359.7 (M+1).

To a mixture of 2-(5-bromo-2-(trifluoromethyl)phenyl)-5-fluoro-1H-benzo[d]imidazole (138 mg, 0.384 mmol, 1 equiv), B$_2$Pin$_2$ (146 mg, 0.576 mmol, 1.5 equiv), Pd(dppf)Cl$_2$ (12 mg, 0.019 mmol, 5 mol %) and KOAc (94 mg, 0.961 mmol, 2.5 equiv), in a sealed microwave vial, was added freshly degassed dioxane (3 mL). The reaction was stirred at 80° C., overnight. The reaction mixture was concentrated in vacuo then diluted with DMF/water. The crude product was purified by HPLC (10-100% ACN/water). (3-(5-fluoro-1H-benzo[d]imidazol-2-yl)-4-(trifluoromethyl)phenyl)boronic acid was isolated. LC-MS m/z: 325.1 (M+1).

Example 36 was prepared analogously to Example 27 using (3-(5-fluoro-1H-benzo[d]imidazol-2-yl)-4-(trifluoromethyl)phenyl)boronic acid (38 mg, 0.117 mmol, 1 equiv) and 8-bromo-3-(2,3-difluorophenyl)imidazo[1,2-a]pyridine (36 mg, 0.117 mmol, 1 equiv). The title compound was isolated. C$_{27}$H$_{14}$F$_6$N$_4$. 509.5 (M+1). 1H NMR (400 MHz, DMSO-d6) δ 8.61-8.49 (m, 3H), 8.14 (d, J=8.4 Hz, 1H), 8.04 (s, 1H), 7.92 (dd, J=7.2, 1.1 Hz, 1H), 7.70 (dd, J=8.8, 4.9 Hz, 1H), 7.63 (ddd, J=10.2, 8.2, 1.8 Hz, 1H), 7.56-7.48 (m, 2H), 7.44 (td, J=8.1, 4.2 Hz, 1H), 7.27 (t, J=7.0 Hz, 1H), 7.17 (ddd, J=9.9, 8.8, 2.5 Hz, 1H). 19F NMR (376 MHz, DMSO-d6) δ −57.52 (s, 3F), −75.36 (s, 3F), −120.13 (m, 1F), −137.51--138.27 (m, 2F).

BIOLOGICAL EXAMPLES

Activity testing was conducted in the Examples below using methods described herein and those well known in the art.

Example B1. Cell-Based (HeLa) Assay for Measurement of IDO1 Inhibition

To measure IDO1 inhibition in tissue culture, HeLa cells were treated with a test compound in the presence of IFNγ, which induces IDO1 expression. Following incubation, cell supernatants were assayed for kynurenine levels, an indicator of IDO1 activity.

H1-HeLa cells (ATCC #CRL-1958) were seeded in 384-well plates (Greiner #82051-282) at a volume of 50 μL/well in DMEM (Corning #15-018-CM) supplemented with 10% FBS (Corning #35-011-CV) and 1% P/S/G (Corning #30-009-CL) at a density of 1,250 cells/well and incubated overnight at 37° C., 5% CO$_2$/100% humidity. The following day, the test compounds were added in DMSO (0.5% final) at various concentrations, and IDO1 was inducibly expressed by the addition of 50 uL/well of 50 ng/mL of INFγ (Peprotech #300-02) in cell plating media. As a positive control, 50 uL of the cell plating media without IFNγ was added to several wells. Following a 48 hour incubation, the plates were spun down at 1,200 RPM for 5 min at 10° C. 65 µL/well of the supernatant was then transferred to new 384-well plates (Thermo #262160) that contained 10 uL/well of 30% TCA (Sigma #TO699), and the plates were sealed and incubated at 60° C. for 30 min. The plates were then centrifuged for 15 min at 2,000 RPM at 10° C. 40 µL/well of the supernatant was transferred to new 384-well plates (Thermo #262160) and was reacted with 40 µL/well of 2% (w/v) p-dimethlyaminobenzaldehyde (Sigma #156417) in glacial acetic acid (Sigma #A6283). The reaction was incubated at room temperature for 10 min and absorbance at 480 nm was read using a PerkinElmer Envision plate reader.

Data in Table 1 were normalized based on positive (-IFNγ) and negative (+IFNγ) controls and EC$_{50}$ values were calculated from the fit of the dose-response curves to a four-parameter equation. All EC$_{50}$ values represent geometric mean values of a minimum of four determinations. These assays generally produced results within 2-fold of the reported mean.

TABLE 1

| Example No. | Name | EC$_{50}$ (nM) |
| --- | --- | --- |
| 1 | 5-(3-(2,3-difluorophenyl)-2-((2-methoxyethoxy)methyl)imidazo[1,2-a]pyridin-8-yl)-N-(4-fluorophenyl)-2-(trifluoromethyl)benzamide | 8679 |
| 2 | N-(4-fluorophenyl)-5-(3-(5-fluoropyridin-3-yl)-2-(hydroxymethyl)imidazo[1,2-a]pyridin-8-yl)-2-methylnicotinamide | 3607 |
| 3 | 2-(3-(2,3-difluorophenyl)imidazo[1,2-a]pyridin-8-yl)-N-(4-fluorophenyl)-5-(trifluoromethyl)isonicotinamide | 2390 |
| 4 | N-(4-fluorophenyl)-5-(3-(6-methylpyridin-3-yl)imidazo[1,2-a]pyridin-8-yl)-2-(trifluoromethyl)benzamide | 2229 |
| 5 | N-(4-fluorophenyl)-2-methyl-5-(3-(2-methylpyridin-3-yl)-[1,2,4]triazolo[4,3-a]pyridin-8-yl)benzamide | 1703 |
| 6 | N-(4-fluorophenyl)-5-(3-(pyridin-4-yl)imidazo[1,2-a]pyridin-8-yl)-2-(trifluoromethyl)benzamide | 1418 |
| 7 | 5-(2-(aminomethyl)-3-(2,3-difluorophenyl)imidazo[1,2-a]pyridin-8-yl)-N-(4-fluorophenyl)-2-(trifluoromethyl)benzamide | 1009 |
| 8 | 2-(3-(2,3-difluorophenyl)imidazo[1,2-a]pyridin-8-yl)-N-(4-fluorophenyl)-5-methylisonicotinamide | 945 |
| 9 | N-(4-fluorophenyl)-5-(3-(2-methylpyridin-3-yl)imidazo[1,2-a]pyridin-8-yl)-2-(trifluoromethyl)benzamide | 535 |
| 10 | 5-(3-(2,3-difluorophenyl)pyrazolo[1,5-a]pyridin-7-yl)-N-(4-fluorophenyl)-2-methylnicotinamide | 441 |
| 11 | 5-(3-(2,3-difluorophenyl)-2-methylimidazo[1,2-a]pyridin-8-yl)-N-(4-fluorophenyl)-2-methylbenzamide | 436 |
| 12 | 5-(3-(2,3-difluorophenyl)imidazo[1,2-a]pyridin-8-yl)-N-(4-fluorophenyl)-2-methylnicotinamide | 403 |
| 13 | 5-(3-(4-cyanopyridin-2-yl)imidazo[1,5-a]pyridin-8-yl)-N-(4-fluorophenyl)-2-(trifluoromethyl)benzamide | 395 |
| 14 | 5-(3-(2,3-difluorophenyl)-2-(hydroxymethyl)imidazo[1,2-a]pyridin-8-yl)-N-(4-fluorophenyl)-2-methylnicotinamide | 372 |
| 15 | 2-chloro-N-(4-fluorophenyl)-5-(2-(hydroxymethyl)-3-(pyridin-3-yl)imidazo[1,2-a]pyridin-8-yl)benzamide | 272 |
| 16 | 6-(3-(2,3-difluorophenyl)imidazo[1,2-a]pyridin-8-yl)-N-(4-fluorophenyl)-3-methylpicolinamide | 168 |
| 17 | N-(4-fluorophenyl)-2-methyl-5-(3-phenylimidazo[1,2-a]pyridin-8-yl)benzamide | 168 |
| 18 | N-(4-fluorophenyl)-5-(2-methyl-3-(pyridin-3-yl)imidazo[1,2-a]pyridin-8-yl)-2-(trifluoromethyl)benzamide | 165 |
| 19 | N-(4-fluorophenyl)-5-(3-(3-fluorophenyl)imidazo[1,2-a]pyridin-8-yl)-2-methylbenzamide | 146 |
| 20 | 5-(3-(2,3-difluorophenyl)imidazo[1,2-a]pyridin-8-yl)-N-(4-fluorophenyl)-2-(trifluoromethyl)nicotinamide | 89 |
| 21 | N-(4-fluorophenyl)-5-(2-(hydroxymethyl)-3-(pyridin-3-yl)imidazo[1,2-a]pyridin-8-yl)-2-(trifluoromethyl)benzamide | 89 |
| 22 | N-(4-fluorophenyl)-5-(3-(2-fluoropyridin-3-yl)imidazo[1,2-a]pyridin-8-yl)-2-(trifluoromethyl)benzamide | 74 |
| 23 | N-(4-fluorophenyl)-5-(3-(2-fluorophenyl)imidazo[1,2-a]pyridin-8-yl)-2-methylbenzamide | 73 |
| 24 | 6-(3-(2,3-difluorophenyl)imidazo[1,2-a]pyridin-8-yl)-N-(4-fluorophenyl)-3-(trifluoromethyl)picolinamide | 64 |
| 25 | N-(4-fluorophenyl)-5-(3-(pyridin-3-yl)imidazo[1,2-a]pyridin-8-yl)-2-(trifluoromethyl)benzamide | 59 |
| 26 | N-(4-fluorophenyl)-5-(3-(5-fluoropyridin-3-yl)imidazo[1,2-a]pyridin-8-yl)-2-(trifluoromethyl)benzamide | 58 |
| 27 | 5-(3-(2,3-difluorophenyl)imidazo[1,2-a]pyridin-8-yl)-N-(4-fluorophenyl)-2-methylbenzamide | 45 |
| 28 | 5-(3-(2,3-difluorophenyl)-2-(hydroxymethyl)imidazo[1,2-a]pyridin-8-yl)-N-(4-fluorophenyl)-2-(trifluoromethyl)benzamide | 40 |
| 29 | 5-(3-(2,3-difluorophenyl)imidazo[1,2-a]pyridin-8-yl)-N-(4-fluorophenyl)-2-(trifluoromethyl)benzamide | 37 |
| 30 | 5-(3-(2,3-difluorophenyl)imidazo[1,2-b]pyridazin-8-yl)-N-(4-fluorophenyl)-2-(trifluoromethyl)benzamide | 25 |
| 31 | N-(4-fluorophenyl)-5-(3-(pyridin-3-yl)imidazo[1,2-b]pyridazin-8-yl)-2-(trifluoromethyl)benzamide | 21 |
| 32 | 5-(3-chloro-1-(2,3-difluorophenyl)imidazo[1,5-a]pyridin-5-yl)-N-(4-fluorophenyl)-2-(trifluoromethyl)benzamide | 19 |
| 33 | 5-(3-(2,3-difluorophenyl)imidazo[1,2-b]pyridazin-8-yl)-N-(4-fluorophenyl)-2-methylbenzamide | 15 |
| 34 | 5-(1-(2,3-difluorophenyl)imidazo[1,5-a]pyridin-5-yl)-N-(4-fluorophenyl)-2-(trifluoromethyl)benzamide | 15 |
| 35 | 5-(3-(2,3-difluorophenyl)pyrazolo[1,5-a]pyridin-7-yl)-N-(4-fluorophenyl)-2-(trifluoromethyl)benzamide | 13 |
| 36 | 2-(5-(3-(2,3-difluorophenyl)imidazo[1,2-a]pyridin-8-yl)-2-(trifluoromethyl)phenyl)-5-fluoro-1H-benzo[d]imidazole | 713 |

The invention claimed is:

1. A compound of Formula (I):

(I)

[chemical structure]

or a pharmaceutically acceptable salt or pharmaceutically acceptable tautomer thereof, wherein:

$Y^1$ is O or N;

----- is a single bond that is present or absent, wherein ----- is absent when $Y^1$ is O and is present when $Y^1$ is N;

$X^1$, $X^2$, $X^3$, and $X^4$ are each independently N or CH; each

[dotted circle]

indicates that the ring in which it is contained is aromatic;

one of $X^5$ and $X^6$ is C and one of $X^5$ and $X^6$ is N;

one of $X^7$ and $X^8$ is $CR^4$ and one of $X^7$ and $X^8$ is N, provided that if $X^5$ is N, $X^8$ is $CR^4$;

n is 0, 1, 2, 3, or 4;

each $R^1$ is independently $C_{1-6}$ alkyl or halo;

$R^2$ is halo, $C_{1-6}$ alkyl, or $C_{1-6}$ haloalkyl;

$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;

$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and each R is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy.

2. The compound of claim 1, wherein the compound is of Formula (Ia):

(Ia)

[chemical structure]

or a pharmaceutically acceptable salt or pharmaceutically acceptable tautomer thereof, wherein:

$X^1$, $X^2$, $X^3$, and $X^4$ are each independently N or CH; each

[dotted circle]

indicates that the ring in which it is contained is aromatic;

one of $X^5$ and $X^6$ is C and one of $X^5$ and $X^6$ is N;

one of $X^7$ and $X^8$ is $CR^4$ and one of $X^7$ and $X^8$ is N, provided that if $X^5$ is N, $X^8$ is $CR^4$;

n is 0, 1, 2, 3, or 4;

each $R^1$ is independently $C_{1-6}$ alkyl or halo;

$R^2$ is halo, $C_{1-6}$ alkyl, or $C_{1-6}$ haloalkyl;

$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;

$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy.

3. The compound of claim 1, wherein the compound is of Formula (Ib):

(Ib)

[chemical structure]

or a pharmaceutically acceptable salt or pharmaceutically acceptable tautomer thereof, wherein:

n is 0, 1, 2, 3, or 4;

each $R^1$ is independently $C_{1-6}$ alkyl or halo;

$R^2$ is halo, $C_{1-6}$ alkyl or $C_{1-6}$ haloalkyl;

$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;

$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy.

4. The compound of claim 1, wherein the compound is of Formula (Ic):

(Ic)

or a pharmaceutically acceptable salt or pharmaceutically acceptable tautomer thereof, wherein:

n is 0, 1, 2, 3, or 4;

each $R^1$ is independently $C_{1-6}$ alkyl or halo;

$R^2$ is halo, $C_{1-6}$ alkyl or $C_{1-6}$ haloalkyl;

$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;

$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy.

5. The compound of claim 1, wherein the compound is of Formula (Id):

(Id)

or a pharmaceutically acceptable salt or pharmaceutically acceptable tautomer thereof, wherein:

n is 0, 1, 2, 3, or 4;

each $R^1$ is independently $C_{1-6}$ alkyl or halo;

$R^2$ is halo, $C_{1-6}$ alkyl or $C_{1-6}$ haloalkyl;

$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;

$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy.

6. The compound of claim 1, wherein the compound is of Formula (Ie):

(Ie)

or a pharmaceutically acceptable salt or pharmaceutically acceptable tautomer thereof, wherein:

$X^1$ is N or CH;

n is 0, 1, 2, 3, or 4;

each $R^1$ is independently $C_{1-6}$ alkyl or halo;

$R^2$ is halo, $C_{1-6}$ alkyl or $C_{1-6}$ haloalkyl;

$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;

$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy.

7. The compound of claim 1, wherein the compound is of Formula (If):

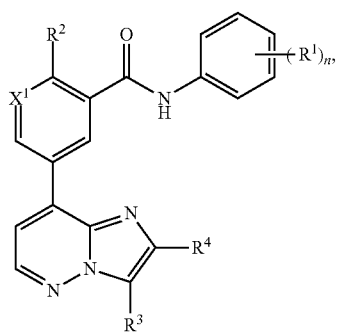

(If)

or a pharmaceutically acceptable salt or pharmaceutically acceptable tautomer thereof, wherein:
$X^1$ is N or CH;
n is 0, 1, 2, 3, or 4;
each $R^1$ is independently $C_{1-6}$ alkyl or halo;
$R^2$ is halo, $C_{1-6}$ alkyl or $C_{1-6}$ haloalkyl;
$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;
$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and
each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy.

8. The compound of claim 1, wherein the compound is of Formula (Ig):

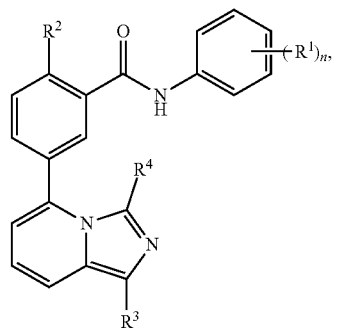

(Ig)

or a pharmaceutically acceptable salt or pharmaceutically acceptable tautomer thereof, wherein:
n is 0, 1, 2, 3, or 4;
each $R^1$ is independently $C_{1-6}$ alkyl or halo;
$R^2$ is halo, $C_{1-6}$ alkyl or $C_{1-6}$ haloalkyl;
$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;
$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and
each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy.

9. The compound of claim 1, wherein the compound is of Formula (Ih):

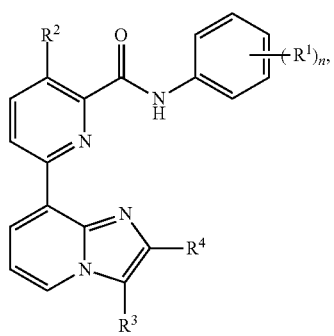

(Ih)

or a pharmaceutically acceptable salt or pharmaceutically acceptable tautomer thereof, wherein:
n is 0, 1, 2, 3, or 4;
each $R^1$ is independently $C_{1-6}$ alkyl or halo;
$R^2$ is halo, $C_{1-6}$ alkyl or $C_{1-6}$ haloalkyl;
$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;
$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and
each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy.

10. The compound of claim 1, wherein the compound is of Formula (Ii):

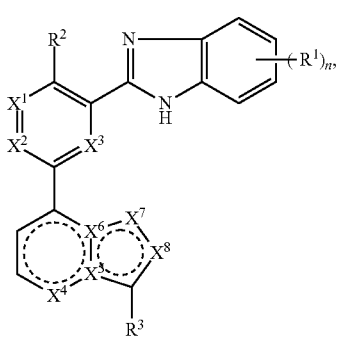

(Ii)

or a pharmaceutically acceptable salt or pharmaceutically acceptable tautomer thereof, wherein:

$X^1$, $X^2$, $X^3$, and $X^4$ are each independently N or CH; each

indicates that the ring in which it is contained is aromatic;

one of $X^5$ and $X^6$ is C and one of $X^5$ and $X^6$ is N;
one of $X^7$ and $X^8$ is $CR^4$ and one of $X^7$ and $X^8$ is N, provided that if $X^5$ is N, $X^8$ is $CR^4$;
n is 0, 1, 2, 3, or 4;
each $R^1$ is independently $C_{1-6}$ alkyl or halo;
$R^2$ is halo, $C_{1-6}$ alkyl or $C_{1-6}$ haloalkyl;
$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;
$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and
each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy.

11. The compound of claim 1, wherein the compound is of Formula (Ij):

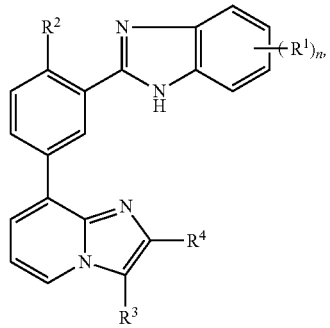

(Ij)

or a pharmaceutically acceptable salt or pharmaceutically acceptable tautomer thereof, wherein:
n is 0, 1, 2, 3, or 4;
each $R^1$ is independently $C_{1-6}$ alkyl or halo;
$R^2$ is halo, $C_{1-6}$ alkyl or $C_{1-6}$ haloalkyl;
$R^3$ is 6-12 membered aryl or 5-12 membered heteroaryl, wherein the 6-12 membered aryl or 5-12 membered heteroaryl of $R^3$ is unsubstituted or substituted with one, two, or three substituents independently selected from halo, CN, $C_{1-6}$ alkyl, and $C_{1-6}$ haloalkyl;
$R^4$ is hydrogen, halo, $C_{1-6}$ alkyl, or $C_{1-6}$ alkoxy, wherein the $C_{1-6}$ alkyl or $C_{1-6}$ alkoxy of $R^4$ is unsubstituted or substituted with one, two, or three $R^5$; and each $R^5$ is independently hydroxyl, amino, $C_{1-4}$ alkyl or $C_{1-4}$ alkoxy, wherein the $C_{1-4}$ alkyl or $C_{1-4}$ alkoxy of $R^5$ is unsubstituted or substituted with $C_{1-3}$ alkyl or $C_{1-3}$ alkoxy.

12. The compound of claim 1, or a pharmaceutically acceptable salt or pharmaceutically acceptable tautomer thereof, wherein n is 0.

13. The compound of claim 1, or a pharmaceutically acceptable salt or pharmaceutically acceptable tautomer thereof, wherein n is 1.

14. The compound of claim 1, or a pharmaceutically acceptable salt or pharmaceutically acceptable tautomer thereof, wherein n is 2.

15. The compound of claim 1, or a pharmaceutically acceptable salt or pharmaceutically acceptable tautomer thereof, wherein each $R^1$ is independently halo.

16. The compound of claim 1, or a pharmaceutically acceptable salt or pharmaceutically acceptable tautomer thereof, wherein $R^1$ is fluoro.

17. The compound of claim 1, or a pharmaceutically acceptable salt or pharmaceutically acceptable tautomer thereof, wherein $R^2$ is methyl, chloro, or —$CF_3$.

18. The compound of claim 1, or a pharmaceutically acceptable salt or pharmaceutically acceptable tautomer thereof, wherein $R^3$ is phenyl or 5-6 membered heteroaryl, wherein the phenyl or 5-6 membered heteroaryl of $R^3$ is unsubstituted or substituted with one or two substituents independently selected from halo and $C_{1-3}$ alkyl.

19. The compound of claim 1, or a pharmaceutically acceptable salt or pharmaceutically acceptable tautomer thereof, wherein $R^3$ is selected from the group consisting of:

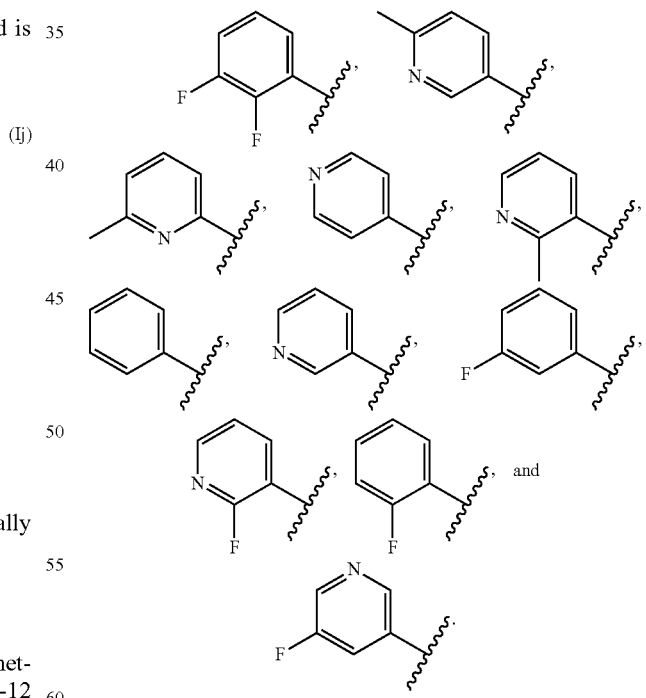

20. The compound of claim 1, or a pharmaceutically acceptable salt or pharmaceutically acceptable tautomer thereof, wherein $R^4$ is hydrogen.

21. The compound of claim 1, or a pharmaceutically acceptable salt or pharmaceutically acceptable tautomer thereof, wherein $R^4$ is halo.

22. The compound of claim 1, or a pharmaceutically acceptable salt or pharmaceutically acceptable tautomer thereof, wherein $R^4$ is $C_{1-6}$ alkyl which is unsubstituted or substituted with one, two, or three $R^5$.

23. The compound of claim 1, or a pharmaceutically acceptable salt or pharmaceutically acceptable tautomer thereof, wherein $R^4$ is selected from the group consisting of:

hydrogen, methyl, chloro,

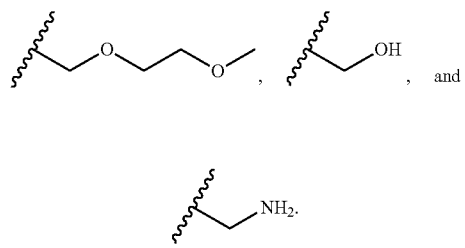, and

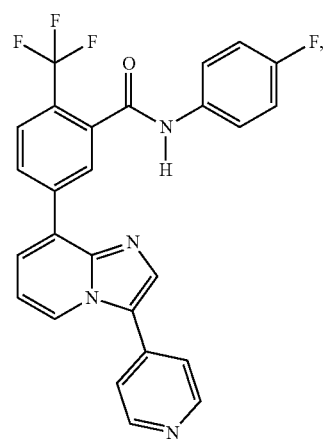

24. A compound selected from the group consisting of:

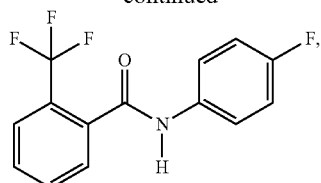

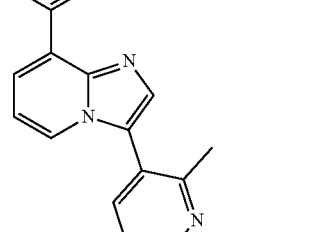

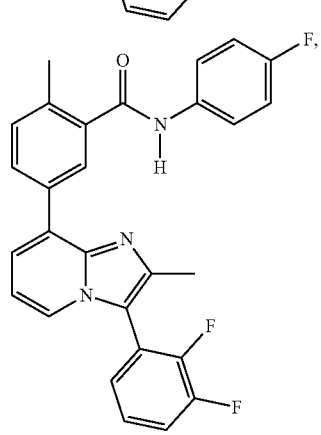

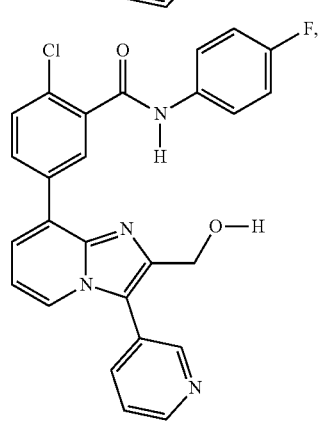

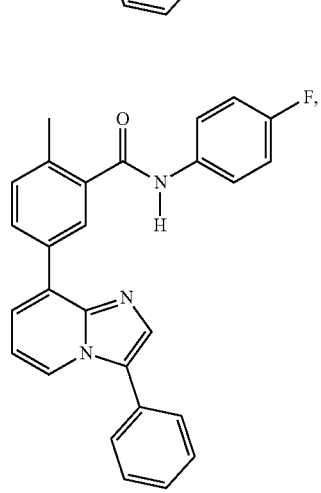

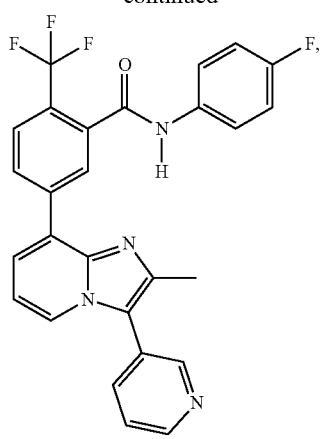
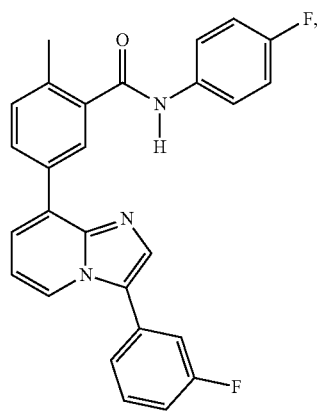
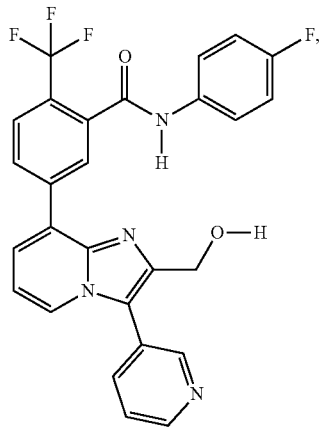
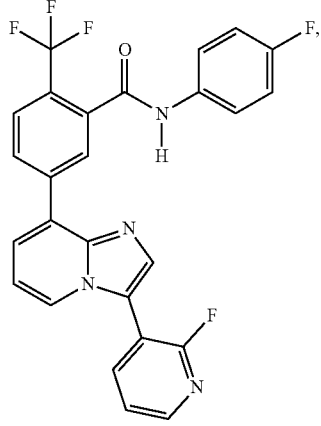
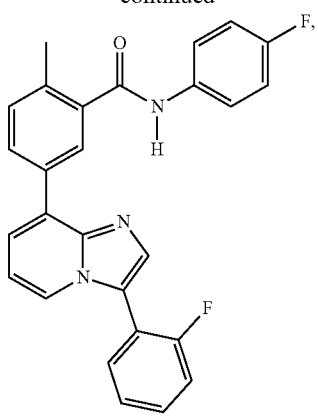
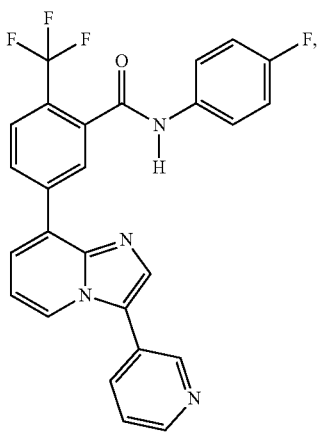
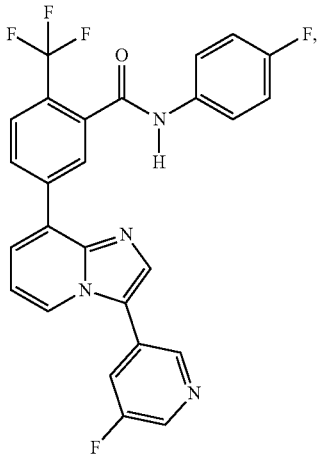
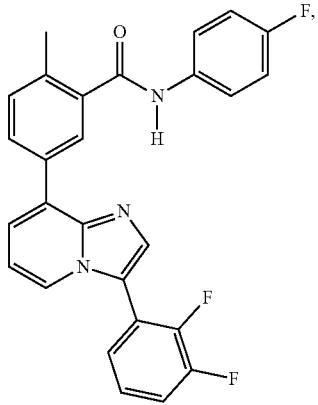

197
-continued
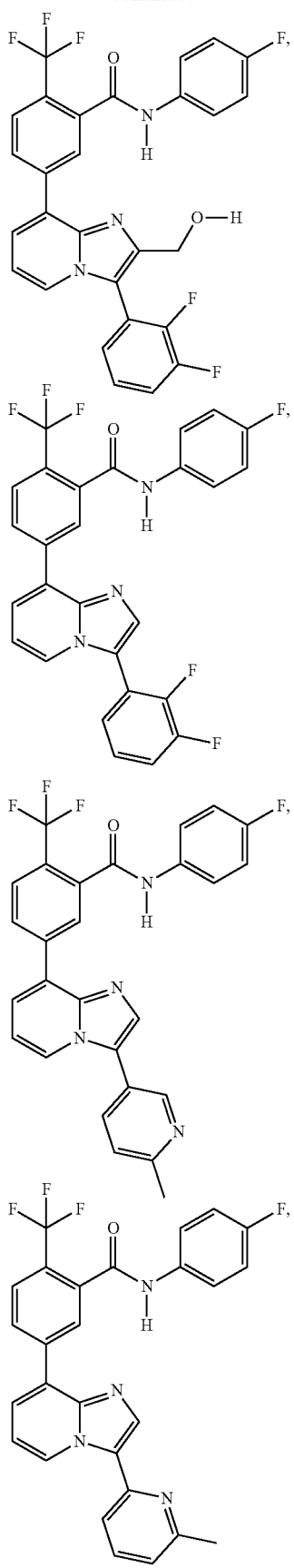
198
-continued
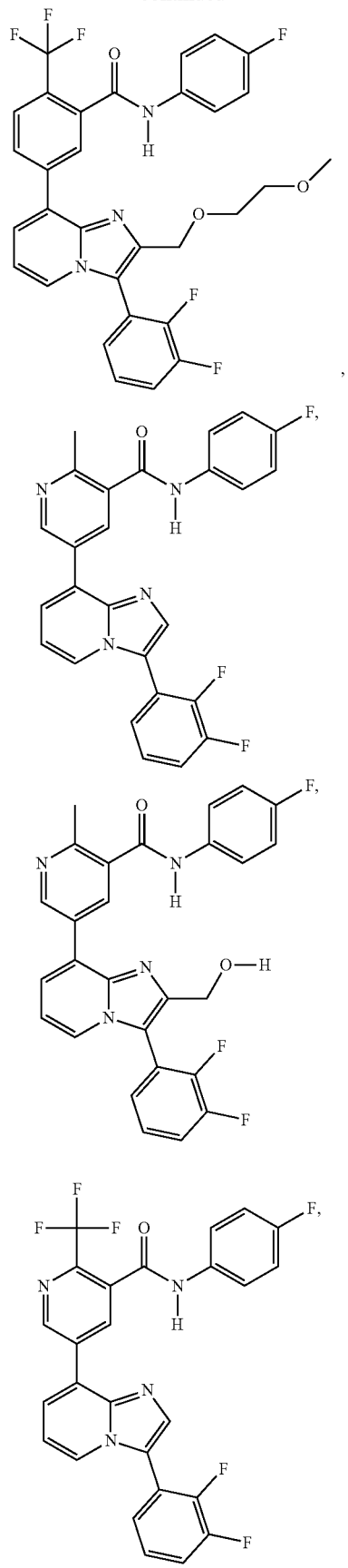

199
-continued
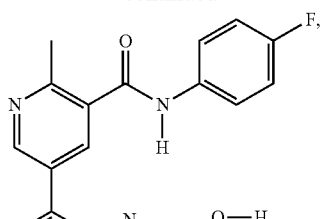
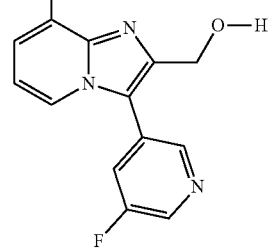
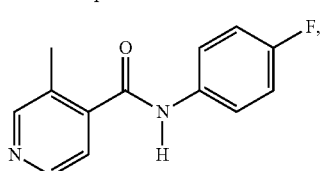
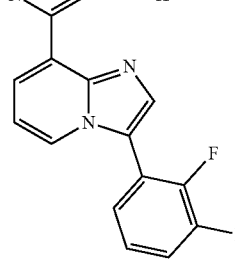
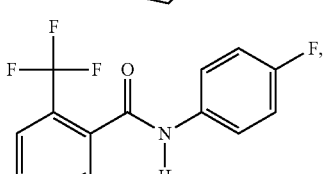
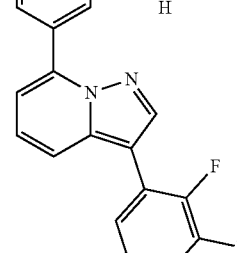
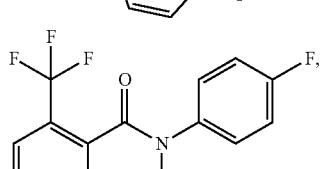
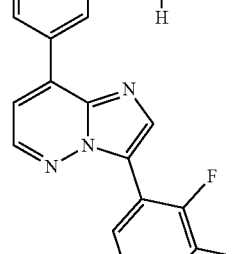
200
-continued
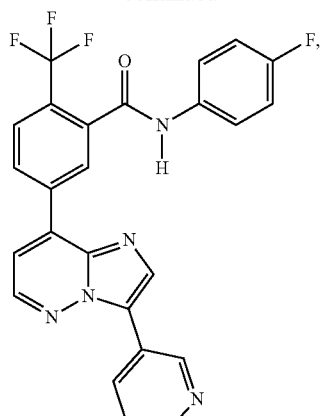
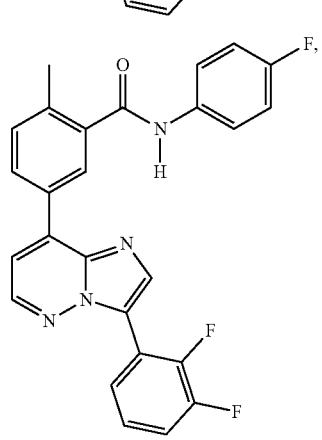
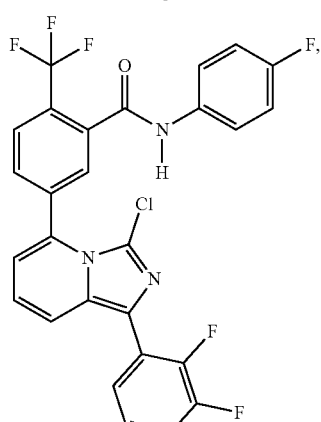
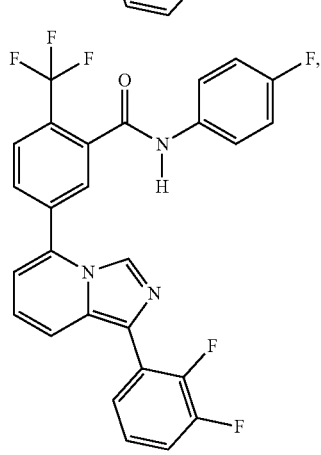

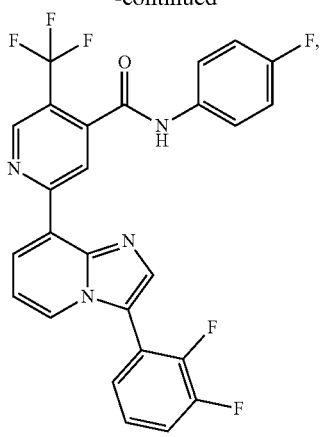
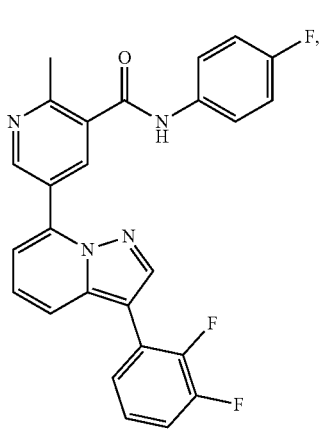
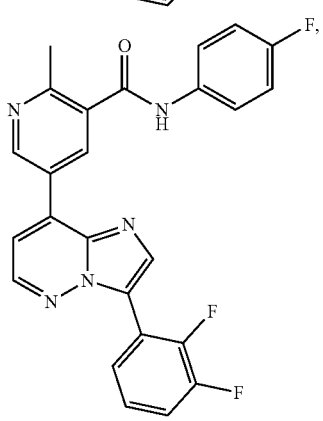
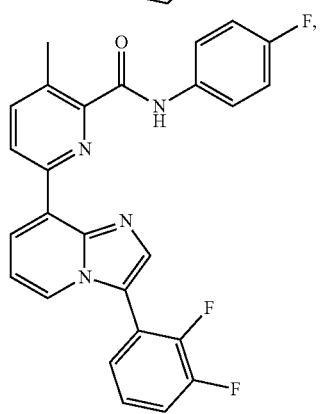
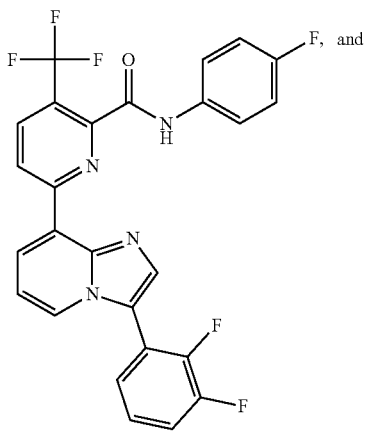
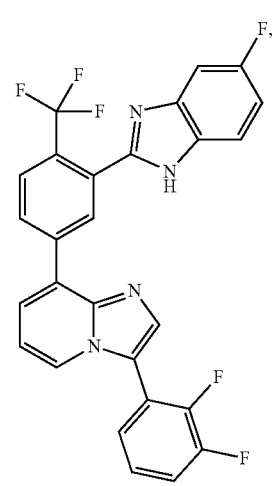 [SMILES: Fc1ccc2[nH]c(-c3cc(-c4cccn5c(-c6cccc(F)c6F)cnc45)ccc3C(F)(F)F)nc2c1]
or a pharmaceutically acceptable salt or pharmaceutically acceptable tautomer thereof.
25. The compound of claim 24, wherein the compound is selected from the group consisting of:
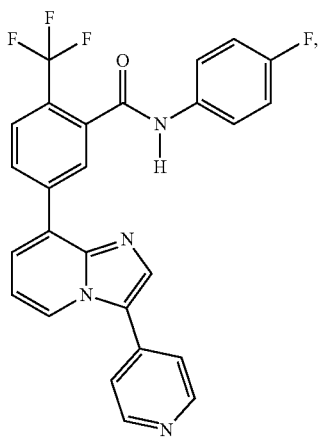

-continued
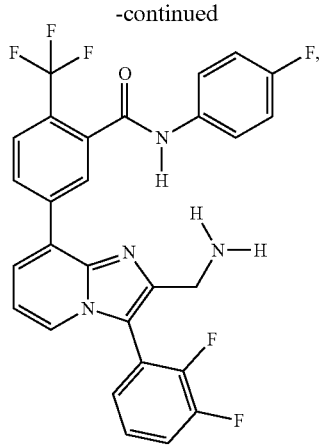
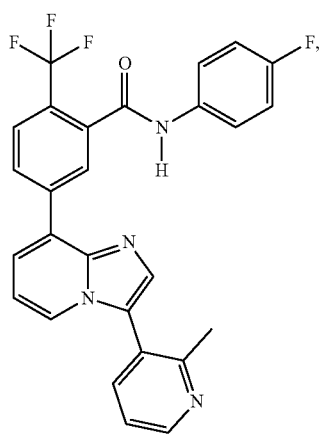
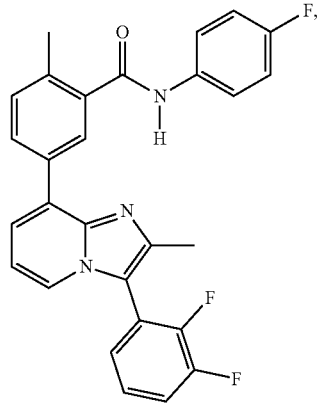
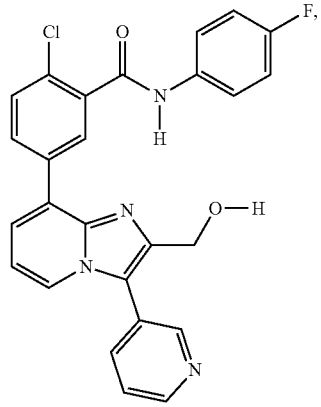
-continued
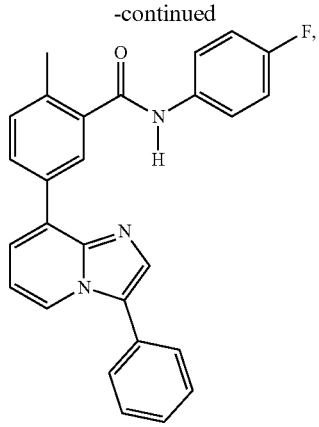
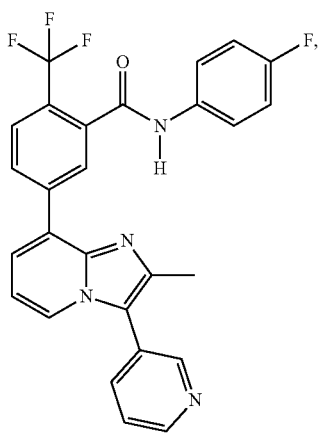
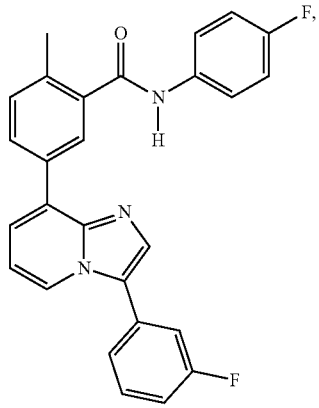
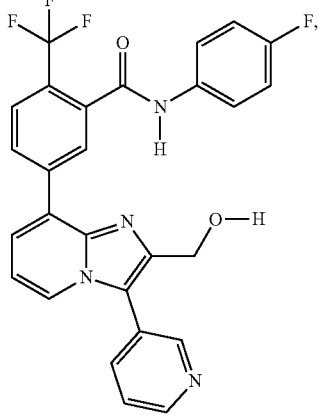

-continued
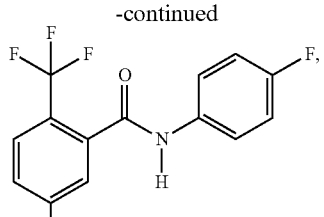
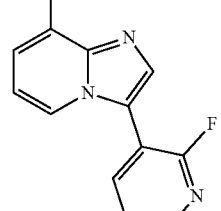
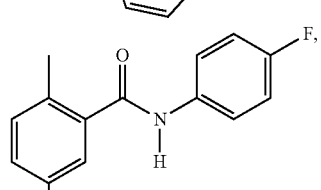
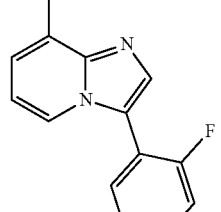
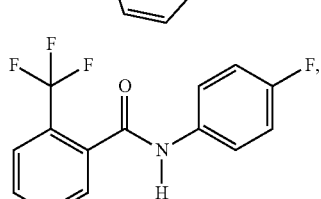
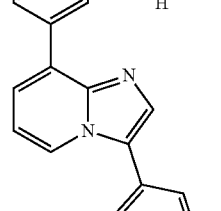
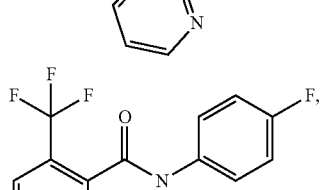
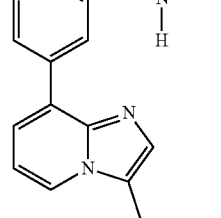
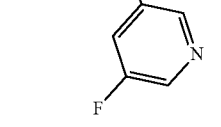
-continued
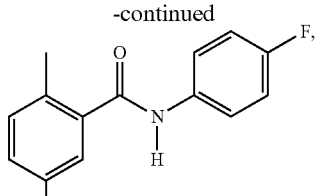
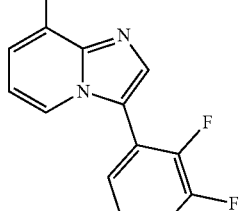
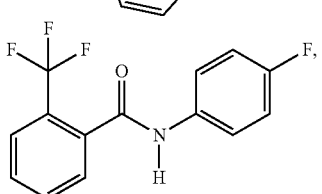
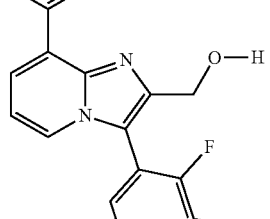
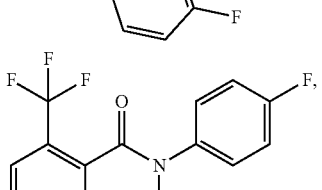
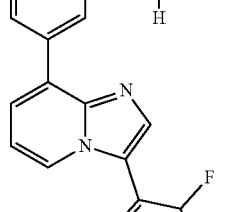
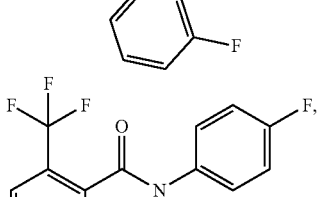
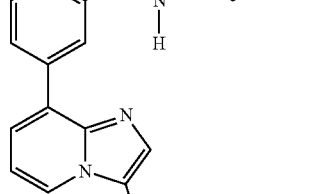
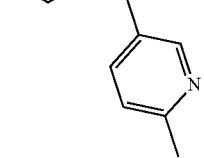

207
-continued

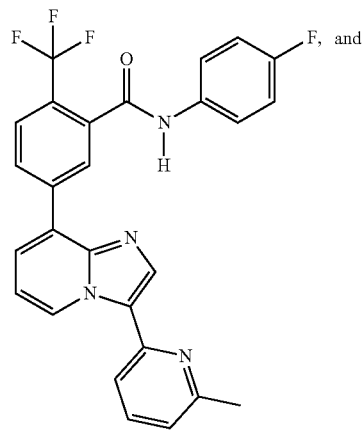

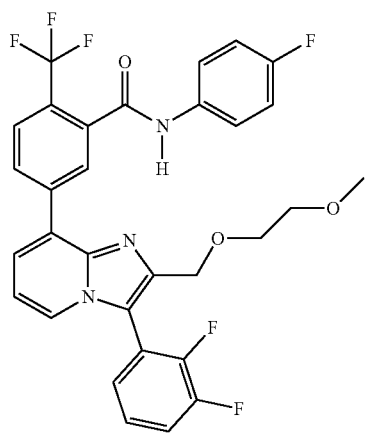

or a pharmaceutically acceptable salt or pharmaceutically acceptable tautomer thereof.

26. The compound of claim 24, wherein the compound is selected from the group consisting of:

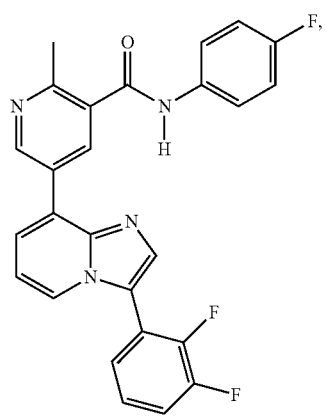

208
-continued

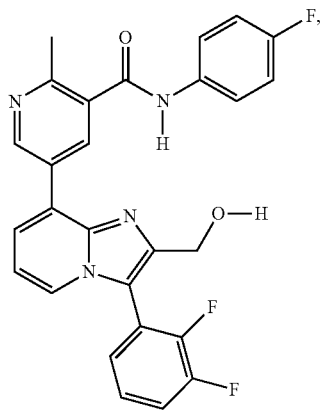

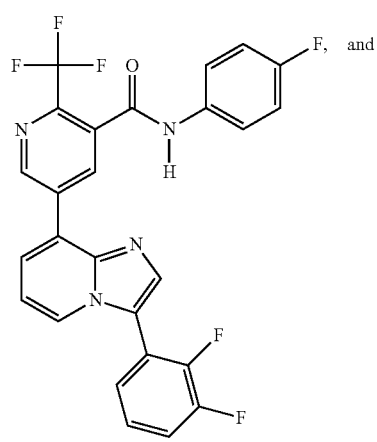

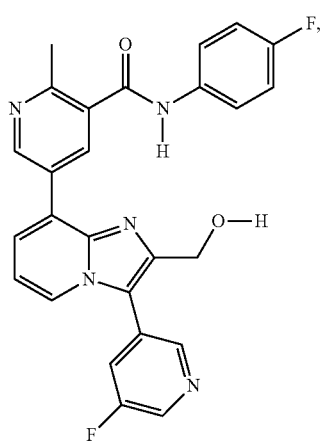

or a pharmaceutically acceptable salt or pharmaceutically acceptable tautomer thereof.

27. The compound of claim 24, wherein the compound is selected from the group consisting of:

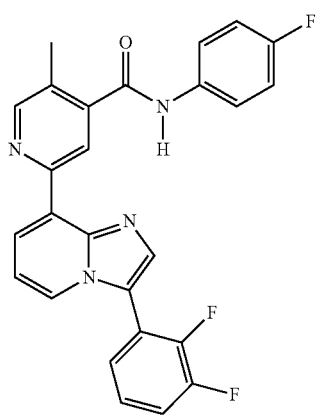
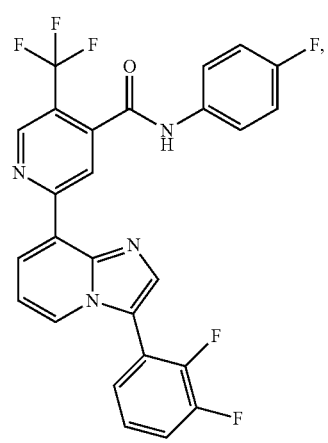
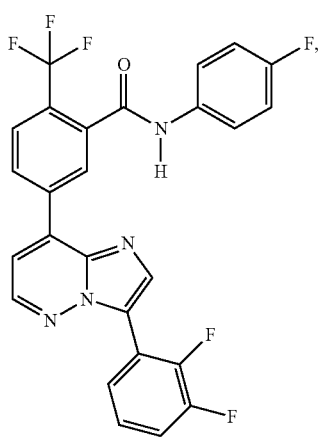
or a pharmaceutically acceptable salt or pharmaceutically acceptable tautomer thereof.
28. The compound of claim 24, wherein the compound is selected from the group consisting of:
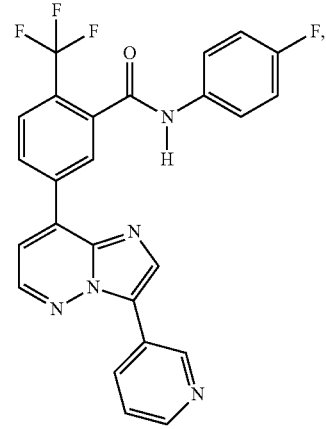
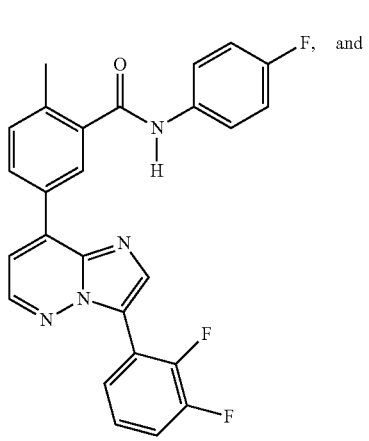
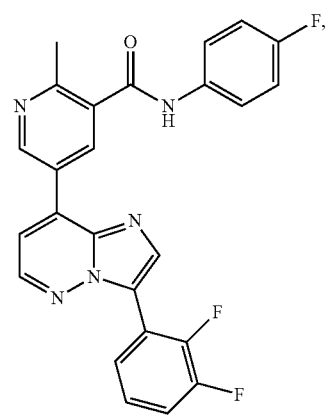
or a pharmaceutically acceptable salt or pharmaceutically acceptable tautomer thereof.
29. The compound of claim 24, wherein the compound is selected from the group consisting of:

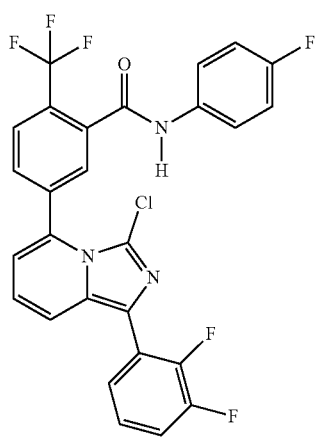

and

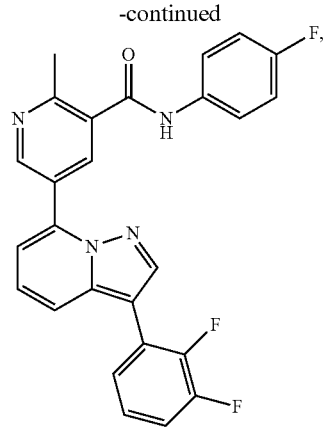

or a pharmaceutically acceptable salt or pharmaceutically acceptable tautomer thereof.

31. The compound of claim 24, wherein the compound is selected from the group consisting of:

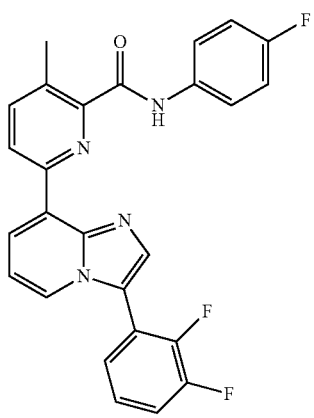

and

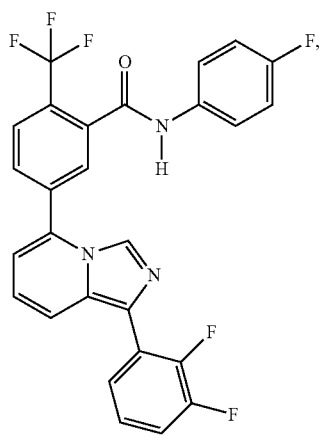

or a pharmaceutically acceptable salt or pharmaceutically acceptable tautomer thereof.

30. The compound of claim 24, wherein the compound is selected from the group consisting of:

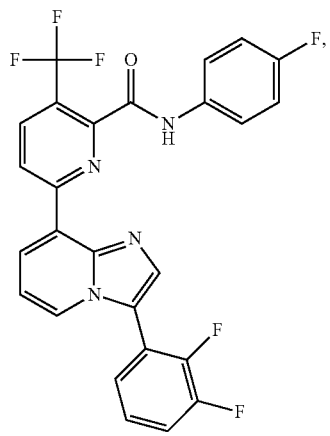

or a pharmaceutically acceptable salt or pharmaceutically acceptable tautomer thereof.

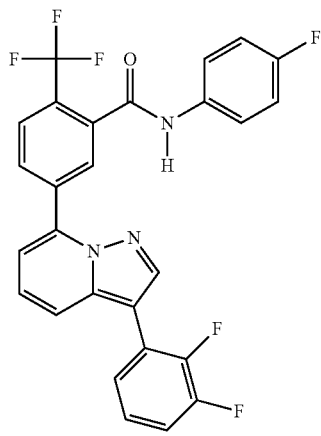

and

32. The compound of claim 24, wherein the compound is:

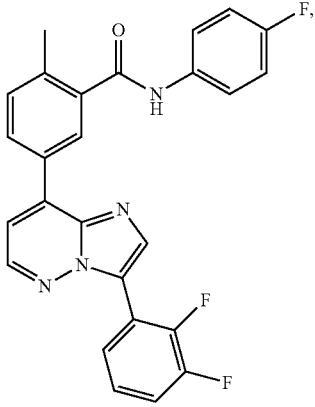 [SMILES: Cc1ccc(-c2ccnn3c(-c4cccc(F)c4F)cnc23)cc1C(=O)Nc1ccc(F)cc1]

or a pharmaceutically acceptable salt or pharmaceutically acceptable tautomer thereof.

33. The compound of claim 24, wherein the compound is:

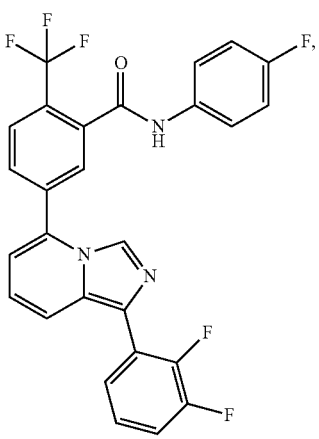 [SMILES: O=C(Nc1ccc(F)cc1)c1cc(-c2cccc3c(-c4cccc(F)c4F)ncn23)ccc1C(F)(F)F]

or a pharmaceutically acceptable salt or pharmaceutically acceptable tautomer thereof.

34. The compound of claim 24, wherein the compound is:

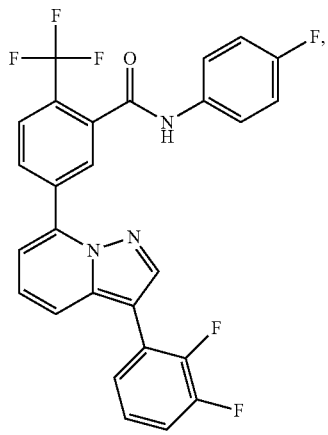 [SMILES: O=C(Nc1ccc(F)cc1)c1cc(-c2cccc3c(-c4cccc(F)c4F)cnn23)ccc1C(F)(F)F]

or a pharmaceutically acceptable salt or pharmaceutically acceptable tautomer thereof.

35. The compound of claim 24, wherein the compound is:

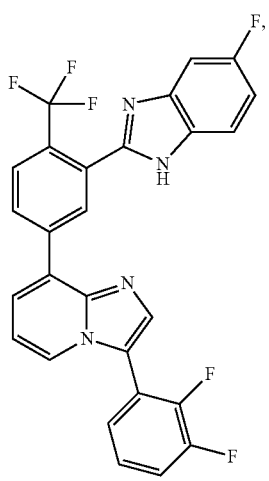 [SMILES: Fc1ccc2[nH]c(-c3cc(-c4cccn5c(-c6cccc(F)c6F)cnc45)ccc3C(F)(F)F)nc2c1]

or a pharmaceutically acceptable salt or pharmaceutically acceptable tautomer thereof.

36. A pharmaceutical composition comprising the compound of claim 1, or a pharmaceutically acceptable salt or pharmaceutically acceptable tautomer thereof, and at least one pharmaceutically acceptable carrier.

* * * * *